(12) United States Patent
Flohr et al.

(10) Patent No.: US 7,652,007 B2
(45) Date of Patent: Jan. 26, 2010

(54) NITROGEN-SUBSTITUTED HEXAHYDROPYRAZINO[1,2-A]PYRIMIDINE-4,7-DIONE DERIVATIVES, PROCESSES FOR THEIR PREPARATION AND THEIR USE AS MEDICAMENTS

(75) Inventors: Stefanie Flohr, Basel (CH); Siegfried Stengelin, Eppstein (DE); Matthias Gossel, Hofheim (DE); Thomas Klabunde, Frankfurt (DE); Petra Stahl, Frankfurt (DE); Pavel Safar, Tucson, AZ (US); James Spoonamore, Tucson, AZ (US); Martin Smrcina, Tucson, AZ (US); Joseph Klein, Neshanic Station, NJ (US); Gregory Merriman, Phillipsburg, NJ (US); Brian Whiteley, Lebanon, NJ (US); Carolina Lanter, Flemington, NJ (US); Kenneth Bordeau, Kintnersville, PA (US); Zhaoxia Yang, Roselle Park, NJ (US)

(73) Assignee: Sanofi-Aventis Deutschland GmbH, Frankfurt am Main (DE)

( * ) Notice: Subject to any disclaimer, the term of this patent is extended or adjusted under 35 U.S.C. 154(b) by 379 days.

(21) Appl. No.: 10/779,439

(22) Filed: Feb. 13, 2004

(65) Prior Publication Data
US 2005/0085483 A1   Apr. 21, 2005

Related U.S. Application Data

(60) Provisional application No. 60/480,423, filed on Jun. 20, 2003.

(30) Foreign Application Priority Data

Feb. 13, 2003  (DE) ................................. 103 05 885
Oct. 24, 2003  (DE) ................................. 103 49 671

(51) Int. Cl.
C07D 487/00 (2006.01)
A61K 31/495 (2006.01)
A01N 43/60 (2006.01)

(52) U.S. Cl. .................... 514/249; 514/259.1; 514/262; 544/350; 544/245; 544/256

(58) Field of Classification Search ................ 514/249, 514/259.1, 262; 544/350, 245, 256
See application file for complete search history.

(56) References Cited

U.S. PATENT DOCUMENTS
2002/0065284 A1   5/2002   Carpino et al.

FOREIGN PATENT DOCUMENTS

| WO | WO 97/26265 | 7/1997 |
|---|---|---|
| WO | WO 97/41097 | 11/1997 |
| WO | WO 98/08871 | 3/1998 |
| WO | WO 99/03861 | 1/1999 |
| WO | WO 01/16135 | 3/2001 |

OTHER PUBLICATIONS

Krchnak, V., et. al., Noninvasive Continuous Monitoring of Solid-Phase Peptide Synthesis by Acid-Base Indicator, Collect. Czech. Chem. Commun. vol. 53, (1988) pp. 2542-2548.

Tyle, P., et. al., Iontophoretic Devices for Drug Delivery, Pharmaceutical Research, 1986, vol. 3, No. 6, 318-326.

Vojkovsky, T., et. al., Solid-Phase Synthesis of Heterocycles Containing an 1-Acyl-3-oxopiperazine Skeleton, J. Org. Chem.; 63; 1998; pp. 3162-3163.

*Primary Examiner*—James O. Wilson
*Assistant Examiner*—Paul V. Ward
(74) *Attorney, Agent, or Firm*—Barbara E. Kurys

(57) ABSTRACT

Nitrogen-substituted hexahydropyrazino[1,2-a]pyrimidine-4,7-dione derivatives, processes for the preparation and their use as medicaments The invention relates to substituted hexahydropyrazino[1,2-a]pyrimidine-4,7-dione derivatives and to the physiologically tolerated salts and physiologically functional derivatives thereof.

Compounds of the formula I in which the radicals have the stated meanings, and the physiologically tolerated salts thereof and processes for preparing them are described. The compounds are suitable for example as anorectic agents.

5 Claims, No Drawings

NITROGEN-SUBSTITUTED HEXAHYDROPYRAZINO[1,2-A]PYRIMIDINE-4,7-DIONE DERIVATIVES, PROCESSES FOR THEIR PREPARATION AND THEIR USE AS MEDICAMENTS

The invention relates to substituted hexahydropyrazino[1,2-a]pyrimidine-4,7-dione derivatives and to the physiologically tolerated salts thereof.

The invention was based on the object of providing compounds which bring about a weight reduction in mammals and are suitable for the prevention and treatment of obesity.

The invention therefore relates to compounds of the formula I,

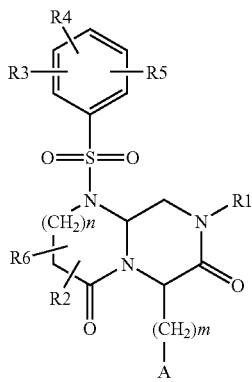

wherein

A is a 3-, 4-, 5-, 6-, 7-, 8-, 9-, 10-, 11-, and 12-membered mono-, bi- or spirobicyclic ring containing one or more heteroatoms selected from the group of N, O and S, and is optionally substituted with F, Cl, Br, $NO_2$, $CF_3$, $OCF_3$, CN, $(C_1-C_6)$-alkyl, aryl, CON(R11)(R12), N(R13)(R14), OH, O—$(C_1-C_6)$-alkyl, S—$(C_1-C_6)$-alkyl, N(R15)CO$(C_1-C_6)$-alkyl or COO—$(C_1-C_6)$-alkyl;

R11, R12, R13, R14, R15 are each independently H, $(C_1-C_6)$-alkyl or a heterocycle;

n is 0 or 1;

m is 0, 1, 2, 3, 4, 5 or 6;

R1 is R8, $(C_1-C_6)$-alkylene-R8, $(C_2-C_6)$-alkenylene-R9, $(SO_2)$—R8, $(SO_2)$—$(C_1-C_6)$-alkylene-R8, $(SO_2)$—$(C_2-C_6)$-alkenylene-R9, (C=O)—R8, (C=O)—$(C_1-C_6)$-alkylene-R8, (C=O)NH—R8, (C=O)—$(C_2-C_6)$-alkenylene-R9, (C=O)—NH—$(C_1-C_6)$-alkylene-R8, (C=O)—NH—$(C_2-C_6)$-alkenylene-R9, COO—R8, COO—$(C_1-C_6)$-alkylene-R8, COO—$(C_2-C_6)$-alkenylene-R9, alkynylene-R9 or $(C_1-C_4$-alkyl)-heterocycle, wherein the alkylene component of said $(C_1-C_6)$-alkylene-R8, $(C_2-C_6)$-alkenylene-R9, $(SO_2)$—$(C_1-C_6)$-alkylene-R8, $(SO_2)$—$(C_2-C_6)$-alkenylene-R9, (C=O)—$(C_1-C_6)$-alkylene-R8, (C=O)—$(C_2-C_6)$-alkenylene-R9, (C=O)—NH—$(C_1-C_6)$-alkylene-R8, (C=O)—NH—$(C_2-C_6)$-alkenylene-R9, COO—$(C_1-C_6)$-alkylene-R8, COO—$(C_2-C_6)$-alkenylene-R9 and alkynylene-R9 groups is optionally substituted by F;

R8, R9 are each independently H, F, Cl, Br, I, OH, $CF_3$, aryl, heterocycle or $(C_3-C_8)$-cycloalkyl, wherein said aryl, heterocycle and $(C_3-C_8)$-cycloalkyl groups are optionally mono-, di- or tri-substituted by F, Cl, Br, I, OH, $CF_3$, $NO_2$, CN, $OCF_3$, O—$(C_1-C_6)$-alkyl, $(C_1-C_6)$-alkyl, $NH_2$, CON(R11)(R12), N(R13)(R14), $SO_2$—$CH_3$, COOH, COO—$(C_1-C_6)$-alkyl or $CONH_2$;

R2 is $NH_2$, $NO_2$, N(R13)(R14), NH—$SO_2$—$CH_3$, NH—$SO_2$—R12, NR11—$SO_2$—R12, N(CO)R11, NHCONR11, N$(C_1-C_6$-alkyl)$N^+(C_1-C_4$-alkyl)$_3$ or a nitrogen-containing heterocycle, wherein said heterocycle is bonded via a nitrogen atom;

R3, R4, R5 are each independently H, F, Cl, Br, I, OH, $CF_3$, $NO_2$, CN, $OCF_3$, O—$(C_1-C_6)$-alkyl, O—$(C_1-C_4)$-alkoxy-$(C_1-C_4)$-alkyl, S—$(C_1-C_6)$-alkyl, $(C_1-C_6)$-alkyl, $(C_2-C_6)$-alkenyl, $(C_3-C_8)$-cycloalkyl, O—$(C_3-C_8)$-cycloalkyl, $(C_3-C_8)$-cycloalkenyl, O—$(C_3-C_8)$-cycloalkenyl, $(C_2-C_6)$-alkynyl, aryl, O-aryl$(C_1-C_8)$-alkylene-aryl, O—$(C_1-C_8)$-alkylene-aryl, S-aryl, N$((C_1-C_6)$-alkyl$)_2$, $SO_2$—$CH_3$, COOH, COO—$(C_1-C_6)$-alkyl or CO—N$((C_1-C_6)$-alkyl$)_2$;

R6 is H, F, Cl, Br, I, OH, $CF_3$, $NO_2$, CN, $OCF_3$, O—$(C_1-C_6)$-alkyl, O—$(C_1-C_4)$-alkoxy-$(C_1-C_4)$-alkyl, S—$(C_1-C_6)$-alkyl, $(C_1-C_6)$-alkyl, $(C_2-C_6)$-alkenyl, $(C_3-C_8)$-cycloalkyl, O—$(C_3-C_8)$-cycloalkyl, $(C_3-C_8)$-cycloalkenyl, O—$(C_3-C_8)$-cycloalkenyl, $(C_2-C_6)$-alkynyl, (CO—$C_8)$-alkylene-aryl, O—(CO—$C_8)$-alkylene-aryl, S-aryl, N$((C_1-C_6)$-alkyl$)_2$, $SO_2$—$CH_3$, COOH, COO—$(C_1-C_6)$-alkyl or CO—N$((C_1-C_6)$-alkyl$)_2$;

and pharmaceutically acceptable salts thereof.

Preference is given to compounds of the formula I of the following structure Ia

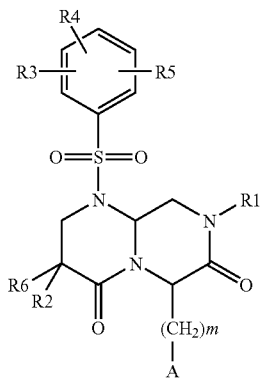

wherein

A is a 3-, 4-, 5-, 6-, 7-, 8-, 9-, 10-, 11-, and 12-membered mono-, bi- or spirobicyclic ring containing one or more heteroatoms selected from the group of N, O and S, and is optionally substituted with F, Cl, Br, $NO_2$, $CF_3$, $OCF_3$, CN, $(C_1-C_6)$-alkyl, aryl, CON(R11)(R12), N(R13)(R14), OH, O—$(C_1-C_6)$-alkyl, S—$(C_1-C_6)$-alkyl, N(R15)CO$(C_1-C_6)$-alkyl or COO—$(C_1-C_6)$-alkyl;

R11, R12, R13, R14, R15 are each independently H, $(C_1-C_6)$-alkyl or a heterocycle;

m is 0, 1, 2, 3, 4, 5 or 6;

R1 is R8, $(C_1-C_6)$-alkylene-R8, $(C_2-C_6)$-alkenylene-R9, $(SO_2)$—R8, $(SO_2)$—$(C_1-C_6)$-alkylene-R8, $(SO_2)$—$(C_2-C_6)$-alkenylene-R9, (C=O)—R8, (C=O)—$(C_1-C_6)$-alkylene-R8, (C=O)NH—R8, (C=O)—$(C_2-C_6)$-alkenylene-R9, (C=O)—NH—$(C_1-C_6)$-alkylene-R8, (C=O)—NH— $(C_2-C_6)$-alkenylene-R9, COO—R8, COO—$(C_1-C_6)$-alkylene-R8, COO—$(C_2-C_6)$-alkenylene-R9, alkynylene-R9 or $(C_1-C_4$-alkyl)-heterocycle;

R8, R9 are each independently H, F, Cl, Br, I, OH, $CF_3$, aryl, heterocycle or $(C_3-C_8)$-cycloalkyl, wherein said aryl, heterocycle and $(C_3-C_8)$-cycloalkyl groups are optionally mono-, di- or tri-substituted by F, Cl, Br, I, OH, $CF_3$, $NO_2$, CN, $OCF_3$, O—$(C_1-C_6)$-alkyl, $(C_1-C_6)$-alkyl, $NH_2$, CON(R11)(R12), N(R13)(R14), $SO_2$—$CH_3$, COOH, COO—$(C_1-C_6)$-alkyl or $CONH_2$;

R2 is $NH_2$, $NO_2$, N(R13)(R14), NH—$SO_2$—$CH_3$, NH—$SO_2$—R12, NR11-$SO_2$—R12, N(CO)R11, NHCONR11, N($C_1$-$C_6$-alkyl)$N^+$($C_1$-$C_4$-alkyl)$_3$ or a nitrogen-containing heterocycle, wherein said heterocycle is bonded via a nitrogen atom;

R3, R4, R5 are each independently H, F, Cl, Br, I, OH, $CF_3$, $NO_2$, CN, $OCF_3$, O—$(C_1-C_6)$-alkyl, O—$(C_1-C_4)$-alkoxy-$(C_1-C_4)$-alkyl, S—$(C_1-C_6)$-alkyl, $(C_1-C_6)$-alkyl, $(C_2-C_6)$-alkenyl, $(C_3-C_8)$-cycloalkyl, O—$(C_3-C_8)$-cycloalkyl, $(C_3-C_8)$-cycloalkenyl, O—$(C_3-C_8)$-cycloalkenyl, $(C_2-C_6)$-alkynyl, aryl, O-aryl$(C_1-C_8)$-alkylene-aryl, O—$(C_1-C_8)$-alkylene-aryl, S-aryl, N(($C_1-C_6$)-alkyl)$_2$, $SO_2$—$CH_3$, COOH, COO—$(C_1-C_6)$-alkyl or CO—N(($C_1-C_6$)-alkyl)$_2$;

R6 is H, F, Cl, Br, I, OH, $CF_3$, $NO_2$, CN, $OCF_3$, O—$(C_1-C_6)$-alkyl, O—$(C_1-C_4)$-alkoxy-$(C_1-C_4)$-alkyl, S—$(C_1-C_6)$-alkyl, $(C_1-C_6)$-alkyl, $(C_2-C_6)$-alkenyl, $(C_3-C_8)$-cycloalkyl, O—$(C_3-C_8)$-cycloalkyl, $(C_3-C_8)$-cycloalkenyl, O—$(C_3-C_8)$-cycloalkenyl, $(C_2-C_6)$-alkynyl, aryl, O-aryl, $(C_1-C_8)$-alkylene-aryl, O—$(C_1-C_8)$-alkylene-aryl, S-aryl, N(($C_1-C_6$)-alkyl)$_2$, $SO_2$—$CH_3$, COOH, COO—$(C_1-C_6)$-alkyl or CO—N(($C_1-C_6$)-alkyl)$_2$;

and pharmaceutically acceptable salts thereof.

Particular preference is given to compounds of the formula Ia wherein

A is aryl wherein said aryl is optionally substituted by F, Cl, Br, $NO_2$, $CF_3$, $OCF_3$, CN, $(C_1-C_6)$-alkyl, aryl, CON(R11)(R12), N(R13)(R14), OH, O—$(C_1-C_6)$-alkyl, S—$(C_1-C_6)$-alkyl, N(R15)CO($C_1-C_6$)-alkyl or COO—$(C_1-C_6)$-alkyl;

R11, R12, R13, R14, R15 are each independently H, $(C_1-C_6)$-alkyl or heterocycle;

m is 1;

R1 is R8, $(C_1-C_6)$-alkylene-R8, $(C_2-C_6)$-alkenylene-R9, ($SO_2$)—R8, ($SO_2$)—$(C_1-C_6)$-alkylene-R8, ($SO_2$)—$(C_2-C_6)$-alkenylene-R9, (C=O)—R8, (C=O)—$(C_1-C_6)$-alkylene-R8, (C=O)NH—R8, (C=O)—$(C_2-C_6)$-alkenylene-R9, (C=O)—NH—$(C_1-C_6)$-alkylene-R8, (C=O)—NH—$(C_2-C_6)$-alkenylene-R9, COO—R8, COO—$(C_1-C_6)$-alkylene-R8, COO—$(C_2-C_6)$-alkenylene-R9, alkynylene-R9 or $(C_1-C_4$-alkyl)-heterocycle;

R8, R9 are each independently H, F, Cl, Br, I, OH, $CF_3$, aryl, heterocycle or $(C_3-C_8)$-cycloalkyl, wherein said aryl, heterocycle and $(C_3-C_8)$-cycloalkyl groups are optionally mono-, di-, or tri-substituted by F, Cl, Br, I, OH, $CF_3$, $NO_2$, CN, $OCF_3$, O—$(C_1-C_6)$-alkyl, $(C_1-C_6)$-alkyl, $NH_2$, CON(R11)(R12), N(R13)(R14), $SO_2$—$CH_3$, COOH, COO—$(C_1-C_6)$-alkyl or $CONH_2$;

R2 is $NH_2$, $NO_2$, N(R13)(R14), NH—$SO_2$—$CH_3$, NH—$SO_2$—R12, NR11-$SO_2$—R12, N(CO)R11, NHCONR11, N($C_1$-$C_6$-alkyl)$N^+$($C_1$-$C_4$-alkyl)$_3$ or a nitrogen-containing heterocycle, wherein said heterocycle is bonded via a nitrogen atom, R3 is H R4, R5 are each independently H, F, Cl, Br, OH, $CF_3$, $OCF_3$, O—$(C_1-C_6)$-alkyl or $(C_1-C_6)$-alkyl;

R6 is H;

and pharmaceutically acceptable salts thereof.

Very particular preference is given to compounds of the formula Ia wherein

A is aryl, wherein said aryl group is optionally substituted by F, Cl, Br, $NO_2$, $CF_3$, $OCF_3$, CN, $(C_1-C_6)$-alkyl, aryl, CON(R11)(R12), N(R13)(R14), OH, O—$(C_1-C_6)$-alkyl, S—$(C_1-C_6)$-alkyl, N(R15)CO($C_1-C_6$)-alkyl or COO—$(C_1-C_6)$-alkyl;

R11, R12, R13, R14, R15 are each independently H, $(C_1-C_6)$-alkyl or heterocycle;

m is 1;

R1 is $(C_1-C_6)$-alkyl or $(C_1-C_6)$-alkylene-R8;

R8, R9 are each independently F, Cl, Br, I, OH or $CF_3$;

R2 is $NH_2$, $NO_2$, CN, N(R13)(R14), NH—$SO_2$—$CH_3$, NH—$SO_2$—R12, NR11-$SO_2$—R12, N(CO)R11, NHCONR11, N($C_1$-$C_6$-alkyl)N+($C_1$-$C_4$-alkyl)$_3$ or a nitrogen-containing heterocycle, wherein said heterocycle is bonded via a nitrogen atom, R3 is H;

R4 is F, Cl, Br, OH, $CF_3$, $OCF_3$, O—$(C_1-C_6)$-alkyl or $(C_1-C_6)$-alkyl;

R5 is H, F, Cl, Br, OH, $CF_3$, $OCF_3$, O—$(C_1-C_6)$-alkyl or $(C_1-C_6)$-alkyl;

R6 is H;

and pharmaceutically acceptable salts thereof.

If radicals or substituents may occur more than once in the compounds of the formula I, such as, for example, CON(R11)(R12), they may all have, independently of one another, the stated meanings and be identical or different.

The invention relates to compounds of the formula I in the form of their racemates, enantiomer-enriched mixtures and pure enantiomers, and to their diastereomers and mixtures thereof.

The alkyl, alkenyl and alkynyl radicals in the substituents A, R1, R2, R3, R4, R5, R6, R8, R9, R10, R11, R12, R13, R14, R15 may be either straight-chain, branched or optionally halogenated.

The term "aryl" means a phenyl or naphthyl group.

Heterocycle or heterocyclic radical means ring systems which, apart from carbon, also comprise heteroatoms such as, for example, nitrogen, oxygen or sulfur. This definition also includes ring systems in which the heterocycle or the heterocyclic radical is fused to benzene nuclei.

Suitable "heterocyclic rings" or "heterocyclic radicals" are acridinyl, azocinyl, benzimidazolyl, benzofuryl, benzothienyl, benzothiophenyl, benzoxazolyl, benzthiazolyl, benztriazolyl, benztetrazolyl, benzisoxazolyl, benzisothiazolyl, benzimidazalinyl, carbazolyl, 4aH-carbazolyl, carbolinyl, quinazolinyl, quinolinyl, 4H-quinolizinyl, quinoxalinyl, quinuclidinyl, chromanyl, chromenyl, cinnolinyl, decahydroquinolinyl, 2H,6H-1,5,2-dithiazinyl, dihydrofuro[2,3-b]-tetrahydrofuran, furyl, furazanyl, imidazolidinyl, imidazolinyl, imidazolyl, 1H-indazolyl, indolinyl, indolizinyl, indolyl, 3H-indolyl, isobenzofuranyl, isochromanyl, isoindazolyl, isoindolinyl, isoindolyl, isoquinolinyl(benzimidazolyl), isothiazolyl, isoxazolyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxazolidinyl, pyrimidinyl, phenanthridinyl, phenanthrolinyl, phenazinyl, phenothiazinyl, phenoxathiinyl, phenoxazinyl, phthalazinyl, piperazinyl, piperidinyl, pteridinyl, purinyl, pyranyl, pyrazinyl, pyrazolidinyl, pyrazolinyl, pyrazolyl, pyridazinyl, pyridooxazoles, pyridoimidazoles, pyridothiazoles, pyridinyl, pyridyl, pyrimidinyl, pyrrolidinyl, pyrrolinyl, 2H-pyrrolyl, pyrrolyl, tetrahydrofuranyl, tetrahydroisoquinolinyl, tetrahydroquinolinyl, 6H-1,2,5-thiadazinyl, thiazolyl, 1,2,3-thiadiazolyl, 1,2,4-thiadiazolyl, 1,2,5-thiadiazolyl, 1,3,4-thiadiazolyl, thienyl, triazolyl, tetrazolyl and xanthenyl.

Pyridyl stands both for 2-, 3- and 4-pyridyl. Thienyl stands both for 2- and 3-thienyl. Furyl stands both for 2- and 3-furyl.

The corresponding N-oxides of these compounds are also included, that is to say, for example, 1-oxy-2-, 3- or 4-pyridyl.

Also included are derivatives of these heterocycles which are benzo-fused one or more times.

The heterocyclic rings or heterocyclic radicals may be substituted one or more times by suitable groups such as, for example, F, Cl, Br, I, $CF_3$, $NO_2$, $N_3$, CN, COOH, COO($C_1$-$C_6$)alkyl, $CONH_2$, CONH($C_1$-$C_6$)alkyl, CON[($C_1$-$C_6$)alkyl]$_2$, ($C_1$-$C_6$)-alkyl, ($C_2$-$C_6$)-alkenyl, ($C_2$-$C_6$)-alkynyl, O—($C_1$-$C_6$)-alkyl, where one or more than one, or all hydrogen(s) in the alkyl radicals may be replaced by fluorine; $PO_3H_2$, $SO_3H$, $SO_2$—$NH_2$, $SO_2NH$($C_1$-$C_6$)-alkyl, $SO_2N$[($C_1$-$C_6$)-alkyl]$_2$, S—($C_1$-$C_6$)-alkyl, S—$(CH_2)_n$-phenyl, SO—($C_1$-$C_6$)-alkyl, SO—$(CH_2)_n$-phenyl, $SO_2$—($C_1$-$C_6$)-alkyl, $SO_2$—$(CH_2)_n$-phenyl, where n can be 0-6, and the phenyl radical may be substituted up to twice by F, Cl, Br, OH, $CF_3$, $NO_2$, CN, $OCF_3$, O—($C_1$-$C_6$)-alkyl, ($C_1$-$C_6$)-alkyl, $NH_2$;
C(NH)($NH_2$), $NH_2$, NH—($C_1$-$C_6$)-alkyl, N(($C_1$-$C_6$)-alkyl)$_2$, NH($C_1$-$C_7$)-acyl, phenyl, O—$(CH_2)_n$-phenyl, where n may be 0-6, and where the phenyl ring may be substituted one to 3 times by F, Cl, Br, I, OH, $CF_3$, $NO_2$, CN, $OCF_3$, O—($C_1$-$C_6$)-alkyl, ($C_1$-$C_6$)-alkyl, $NH_2$, NH($C_1$-$C_6$)-alkyl, N(($C_1$-$C_6$)-alkyl)$_2$, $SO_2$—$CH_3$, COOH, COO—($C_1$-$C_6$)-alkyl, $CONH_2$.

Pharmaceutically acceptable salts are particularly suitable for medical applications because their solubility in water is higher than the initial or basic compounds. These salts must have a pharmaceutically acceptable anion or cation. Suitable pharmaceutically acceptable acid addition salts of the compounds of the invention are salts of inorganic acids such as hydrochloric acid, hydrobromic acid, phosphoric, metaphosphoric, nitric, sulfamic and sulfuric acids, and organic acids such as, for example, acetic acid, benzenesulfonic, benzoic, citric, ethanesulfonic, fumaric, gluconic, glycolic, isethionic, lactic, lactobionic, maleic, malic, methanesulfonic, succinic, p-toluenesulfonic, tartaric and trifluoroacetic acids. The chloride salt is particularly preferably used for medical purposes. Suitable pharmaceutically acceptable basic salts are ammonium salts, alkali metal salts (such as sodium and potassium salts) and alkaline earth metal salts (such as magnesium and calcium salts).

Salts with a pharmaceutically unacceptable anion likewise fall within the scope of the invention as useful intermediates for preparing or purifying pharmaceutically acceptable salts and/or for use in nontherapeutic, for example in vitro, applications.

As used herein, the following definitions apply:

"Patient" means a warm blooded animal, such as for example rat, mice, dogs, cats, guinea pigs, and primates such as humans.

"Treat" or "treating" means to alleviate symptoms, eliminate the causation of the symptoms either on a temporary or permanent basis, or to prevent or slow the appearance of symptoms of the named disorder or condition.

"Therapeutically effective amount" means a quantity of the compound which is effective in treating the named disorder or condition.

"Pharmaceutically acceptable carrier" is a non-toxic solvent, dispersant, excipient, adjuvant or other material which is mixed with the active ingredient in order to permit the formation of a pharmaceutical composition, i.e., a dosage form capable of administration to the patient. One example of such a carrier is a pharmaceutically acceptable oil typically used for parenteral administration.

The term "physiologically functional derivative" used herein refers to any physiologically tolerated derivative of a compound according to the invention of the formula I, for example an ester, which is able on administration to a mammal such as, for example, a human to form (directly or indirectly) a compound of the formula I or an active metabolite thereof.

The physiologically functional derivatives also include prodrugs of the compounds according to the invention. Such prodrugs can be metabolized in vivo to a compound according to the invention. These prodrugs may themselves be active or not.

The compounds according to the invention may also exist in various polymorphous forms, for example as amorphous and crystalline polymorphous forms. All polymorphous forms of the compounds according to the invention lie within the scope of the invention and are a further aspect of the invention.

All references hereinafter to "compound(s) of formula (I)" refer to compound(s) of the formula (I) as described above, and the salts, solvates and physiologically functional derivatives thereof as described herein.

The amount of a compound of formula (I) which is necessary to achieve the desired biological effect depends on a number of factors, for example the specific compound chosen, the intended use, the mode of administration and the clinical condition of the patient. In general, the daily dose is in the range from 0.3 mg to 100 mg (typically from 3 mg to 50 mg) per day and per kilogram of body weight, for example 3-10 mg/kg/day. An intravenous dose may be, for example, in the range from 0.3 mg to 1.0 mg/kg, which can most suitably be administered as infusion of from 10 ng to 100 ng per kilogram and per minute. Suitable infusion solutions for these purposes may contain, for example, from 0.1 ng to 10 mg, typically from 1 ng to 10 mg, per milliliter. Single doses may contain, for example, from 1 mg to 10 g of the active ingredient. It is thus possible for ampoules for injections to contain, for example, from 1 mg to 100 mg, and single-dose formulations which can be administered orally, such as, for example, tablets or capsules, to contain, for example, from 1.0 to 1000 mg, typically from 10 to 600 mg. In the case of pharmaceutically acceptable salts, the aforementioned weight data are based on the weight of the salt—underlying free compound. For the prophylaxis or therapy of the abovementioned conditions, the compounds of formula (I) can be used as the compound itself, but they are preferably in the form of a pharmaceutical composition with an acceptable carrier. The carrier must, of course, be acceptable in the sense that it is compatible with the other ingredients of the composition and is not hazardous for the patient's health. The carrier may be a solid or a liquid or both and is preferably formulated with the compound as single dose, for example as tablet which may contain from 0.05% to 95% by weight of the active ingredient. Further pharmaceutically active substances may likewise be present, including other compounds of formula (I). The pharmaceutical compositions according to the invention can be produced by one of the known pharmaceutical methods which essentially consist of mixing the ingredients with pharmacologically acceptable carriers and/or excipients.

Pharmaceutical compositions according to the invention are those suitable for oral, rectal, topical, peroral (for example sublingual) and parenteral (for example subcutaneous, intramuscular, intradermal or intravenous) administration although the most suitable mode of administration in each individual case depends on the nature and severity of the condition to be treated and on the nature of the compound of formula (I) used in each case. Coated formulations and coated slow-release formulations also lie within the scope of the invention. Formulations resistant to acid and gastric fluid are preferred. Suitable coatings resistant to gastric fluid comprise cellulose acetate phthalate, polyvinyl acetate phthalate, hydroxypropylmethylcellulose phthalate and anionic polymers of methacrylic acid and methyl methacrylate.

Suitable pharmaceutical compounds for oral administration may be in the form of separate units such as, for example, capsules, cachets, suckable tablets or tablets, each of which contain a defined amount of the compound of formula (I); as powders or granules; as solution or suspension in an aqueous or nonaqueous liquid; or as an oil-in-water or water-in-oil emulsion. These compositions may, as already mentioned, be prepared by any suitable pharmaceutical method which includes a step in which the active ingredient and the carrier (which may consist of one or more additional ingredients) are brought into contact. In general, the compositions are produced by uniform and homogeneous mixing of the active ingredient with a liquid and/or finely divided solid carrier, after which the product is shaped if necessary. Thus, for example, a tablet can be produced by compressing or molding a powder or granules of the compound, where appropriate with one or more additional ingredients. Compressed tablets can be produced by tableting the compound in free-flowing form, such as, for example, a powder or granules, where appropriate mixed with a binder, lubricant, inert diluent and/or a (plurality of) surface-active/dispersing agent(s) in a suitable machine. Molded tablets can be produced by molding the compound which is in powder form and is moistened with an inert liquid diluent in a suitable machine.

Pharmaceutical compositions suitable for peroral (sublingual) administration comprise suckable tablets which contain a compound of formula (I) with a flavoring, normally sucrose and gum arabic or tragacanth, and pastilles which comprise the compound in an inert base such as gelatin and glycerol or sucrose and gum arabic.

Suitable pharmaceutical compositions for parenteral administration comprise preferably sterile aqueous preparations of a compound of formula (I), which are preferably isotonic with the blood of the intended recipient. These preparations are preferably administered intravenously, although administration may also take place by subcutaneous, intramuscular or intradermal injection. These preparations can preferably be produced by mixing the compound with water and making the resulting solution sterile and isotonic with blood. Injectable compositions according to the invention generally contain from 0.1 to 5% by weight of the active compound.

Suitable pharmaceutical compositions for rectal administration are preferably in the form of single-dose suppositories. These can be produced by mixing a compound of formula (I) with one or more conventional solid carriers, for example cocoa butter, and shaping the resulting mixture.

Suitable pharmaceutical compositions for topical application to the skin are preferably in the form of ointment, cream, lotion, paste, spray, aerosol or oil. Carriers which can be used are petrolatum, lanolin, polyethylene glycols, alcohols and combinations of two or more of these substances. The active ingredient is generally present in a concentration of from 0.1 to 15% by weight of the composition, for example from 0.5 to 2%.

Transdermal administration is also possible. Suitable pharmaceutical compositions for transdermal uses can be in the form of single plasters which are suitable for long-term close contact with the patient's epidermis. Such plasters suitably contain the active ingredient in an optionally buffered aqueous solution, dissolved and/or dispersed in an adhesive or dispersed in a polymer. A suitable active ingredient concentration is about 1% to 35%, preferably about 3% to 15%. As a special possibility, the active ingredient can be released as described, for example, in Pharmaceutical Research, 2(6): 318 (1986) by electrotransport or iontophoresis.

The compounds of the formula I are distinguished by beneficial effects on lipid metabolism, and they are particularly suitable for weight reduction and for maintaining a reduced weight after weight reduction has taken place in mammals and as anorectic agents. The compounds are distinguished by their low toxicity and their few side effects. The compounds can be employed alone or in combination with other weight-reducing or anorectic active ingredients. Further anorectic active ingredients of this type are mentioned, for example, in the Rote Liste, chapter 01 under weight-reducing agents/appetite suppressants, and may also include active ingredients which increase the energy turnover of the organism and thus lead to weight reduction or else those which influence the general metabolism of the organism in such a way that an increased calorie intake does not lead to an enlargement of the fat depots and a normal calorie intake leads to a reduction of the fat depots of the organism. The compounds are suitable for the prophylaxis and, in particular, for the treatment of excessive weight or obesity. The compounds are further suitable for the prophylaxis and, in particular, for the treatment of type II diabetes, of arteriosclerosis and for normalizing lipid metabolism and for the treatment of high blood pressure. The compounds act as melanocortin receptor agonists and are also suitable for the treatment of disturbances of wellbeing and other psychiatric indications such as, for example, depressions, anxiety states, anxiety neuroses, schizophrenia and for the treatment of disorders associated with the circadian rhythm and for the treatment of drug abuse.

They are additionally suitable for the treatment of cancer, arthritis, sleep disorders, sleep apnoea, female and male sexual disorders, inflammations, acne, pigmentation of the skin, of metabolic syndrome, disorders of steroid metabolism, skin diseases, psoriasis, mycoses, neurodegenerative diseases and Alzheimer's disease.

In a further aspect of the invention, the compounds of the formula I can be administered in combination with one or more other pharmacologically active substances which are selected, for example, from antidiabetics, antiobesity agents, active ingredients which lower blood pressure, lipid-lowering agents and active ingredients for the treatment and/or prevention of complications caused by diabetes or associated with diabetes.

Suitable antidiabetics include insulins, amylin, derivatives of GLP-1 and GLP-2 such as, for example, those disclosed in WO 98/08871 of Novo Nordisk A/S, and orally active hypoglycemic active ingredients.

The orally active hypoglycemic active ingredients preferably comprise sulfonylureas, biguanides, meglitinides, oxadiazolidinediones, thiazolidinediones, glucosidase inhibitors, glucagon receptor antagonists, GLP-1 agonists, potassium channel openers such as, for example, those disclosed in WO 97/26265 and WO 99/03861 of Novo Nordisk A/S, insulin sensitizers, activators of insulin receptor kinase, inhibitors of liver enzymes involved in the stimulation of gluconeogenesis and/or glycogenolysis, for example inhibitors of glycogen phosphorylase, modulators of glucose uptake and glucose excretion, compounds which alter lipid metabolism, such as antihyperlipidemic active ingredients and antilipidemic active ingredients, for example HMGCoA reductase inhibitors, inhibitors of cholesterol transport/of cholesterol uptake, inhibitors of bile acid reabsorption or inhibitors of the microsomal triglyceride transfer protein (MTP), compounds which reduce food intake, PPAR and RXR agonists and active ingredients which act on the ATP-dependent potassium channel of the beta cells.

In one embodiment of the invention, the present compounds are administered in combination with insulin.

In a further embodiment, the present compounds are administered in combination with a sulfonylurea such as, for example, tolbutamide, glibenclamide, glimepiride, glipizide, gliquidone, glisoxepide, glibornuride or gliclazide.

In another embodiment, the present compounds are administered in combination with a biguanide such as, for example, metformin.

In yet another embodiment, the present compounds are administered in combination with a meglitinide such as, for example, repaglinide.

In yet a further embodiment, the present compounds are administered in combination with a thiazolidinedione such as, for example, troglitazone, ciglitazone, pioglitazone, rosiglitazone or the compounds disclosed in WO 97/41097 of Dr. Reddy's Research Foundation, in particular 5-[[4-[(3,4-dihydro-3-methyl-4-oxo-2-quinazolinylmethoxy]phenyl]methyl]-2,4-thiazolidinedione.

In a further embodiment, the present compounds are administered in combination with an α-glucosidase inhibitor such as, for example, miglitol or acarbose.

In another embodiment, the present compounds are administered in combination with an active ingredient which acts on the ATP-dependent potassium channel of the beta cells, such as, for example, tolbutamide, glibenclamide, glimepiride, glipizide, gliclazide or repaglinide.

In yet another embodiment, the present compounds are administered in combination with an antihyperlipidemic active ingredient or an antilipidemic active ingredient such as, for example, cholestyramine, colestipol, clofibrate, fenofibrate, gemfibrozil, lovastatin, pravastatin, simvastatin, atorvastatin, cerivastatin, fluvastatin, probucol, ezetimibe or dextrothyroxine.

In a further embodiment, the present compounds are administered in combination with more than one of the aforementioned compounds, e.g. in combination with a sulfonylurea and metformin, a sulfonylurea and acarbose, repaglinide and metformin, insulin and a sulfonylurea, insulin and metformin, insulin and troglitazone, insulin and lovastatin, etc.

The compounds of the invention may additionally be administered in combination with one or more antiobesity agents or appetite-regulating active ingredients.

Active ingredients of these types may be selected from the group consisting of CART agonists, NPY antagonists, MCH antagonists, orexin antagonists, H3 antagonists, TNF agonists, CRF agonists, CRF BP antagonists, urocortin agonists, β3 agonists, MSH (melanocyte-stimulating hormone) agonists, CCK agonists, serotonin-reuptake inhibitors, mixed serotonin- and noradrenaline-reuptake inhibitors, 5HT modulators, MAO inhibitors, bombesin agonists, galanin antagonists, growth hormone, growth hormone-releasing compounds, TRH agonists, modulators of uncoupling proteins 2 or 3, leptin agonists, dopamine agonists (bromocriptine, Doprexin), lipase/amylase inhibitors, antagonists of cannabinoid receptor 1, modulators of acylation-stimulating protein (ASP), PPAR modulators, RXR modulators, hCNTF agonists or TR-β agonists.

In one embodiment of the invention, the antiobesity agent is leptin or modified leptin.

In another embodiment, the antiobesity agent is dexamphetamine or amphetamine.

In another embodiment, the antiobesity agent is fenfluramine or dexfenfluramine.

In yet another embodiment, the antiobesity agent is sibutramine or the mono- and bisdemethylated active metabolites of sibutramine.

In a further embodiment, the antiobesity agent is orlistat.

In another embodiment, the antiobesity agent is mazindol, diethylpropion or phentermine.

The present compounds may additionally be administered in combination with one or more antihypertensive active ingredients. Examples of antihypertensive active ingredients are beta blockers such as alprenolol, atenol, timolol, pindolol, propranolol and metoprolol, ACE (angiotensin converting enzyme) inhibitors such as, for example, benazepril, captopril, enalapril, fosinopril, lisinopril, quinapril and rampril, calcium channel blockers such as nifedipine, felodipine, nicardipine, isradipine, nimodipine, diltiazem and verapamil, and alpha blockers such as doxazosin, urapidil, prazosin and terazosin. Reference may furthermore be made to Remington: The Science and Practice of Pharmacy, 19th edition, Gennaro, editor, Mack Publishing Co., Easton, Pa., 1995.

It will be appreciated that every suitable combination of the compounds of the invention with one or more of the aforementioned compounds and optionally one or more other pharmacologically active substances is to be regarded as covered by the scope of protection of the present invention.

The efficacy of the compounds was tested as follows:

Biological Test Model:

The anorectic effect was tested on female NMRI mice. After withdrawal of food for 24 hours, the test product was administered by gavage. The animals were housed singly with free access to drinking water and were offered condensed milk 30 minutes after administration of the product. The condensed milk consumption was determined every half hour for 7 hours, and the general wellbeing of the animals was observed. The measured milk consumption was compared with the vehicle-treated control animals.

TABLE 1

Anorectic effect measured as the reduction in the cumulative milk consumption of treated compared with control animals.

| Example | Oral dose [mg/kg] | Number of animals/ cumulative milk consumption of the treated animals N/[ml] | Number of animals/ cumulative milk consumption of the control animals N/[ml] | Reduction in the cumulative milk consumption as % of the control |
|---|---|---|---|---|
| 5 | 50 | 5/2.4 | 5/3.40 | 31 |
| 9 | 50 | 5/2.06 | 5/3.86 | 47 |

It is evident from the table that the compounds of the formula I show a good anorectic effect and are thus very suitable as antiobesity agent.

The examples and preparation methods detailed below serve to illustrate the invention without, however, restricting it.

General Processes

The starting materials used in the synthesis were purchased from chemical suppliers such as Aldrich, Acros, Sigma, Fluka, Nova Biochem, Advanced Chemtech, Bachem, Lancaster and other companies.

In the synthesis, the functional groups of the amino acid derivatives used were protected by protective groups to prevent side reactions during the coupling steps. Examples of suitable protective groups and their use are described in The Peptides, supra, 1981 and in Vol. 9, Udenfriend and Meienhofer (Editors) 1987 (included herein by reference).

General methods of solid-phase synthesis were used to prepare the compounds of the invention. Methods of this type are described for example by Steward and Young in Solid Phase Peptide Synthesis (Freeman & Co., San Francisco 1969) (included herein by reference).

Unless indicated otherwise, the compounds were synthesized using TentaGel HL12019 Resin (Rapp Polymere, Tübingen). This commercially available polymer contains a bromoacetal linker. This type of coupling can be incorporated in all types of hydroxy-tentagel by the process described by Vojkovsky, T. et al., J. Org. Chem. 1998, 63, 3162-3163, and Patek, M., Contribution to Combinatorial Chemistry 2000, London, 11.-14. 7. 2000 (included herein by reference).

In the first synthesis step (see scheme 1 for general synthetic scheme), amine was used in DMSO to replace bromine in the bromoacetal link at an elevated temperature. Fmoc-protected amino acid was coupled onto the secondary amine produced thereby on the polymer. The coupling was effected by means of DIC/HOAt or HATU/DIEA, usually in DMF. The coupling was carried out at room temperature (RT) for 16 hours or at 55° C. for 4-5 hours. Protection by the Fmoc group was eliminated by using 50% piperidine in DMF (5+15 minutes). The substitution can be determined by measuring the amount of liberated Fmoc from the absorbance of the solution at 302 nm after elimination of the protection, the volume of the washing liquid and the weight of the polymer employed in the synthesis in accordance with the description in Krchnak, V. et al., Collect. Czech. Chem. Commun. 53 (1988) 2542 (incorporated herein by reference).

The free amino group of the structure bound to the solid phase was then coupled to Fmoc-beta-alanine (or Fmoc-alpha-amino acid or substituted beta-amino acid). The coupling was effected with N,N'-diisopropylcarbodiimide (DIC) in the presence of HOBt, usually in DMF. The completeness of the coupling was monitored by the ninhydrin test.

A protection by the Fmoc group was eliminated with 50% piperidine in DMF for 5+15 minutes. The amount of liberated Fmoc was measured from the absorbance of the solution at 302 nm after elimination of the protection, the volume of the washing liquid and the weight of the polymer employed in the synthesis.

The free amino groups of the structure bound to the solid phase was then sulfonylated with up to 2 equivalents of a suitable sulfonyl chloride/DIEA in DCM or acetonitrile. The completeness of the sulfonylation was monitored by the ninhydrin test.

After completion of the assembly of the precursor of the linear compound on the polymer, the solid phase was washed successively with DMF and DCM or THF and dried in vacuo.

The desired compound was subjected to cyclative cleavage off with formic acid at room temperature for 18-24 hours, at 50° C. for 6 hours or by a combination of the two conditions. The polymer was filtered off and washed with DCM or formic acid. The washing liquid was introduced into the formic acid solution. The solution was evaporated. The residue was dissolved in a mixture of water and acetonitrile and freeze dried.

The dried compound was purified with HPLC with a suitable gradient of 0.1% TFA in water and acetonitrile (ACN). After collection of the peak containing the desired synthetic product, the solution of the compound was freeze dried. To confirm that the correct compound had been synthesized, the compound was subjected to a qualitative determination with electrospray mass spectrum (LC/MS) and/or an NMR analysis.

For HPLC analysis a sample of the compound was analyzed with the Beckman HPLC system (consisting of the solvent supply system 126, the programmable detector module 166 and the autosampler 507e and controlled by data station with Gold Nouveau sofware) using a YMC ODS-AM 4.6×250 mm column (S-5 (5 μm), YMC, Inc. Wilmington, N.C., USA) at 230 nm. With this setting, a flow rate of 1 ml/min was used and a gradient of water/0.1% TFA buffer and ACN(HPL quality) was used as eluent.

Scheme 1:

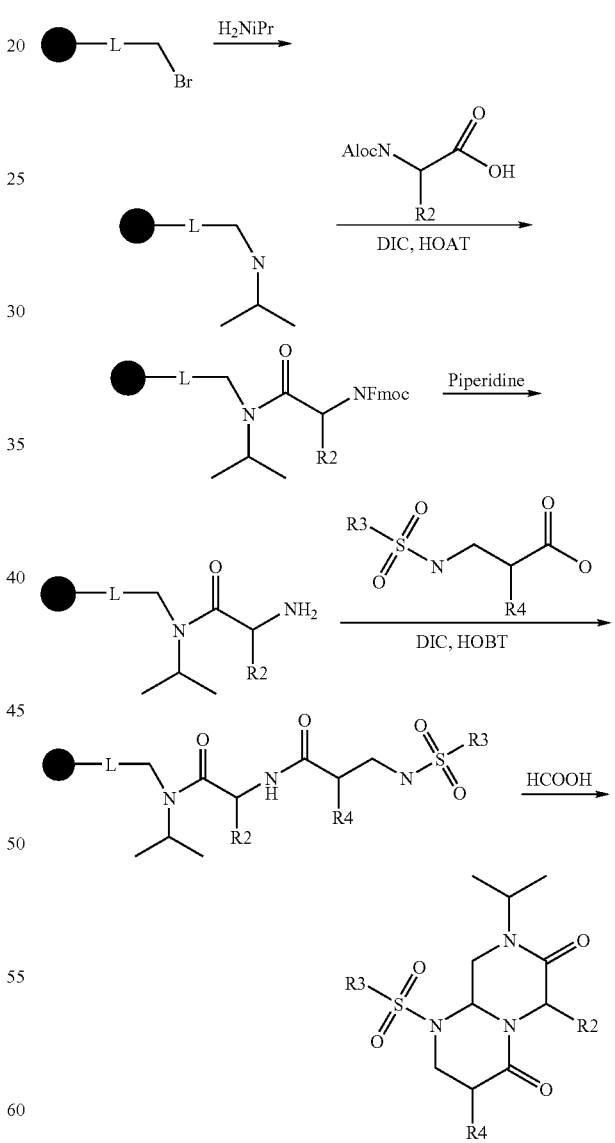

The compounds can also be prepared in solution in analogy to the described synthesis on the resin. (Scheme 2). In place of the functionalized resin, in the first stage 2-bromo-1,1-diethoxyethane is reacted with a primary amine.

Scheme 2:

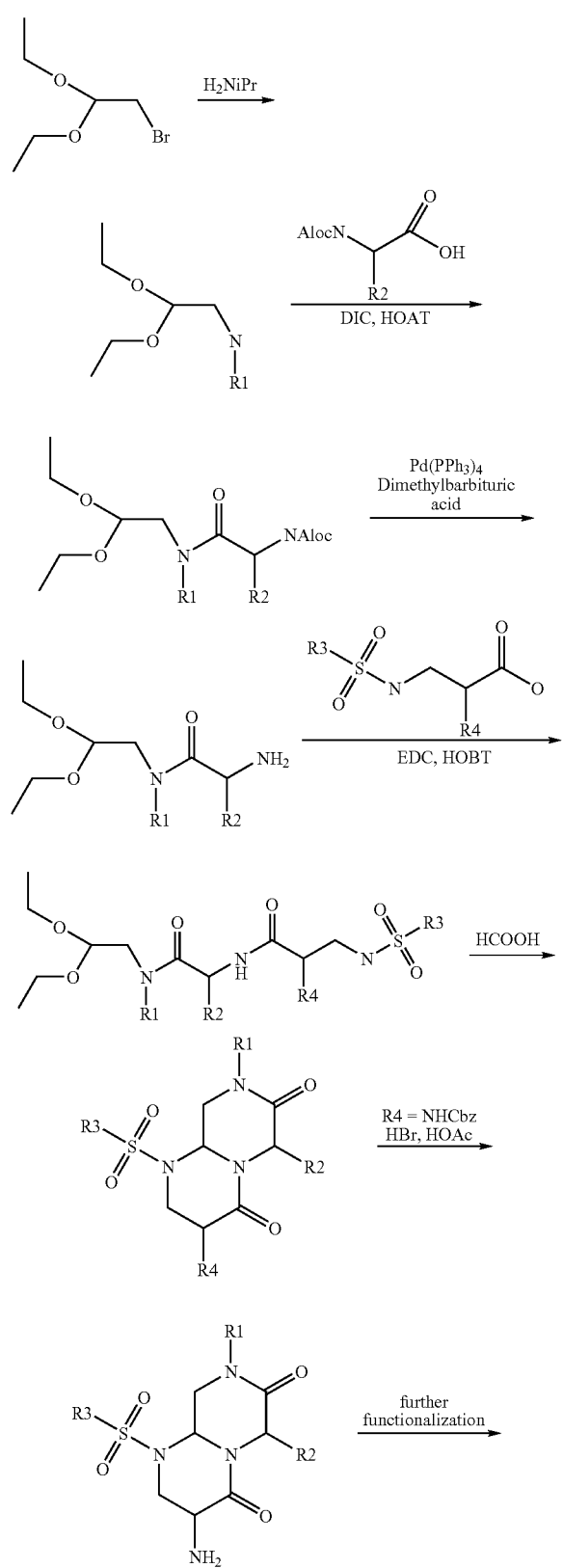
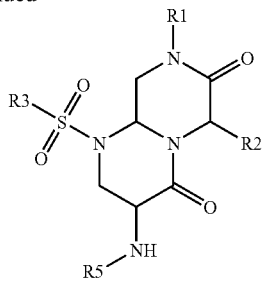

The resulting product is reacted with the amino acid in analogy to the solid-phase synthesis. The allyloxycarbonyl protective group (Aloc) can be used in place of FMOC as amino-protective group for the amino acid, and is introduced (Aloc-Cl, triethylamine) and eliminated (Pd(PPh$_3$)$_4$, dimethylbarbituric acid) by methods known from the literature.

The amino carboxylic acid with the radical R4 is reacted with the sulfonyl chloride in the presence of triethylamine. The free carboxylic acid is coupled by the carbodiimide method (EDC, HOBt) or with use of uronium salts (HATU, HOAt) to the free amine which has been obtained by elimination of the Aloc group.

The cyclization proceeds under acidic conditions and the benzyloxycarbonyl (Cbz) group is eliminated with HBr in glacial acid. Subsequent functionalization proceeds in analogy to the above description.

The product was purified by developing a sample of the freeze-dried crude substance in a mixture of 0.1% strength aqueous TFA with 10-50% acetonitrile or in acetic acid. The solution of the compound was usually filtered through a syringe connected to an ACRODISC 13 CR PTFE 0.45 μm filter (Gelman Sciences; Ann Arbor, Mich., USA). An appropriate volume of the filtered solution of the compound was injected into a semipreparative C 18 column (YMC ODS-AM, S-5 (5 μm), 20×150 mm, YMC, Inc., Wilmington, N.C., USA). The flow rate of the gradient of water/0.1% TFA buffer and ACN (HPL quality) as eluent was maintained by means of the Beckman SYSTEM GOLD HPLC (System Gold, programmable solvent module 126 and programmable detector module 166, controlled by SYSTEM GOLD software). Elution of the compound was monitored by UV detection at 230 or 280 nm. After identification of the peak of the compound to be synthesized by LC/MS, the compound was collected, freeze dried and subjected to biological testing.

After purification, compounds with basic groups were obtained as trifluoroacetates. Hydrochlorides of these compounds can easily be prepared by treating the trifluoroacetate of the compound with an excess of HCl/dioxane. After evaporation of the solvents, the hydrochloride of the compound was precipitated with diethyl ether and isolated by filtration.

LC/MS was carried out with PE Sciex API 150EX and Sciex MassChrom software, equipped with a Gilson 215 liquid handler, two Shimadzu LC-10AD liquid modules, a Shimadzu SPD-10A detector, a Keystone Betasil C-18 column (2×30 mm, 3 μm, flow rate of the acetonitrile/water/0.1% TFA gradient 0.7 m/min) in ES+ mode.

For the NMR analysis, the samples were measured in DMSO-d$_6$ (Aldrich) with a Bruker Avance DPX 300.

Scheme 3:

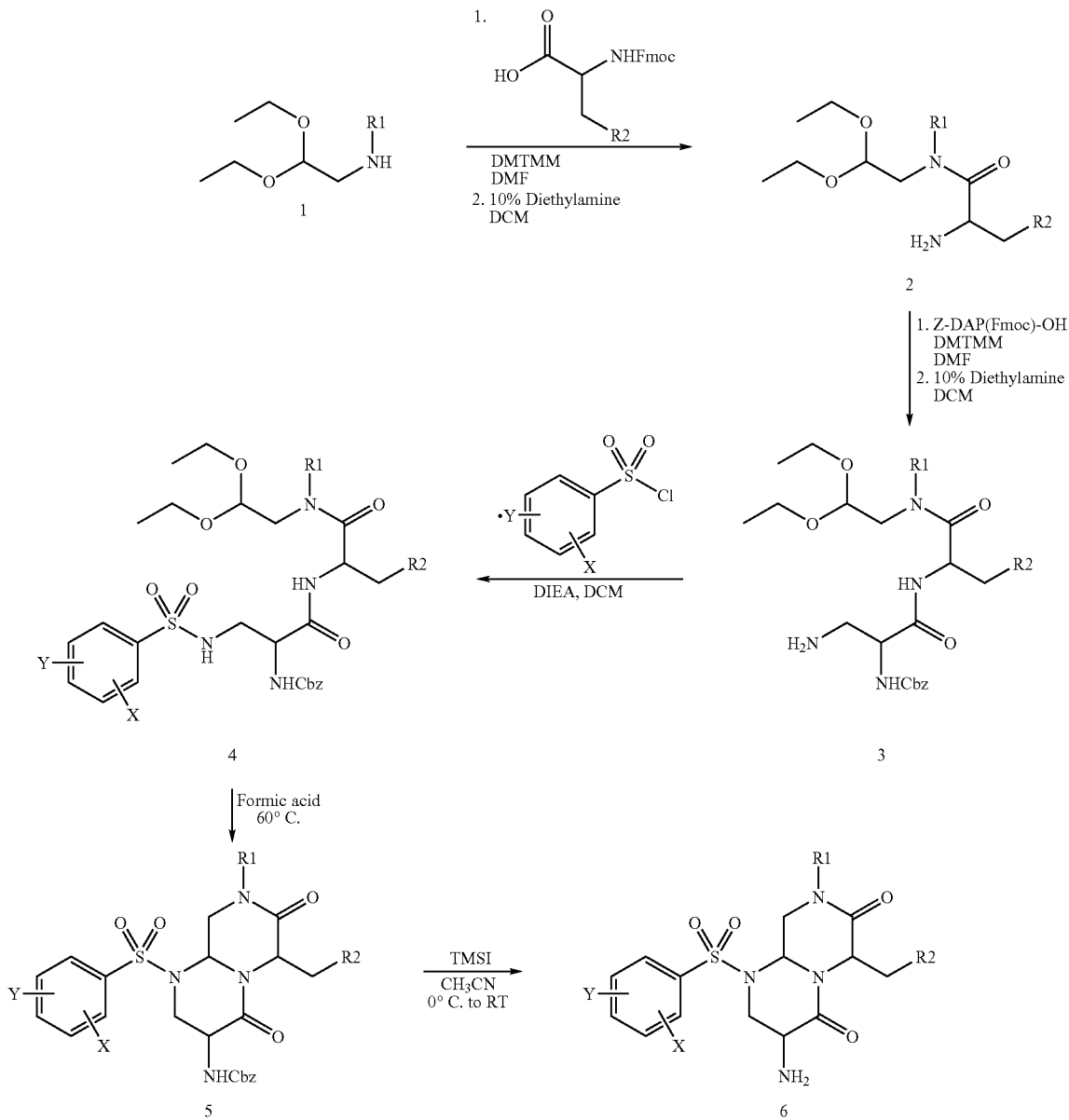

The synthesis shown in Scheme 3 was carried out in analogy to the other solution synthesis. In this case, the amide couplings were carried out in each case with DMTMM as coupling reagent. In addition, Fmoc was employed as protective group in the solid-phase chemistry, and was eliminated again with diethylamine. The sulfonamide was not introduced along with the second amide coupling, but was formed after the latter with use of diethylamine as base. The Cbz group was eliminated with TMSI in acetonitrile. All further functionalizations were carried out in analogy to the above description.

The reagents and building blocks used in the syntheses originated from various suppliers such as Aldrich, Acros, Sigma, Fluka, Nova Biochem, Advanced Chemtech, Bachem, Lancaster, Rapp Polymere etc.

Unless indicated otherwise, the following methods were used for the chemical analysis: liquid chromatography/mass spectrometry analysis (LC/MS): Agilent 1100 LC with mass spectrometer detector. The following were used: Waters (YMC) Combiscreen Pro C18 4.6×33.5μ, 120 A, 3 minutes with 10% acetonitrile (0.1% trifluoroacetic acid) and 90% water (0.1% trifluoroacetic acid) to 0% acetonitrile (0.1% trifluoroacetic acid) and 100% water (0.1% trifluoroacetic acid). 1-minute flow-through time and subsequently 1-minute equilibration to the starting conditions.

Electrospraying mass spectrometry, positive mode (unless indicated otherwise). Preparative LC: semipreparative liquid chromatograms were recorded with a Gilson 215 liquid handler, an apparatus which is suitable for analyses and semipreparative processes. Mobile phase: water (0.1% TFA) and acetonitrile (0.1% TFA). The samples were initially investigated by analytical methods. An appropriate semipreparative process was then used. 5% to 100% acetonitrile, 12 minutes (unless indicated otherwise). Waters (YMC) Combiscreen columns for analysis, 4.6×50 per C18, 5µ, 120 A are used. Waters Combiscreen 20×50.5µ, 120 A semipreparative columns.

Thin-layer chromatograms (TLC) were recorded with glass-reinforced 60F-254 silica gel plates 0.25 mm thick.

Flash chromatography: this process was carried out by the method described by Still, W. C., Kahn, M. and Mitra, A. in J. Org. Chem. 1978, 43, 2923, or adapted to commercially available systems such as Biotage Horizon, Isco Opix or Companion. The solvent systems indicated in the experimental examples were used in these cases.

Microwave synthesis: unless indicated otherwise, the microwave reactions were carried out in a personal chemistry creator, optimizer or synthesizer.

All the calculated masses indicated are monoisotopic.

Abbreviations

Unless indicated otherwise, the abbreviations in the examples below have the following meaning:
ACN=Acetonitrile
Aloc=Allyloxycarbonyl
DIC=Diisopropylcarbodiimide
EDC=1-(3-Dimethylaminopropyl)-3-ethylcarbodiimide
FMOC=9-Fluorenylmethyloxycarbonyl
DCE=1,2-Dichloroethane
DEA=Diethylamine
DIEA=Diisopropylethylamine
$NaBH_3CN$=Sodium cyanoborohydride
DMAP=N,N-Dimethylaminopyridine
DMF=N,N-Dimethylformamide
THF=Tetrahydrofuran
DIC=Diisopropylcarbodiimide
DMSO=Dimethyl sulfoxide
DCM=Dichloromethane (also referred to as methylene chloride)
DMTMM=4-(4,6-Dimethoxy[1,3,5]triazin-2-yl]-4-methyl-morpholinium chloride
HOBt=1-Hydroxybenzotriazole
HOAt=1-Hydroxy-7-azabenzotriazole
HATU=Dimethylamino([1,2,3]triazolo[4,5-b]pyridin-3-yloxy)methylenedimethyl-ammonium hexafluorophosphate
EtOAc=Ethyl acetate
HOAc=Acetic acid
$Et_3N$=Triethylamine
HCl=Hydrochloric acid
HBr=Hydrobromic acid
HPLC=High performance liquid chromatography
TEA=Triethylamine
TMSI=Trimethylsilyl iodide The citation of any reference herein should not be construed as an admission that such reference is available as "Prior Art" to the instant application.

Various publications are cited herein, the disclosures of which are incorporated by reference in their entireties.

The following examples serve to explain the invention in more detail. The present invention is not to be limited in scope by the specific embodiments describe herein. Indeed, various modifications of the invention in addition to those described herein will become apparent to those skilled in the art from the foregoing description and the accompanying figures. Such modifications are intended to fall within the scope of the claims.

EXAMPLE 1

3-Amino-6-(4-chlorobenzyl)-1-(5-chloro-2-methoxybenzenesulfonyl)-8-isopropylhexahydropyrazino[1,2-a]pyrimidine-4,7-dione Structure:

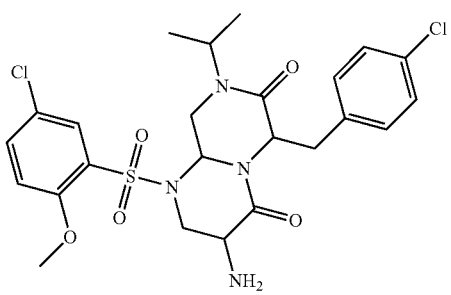

0.35 g of TentaGel HL12019 (bromoacetal linker, S=0.5 mmol/g, Rapp Polymere, Tubingen) was washed with DMSO. 20 equivalents of 2M isopropylamine solution in DMSO were added, and the mixture was kept in a closed vessel at 60° C. for 15 hours. The polymer was washed 7 times with DMF.

Fmoc-(S)-4-chlorophenylalanine (3 equivalents) were coupled to the secondary amine on the polymer using HOAt (3 equivalents) and DIC (3 equivalents) in DMF. The final concentration was 0.2-0.3 M. The reaction mixture was left to stand at room temperature overnight. The polymer was washed 6 times with DMF. The Fmoc protective group was eliminated with 50% piperidine in DMF (5+15 minutes).

Z-Dap(Fmoc) (3 equivalents) were then coupled on using HOBt (3 equivalents) and DIC (3 equivalents) in DMF (final concentration: about 0.2 M) over a period of at least 4 hours. The Fmoc protective group was eliminated with 50% piperidine in DMF (5+15 minutes). The polymer was washed 5 times with DMF and 4 times with DCM and mixed with a solution of 1.5 equivalents of 2-methoxy-5-chlorobenzenesulfonyl chloride and 3 equivalents of DIEA in DCM (final concentration: 0.1-0.15 M) and reacted at room temperature for 5 hours. It was then washed 5 times with DMF and 5 times with DCM and dried in vacuo.

For the cyclative cleavage off, the dried polymer was mixed with 10 ml of formic acid and shaken at room temperature for 16 hours and at 50-55° C. for 6 hours. The polymer was filtered off and washed with DCM. The combined filtrates were evaporated in vacuo. The residue was treated with 5 ml of 37% HBr/HOAc at room temperature for 2 hours and evaporated in vacuo. The hydrobromide of the product was precipitated by adding diethyl ether and was filtered off. The pure title compound was removed after purification by HPLC. The system and process described under "general process" was used for this. MW=554.12 (calculated, monoisotopic); measured value $(M+H)^+$: 555.3.

EXAMPLE 2

3-Amino-6-(4-chlorobenzyl)-1-(2,4-dichlorobenzenesulfonyl)-8-isopropylhexahydropyrazino[1,2-a]pyrimidine-4,7-dione Structure:

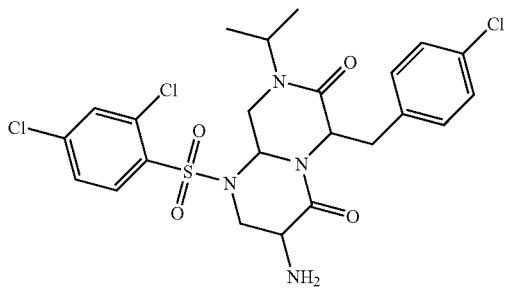

0.7 g of TentaGel HL12019 (bromoacetal linker, S=0.5 mmol/g, Rapp Polymere, Tübingen) was washed with DMSO. 20 equivalents of 2M isopropylamine solution in DMSO were added, and the mixture was kept in a closed vessel at 60° C. for 15 hours. The polymer was washed 7 times with DMF.

Fmoc-4-chlorophenylalanine (3 equivalents) were coupled to the secondary amine on the polymer using HOAt (3 equivalents) and DIC (3 equivalents) in DMF. The final concentration was 0.2-0.3 M. The reaction mixture was left to stand at room temperature overnight. The polymer was washed 6 times with DMF. The Fmoc protective group was eliminated with 50% piperidine in DMF (5+15 minutes).

Cbz-Dap(Fmoc) (3 equivalents) were then coupled on using HOBt (3 equivalents) and DIC (3 equivalents) in DMF (final concentration: about 0.2 M) over a period of at least 4 hours. The Fmoc protective group was eliminated with 50% piperidine in DMF (5+15 minutes). The polymer was washed 5 times with DMF and 4 times with DCM and mixed with a solution of 1.5 equivalents of 2,4-dichlorobenzenesulfonyl chloride and 3 equivalents of DIEA in DCM (final concentration: 0.1-0.15 M) and reacted at room temperature for 5 hours. It was then washed 5 times with DMF and 5 times with DCM and dried in vacuo. For the cyclative cleavage off, the dried polymer was mixed with 15 ml of formic acid and shaken at room temperature for 16 hours and at 50-55° C. for 6 hours. The polymer was filtered off and washed with DCM. The combined filtrates were evaporated in vacuo. The residue was treated with 10 ml of 37% HBr/HOAc at room temperature for 2 hours and evaporated in vacuo. The hydrobromide of the product was precipitated by adding diethyl ether and was filtered off. The pure title compound was removed after purification by HPLC. The system and process described under "general processes" was used for this. MW=558.07 (calculated, monoisotopic); measured value (M+H)+: 559.3.

EXAMPLE 3

6-(4-Chlorobenzyl)-1-(5-chloro-2-methoxybenzenesulfonyl)-3-diethylamino-8-isopropylhexahydropyrazino[1,2-a]pyrimidine-4,7-dione Structure:

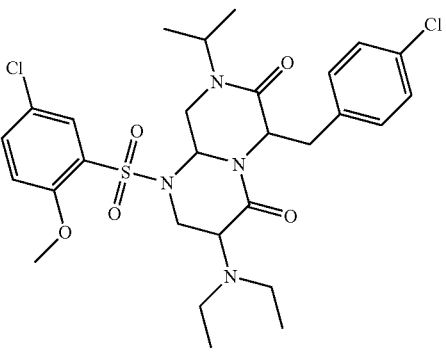

50 mg of 6-(4-chlorobenzyl)-1-(2-methoxy-5-chlorobenzenesulfonyl)-3-amino-8-isopropylhexahydropyrazino[1,2-a]pyrimidine-4,7-dione hydrochloride (Example 1) were dissolved in 3 ml of methanol, and 100 µl of acetic acid were added. 100 µl of acetaldehyde and 1 ml of 1M sodium cyanoborohydride solution in THF were added to this solution. After 2 hours, the reaction mixture was evaporated, suspended in 5% Et₃N in ethyl acetate and filtered through a small silica gel column. The eluent was evaporated, and the crude substance was dissolved in a mixture of acetonitrile and water and freeze dried. The pure title compound was removed after purification by HPLC. The system and process described under "general processes" was used for this. MW=610.18 (calculated, monoisotopic); measured value (M+H)+: 611.4.

EXAMPLE 4

6-(4-Chlorobenzyl)-1-(5-chloro-2-methoxybenzenesulfonyl)-8-isopropyl-3-isopropylaminohexahydropyrazino[1,2-a]pyrimidine-4,7-dione Structure:

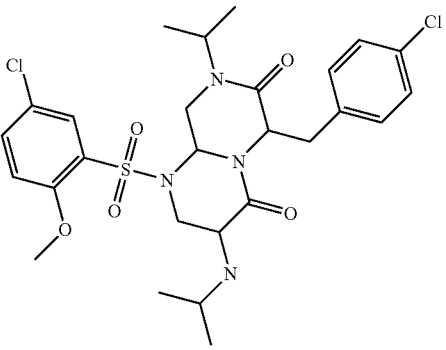

50 mg of 6-(4-chlorobenzyl)-1-(2-methoxy-5-chlorobenzenesulfonyl)-3-amino-8-isopropylhexahydropyrazino[1,2-a]pyrimidine-4,7-dione (Example 1) were dissolved in ml of methanol, and 200 μl of acetic acid were added. 400 μl of acetone and 1 ml of 1M sodium cyanoborohydride solution in THF were added to this solution. After 3 hours, the reaction mixture was evaporated, suspended in 5% Et$_3$N in ethyl acetate and filtered through a small silica gel column. The eluent was evaporated, and the crude substance was dissolved in a mixture of acetonitrile and water and freeze dried. The pure title compound was removed after purification by HPLC. The system and process described under "general processes" was used for this. MW=596.16 (calculated, monoisotopic); measured value (M+H)$^+$: 597.3.

EXAMPLE 5

6-(4-Chlorobenzyl)-1-(2,4-dichlorobenzenesulfonyl)-3-dimethylamino-8-isopropylhexahydropyrazino[1,2-a]pyrimidine-4,7-dione Structure:

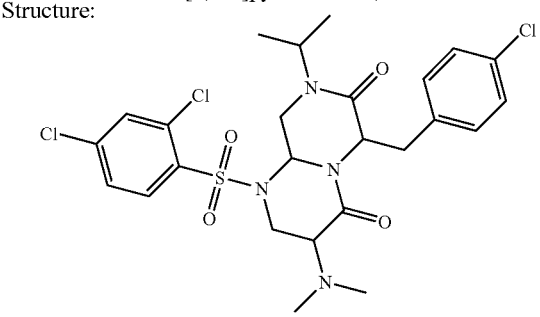

200 mg of 6-(4-chlorobenzyl)-1-(2,4-dichlorobenzenesulfonyl)-3-amino-8-isopropylhexahydropyrazino[1,2-a]pyrimidine-4,7-dione hydrobromide (Example 2) were dissolved in 15 ml of methanol, and 600 μl of acetic acid were added. 0.5 ml of 37% strength aqueous formaldehyde and 3 ml of 1M sodium cyanoborohydride solution in THF were added to this solution. After 2 hours, the reaction mixture was evaporated, suspended in 5% Et$_3$N in ethyl acetate and filtered through a small silica gel column. The eluent was evaporated, and the crude substance was dissolved in a mixture of acetonitrile and water and freeze dried. The pure title compound was removed after purification by HPLC. The system and process described under "general processes" was used for this. MW=586.10 (calculated, monoisotopic); measured value (M+H)$^+$: 587.3.

EXAMPLE 6

6-(4-Chlorobenzyl)-1-(2,4-dichlorobenzenesulfonyl)-8-isopropyl-3-pyrrol-1-ylhexahydropyrazino[1,2-a]pyrimidine-4,7-dione Structure:

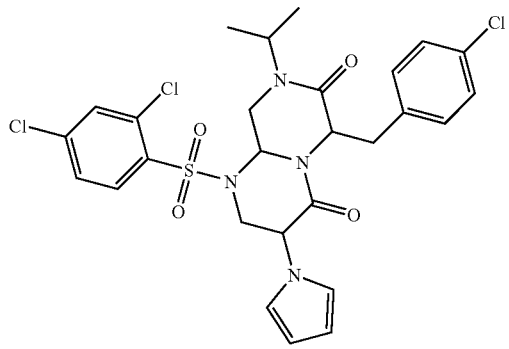

64 mg of 6-(4-chlorobenzyl)-1-(2,4-dichlorobenzenesulfonyl)-3-amino-8-isopropylhexahydropyrazino[1,2-a]pyrimidine-4,7-dione hydrobromide (Example 2) were suspended in 1 ml of water, and 1 ml of DCE was added. This mixture was mixed with 2 equivalents of 2,5-dimethoxytetrahydrofuran and stirred at 80° C. for 1 hour. The DCE phase was removed and the aqueous phase was extracted twice with DCE. The combined extracts were evaporated, and the crude substance was dissolved in a mixture of acetonitrile and water and freeze dried. The pure title compound was removed after purification by HPLC. The system and process described under "general processes" was used for this. MW=608.08 (calculated, monoisotopic); measured value (M+H)$^+$: 609.4.

EXAMPLE 7

3-Azetidin-1-yl-6-(4-chlorobenzyl)-1-(2,4-dichlorobenzenesulfonyl)-8-isopropylhexahydro-pyrazino[1,2-a]pyrimidine-4,7-dione Structure:

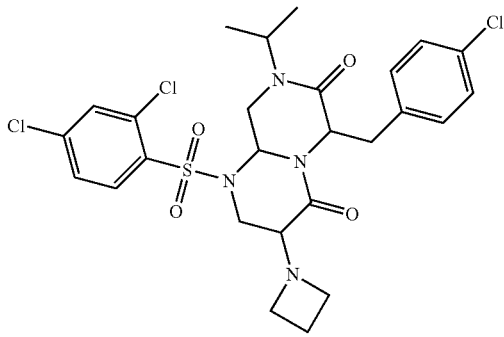

32 mg of 6-(4-chlorobenzyl)-1-(2,4-dichlorobenzenesulfonyl)-3-amino-8-isopropylhexahydropyrazino[1,2-a]pyrimidine-4,7-dione hydrobromide (Example 2) were suspended in 1 ml of water, and 2 ml of 1-butanol were added. 1 mmol of potassium carbonate and 200 μl of 1,3-dibromopropane were added to this mixture. The reaction mixture was stirred at 90° C. for 16 hours and evaporated. The residue was suspended in 5% Et$_3$N/ethyl acetate, filtered and evaporated. The pure title compound was removed after purification by HPLC. The system and process described under "general processes" was used for this. MW=598.10 (calculated, monoisotopic); measured value (M+H)$^+$: 599.3.

EXAMPLE 8

6-(4-Chlorobenzyl)-1-(2,4-dichlorobenzenesulfonyl)-8-isopropyl-3-pyrrolidin-1-yl-hexahydropyrazino[1,2-a]pyrimidine-4,7-dione Structure:

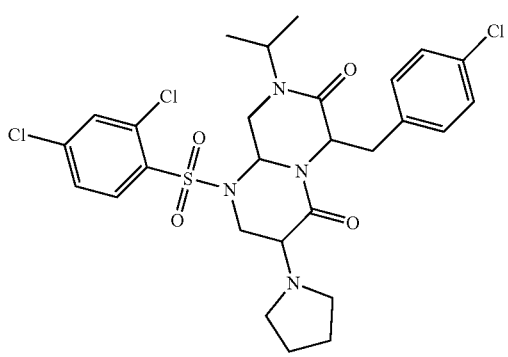

32 mg of 6-(4-chlorobenzyl)-1-(2,4-dichlorobenzenesulfonyl)-3-amino-8-isopropylhexahydropyrazino[1,2-a]pyrimidine-4,7-dione hydrobromide (Example 2) were suspended in 1 ml of water, and 2 ml of 1-butanol were added. 1 mmol of potassium carbonate and 200 µl of 1,4-dibromobutane were added to this mixture. The reaction mixture was stirred at 90° C. for 16 hours and evaporated. The residue was suspended in 5% Et$_3$N/ethyl acetate, filtered and evaporated. The pure title compound was removed after purification by HPLC. The system and process described under "general processes" was used for this. MW=612.11 (calculated, monoisotopic); measured value (M+H)$^+$: 613.4.

EXAMPLE 9

N-[6-(4-Chlorobenzyl)-1-(2,4-dichlorobenzenesulfonyl)-8-isopropyl-4,7-dioxooctahydropyrazino[1,2-a]pyrimidin-3-yl]methanesulfonamide Structure:

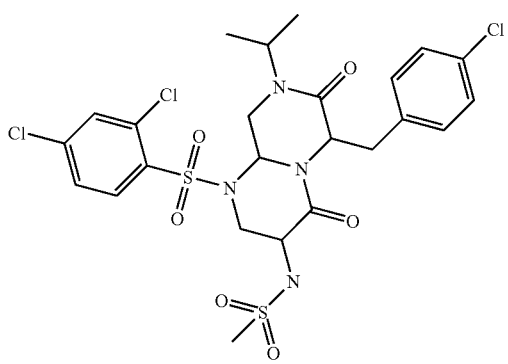

64 mg of 6-(4-chlorobenzyl)-1-(2,4-dichlorobenzenesulfonyl)-3-amino-8-isopropylhexahydropyrazino[1,2-a]pyrimidine-4,7-dione hydrobromide (Example 2) were dissolved in 3 ml of DCM. 0.5 mmol of triethylamine and 1.5 equivalents of methanesulfonyl chloride were added to the solution. After 2 hours, 0.5 ml of dimethylamine in THF was added, and the solvent was evaporated in vacuo. The pure title compound was removed after purification by HPLC. The system and process described under "general processes" was used for this. MW=636.04 (calculated, monoisotopic); measured value (M+H)$^+$: 637.4.

EXAMPLE 10

6-(4-Chlorobenzyl)-1-(5-chloro-2-methoxybenzenesulfonyl)-3-dimethylamino-8-isopropylhexahydropyrazino[1,2-a]pyrimidine-4,7-dione Structure:

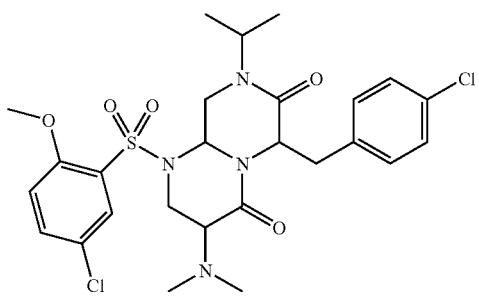

The compound in Example 10 was synthesized by the process described in Example 5 starting from 6-(4-chlorobenzyl)-1-(2-methoxy-5-chlorobenzenesulfonyl)-3-amino-8-isopropylhexahydropyrazino[1,2-a]pyrimidine-4,7-dione (Example 1). MW=582.15 (calculated, monoisotopic); measured value (M+H)$^+$: 583.3.

EXAMPLE 11

3-(Biscyclopropylmethylamino)-6-(4-chlorobenzyl)-1-(5-chloro-2-methoxybenzenesulfonyl)-8-isopropylhexahydropyrazino[1,2-a]pyrimidine-4,7-dione Structure:

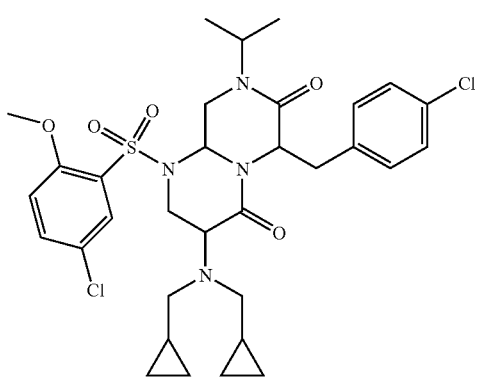

The compound in Example 11 was synthesized by the process described in Example 3 using 10 equivalents of cyclopropanecarboxaldehyde.

MW=662.21 (calculated monoisotopic) measured value (M+H)$^+$: 663.4.

EXAMPLE 12

6-(4-Chlorobenzyl)-1-(2,4-dichlorobenzenesulfonyl)-3-isobutylamino-8-isopropylhexahydropyrazino[1,2-a]pyrimidine-4,7-dione Structure:

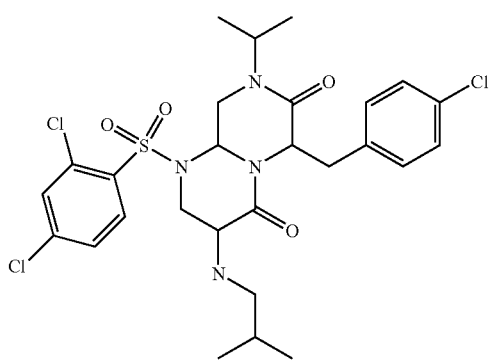

The compound in Example 12 was synthesized by the process described in Example 4 using 4 equivalents of isobutyraldehyde.

MW=614.13 (calculated, monoisotopic); measured value (M+H)$^+$: 615.4.

EXAMPLE 13

6-(4-Chlorobenzyl)-1-(2,4-dichlorobenzenesulfonyl)-3-diisobutylamino-8-isopropylhexahydropyrazino[1,2-a]pyrimidine-4,7-dione Structure:

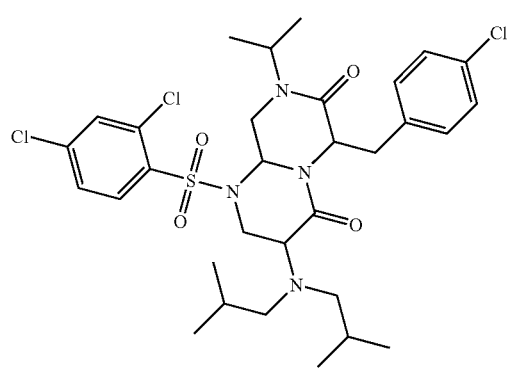

The compound in Example 13 was synthesized by the process described in Example 3 using 20 equivalents of isobutyraldehyde.

MW=670.19 (calculated, monoisotopic); measured value (M+H)$^+$: 671.3.

EXAMPLE 14

6-(4-Chlorobenzyl)-3-(cyclopropylmethylamino)-1-(2,4-dichlorobenzenesulfonyl)-8-isopropylhexahydropyrazino[1,2-a]pyrimidine-4,7-dione Structure:

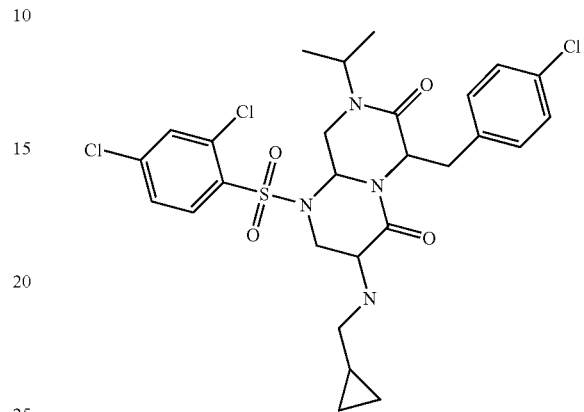

The compound in Example 14 was synthesized by the process described in Example 4 using 5 equivalents of cyclopropanecarboxaldehyde.

MW=612.11 (calculated monoisotopic); measured value (M+H)$^+$: 613.4.

EXAMPLE 15

6-(4-Chlorobenzyl)-1-(2,4-dichlorobenzenesulfonyl)-3-diethylamino-8-isopropylhexahydropyrazino[1,2-a]pyrimidine-4,7-dione Structure:

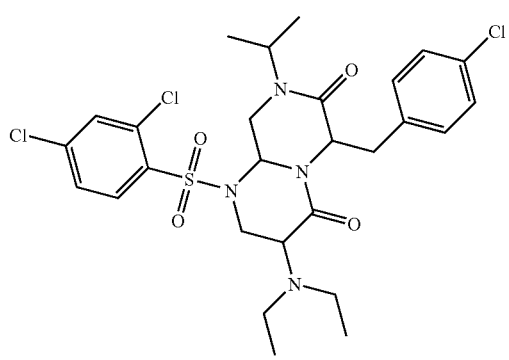

The compound in Example 15 was synthesized by the process described in Example 3 starting from 6-(4-chlorobenzyl)-1-(2,4-dichlorobenzenesulfonyl)-3-amino-8-isopropylhexahydropyrazino[1,2-a]pyrimidine-4,7-dione (Example 2). MW=614.13 (calculated, monoisotopic); measured value (M+H)$^+$: 615.3.

EXAMPLE 16

6-(4-Chlorobenzyl)-1-(2,4-dichlorobenzenesulfonyl)-8-isopropyl-3-isopropylaminohexahydropyrazino[1,2-a]pyrimidine-4,7-dione Structure:

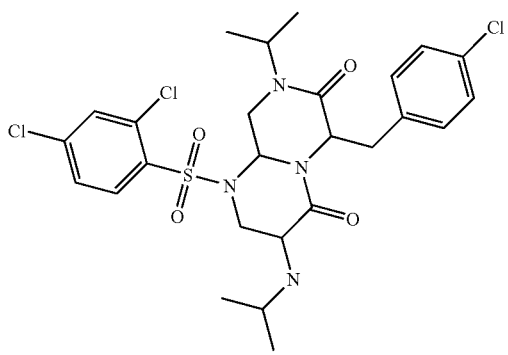

The compound in Example 16 was synthesized by the process described in Example 4 starting from 6-(4-chlorobenzyl)-1-(2,4-dichlorobenzenesulfonyl)-3-amino-8-isopropylhexahydropyrazino[1,2-a]pyrimidine-4,7-dione (Example 2).

MW=600.11 (calculated, monoisotopic); measured value (M+H)$^+$: 601.3.

EXAMPLE 17

6-(4-Chlorobenzyl)-1-(2,4-dichlorobenzenesulfonyl)-8-isopropyl-3-(isopropylmethylamino)hexahydropyrazino[1,2-a]pyrimidine-4,7-dione Structure:

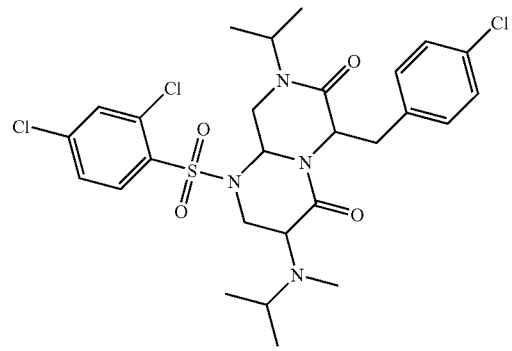

The compound in Example 17 was synthesized by the process described in Example 5 starting from 6-(4-chlorobenzyl)-1-(2,4-dichlorobenzenesulfonyl)-8-isopropyl-3-isopropylaminohexahydropyrazino[1,2-a]pyrimidine-4,7-dione (Example 16). MW=614.13 (calculated, monoisotopic); measured value (M+H)$^+$: 615.4.

EXAMPLE 18

6-(4-Chlorobenzyl)-1-(5-chloro-2-methoxybenzenesulfonyl)-8-isopropyl-3-pyrrolidin-1-yl-hexahydropyrazino[1,2-a]pyrimidine-4,7-dione Structure:

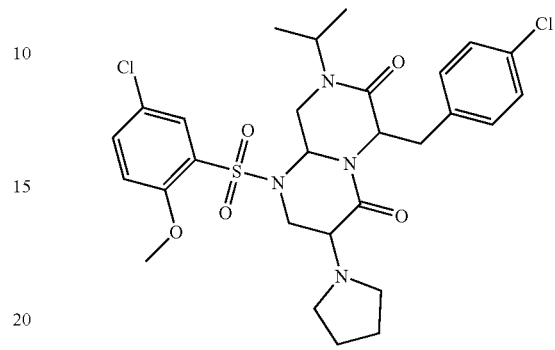

The compound in Example 18 was synthesized by the process described in Example 8 starting from 3-amino-6-(4-chlorobenzyl)-1-(5-chloro-2-methoxybenzenesulfonyl)-8-isopropylhexahydropyrazino[1,2-a]pyrimidine-4,7-dione (Example 1).

MW=608.16 (calculated monoisotopic); measured value (M+H)$^+$: 609.4.

EXAMPLE 19

{4-[6-(4-Chlorobenzyl)-1-(2,4-dichlorobenzenesulfonyl)-8-isopropyl-4,7-dioxooctahydropyrazino[1,2-a]pyrimidin-3-ylamino]butyl}triethylammonium Structure:

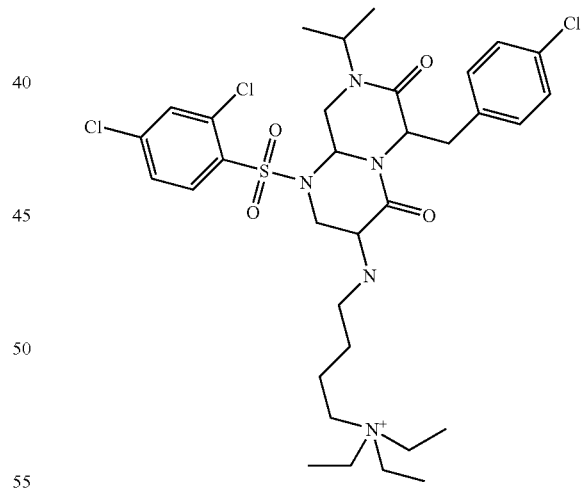

32 mg of 6-(4-chlorobenzyl)-1-(2,4-dichlorobenzenesulfonyl)-3-amino-8-isopropylhexahydropyrazino[1,2-a]pyrimidine-4,7-dione hydrobromide (Example 2) in 1 ml of dichloroethane were treated with 200 µl of triethylamine and 100 µl of 1,4-dibromobutane. The reaction mixture was kept at 60° C. for 60 hours. The precipitate was filtered off, and the filtrate was evaporated in vacuo. The pure title compound trifluoroacetate was removed after purification of the filter residue by HPLC. The system and process described under "general processes" was used for this.

MW=714.24 (calculated, monoisotopic); measured value (M): 714.4.

EXAMPLE 20

{3-[6-(4-Chlorobenzyl)-1-(2,4-dichlorobenzene-sulfonyl)-8-isopropyl-4,7-dioxooctahydropyrazino[1,2-a]pyrimidin-3-ylamino]propyl} triethylammonium Structure:

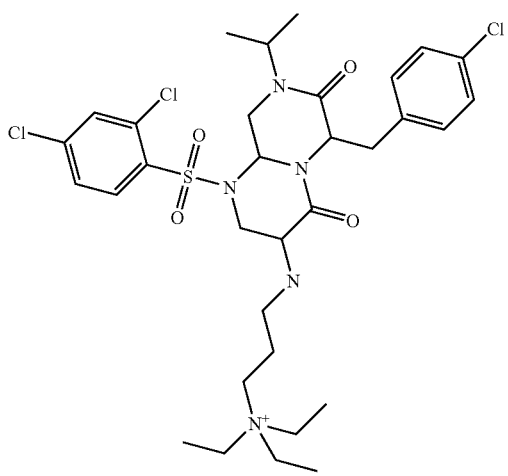

32 mg of 6-(4-chlorobenzyl)-1-(2,4-dichlorobenzene-sulfonyl)-3-amino-8-isopropylhexahydropyrazino[1,2-a]pyrimidine-4,7-dione hydrobromide (Example 2) in 1 ml of dichloroethane were treated with 200 µl of triethylamine and 100 µl of 1,3-dibromopropane. The reaction mixture was kept at 60° C. for 60 hours. The precipitate was filtered off, and the filtrate was evaporated in vacuo. The pure title compound trifluoroacetate was removed after purification of the filter residue by HPLC. The system and process described under "general processes" was used for this.

MW=700.23 (calculated, monoisotopic); measured value (M): 700.4.

EXAMPLE 21

N-[6-(4-Chlorobenzyl)-1-(5-chloro-2-methoxyben-zenesulfonyl)-8-isopropyl-4,7-dioxooctahydropy-razino[1,2-a]pyrimidin-3-yl]acetamide Structure:

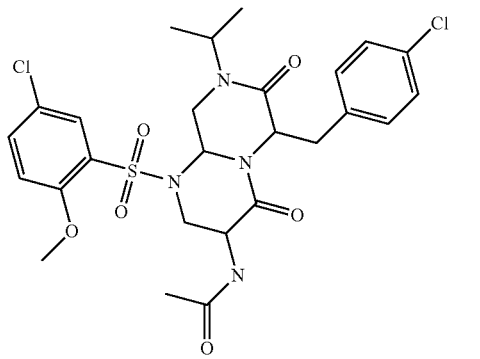

a) 2-Allyloxycarbonylamino-3-(4-chlorophenyl)propionic Acid

The product is obtained by methods (ET$_3$N, methanol) known from the literature starting from 10 g of 4-chlo-rophenylalanine and 8 ml of allyl chloroformate. MW=283.71 (calculated monoisotopic); measured value (M+H)$^+$: 284.1.

b) Allyl {2-(4-chlorophenyl)-1-[(2,2-diethoxyethyl)isopropylcarbamoyl]ethyl}-carbamate 7.8 ml of DIC are added dropwise to a solution of 5.7 g of 2-allyloxycarbonylamino-3-(4-chlorophenyl)propionic acid, 3.5 g of (2,2-diethoxyethyl)isopropylamine, 6.8 g of HOAt in 30 ml of DMF and the mixture is stirred for 12 h. The reaction solution is concentrated under reduced pressure and purified by flash chromatography on silica gel with the eluent ethyl acetate/n-heptane=1/3. The desired product is obtained with MW=440.97 (calculated monoisotopic); measured value (M+H)$^+$: 441.15 c) 2-Amino-3-(4-chlorophenyl)-N-(2,2-diethoxy-ethyl)-N-isopropylpropionamide 10 mg of palladium tetrakistriphenylphosphine are added to a solution of 13.2 g of allyl {2-(4-chlorophenyl)-1-[(2,2-diethoxyethyl)isopropylcarbamoyl]ethyl}carbamate, 18.9 g of dimethylbarbituric acid in 140 ml of methylene chloride under a protective argon gas atmosphere, and the mixture is stirred for 12 h. The reaction solution is concentrated under reduced pressure and [lacuna] by flash chromatography on silica gel (eluent methylene chloride, 1% Et$_3$N, 0-10% methanol). The desired product is obtained with MW=356.90 (calculated monoisotopic); measured value (M-C$_2$H$_6$O+H)$^+$: 311.10 d) 2-Benzyloxycarbonylamino-3-(5-chloro-2-methoxybenzenesulfonylamino)-propionic Acid A solution of 3.8 g of 5-chloro-2-methoxybenzenesulfonyl chloride in 5 ml of dioxane is added dropwise to a solution of 2.3 g of 3-amino-2-benzyloxycarbonylamino-propionic acid in 20 ml of 1N NaOH solution. The mixture is left to stir while controlling the pH (pH>7) for 12 h, the pH is reduced below 7 by adding citric acid, and the reaction solution is then extracted with methylene chloride. The organic phase is dried over magnesium sulfate, concentrated under reduced pressure and employed without further purification in the next reaction step.

Product with MW=442.06 (calculated monoisotopic); measured value (M+H)$^+$: 442.95 e) Benzyl(2-(5-chloro-2-methoxybenzenesulfony-lamino)-1-{2-(4-chlorophenyl)-1-[(2,2-diethoxy-ethyl)isopropylcarbamoyl]ethylcarbamoyl}ethyl) carbamate ester 52 mg of EDC, 45 mg of HOBt and 100 µl of N-ethylmorpholine are added to a solution of 124 mg of 2-benzyloxycarbonylamino-3-(5-chloro-2-methoxybenzene-sulfonylamino)propionic acid in 1 ml of DMF. A solution of 100 mg of 2-amino-3-(4-chlorophenyl)-N-(2,2-diethoxyethyl)-N-isopropylpropionamide in 1 ml of DMF is added dropwise thereto, and the mixture is left to stir for 12 h. The reaction solution is filtered mixed with ethyl acetate and then extracted with 5% aqueous sodium bicarbonate solution and aqueous sodium chloride solution. Drying of the organic phase with Chromabond XTR is followed by concentration under reduced pressure, and the residue is separated by HPLC (Knauer Eurospher-100-10-C18, water (0.1% trifluoroacetic acid)/acetonitrile (0.1% trifluoroacetic acid)=80/20→10/90). The desired product is obtained with MW=780.24 (calculated); measured value (M-C$_2$H$_6$O+H)$^+$: 735.1 f) Benzyl[6-(4-chlorobenzyl)-1-(5-chloro-2-methoxybenzenesulfonyl)-8-isopropyl-4,7-dioxooctahydropyrazino[1,2-a]pyrimidin-3-yl]carbamate A solution of 218 mg of benzyl(2-(5-chloro-2-methoxybenzenesulfonylamino)-1-{2-(4-chlorophenyl)-1-[(2,2-diethoxyethyl)isopropylcarbamoyl]ethylcarbamoyl}ethyl)-carbamate in 3 ml of formic acid is stirred at room temperature for 12 h and then at 55° C. for 5 h. The reaction solution is concentrated under reduced pressure, and the residue is separated by HPLC (Knauer Eurospher-100-10-C18, water (0.1% trifluoroacetic acid)/acetonitrile (0.1% trifluoroacetic acid)=80/20→10/90). The desired product is obtained with MW=688.15 (calculated monoisotopic); measured value (M+H)$^+$: 689.41 g) 3-Amino-6-(4-chlorobenzyl)-1-(5-chloro-2-methoxybenzenesulfonyl)-8-isopropylhexahydropyrazino[1,2-a]pyrimidine-4,7-dione A solution of 79 mg of benzyl[6-(4-chlorobenzyl)-1-(5-chloro-2-methoxybenzenesulfonyl)-8-isopropyl-4,7-dioxooctahydropyrazino[1,2-a]pyrimidin-3-yl]carbamate in 2 ml of a 33% solution of HBr in glacial acetic acid is stirred for 2 h. The reaction solution is mixed with aqueous sodium carbonate solution and extracted with ethyl acetate. The organic phase is dried over magnesium carbonate and concentrated under reduced pressure, and the residue is separated by HPLC (Knauer Eurospher-100-10-C18, water (0.1% trifluoroacetic acid)/acetonitrile (0.1% trifluoroacetic acid)=80/20→10/90). The desired product is obtained with MW=554.12 (calculated monoisotopic); measured value (M+H)$^+$: 555.12 h) N-[6-(4-Chlorobenzyl)-1-(5-chloro-2-methoxybenzenesulfonyl)-8-isopropyl-4,7-dioxooctahydropyrazino[1,2-a]pyrimidin-3-yl]acetamide A solution of 7 mg of 3-amino-6-(4-chlorobenzyl)-1-(5-chloro-2-methoxybenzenesulfonyl)-8-isopropylhexahydropyrazino[1,2-a]pyrimidine-4,7-dione, 2.4 µl of acetic anhydride, 0.5 mg of DMAP in 1.5 ml of pyridine is stirred for 12 h. The reaction solution is concentrated and purified by flash chromatography on silica gel with the eluent methylene chloride with a gradient of 0-10% methanol.

The desired product is obtained with MW=596.13 (calculated monoisotopic); measured value (M+H)$^+$: 597.13

EXAMPLE 22

N-[6-(4-Chlorobenzyl)-1-(5-chloro-2-methoxybenzenesulfonyl)-8-isopropyl-4,7-dioxooctahydropyrazino[1,2-a]pyrimidin-3-yl]cyclopropanecarboxamide

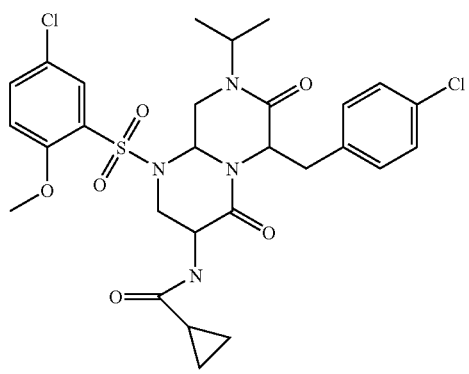

11 mg (0.105 mmol) of cyclopropanecarbonyl chloride are added to a solution of 3-amino-6-(4-chlorobenzyl)-1-(5-chloro-2-methoxybenzenesulfonyl)-8-isopropylhexahydropyrazino[1,2-a]pyrimidine-4,7-dione (56 mg, 0.10 mmol) in 1 ml of dichloromethane and 26 mg (0.20 mmol) of diisopropylethylamine. After stirring at room temperature for two hours, the reaction mixture is purified by chromatography on 1 g of silica gel (eluent EtOAc/DCM; gradient 0-20%). 42 mg of the desired product are obtained.

MW=622 (calculated, monoisotopic), measured value (M+H)$^+$=623.10

EXAMPLE 23

N-[6-(4-Chlorobenzyl)-1-(5-chloro-2-methoxybenzenesulfonyl)-8-isopropyl-4,7-dioxooctahydropyrazino[1,2-a]pyrimidin-3-yl]cyclobutanecarboxamide

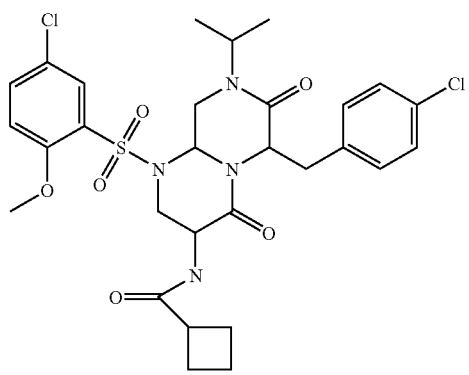

Synthesis took place in analogy to Example 22 using cyclobutanecarbonyl chloride. The desired product is obtained with MW=636.16 (calculated, monoisotopic); measured value (M+H)$^+$: 637.11

EXAMPLE 24

N-[6-(4-Chlorobenzyl)-1-(5-chloro-2-methoxyben-zenesulfonyl)-8-isopropyl-4,7-dioxooctahydropy-razino[1,2-a]pyrimidin-3-yl]cyclopentanecarboxam-ide Structure:

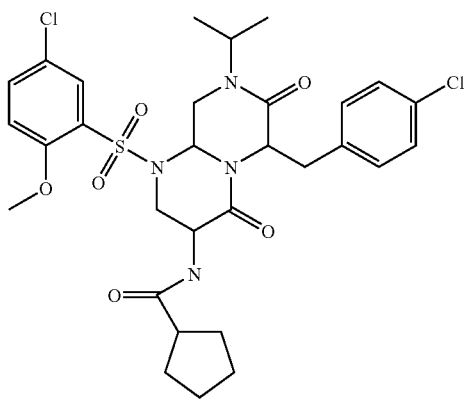

Synthesis took place in analogy to Example 22 using cyclopentanecarbonyl chloride. The desired product is obtained with MW=650.17 (calculated, monoisotopic); measured value (M+H)$^+$: 651.12

EXAMPLE 25

4-Dimethylamino-N-[6-(4-chlorobenzyl)-1-(5-chloro-2-methoxybenzenesulfonyl)-8-isopropyl-4,7-dioxooctahydropyrazino[1,2-a]pyrimidin-3-yl]benza-mide Structure:

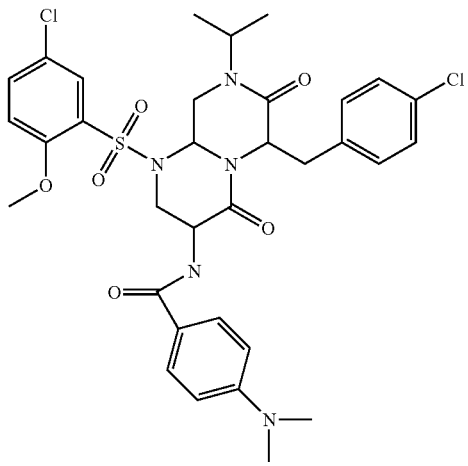

Synthesis took place in analogy to Example 22 using 4-dimethylaminobenzoyl chloride. The desired product is obtained with MW=701.18 (calculated, monoisotopic); measured value (M+H)$^+$: 702.12

EXAMPLE 26

N-[6-(4-Chlorobenzyl)-1-(5-chloro-2-methoxyben-zenesulfonyl)-8-isopropyl-4,7-dioxooctahydropy-razino[1,2-a]pyrimidin-3-yl]methanesulfonamide Structure:

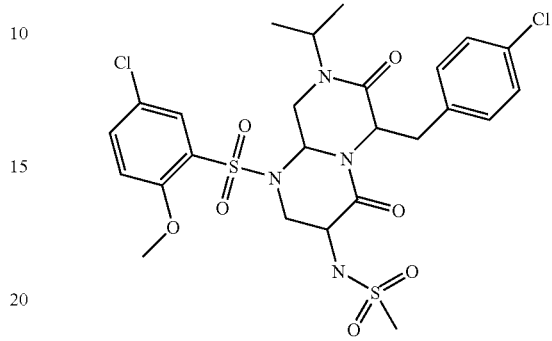

1.8 µl of mesyl chloride are added dropwise to a solution of 5 mg of 3-amino-6-(4-chlorobenzyl)-1-(5-chloro-2-methoxybenzenesulfonyl)-8-isopropylhexahydropyrazino[1,2-a]pyrimidine-4,7-dione in 1 ml of methylene chloride and 3 µl of Et$_3$N at 0° C. The mixture is stirred for 2 h and then washed with aqueous sodium chloride solution. The organic phase is dried over magnesium sulfate and concentrated under reduced pressure.

The desired product is obtained as residue with MW=632.09 (calculated, monoisotopic); measured value (M+H)$^+$: 633.10

EXAMPLE 27

N-[6-(4-Chlorobenzyl)-1-(5-chloro-2-methoxyben-zenesulfonyl)-8-isopropyl-4,7-dioxooctahydropy-razino[1,2-a]pyrimidin-3-yl]cyclopropanesulfona-mide Structure:

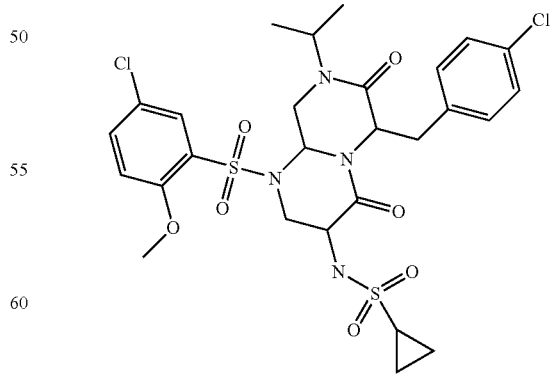

Synthesis took place in analogy to Example 26 using cyclopropanesulfonyl chloride. The desired product is obtained with MW=658.11 (calculated, monoisotopic); measured value (M+H)$^+$:659.10

EXAMPLE 28

1-tert-Butyl-3-[6-(4-chlorobenzyl)-1-(5-chloro-2-methoxybenzenesulfonyl)-8-isopropyl-4,7-dioxooctahydropyrazino[1,2-a]pyrimidin-3-yl]urea Structure:

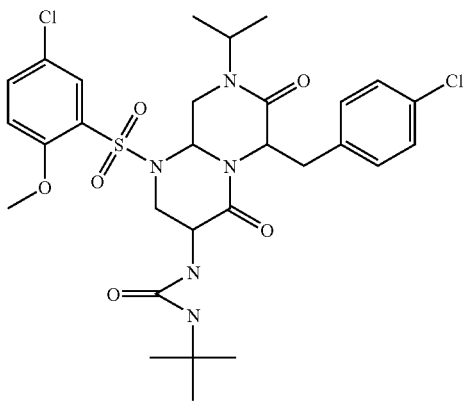

5.4 mg of tert-butyl isocyanate are added to a solution of 30 mg of 3-amino-6-(4-chlorobenzyl)-1-(5-chloro-2-methoxybenzenesulfonyl)-8-isopropylhexahydropyrazino[1,2-a]pyrimidine-4,7-dione and 7.6 µl of $Et_3N$ in 500 µl of dioxane. The solution is heated at 50° C. for 6 h. The solvent is removed in vacuo. The residue is separated by HPLC (Waters-Xterra™ MS C18, 5 µm, water (0.1% trifluoroacetic acid)/acetonitrile (0.1% trifluoroacetic acid)=80/20 10/90).

The desired product is obtained with MW=653.18 (calculated, monoisotopic); measured value $(M+H)^+$: 654.13

EXAMPLE 29

N-[6-(4-Chlorobenzyl)-1-(2,4-dichlorobenzenesulfonyl)-8-isopropyl-4,7-dioxooctahydropyrazino[1,2-a]pyrimidin-3-yl]cyclopropanecarboxamide Structure:

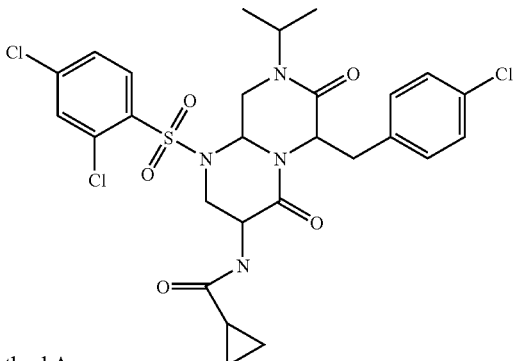

Method A:

a) 2-Benzyloxycarbonylamino-3-(2,4-dichlorobenzenesulfonylamino)propionic Acid Synthesis takes place in analogy to Example 21d) starting from 2,4-dichlorobenzenesulfonyl chloride. The desired product is obtained with MW=446.01 (calculated, monoisotopic); measured value $(M+H-CO_2)^+$: 403.00.

b) N-{2-(4-Chlorophenyl)-1-[(2,2-diethoxyethyl)isopropylcarbamoyl]ethyl}-3-(2,4-dichlorobenzenesulfonylamino)-2-methanesulfonylaminopropionamide Synthesis takes place in analogy to Example 21e) starting from 2-benzyloxycarbonylamino-3-(2,4-dichlorobenzenesulfonylamino)propionic acid. The desired product is obtained with MW=784.186 (calculated, monoisotopic); measured value $(M-CO_2+H)^+$: 741.10 c) Benzyl[6-(4-chlorobenzyl)-1-(2,4-dichlorobenzenesulfonyl)-8-isopropyl-4,7-dioxooctahydropyrazino[1,2-a]pyrimidin-3-yl]carbamate Synthesis takes place in analogy to Example 21f) starting from N-{2-(4-chlorophenyl)-1-[(2,2-diethoxyethyl)isopropylcarbamoyl]ethyl}-3-(2,4-dichlorobenzenesulfonylamino)-2-methanesulfonylaminopropionamide. The desired product is obtained with MW=692.10 (calculated, monoisotopic); measured value $(M+H)^+$: 693.05 d) 3-Amino-6-(4-chlorobenzyl)-1-(2,4-dichlorobenzenesulfonyl)-8-isopropylhexahydropyrazino[1,2-a]pyrimidine-4,7-dione Synthesis takes place in analogy to Example 21g) starting from benzyl[6-(4-chlorobenzyl)-1-(2,4-dichlorobenzenesulfonyl)-8-isopropyl-4,7-dioxooctahydropyrazino[1,2-a]pyrimidin-3-yl]carbamate. The desired product is obtained with MW=558.07 (calculated, monoisotopic); measured value $(M+H)^+$: 559.10 e) N-[6-(4-Chlorobenzyl)-1-(2,4-dichlorobenzenesulfonyl)-8-isopropyl-4,7-dioxooctahydropyrazino[1,2-a]pyrimidin-3-yl]cyclopropanecarboxamide A solution of 15 mg of 3-amino-6-(4-chlorobenzyl)-1-(2,4-dichlorobenzenesulfonyl)-8-isopropylhexahydropyrazino[1,2-a]pyrimidine-4,7-dione, 3.2 mg of cyclopropanecarboxylic acid in 110 µl of DMF is cooled to 0° C., and 11.2 mg of HATU, 4.1 mg of HOAt and 11.6 µl of $Et_3N$ are added. The solution is stirred at 0° C. for 10 min and then at room temperature for 4 h. The solvent is removed in vacuo. The residue is then taken up in ethyl acetate and water. The aqueous phase extracted twice with ethyl acetate. The combined organic phase is dried over $Na_2SO_4$ and the solvent removed in vacuo. The crude product is separated by HPLC (Waters-Xterra™ MS C18, 5 µm, water (0.1% trifluoroacetic acid)/acetonitrile (0.1% trifluoroacetic acid)=80/20 10/90).

The desired product is obtained with MW=626.09 (calculated, monoisotopic); measured value $(M+H)^+$: 627.13

Method B a) 9H-Fluoren-9-ylmethyl{2-(4-chlorophenyl)-1-[(2,2-diethoxyethyl)isopropylcarbamoyl]ethyl}carbamate 210 mg (1.2 mmol) of (2,2-diethoxyethyl)isopropylamine and 376 mg (1.20 mmol) of DMTMM are added to a solution of 505 mg (1.2 mmol) of N-Fmoc-4-Cl-Phe-OH in 2 ml of DMF. The reaction mixture is stirred at room temperature overnight. It is then extracted with 40 ml of diethyl ether and washed with 10 ml of water. The combined organic phases are dried over $MgSO_4$ and concentrated in vacuo. The crude product is purified by chromatography on 10 g $SiO_2$ (eluent DCM followed by 20% EtOAc/DCM). 530 mg of the desired product are obtained as an oil. MW=578.26 (calculated, monoisotopic); measured value (M+H)⁺: 579 b) 2-Amino-3-(4-chlorophenyl)-N-(2,2-diethoxyethyl)-N-isopropylpropionamide

A solution of 530 mg (0.915 mmol) of 3-(4-chlorophenyl)-N-(2,2-diethoxyethyl)-N-isopropyl-2-methylpropionamide in 15 ml of a 20% diethylamine DCM solution is stirred at room temperature overnight. The reaction mixture is concentrated in vacuo and purified by chromatography on 5 g of $SiO_2$ (eluent DCM followed by 20% EtOAc/DCM followed by 20% MeOH/DCM). 320 mg of the desired product are obtained as an oil. MW=356.19 (calculated, monoisotopic); measured value (M+H)⁺=357 c) 9H-Fluoren-9-ylmethyl(2-benzyloxycarbonylamino-2-{2-(4-chlorophenyl)-1-[(2,2-diethoxyethyl)isopropylcarbamoyl]ethylcarbamoyl}ethyl)carbamate Z-Dap-Fmoc-OH was coupled with 2-amino-3-(4-chlorophenyl)-N-(2,2-diethoxyethyl)-N-isopropylpropionamide under the same conditions as described under a). The desired product is obtained with MW=798.34 (calculated, monoisotopic); measured value (M+Na)⁺=821.43 d) Benzyl(2-amino-1-{2-(4-chlorophenyl)-1-[(2,2-diethoxyethyl)isopropylcarbamoyl]-ethylcarbamoyl}ethyl)carbamate The Fmoc protective group was eliminated from 9H-fluoren-9-ylmethyl(2-benzyloxycarbonylamino-2-{2-(4-chlorophenyl)-1-[(2,2-diethoxyethyl)isopropylcarbamoyl]ethylcarbamoyl}ethyl)carbamate using diethylamine and employing the method as described under b). The desired product is obtained with MW=576.27 (calculated, monoisotopic); measured value (M+H)⁺=577.22 e) Benzyl[1-{2-(4-chlorophenyl)-1-[(2,2-diethoxyethyl)isopropylcarbamoyl]-ethylcarbamoyl}-2-(2,4-dichlorobenzenesulfonylamino)ethyl]carbamate 1.94 ml (11.09 mmol) of DIEA and 1.5 g (6.1 mmol) of 2,4-dichlorophenylsulfonyl chloride are added to a solution of 3.2 g (5.54 mmol) of benzyl(2-amino-1-{2-(4-chlorophenyl)-1-[(2,2-diethoxyethyl)isopropylcarbamoyl]ethylcarbamoyl}ethyl)carbamate in 75 ml of DCM. The solution is stirred at room temperature overnight. The solution is then concentrated in vacuo, and the residue is purified by column chromatography on 100 g of $SiO_2$ (eluent DCM followed by 20% EtOAc/DCM). 2.78 g of the desired product are obtained as a colorless foam. MW=784.19 (calculated, monoisotopic); measured value (M+Na)⁺=807.24 f) Benzyl[6-(4-chlorobenzyl)-1-(2,4-dichlorobenzenesulfonyl)-8-isopropyl-4,7-dioxooctahydropyrazino[1,2-a]pyrimidin-3-yl]carbamate A solution of 2.74 g (3.49 mmol) of benzyl[1-{2-(4-chlorophenyl)-1-[(2,2-diethoxyethyl)-isopropylcarbamoyl]ethylcarbamoyl}-2-(2,4-dichlorobenzenesulfonylamino)ethyl]carbamate in 45 ml of formic acid was heated at 60° C. for 6 h. The reaction mixture was then concentrated in vacuo, and the residue was purified by chromatography on 40 g of $SiO_2$ (eluent DCM followed by 20% EtOAc/DCM). 2.25 g of the cyclized compound are obtained as a colorless solid.

LC/MS MW=692.1 (calculated, monoisotopic); measured value (M+H)⁺=693 g) 3-Amino-6-(4-chlorobenzyl)-1-(2,4-dichlorobenzenesulfonyl)-8-isopropylhexahydropyrazino[1,2-a]pyrimidine-4,7-dione 206 ml (1.44 mmol) of trimethylsilyl iodide (TMSI) are added to a solution of 250 mg (0.36 mmol) of benzyl[6-(4-chlorobenzyl)-1-(2,4-dichlorobenzenesulfonyl)-8-isopropyl-4,7-dioxooctahydropyrazino[1,2-a]pyrimidin-3-yl]carbamate in 10 ml of $CH_3CN$ at 0° C. The reaction solution is allowed to reach room temperature and is stirred at this temperature for 2 h. 5 ml of MeOH are added to the reaction solution, and then the solution is concentrated in vacuo. The residue is purified on a 5 g SCX cartridge (eluted with MeOH followed by 3N $NH_3$/MeOH). 185 mg of the desired compound are obtained as a white powder. LC/MS 558.07 (calculated, monoisotopic); measured value (M+H)⁺: 559.10 g) N-[6-(4-Chlorobenzyl)-1-(2,4-dichlorobenzenesulfonyl)-8-isopropyl-4,7-dioxooctahydropyrazino[1,2-a]pyrimidin-3-yl]cyclopropanecarboxamide Synthesis took place in analogy to Example 22.

EXAMPLE 30

N-[6-(4-Chlorobenzyl)-1-(2,4-dichlorobenzenesulfonyl)-8-isopropyl-4,7-dioxooctahydropyrazino[1,2-a]pyrimidin-3-yl]cyclobutanecarboxamide Structure:

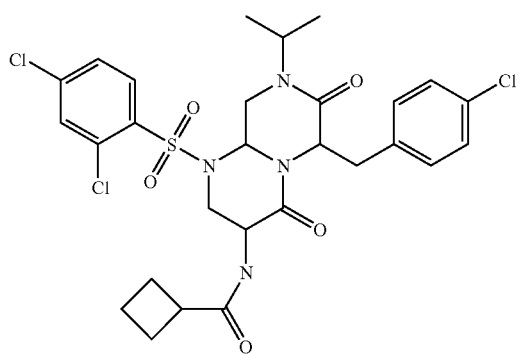

Synthesis took place in analogy to Example 22 using cyclobutanecarbonyl chloride and 3-amino-6-(4-chlorobenzyl)-1-(2,4-dichlorobenzenesulfonyl)-8-isopropylhexahydropyrazino[1,2-a]pyrimidine-4,7-dione. The desired product is obtained with MW=640.11 (calculated, monoisotopic); measured value (M+H)⁺: 641.09

EXAMPLE 31

N-[6-(4-Chlorobenzyl)-1-(2,4-dichlorobenzenesulfonyl)-8-isopropyl-4,7-dioxooctahydropyrazino[1,2-a]pyrimidin-3-yl]cyclopentanecarboxamide Structure:

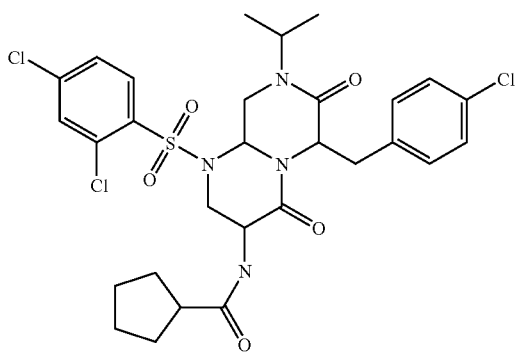

Synthesis took place in analogy to Example 22 using cyclopentanecarbonyl chloride and 3-amino-6-(4-chlorobenzyl)-1-(2,4-dichlorobenzenesulfonyl)-8-isopropylhexahydropyrazino[1,2-a]pyrimidine-4,7-dione. The desired product is obtained with MW=654.12 (calculated, monoisotopic); measured value (M+H)$^+$: 655.1

EXAMPLE 32

N-[6-(4-Chlorobenzyl)-1-(2,4-dichlorobenzenesulfonyl)-8-isopropyl-4,7-dioxooctahydropyrazino[1,2-a]pyrimidin-3-yl]cyclohexanecarboxamide Structure:

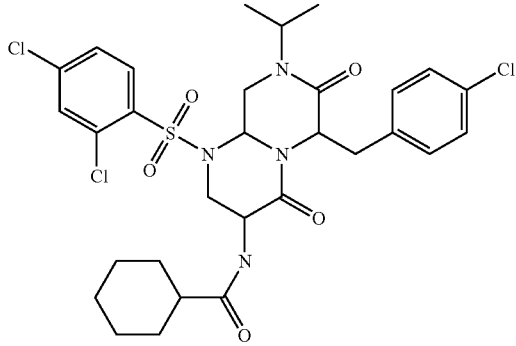

Synthesis took place in analogy to Example 22 using cyclohexanecarbonyl chloride and 3-amino-6-(4-chlorobenzyl)-1-(2,4-dichlorobenzenesulfonyl)-8-isopropylhexahydropyrazino[1,2-a]pyrimidine-4,7-dione. The desired product is obtained with MW=668.14 (calculated, monoisotopic); measured value (M+H)$^+$: 669.11

EXAMPLE 33

N-[6-(4-Chlorobenzyl)-1-(2,4-dichlorobenzenesulfonyl)-8-isopropyl-4,7-dioxooctahydropyrazino[1,2-a]pyrimidin-3-yl]-2,2,2-trifluoroacetamide

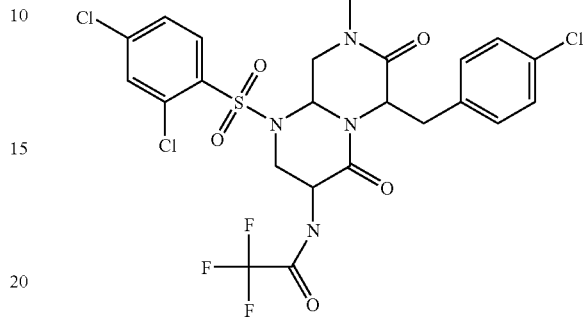

40 mg (0.071 mmol) of 3-amino-6-(4-chlorobenzyl)-1-(2,4-dichlorobenzenesulfonyl)-8-isopropylhexahydropyrazino[1,2-a]pyrimidine-4,7-dione were dissolved in 1.5 ml of DCM, and 0.024 ml (0.17 mmol) of trifluoroacetic anhydride and 0.075 ml (0.43 mmol) of DIEA were added. The reaction mixture was stirred at 50° C. for 1 hour. After addition of 1 ml of water, the organic phase was isolated, dried (MgSO$_4$) and concentrated in vacuo. Purification by flash chromatography on 4 g SiO$_2$ (elution with MeOH/DCM, gradient 0-4%) afforded 21 mg of substance. MW (calculated, monoisotopic)=654.05; MW (measured value)=655.06.

EXAMPLE 34

N-[6-(4-Chlorobenzyl)-1-(2,4-dichlorobenzenesulfonyl)-8-isopropyl-4,7-dioxooctahydropyrazino[1,2-a]pyrimidin-3-yl]-N-isopropylcyclopropanecarboxamide

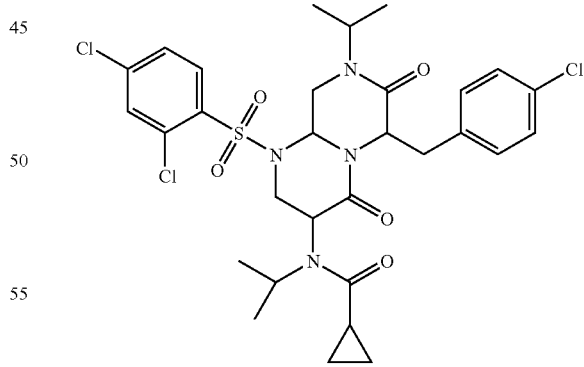

0.2 g (0.36 mmol) of 3-amino-6-(4-chlorobenzyl)-1-(2,4-dichlorobenzenesulfonyl)-8-isopropylhexahydropyrazino[1,2-a]pyrimidine-4,7-dione was dissolved in 12 ml of MeOH, and 1.6 ml of acetone and then 0.8 ml of CH$_3$COOH and 4 ml of NaCNBH$_3$ (1.0M in THF) were added. After 1 hour, the mixture was concentrated in vacuo, mixed with 5 ml of EtOAc and washed with 5 ml of water. The organic phase was isolated, dried (MgSO$_4$) and concentrated in vacuo. Flash chromatography of the crude substance on 20 g of SiO$_2$ (elution with EtOAc/DCM, gradient 0-50%) afforded 182 mg of the intermediate as an oil which was used for the subsequent coupling step. 30 mg (0.05 mm) of the intermediate were mixed in 1 ml of DCM with 0.026 ml (0.149 mmol) of DIEA and 0.0055 ml (0.0598 mmol) of cyclopropanecarbonyl chloride and stirred at room temperature overnight. After addition of 2 ml of water, the organic phase was isolated, dried (MgSO$_4$) and concentrated in vacuo. The crude substance was chromatographed on 4 g of SiO$_2$ (elution with MeOH/DCM, gradient 0-5%). 21.4 mg of the desired compound were obtained. MW (calculated, monoisotopic)= 668.14; MW (measured value) (M$^+$H)=669.

EXAMPLE 35

N-[6-(4-Chlorobenzyl)-1-(2,4-dichlorobenzenesulfonyl)-8-isopropyl-4,7-dioxooctahydropyrazino[1,2-a]pyrimidin-3-yl]-N-cyclohexylcyclopentanecarboxamide

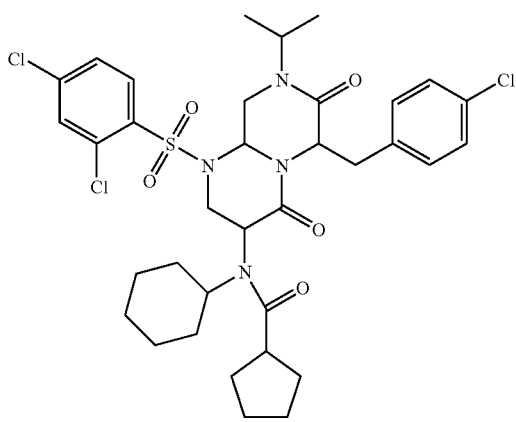

Example 35 was synthesized in analogy to Example 34 using cyclohexanone in the reductive amination. Cyclopentanecarbonyl chloride was used for the amide coupling. The desired product is obtained with MW=736.20 (calculated, monoisotopic), measured value: (M+H)$^+$=737.15

EXAMPLE 36

N-[6-(4-Chlorobenzyl)-1-(2,4-dichlorobenzenesulfonyl)-8-isopropyl-4,7-dioxooctahydropyrazino[1,2-a]pyrimidin-3-yl]-1-methylpiperidine-4-carboxamide

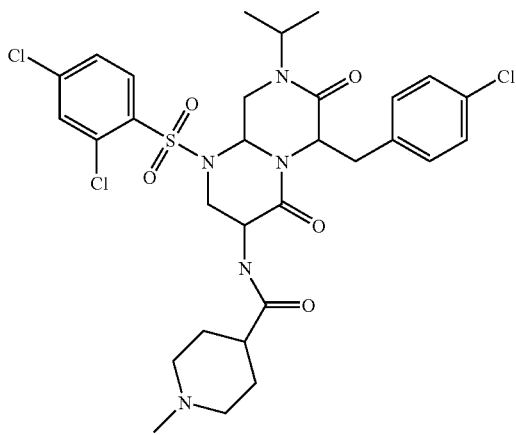

Synthesis took place in analogy to Example 29e using 1-methylpiperidin-4-carboxylic acid hydrochloride. The desired product is obtained with MW=683.15 (calculated, monoisotopic); measured value (M+H)$^+$: 684.38

EXAMPLE 37

N-[6-(4-Chlorobenzyl)-1-(2,4-dichlorobenzenesulfonyl)-8-isopropyl-4,7-dioxooctahydropyrazino[1,2-a]pyrimidin-3-yl]piperidine-4-carboxamide

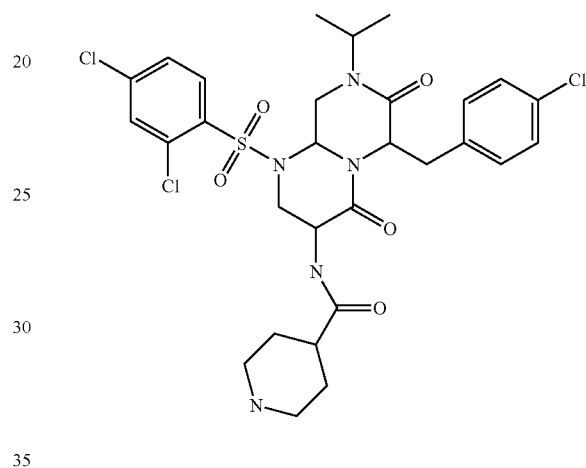

A mixture of 100 mg (0.179 mmol) of 3-amino-6-(4-chlorobenzyl)-1-(2,4-dichlorobenzenesulfonyl)-8-isopropylhexahydropyrazino[1,2-a]pyrimidine-4,7-dione, 2 ml of DCM, 23 mg (0.178 mmol) of DIEA and 51 mg (0.181 mmol) of benzyl 4-(chlorocarbonyl)tetrahydro-1(2H)-pyridinecarboxylate was stirred at room temperature for 1 hour. The mixture was subjected to a flash chromatography on 2 g of SiO$_2$ (elution with EtOAc/DCM, gradient 0-20%). 119 mg of the intermediate benzyl 4-[6-(4-chlorobenzyl)-1-(2,4-dichlorobenzenesulfonyl)-8-isopropyl-4,7-dioxooctahydropyrazino [1,2-a]pyrimidin-3-ylcarbamoyl]piperidine-1-carboxylate were obtained. The results obtained in LC/MS (expected monoisotopic MW=803, measured value (M$^+$H)= 804) agreed with the structure.

103 mg (0.517 mmol) of iodotrimethylsilane were added to a solution of 104 mg (0.129 mmol) of benzyl 4-[6-(4-chlorobenzyl)-1-(2,4-dichlorobenzenesulfonyl)-8-isopropyl-4,7-dioxooctahydropyrazino[1,2-a]pyrimidin-3-ylcarbamoyl]piperidine-1-carboxylate in 2.5 ml of acetonitrile at room temperature with stirring. After 2 hours, the mixture was concentrated. The residue was purified on a Varian Bond-Elut SCX ion exchange cartridge (elution with methanol, then with 3N—NH$_3$ in methanol). The purified amine was converted into the hydrochloride salt. 75 mg of the desired compound were obtained. LC/MS (expected monoisotopic MW=669.13; measured value (M$^+$H)=670)

EXAMPLE 38

N-[6-(4-Chlorobenzyl)-1-(2,4-dichlorobenzenesulfonyl)-8-isopropyl-4,7-dioxooctahydropyrazino[1,2-a]pyrimidin-3-yl]morpholine-4-carboxamide

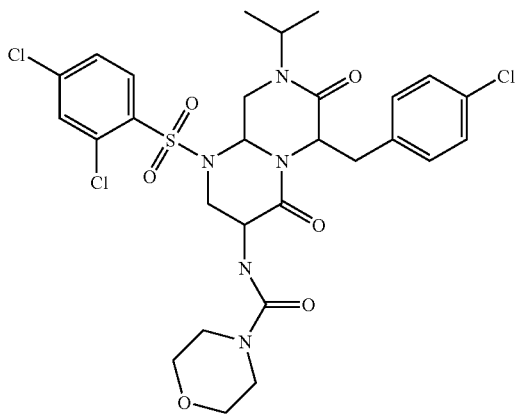

47 µl (0.268 mmol) of Hünig's base were added to a solution of 50 mg (0.089 mmol) of the amine 3-amino-6-(4-chlorobenzyl)-1-(2,4-dichlorobenzenesulfonyl)-8-isopropylhexahydropyrazino[1,2-a]pyrimidine-4,7-dione in 1.8 ml of DCM/THF (1:1). Then 80 mg (0.268 mmol) of triphosgene were slowly added to the reaction mixture. The mixture was stirred at room temperature overnight. The reaction mixture was then diluted with EtOAc, washed with $H_2O$, dried over $MgSO_4$ and concentrated in vacuo. This intermediate was dissolved in 1 ml of THF, and 31 µl (0.178 mmol) of Hünig's base and 12 mg (0.134 mmol) of morpholine were added. The reaction mixture was stirred at room temperature overnight, diluted with EtOAc, washed with $H_2O$, dried over $MgSO_4$ and concentrated. The residue was chromatographed on 4 g of $SiO_2$ (elution with MeOH/DCM, gradient 1-8%). 36 mg of the desired substance were obtained as a colorless solid. LC/MS (expected MW=671.11; measured value $(M^+H)$=672).

EXAMPLE 39

N-[6-(4-Chlorobenzyl)-1-(2,4-dichlorobenzenesulfonyl)-8-isopropyl-4,7-dioxooctahydropyrazino[1,2-a]pyrimidin-3-yl]piperidine-2-carboxamide

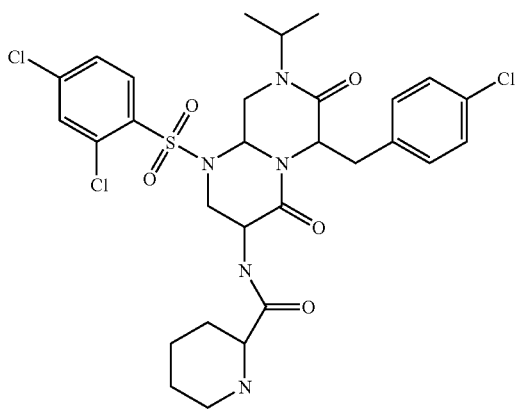

24.7 mg (0.089 mmol) of 4-(4,6-dimethoxy[1,3,5]triazin-2-yl)$_4$-methylmorpholine chloride×$H_2O$ (DMTMM) and then 31.3 mg (0.089 mmol) of Fmoc-Pip-OH were added to a solution of 0.05 g (0.089 mmol) of 3-amino-6-(4-chlorobenzyl)-1-(2,4-dichlorobenzenesulfonyl)-8-isopropylhexahydropyrazino[1,2-a]pyrimidine-4,7-dione in 2 ml of DMF. The reaction mixture was stirred at room temperature overnight. Then 8 ml of diethyl ether and 5 ml of water were added. The organic phase was isolated, again washed with 5 ml of water, dried ($MgSO_4$) and concentrated in vacuo. Purification takes place by flash chromatography on 4 g of $SiO_2$ (MeOH/DCM as eluent system, gradient 0-2%) and afforded 82 mg of the FMOC-protected intermediate in the form of a white solid. It was possible to show by LC/MS that the product was the desired intermediate. A solution of 70 mg (0.078 mmol) of the FMOC intermediate in 2 ml of 10% strength diethylamine in DCM was stirred at room temperature overnight. The reaction mixture was concentrated in vacuo and purified by preparative HPLC in a Gilson C18 apparatus ($CH_3CN$ (0.1% TFA)/$H_2O$ (0.1% TFA), gradient 5-100%). The desired fractions were concentrated in vacuo. 33.9 mg of the corresponding TFA salt of the desired compound were obtained. LC/MS MW (calculated, monoisotopic)=669.13; measured value $(M^+H)$=670.11.

EXAMPLE 40

N-[6-(4-Chlorobenzyl)-1-(2,4-dichlorobenzenesulfonyl)-8-isopropyl-4,7-dioxooctahydropyrazino[1,2-a]pyrimidin-3-yl]pyrrolidine-2-carboxamide

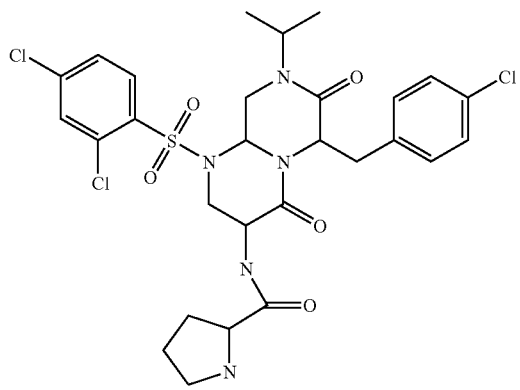

A mixture of 50 mg (0.089 mmol) of 3-amino-6-(4-chlorobenzyl)-1-(2,4-dichlorobenzenesulfonyl)-8-isopropylhexahydropyrazino[1,2-a]pyrimidine-4,7-dione, 1 ml of DCM, 23 mg (0.178 mmol) of DIEA and 32 mg (0.090 mmol) of Fmoc-Pro-Cl was stirred at room temperature for 1 hour. The mixture was purified by chromatography on 2 g of $SiO_2$ (elution with EtOAc/DCM, gradient 0-20%). 72 mg of the intermediate 9H-fluoren-9-ylmethyl 2-[6-(4-chlorobenzyl)-1-(2,4-dichlorobenzenesulfonyl)-8-isopropyl-4,7-dioxooctahydropyrazino[1,2-a]pyrimidin-3-ylcarbamoyl]pyrrolidine-1-carboxylate were obtained. LC/MS: (calculated, monoisotopic MW=877, measured value $(M^+H)$=878) A mixture of 60 mg (0.068 mmol) of 9H-fluoren-9-ylmethyl 2-[6-(4-chlorobenzyl)-1-(2,4-dichlorobenzenesulfonyl)-8-isopropyl-4,7-dioxooctahydropyrazino[1,2-a]pyrimidin-3-ylcarbamoyl]pyrrolidine-1-carboxylate and 2 ml of 15% strength diethylamine in DCM was stirred at room temperature overnight. The mixture was concentrated and subjected to a flash chromatography on 2 g of $SiO_2$ (elution with DCM, EtOAc and then with 10% methanol/EtOAc). The amine was converted into the hydrochloride salt. 30 mg of solid were obtained. This was further purified by preparative reverse phase (RP)HPLC. 17 mg of the desired compound were obtained. LC/MS (calculated, monoisotopic MW=655.12; measured value (M+H)=656)

EXAMPLE 41

N-[6-(4-Chlorobenzyl)-1-(2,4-dichlorobenzenesulfonyl)-8-isopropyl-4,7-dioxooctahydropyrazino[1,2-a]pyrimidin-3-yl]-1-methylpyrrolidine-2-carboxamide

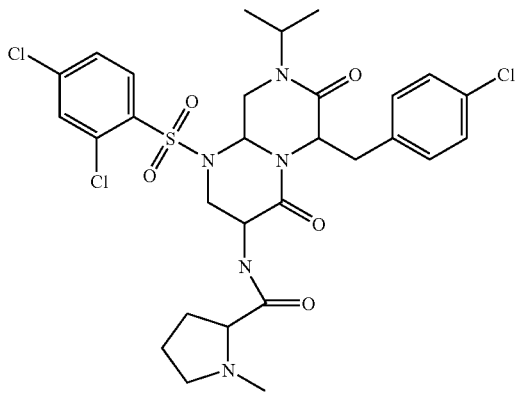

0.3 ml (5.2 mmol) of acetic acid, 0.25 ml (3.33 mmol) of formaldehyde (37% in water) and 1.5 ml (1.5 mmol) of sodium cyanoborohydride (1M in THF) were added to a solution of 93 mg (0.142 mmol) of the amine from Example 40 in 7.5 ml of methanol. The reaction mixture was stirred at room temperature for 2 hours and concentrated in vacuo. The residue was diluted with 10 ml of DCM, basified with 7N—$NH_3$ in methanol, filtered and concentrated. This residue was purified by preparative RP-HPLC. 50 mg of the desired compound were obtained. LC/MS (calculated, monoisotopic MW=669; measured value (M+H)=670)

EXAMPLE 42

N-[6-(4-Chlorobenzyl)-1-(2,4-dichlorobenzenesulfonyl)-8-isopropyl-4,7-dioxooctahydropyrazino[1,2-a]pyrimidin-3-yl]azetidine-3-carboxamide

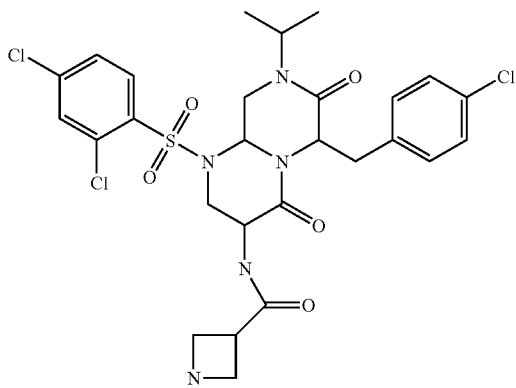

49.5 mg (0.179 mmol) of 4-(4,6-dimethoxy[1,3,5]triazin-2-yl)-4-methylmorpholine chloride×$H_2O$ (DMTMM) and then 58 mg (0.179 mmol) of 1-Fmoc-azetidine-3-carboxylic acid were added to a solution of 0.1 g (0.179 mmol) of the amine 3-amino-6-(4-chlorobenzyl)-1-(2,4-dichlorobenzenesulfonyl)-8-isopropylhexahydropyrazino[1,2-a]pyrimidine-4,7-dione in 5 ml of DMF. The reaction mixture was stirred at room temperature overnight. Then 50 ml of diethyl ether and 50 ml of water were added. The organic phase was isolated, washed twice with 50 ml of water each time, dried ($MgSO_4$) and concentrated in vacuo. Purification by flash chromatography on 20 g of $SiO_2$ (MeOH/DCM as eluent system, gradient 0-10%) afforded 117 mg of the FMOC-protected intermediate in the form of a white solid. This was used in the next step. A solution of 50 mg (0,058 mmol) of the FMOC intermediate in 1.5 ml of 10% strength diethylamine in DCM was stirred at room temperature overnight. The reaction mixture was concentrated in vacuo and purified by preparative HPLC in a Gilson C18 apparatus ($CH_3CN$ (0.1% TFA)/$H_2O$ (0.1% TFA)). The fractions were concentrated in vacuo. 21.6 mg of the TFA salt of the desired product were obtained. MW (calculated, monoisotopic)=641.11; measured value (M+H)= 641.99.

EXAMPLE 43

N-[6-(4-Chlorobenzyl)-1-(2,4-dichlorobenzenesulfonyl)-8-isopropyl-4,7-dioxooctahydropyrazino[1,2-a]pyrimidin-3-yl]-N',N'-dimethylsuccinamide

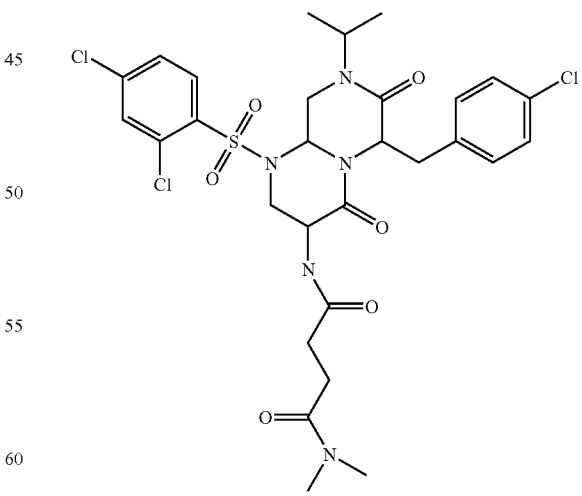

Synthesis took place in analogy to Example 29e using N,N-dimethylsuccinamic acid. The desired product is obtained with MW=685.13 (calculated, monoisotopic); measured value (M+H)+: 686.30

EXAMPLE 44

N-[6-(4-Chlorobenzyl)-1-(2,4-dichlorobenzenesulfonyl)-8-isopropyl-4,7-dioxooctahydropyrazino[1,2-a]pyrimidin-3-yl]-N-isopropylcyclohexanecarboxamide Structure:

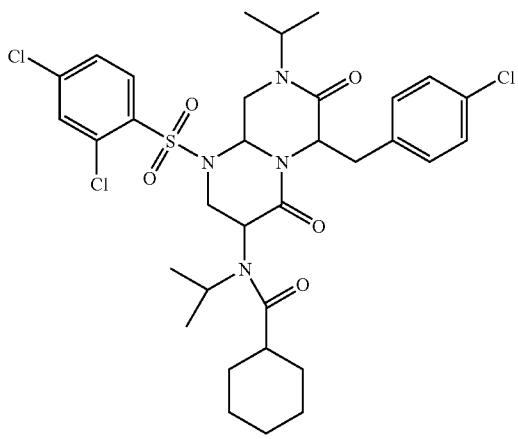

Example 44 was synthesized in analogy to Example 34 using cyclohexanecarbonyl chloride in the amide coupling step. The desired product is obtained with MW=710.19 (calculated, monoisotopic); measured value (M+H)$^+$: 711.18

EXAMPLE 45

N-[6-(4-Chlorobenzyl)-1-(2,4-dichlorobenzenesulfonyl)-8-isopropyl-4,7-dioxooctahydropyrazino[1,2-a]pyrimidin-3-yl]-N-isopropylcyclopentanecarboxamide Structure:

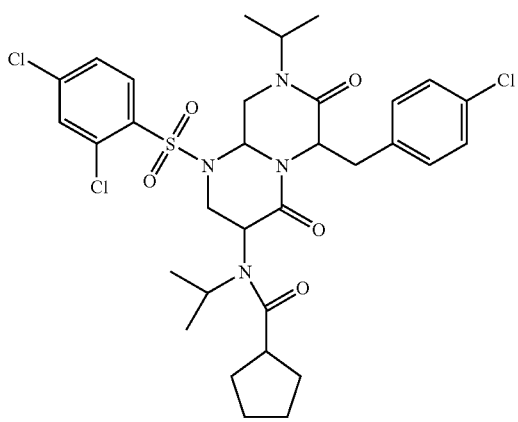

Example 45 was synthesized in analogy to Example 34 using cyclopentanecarbonyl chloride in the amide coupling step. The desired product is obtained with MW=696.17 (calculated, monoisotopic); measured value (M+H)$^+$: 697.17

EXAMPLE 46

N-[6-(4-Chlorobenzyl)-1-(2,4-dichlorobenzenesulfonyl)-8-isopropyl-4,7-dioxooctahydropyrazino[1,2-a]pyrimidin-3-yl]-N-isopropylpiperidine-4-carboxamide Structure:

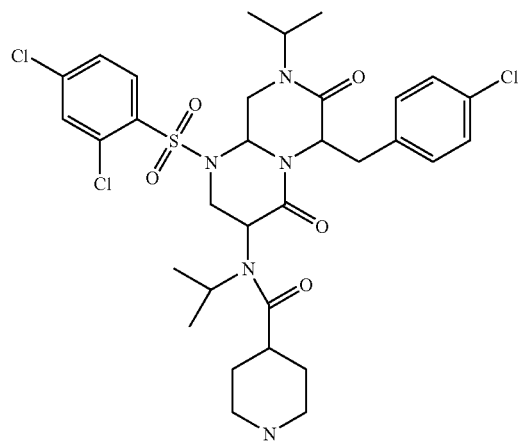

Synthesis in Example 46 took place by the process described for 34. Benzyl 4-chlorocarbonylpiperidine-1-carboxylate was used in the coupling step and afforded the Cbz-protected compound. The Cbz protective group was eliminated by adding 0.0283 ml (0.199 mmol) of TMSI and 2 ml of CH$_3$CN at 0° C. The reaction mixture was stirred for 3 days, concentrated in vacuo and eluted through a column packed with 1 g of SCX and moistened with MeOH. The impurities were eluted with MeOH. The desired amine was obtained by elution with 2N-NH$_3$ in MeOH. This was followed by concentration in vacuo and addition of 0.1 ml of 1.0 M HCl in diethyl ether. The salt produced in this way was ground, washed 4 times with 2 ml of diethyl ether each time and dried. 0.025 g of the desired compound was obtained.

LC/MS: MW (calculated, monoisotopic)=711.18; measured value (M$^+$H)=712.11.

EXAMPLE 47

N-[6-(4-Chlorobenzyl)-1-(2,4-dichlorobenzenesulfo-
nyl)-8-isopropyl-4,7-dioxooctahydropyrazino[1,2-a]
pyrimidin-3-yl]-4-dimethylaminobenzamide Structure:

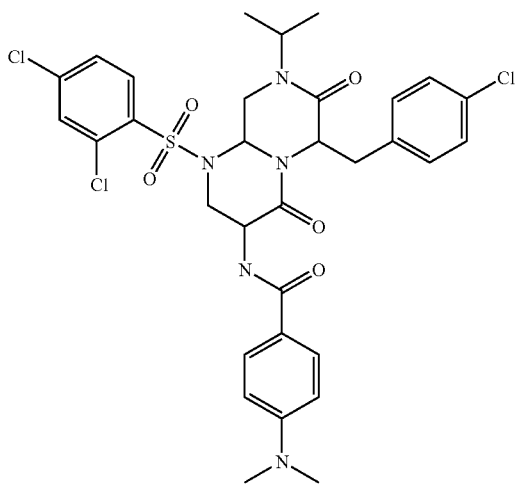

Synthesis took place in analogy to Example 29e using 4-dimethylaminobenzoic acid. The desired product is obtained with MW=705.13 (calculated, monoisotopic); measured value (M+H)$^+$: 706.21

EXAMPLE 48

N-[6-(4-Chlorobenzyl)-1-(2,4-dichlorobenzenesulfo-
nyl)-8-isopropyl-4,7-dioxooctahydropyrazino[1,2-a]
pyrimidin-3-yl]-2-pyridin-3-ylacetamide

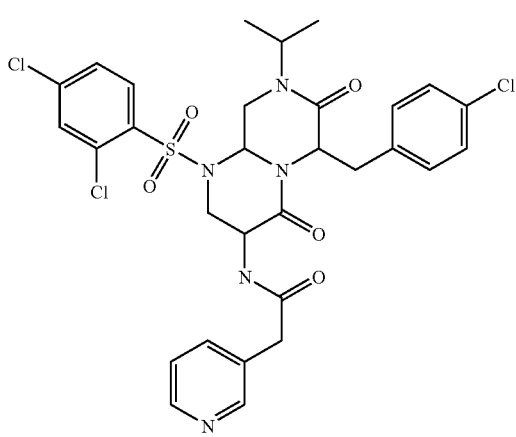

Synthesis took place in analogy to Example 29e using 3-pyridylacetic acid. The desired product is obtained with MW=677.10 (calculated, monoisotopic); measured value (M+H)$^+$: 678.07

EXAMPLE 49

N-[6-(4-Chlorobenzyl)-1-(2,4-dichlorobenzenesulfo-
nyl)-8-isopropyl-4,7-dioxooctahydropyrazino[1,2-a]
pyrimidin-3-yl]pyridine-2-carboxamide

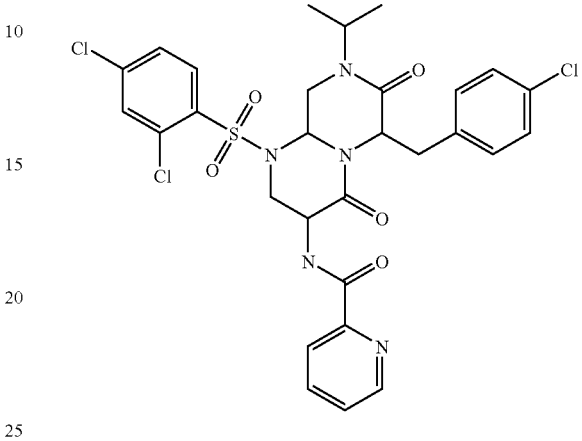

Synthesis took place in analogy to Example 29e using picolinic acid. The desired product is obtained with MW=663.09 (calculated, monoisotopic); measured value (M+H)$^+$: 664.22

EXAMPLE 50

N-[6-(4-Chlorobenzyl)-1-(2,4-dichlorobenzenesulfo-
nyl)-8-isopropyl-4,7-dioxooctahydropyrazino[1,2-a]
pyrimidin-3-yl]nicotinamide Structure:

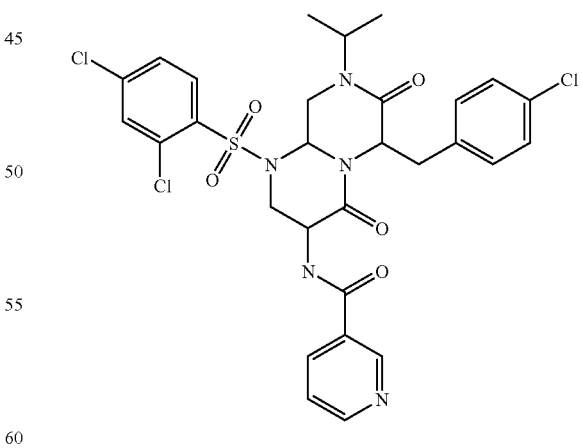

Synthesis took place in analogy to Example 22 using nicotinoyl chloride *HCl and 3-amino-6-(4-chlorobenzyl)-1-(2,4-dichlorobenzenesulfonyl)-8-isopropyl-hexahydropyrazino[1,2-a]pyrimidine-4,7-dione. The desired product is obtained with MW=663.09 (calculated, monoisotopic); measured value (M+H)$^+$: 664.11

EXAMPLE 51

N-[6-(4-Chlorobenzyl)-1-(2,4-dichlorobenzenesulfonyl)-8-isopropyl-4,7-dioxooctahydropyrazino[1,2-a]pyrimidin-3-yl]-6-trifluoromethylnicotinamide Structure:

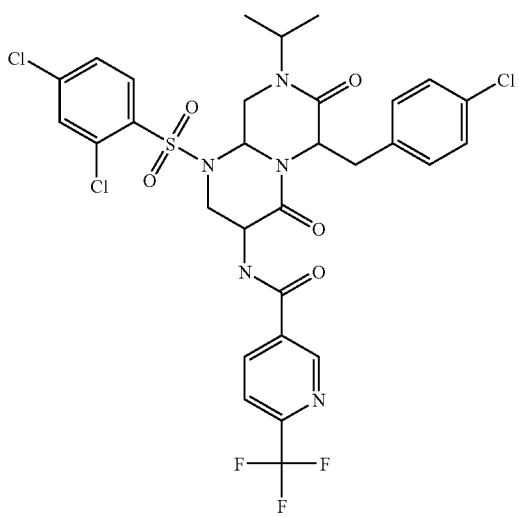

Synthesis took place in analogy to Example 22 using 6-(trifluoromethyl)nicotinoyl chloride and 3-amino-6-(4-chlorobenzyl)-1-(2,4-dichlorobenzenesulfonyl)-8-isopropyl-hexahydropyrazino[1,2-a]pyrimidine-4,7-dione. The desired product is obtained with MW=731.08 (calculated, monoisotopic); measured value (M+H)$^+$: 732.01

EXAMPLE 52

N-[6-(4-Chlorobenzyl)-1-(2,4-dichlorobenzenesulfonyl)-8-isopropyl-4,7-dioxooctahydropyrazino[1,2-a]pyrimidin-3-yl]4-trifluoromethylnicotinamide Structure:

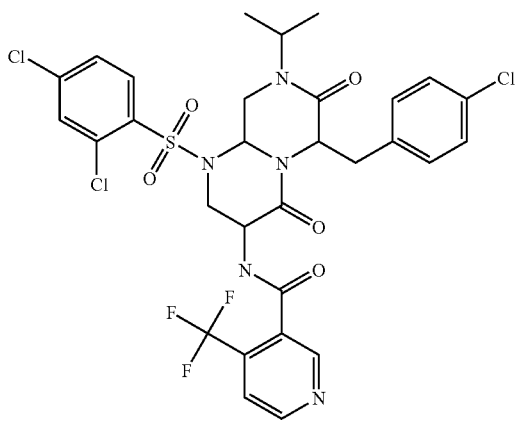

Synthesis took place in analogy to Example 29e using 4-(trifluoromethyl)nicotinic acid and 3-amino-6-(4-chlorobenzyl)-1-(2,4-dichlorobenzenesulfonyl)-8-isopropyl-hexahydropyrazino[1,2-a]pyrimidine-4,7-dione. The desired product is obtained with MW=731.08 (calculated, monoisotopic); measured value (M+H)$^+$: 732.07

EXAMPLE 53

N-[6-(4-Chlorobenzyl)-1-(2,4-dichlorobenzenesulfonyl)-8-isopropyl-4,7-dioxooctahydropyrazino[1,2-a]pyrimidin-3-yl]-5-methylpyrazine-2-carboxamide Structure:

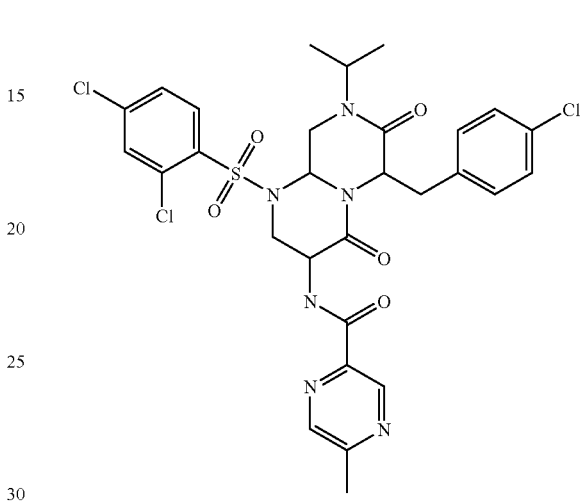

Synthesis took place in analogy to Example 29e using 5-methylpyrazine-2-carboxylic acid and 3-amino-6-(4-chlorobenzyl)-1-(2,4-dichlorobenzenesulfonyl)-8-isopropyl-hexahydropyrazino[1,2-a]pyrimidine-4,7-dione. The desired product is obtained with MW=678.10 (calculated, monoisotopic); measured value (M+H)$^+$: 679.06

EXAMPLE 54

N-[6-(4-Chlorobenzyl)-1-(2,4-dichlorobenzenesulfonyl)-8-isopropyl-4,7-dioxooctahydropyrazino[1,2-a]pyrimidin-3-yl]pyrazine-2-carboxamide Structure:

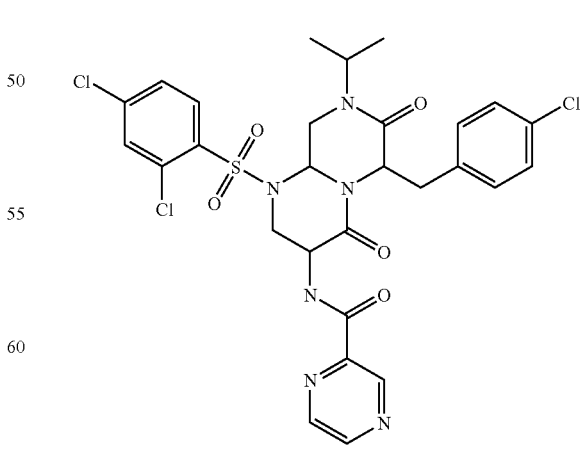

Synthesis took place in analogy to Example 22 using pyrazine-2-carbonyl chloride and 3-amino-6-(4-chlorobenzyl)-1-

(2,4-dichlorobenzenesulfonyl)-8-isopropylhexahydropyrazino[1,2-a]pyrimidine-4,7-dione. The desired product is obtained with MW=664.08 (calculated, monoisotopic); measured value (M+H)+: 665.05

EXAMPLE 55

N-[6-(4-Chlorobenzyl)-1-(2,4-dichlorobenzenesulfonyl)-8-isopropyl-4,7-dioxooctahydropyrazino[1,2-a]pyrimidin-3-yl]quinoline-3-carboxamide Structure:

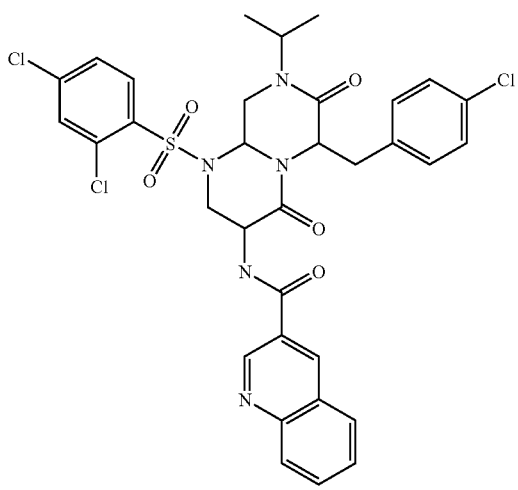

Synthesis took place in analogy to Example 29e using 3-quinolinecarboxylic acid and 3-amino-6-(4-chlorobenzyl)-1-(2,4-dichlorobenzenesulfonyl)-8-isopropyl-hexahydropyrazino[1,2-a]pyrimidine-4,7-dione. The desired product is obtained with MW=713.10 (calculated, monoisotopic); measured value (M+H)+:714

EXAMPLE 56

1-tert-Butyl-3-[6-(4-chlorobenzyl)-1-(2,4-dichlorobenzenesulfonyl)-8-isopropyl-4,7-dioxooctahydropyrazino[1,2-a]pyrimidin-3-yl]urea Structure:

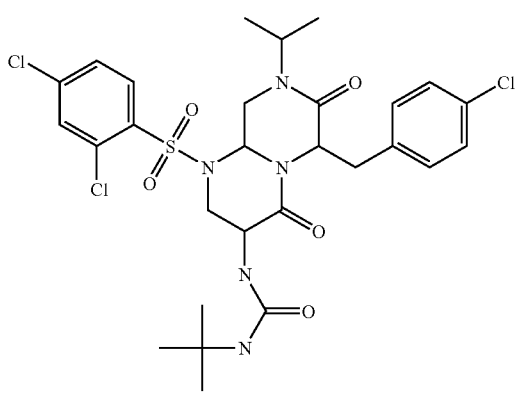

Synthesis takes place in analogy to Example 28 starting from 3-amino-6-(4-chlorobenzyl)-1-(2,4-dichlorobenzenesulfonyl)-8-isopropylhexahydropyrazino[1,2-a]pyrimidine-4,7-dione. The desired product is obtained with MW=657.13 (calculated, monoisotopic); measured value (M+H)+: 658.26

EXAMPLE 57

1-Ethyl-3-[6-(4-chlorobenzyl)-1-(2,4-dichlorobenzenesulfonyl)-8-isopropyl-4,7-dioxooctahydropyrazino[1,2-a]pyrimidin-3-yl]urea

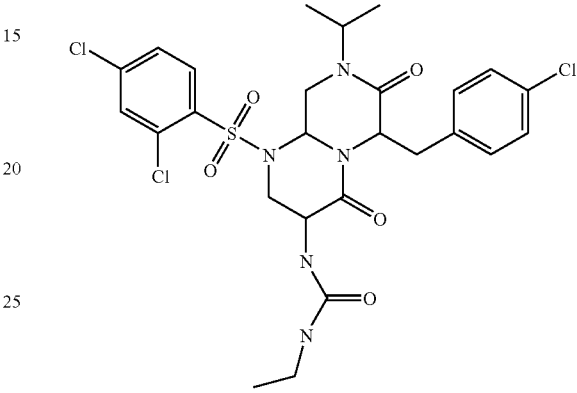

Synthesis took place in analogy to Example 56 using ethyl isocyanate. The desired product is obtained with MW=629.10 (calculated, monoisotopic); measured value (M+H)+: 630.13

EXAMPLE 58

N-[6-(4-Chlorobenzyl)-1-(2,4-dichlorobenzenesulfonyl)-8-isopropyl-4,7-dioxooctahydropyrazino[1,2-a]pyrimidin-3-yl]cyclopropanesulfonamide Structure:

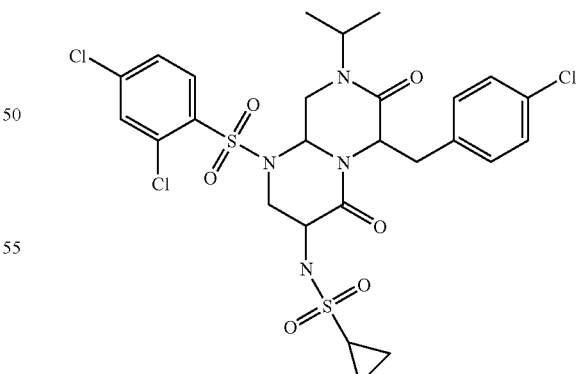

Synthesis takes place in analogy to Example 27 starting from 3-amino-6-(4-chlorobenzyl)-1-(2,4-dichlorobenzenesulfonyl)-8-isopropylhexahydropyrazino[1,2-a]pyrimidine-4,7-dione. The desired product is obtained with MW=662.06 (calculated, monoisotopic); measured value (M+H)+: 663.05.

EXAMPLE 59

6-(4-Chlorobenzyl)-1-(2,4-dichlorobenzenesulfonyl)-8-isopropyl-3-piperidin-1-ylhexahydropyrazino[1,2-a]pyrimidine-4,7-dione

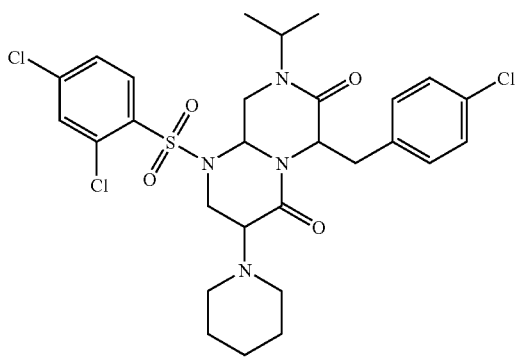

A mixture of 50 mg (0.089 mmol) of 3-amino-6-(4-chlorobenzyl)-1-(2,4-dichlorobenzenesulfonyl)-8-isopropyl-hexahydropyrazino[1,2-a]pyrimidine-4,7-dione, 2,0 ml of acetonitrile, 0.2 ml (0.2 mmol) of 1M ($H_2O$)—$NaHCO_3$ and 83 mg (0.361 mmol) of 1,5-dibromopropane was heated with stirring in a microwave oven at 175° C. for 800 seconds. After cooling, the mixture was concentrated. The residue was subjected to a flash chromatography on 2 g of $SiO_2$ (elution with EtOAc/DCM, gradient 0-20%). The purified amine was converted into the hydrochloride salt. 38 mg of the desired compound were obtained. LC/MS: (MW calculated, monoisotopic=626.13; measured value ($M^+H$)=627.15)

EXAMPLE 60

6-(4-Chlorobenzyl)-1-(2,4-dichlorobenzenesulfonyl)-8-isopropyl-3-morpholin-4-yl-hexahydropyrazino[1,2-a]pyrimidine-4,7-dione Structure:

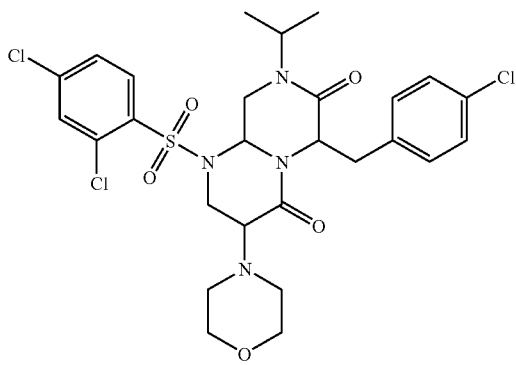

149 mg (0.64 mmol, 4.0 equiv.) of 2-bromoethyl ether and then 0.2 ml of 1N $NaHCO_3$ solution were added to a solution of 90 mg (0.16 mmol) of the amine 3-amino-6-(4-chlorobenzyl)-1-(2,4-dichlorobenzenesulfonyl)-8-isopropylhexahydropyrazino[1,2-a]pyrimidine-4,7-dione in 2 ml of $CH_3CN$. The reaction mixture was heated at 200° C. in a microwave oven (Smith Creator) for 120 seconds. Cooling was followed by dilution with DCM and washing with 1N $NaHCO_3$. The organic phase was dried over $MgSO_4$ and concentrated. The residue was chromatographed on 12 g of $SiO_2$ (elution with MeOH/DCM, gradient 0-10%). 48 mg of the desired substance were obtained as a white solid. LC/MS (calculated, monoisotopic MW=628.18; measured value ($M^+H$)=629.1) agree with the structure.

EXAMPLE 61

6-(4-Chlorobenzyl)-1-(2,4-dichlorobenzenesulfonyl)-8-isopropyl-3-(4-methylpiperazin-1-yl)hexahydropyrazino[1,2-a]pyrimidine-4,7-dione Structure:

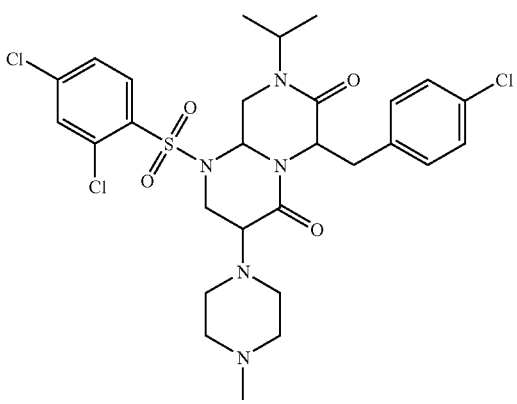

50 mg of 3-amino-6-(4-chlorobenzyl)-1-(2,4-dichlorobenzenesulfonyl)-8-isopropylhexahydropyrazino[1,2-a]pyrimidine-4,7-dione, 14.4 mg of mechlorethamine hydrochloride, 13 mg of $NaHCO_3$ are dissolved in just enough ethylene glycol to result a solution. 1.6 mg of NaI are added to this solution, and the solution is heated at 110° C. for 6 h. After cooling, the solution is mixed with water and extracted three times with 40 ml of ethyl acetate each time. The combined organic phases are dried over $Na_2SO_4$, and the solvent is removed in vacuo. The residue is separated by HPLC (Waters-Xterra™ MS C18, 5 µm, water (0.1% trifluoroacetic acid)/acetonitrile (0.1% trifluoroacetic acid)=80/20→10/90).

The desired product is obtained with MW=641.14 (calculated, monoisotopic); measured value $(M+H)^+$: 642.25

EXAMPLE 62

3-(1-Benzylpiperidin-4-ylamino)-6-(4-chlorobenzyl)-1-(2,4-dichlorobenzenesulfonyl)-8-isopropyl-hexahydropyrazino[1,2-a]pyrimidine-4,7-dione Structure:

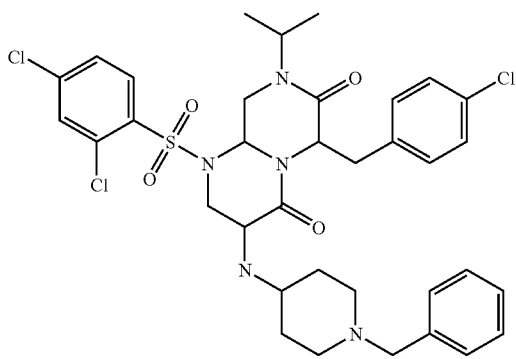

115 mg (0.61 mmol) of 1-benzyl-4-piperidone and then 130 mg (4.1 mmol/g) of (polystyrylmethyl)trimethylammonium cyanoborohydride were added to a solution of 100 mg (0.18 mmol) of 3-amino-6-(4-chlorobenzyl)-1-(2,4-dichlorobenzenesulfonyl)-8-isopropylhexahydropyrazino[1,2-a]pyrimidine-4,7-dione in 1.2 ml of 5% HOAc/CH₃CN and 3 drops of MeOH. The reaction mixture was shaken at room temperature for 18 hours, filtered and concentrated. 160 mg of beige oil were obtained. The crude product was isolated by flash chromatography in a column packed with 4 g of silica gel (elution with 5% MeOH/EtOAc). Concentration of the appropriate fractions resulted in 110 mg (85%) of the above compound in the form of a clear oil. LC/MS (expected, monoisotopic MW=731.19; measured value (M⁺H)=732.20)

EXAMPLE 63

6-(4-Chlorobenzyl)-1-(2,4-dichlorobenzenesulfonyl)-8-isopropyl-3-(2-oxopyrrolidin-1-yl)-hexahydropyrazino[1,2-a]pyrimidine-4,7-dione Structure:

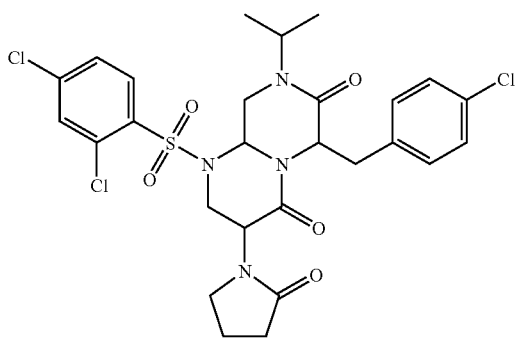

A solution of 50 mg (0.089 mmol) of 3-amino-6-(4-chlorobenzyl)-1-(2,4-dichlorobenzenesulfonyl)-8-isopropyl-hexahydropyrazino[1,2-a]pyrimidine-4,7-dione, 0.012 ml (0.107 mmol) of 4-chlorobutyryl chloride and 0.031 ml of DIEA in 2 ml of DCM was stirred at room temperature overnight. After addition of 2 ml of water, the organic phase was isolated, washed with 2 ml of brine, dried (MgSO₄) and concentrated in vacuo. The crude substance was chromatographed on 4 g of SiO₂ (elution with MeOH/DCM, gradient 0-6%). The concentrated fractions afforded 45.8 mg of chlorobutyramide intermediate in the form of a white solid and were used in the following step. 60 mg (0.36 mmol) of potassium iodide and 277 mg (2 mmol) of K₂CO₃ were added to 45 mg (0.068 mmol) of the chloro amide intermediate dissolved in 2 ml of acetone. The mixture was heated at 130° C. in a microwave oven for 600 seconds, and then concentrated in vacuo and purified by flash chromatography on 4 g of SiO₂ (elution with MeOH/DCM, gradient 0-5%). 16.2 mg of white solid were obtained. LC/MS agreed with the desired structure. MW (calculated, monoisotopic)=626.09; measured value (M⁺H)=627.1.

EXAMPLE 64

6-(4-Chlorobenzyl)-1-(2,4-dichlorobenzenesulfonyl)-8-isopropyl-3-(2-oxopiperidin-1-yl)-hexahydropyrazino[1,2-a]pyrimidine-4,7-dione Structure:

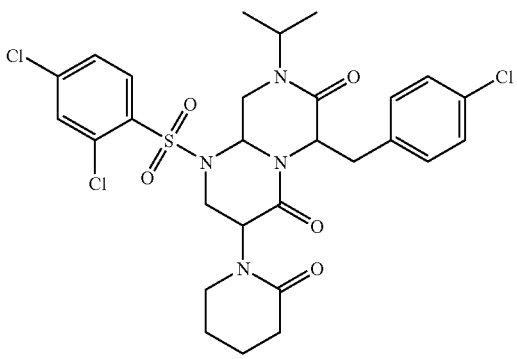

Example 64 was synthesized in analogy to Example 63 using 5-chloropentanoyl chloride in the amide coupling step. The desired product is obtained with MW=640.11 (calculated, monoisotopic); measured value (M+H)⁺: 641.1

EXAMPLE 65

6-(4-Chlorobenzyl)-1-(2,4-dichlorobenzenesulfonyl)-8-isopropyl-3-(2-oxoazepan-1-yl)-hexahydropyrazino[1,2-a]pyrimidine-4,7-dione Structure:

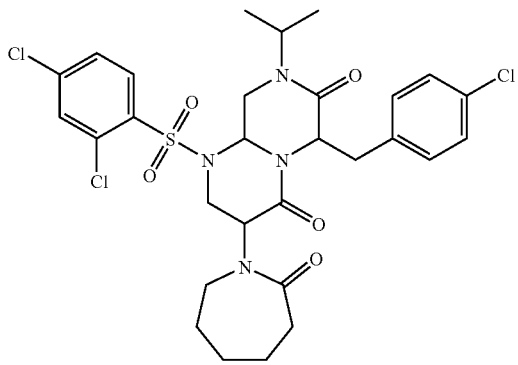

Example 65 was synthesized in analogy to Example 63 using 6-chlorohexanoyl chloride in the amide coupling step. The desired product is obtained with MW=654.12 (calculated, monoisotopic); measured value (M+H)$^+$: 655.11.

EXAMPLE 66

N-[6-(4-Chlorobenzyl)-1-(5-fluoro-2-methoxybenzenesulfonyl)-8-isopropyl-4,7-dioxooctahydropyrazino[1,2-a]pyrimidin-3-yl)acetamide

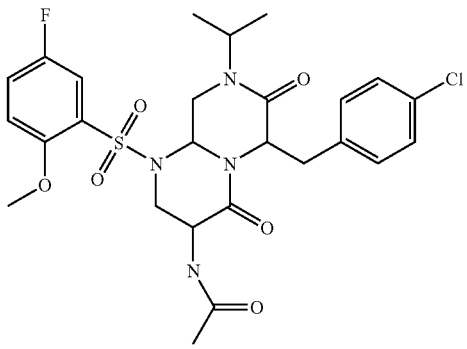

a) Benzyl[6-(4-chlorobenzyl)-1-(5-fluoro-2-methoxybenzenesulfonyl)-8-isopropyl-4,7-dioxooctahydropyrazino[1,2-a]pyrimidin-3-yl]carbamate Solid-Phase Route:

7 g (3.64 mmol) of Tentagel HL 12 019 (Rapp Polymer GmbH loaded with bromoacetal linker) is heated in 26 ml of DMSO and 6 ml (70.44 mmol) of isopropylamine at 60° C. in a solid-phase reactor overnight. The resin is washed four times each with DMSO, MeOH, DCM and diethyl ether (30 ml each time) and then dried in vacuo. DEA (5.7 ml, 32.76 mmol) and HATU (4.15 g, 10.92 mmol) in 30 ml of DMF are added for the coupling with Fmoc(4-ClPhe)OH (4.6 g, 10.92 mmol). The reaction mixture is heated at 55° C. for 3 h. The resin is washed in analogy to the first step. The Fmoc group is eliminated by treating the resin twice with 30 ml of 20% piperidine in DMF each time, for 20 minutes each time, and it is then washed as described above. The resin is next reacted with Fmoc-ZDap(OH) (5.02 g, 10.92 mmol), DIC (1.71 ml, 10.92 mmol) and HOBt (1.47 g, 10.92 mmol) in 30 ml of DMF at room temperature overnight. Washing was carried out in analogy to the procedure described above. 0.613 g (2.73 mmol) of 5-fluoro-2-methoxybenzenesulfonyl chloride (Butt Park 49/07-57), 0.95 ml (5.46 mmol) of DEA and 30 ml of DCM were added to half of the resin (1.82 mmol). The reaction solution was shaken at room temperature overnight. The resin was then washed as described above. The resin is subsequently mixed with 30 ml of 99% HCOOH and shaken at room temperature overnight. The resin is decanted off and washed twice with 20 ml of HCOOH each time. The combined filtrates are heated at 60° C. for 3 h. The reaction solution is concentrated in vacuo, and the crude product is purified by chromatography (100 g SiO$_2$, eluent EtOAc/DCM (gradient 0-50%)). 0.778 g of the desired product is obtained as a white solid of MW=672.18 (calculated, monoisotopic); measured value (M+H)$^+$: 673.1 b) 3-Amino-6-(4-chlorobenzyl)-1-(5-fluoro-2-methoxybenzenesulfonyl)-8-isopropylhexahydropyrazino[1,2-a]pyrimidine-4,7-dione Synthesis takes place in analogy to Example 22g (Method B) starting from benzyl[6-(4-chlorobenzyl)-1-(5-fluoro-2-methoxybenzenesulfonyl)-8-isopropyl-4,7-dioxooctahydropyrazino[1,2-a]pyrimidin-3-yl]carbamate.

The desired product is obtained with MW=538.14 (calculated, monoisotopic); measured value (M+H)$^+$: 539.14 c) N-[6-(4-Chlorobenzyl)-1-(5-fluoro-2-methoxybenzenesulfonyl)-8-isopropyl-4,7-dioxooctahydropyrazino[1,2-a]pyrimidin-3-yl]acetamide Synthesis takes place in analogy to Example 21h starting from 3-amino-6-(4-chlorobenzyl)-1-(5-fluoro-2-methoxybenzenesulfonyl)-8-isopropylhexahydropyrazino[1,2-a]pyrimidine-4,7-dione. The desired product is obtained with MW=580.16 (calculated, monoisotopic); measured value (M+H)$^+$: 581.13

EXAMPLE 67

N-[6-(4-Chlorobenzyl)-1-(5-fluoro-2-methoxybenzenesulfonyl)-8-isopropyl-4,7-dioxooctahydropyrazino[1,2-a]pyrimidin-3-yl]cyclopropanecarboxamide Structure:

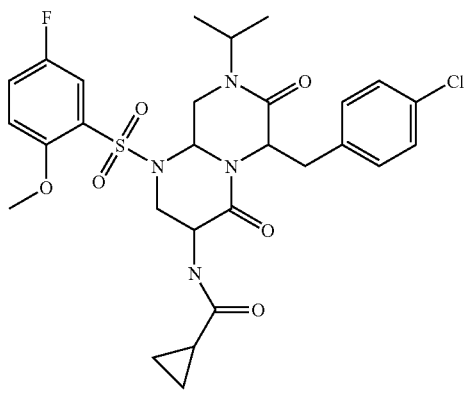

Synthesis takes place in analogy to Example 22 starting from 3-amino-6-(4-chlorobenzyl)-1-(5-fluoro-2-methoxybenzenesulfonyl)-8-isopropylhexahydropyrazino[1,2-a]pyrimidine-4,7-dione. The desired product is obtained with MW=606.17 (calculated, monoisotopic); measured value (M+H)+: 607.14

EXAMPLE 68

N-[6-(4-Chlorobenzyl)-1-(5-fluoro-2-methoxybenzenesulfonyl)-8-isopropyl-4,7-dioxooctahydropyrazino[1,2-a]pyrimidin-3-yl]cyclobutanecarboxamide Structure:

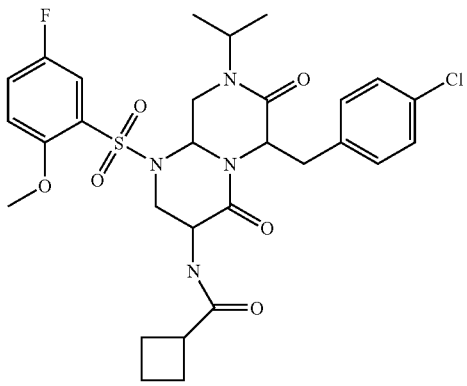

Synthesis takes place in analogy to Example 30 starting from 3-amino-6-(4-chlorobenzyl)-1-(5-fluoro-2-methoxybenzenesulfonyl)-8-isopropylhexahydropyrazino[1,2-a]pyrimidine-4,7-dione. The desired product is obtained with MW=620.19 (calculated, monoisotopic); measured value (M+H)+: 621.16

EXAMPLE 69

N-[6-(4-Chlorobenzyl)-1-(5-fluoro-2-methoxybenzenesulfonyl)-8-isopropyl-4,7-dioxooctahydropyrazino[1,2-a]pyrimidin-3-yl]cyclopentanecarboxamide Structure:

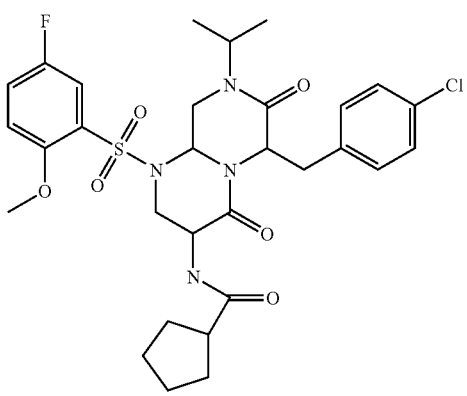

Synthesis takes place in analogy to Example 31 starting from 3-amino-6-(4-chlorobenzyl)-1-(5-fluoro-2-methoxybenzenesulfonyl)-8-isopropylhexahydropyrazino[1,2-a]pyrimidine-4,7-dione. The desired product is obtained with MW=634.20 (calculated, monoisotopic); measured value (M+H)+: 635.17

EXAMPLE 70

1-tert-Butyl-3-[6-(4-chlorobenzyl)-1-(5-fluoro-2-methoxybenzenesulfonyl)-8-isopropyl-4,7-dioxooctahydropyrazino[1,2-a]pyrimidin-3-yl]urea Structure:

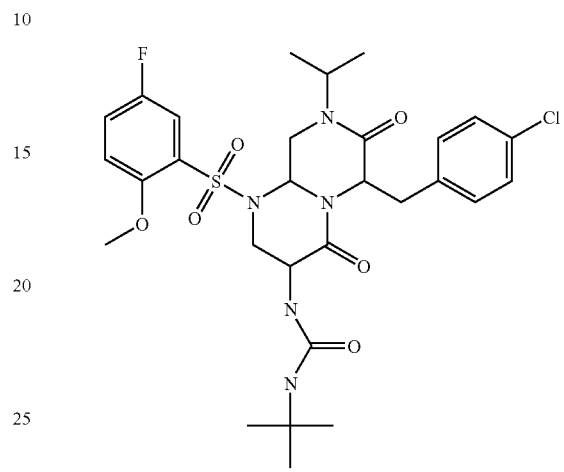

Synthesis takes place in analogy to Example 28 starting from 3-amino-6-(4-chlorobenzyl)-1-(5-fluoro-2-methoxybenzenesulfonyl)-8-isopropylhexahydropyrazino[1,2-a]pyrimidine-4,7-dione. The desired product is obtained with MW=637.31 (calculated, monoisotopic); measured value (M+Na)+: 660.17

EXAMPLE 71

N-[6-(4-Chlorobenzyl)-1-(5-fluoro-2-methoxybenzenesulfonyl)-8-isopropyl-4,7-dioxooctahydropyrazino[1,2-a]pyrimidin-3-yl]methanesulfonamide Structure:

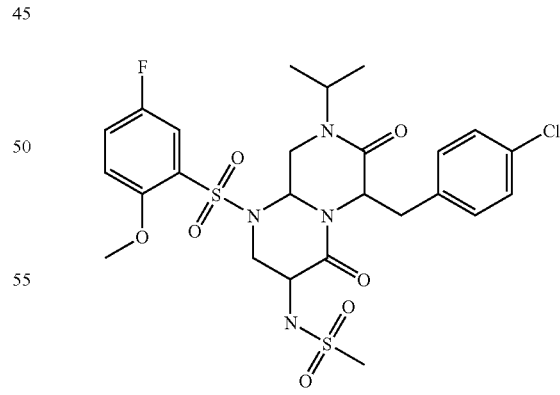

Synthesis takes place in analogy to Example 26 starting from 3-amino-6-(4-chlorobenzyl)-1-(5-fluoro-2-methoxybenzenesulfonyl)-8-isopropylhexahydropyrazino[1,2-a]pyrimidine-4,7-dione. The desired product is obtained with MW=616.12 (calculated, monoisotopic); measured value (M+H)+: 617.14.

EXAMPLE 72

6-(4-Chlorobenzyl)-3-dimethylamino-1-(5-fluoro-2-methoxybenzenesulfonyl)-8-isopropylhexahydropyrazino[1,2-a]pyrimidine-4,7-dione Structure:

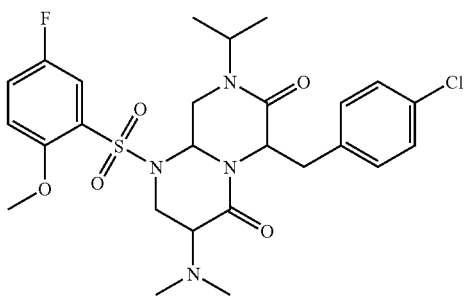

35 mg (0.065 mmol) of 3-amino-6-(4-chlorobenzyl)-1-(5-fluoro-2-methoxybenzenesulfonyl)-8-isopropylhexahydropyrazino[1,2-a]pyrimidine-4,7-dione were dissolved in 3.5 ml of MeOH. Addition of 0.1 ml of $CH_3COOH$, 0.1 ml of formaldehyde (37% in water) and 0.7 ml of $NaCNBH_3$ (1.0M in THF) was followed by stirring at room temperature overnight. The mixture was then concentrated in vacuo, mixed with 1 ml of water and extracted twice with 1 ml of EtOAc each time. The organic phase was isolated, dried ($MgSO_4$) and concentrated. Further purification by flash chromatography on 4 g of $SiO_2$ (elution with MeOH/DCM, gradient 0-5% MeOH) resulted in the amine. The amine was triturated after addition of 0.2 ml of 1.0M HCl in diethyl ether. The solid was washed 4 times with 1 ml of diethyl ether each time and dried in vacuo. 16.1 mg of HCl salt of the desired compound were obtained. LC/MS: MW (calculated, monoisotopic)=567.08; measured value ($M^+H$)=567.14.

EXAMPLE 73

3-Azetidin-1-yl-6-(4-chlorobenzyl)-1-(5-fluoro-2-methoxybenzenesulfonyl)-8-isopropylhexahydropyrazino[1,2-a]pyrimidine-4,7-dione Structure:

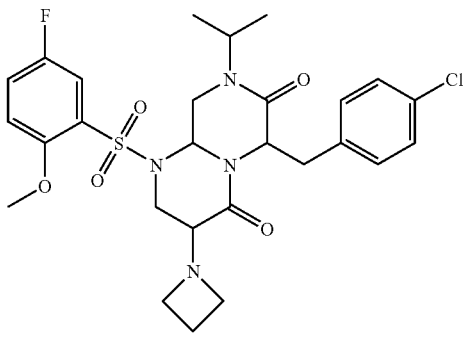

50 mg (0.093 mmol) of 3-amino-6-(4-chlorobenzyl)-1-(5-fluoro-2-methoxybenzenesulfonyl)-8-isopropylhexahydropyrazino[1,2-a]pyrimidine-4,7-dione were introduced into a 2-5 ml microwave vessel and dissolved in 2 ml of $CH_3CN$. 0.25 ml of $NaHCO_3$ (1.0M, in water) and 0.0375 ml of dibromopropane were added to this solution. The reaction mixture was heated at 180° C. in a Personal Chemistry Smith Synthesizer microwave oven (higher absorption mode with 30 seconds' preliminary stirring time) for 1000 seconds. The mixture was then concentrated in vacuo, mixed with 2 ml of EtOAc and washed with 2 ml of water. The organic phase was isolated, dried ($MgSO_4$) and concentrated in vacuo. Purification took place by preparative RP HPLC in GILSON apparatus ($CH_3CN$ (0.1% TFA)/$H_2O$ (0.1% TFA), gradient 5-100%). 6.9 mg of TFA salt of the desired compound were obtained. LC/MS: MW (calculated, monoisotopic)=578.18; measured value ($M^+H$)=579.17.

EXAMPLE 74

6-(4-Chlorobenzyl)-1-(5-fluoro-2-methoxybenzenesulfonyl)-8-isopropyl-3-pyrrolidin-1-yl-hexahydropyrazino[1,2-a]pyrimidine-4,7-dione Structure:

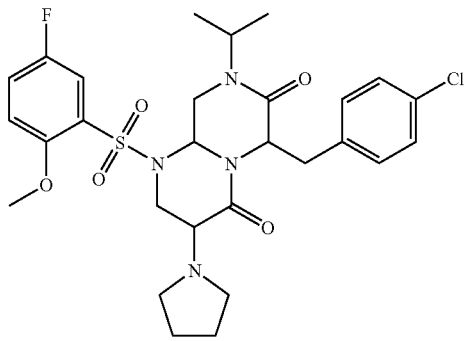

40 mg (0.074 mmol) of 3-amino-6-(4-chlorobenzyl)-1-(5-fluoro-2-methoxybenzenesulfonyl)-8-isopropylhexahydropyrazino[1,2-a]pyrimidine-4,7-dione were introduced into a 2-5 ml microwave vessel and dissolved in 2 ml of $CH_3CN$. 0.2 ml of $NaHCO_3$ (1.0M, in water) and 0.036 ml of dibromobutane were added to this solution. The reaction mixture was heated at 190° C. in a Personal Chemistry Smith Synthesizer microwave oven (high absorption mode with 30 seconds' preliminary stirring time) for 800 seconds. The mixture was then concentrated in vacuo, mixed with 1 ml of EtOAc and washed with 1 ml of water. The organic phase was isolated, dried ($MgSO_4$) and concentrated in vacuo. Purification took place by flash chromatography on 4 g of $SiO_2$ (MeOH/DCM, gradient 0-5%). The concentrated substance was converted into the HCl salt by adding 0.2 ml of 1.0M HCl in diethyl ether. The solid was ground, washed 4 times with diethyl ether and dried in vacuo. 22.7 mg of HCl salt of the desired compound were obtained. LC/MS: MW (calculated, monoisotopic)=592.19; measured value ($M^+H$)=593.18.

EXAMPLE 75

6-(4-Chlorobenzyl)-1-(5-fluoro-2-methoxybenzene-sulfonyl)-8-isopropyl-3-piperidin-1-yl-hexahydropy-razino[1,2-a]pyrimidine-4,7-dione Structure:

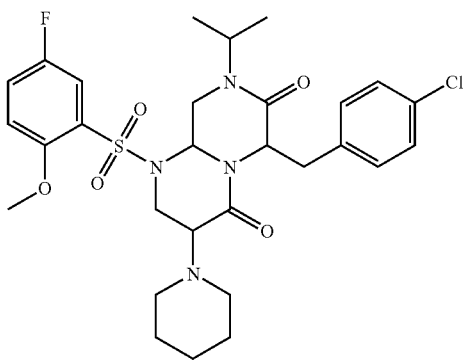

Synthesis takes place in analogy to Example 59 starting from 3-amino-6-(4-chlorobenzyl)-1-(5-fluoro-2-methoxy-benzenesulfonyl)-8-isopropylhexahydropyrazino[1,2-a]pyrimidine-4,7-dione. The desired product is obtained with MW=606.21 (calculated, monoisotopic); measured value (M+H)$^+$:607.19

EXAMPLE 76

6-(4-Chlorobenzyl)-1-(5-fluoro-2-methoxybenzene-sulfonyl)-8-isopropyl-3-morpholin-4-ylhexahydropy-razino[1,2-a]pyrimidine-4,7-dione Structure:

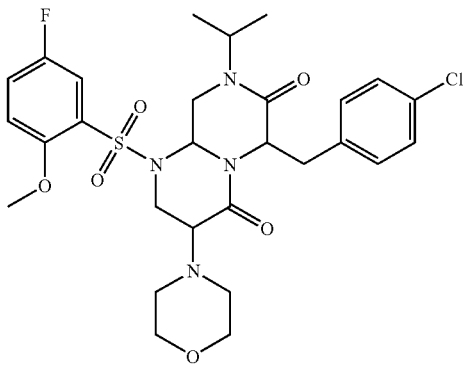

Synthesis takes place in analogy to Example 60 starting from 3-amino-6-(4-chlorobenzyl)-1-(5-fluoro-2-methoxy-benzenesulfonyl)-8-isopropylhexahydropyrazino [1,2-a]py-rimidine-4,7-dione. The desired product is obtained with MW=608.19 (calculated, monoisotopic); measured value (M+H)$^+$:609.16

EXAMPLE 77

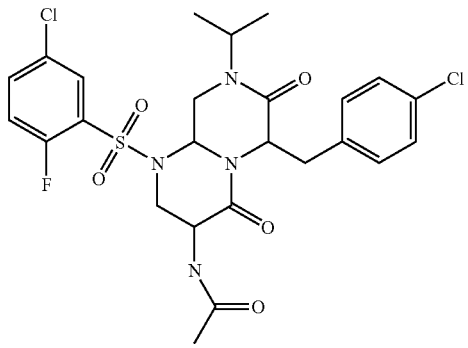

a) Benzyl[6-(4-chlorobenzyl)-1-(5-chloro-2-fluo-robenzenesulfonyl)-8-isopropyl-4,7-dioxooctahydro-pyrazino[1,2-a]pyrimidin-3-yl]carbamate Synthesis takes place in analogy to Example 66a) using 5-chloro-2-fluorobenzenesulfonyl chloride. The desired product is obtained with MW=676.13 (calculated, monoiso-topic); measured value (M+H)$^+$: 677.1 b) 3-Amino-6-(4-chlorobenzyl)-1-(5-chloro-2-fluo-robenzenesulfonyl)-8-isopropylhexahydropyrazino [1,2-a]pyrimidine-4,7-dione Synthesis takes in analogy to Example 66b) starting from benzyl[6-(4-chlorobenzyl)-1-(5-chloro-2-fluorobenzene-sulfonyl)-8-isopropyl-4,7-dioxooctahydropyrazino[1,2-a] pyrimidin-3-yl]carbamate. The desired product is obtained with MW=542.1 (calculated, monoisotopic); measured value (M+H)$^+$: 543.1 c) N-[6-(4-Chlorobenzyl)-1-(5-chloro-2-fluorobenzene-sulfonyl)-8-isopropyl-4,7-dioxooctahydropyrazino[1,2-a] pyrimidin-3-yl]acetamide. Synthesis takes place in analogy to Example 66c) starting from 3-amino-6-(4-chlorobenzyl)-1-(5-chloro-2-fluorobenzenesulfonyl)-8-isopropylhexahy-dropyrazino[1,2-a]pyrimidine-4,7-dione. The desired prod-uct is obtained with MW=584.11 (calculated, monoisotopic); measured value (M+H)$^+$: 585.08

EXAMPLE 78

N-[6-(4-Chlorobenzyl)-1-(5-chloro-2-fluorobenzene-sulfonyl)-8-isopropyl-4,7-dioxooctahydropyrazino[1, 2-a]pyrimidin-3-yl]cyclopropanecarboxamide Structure:

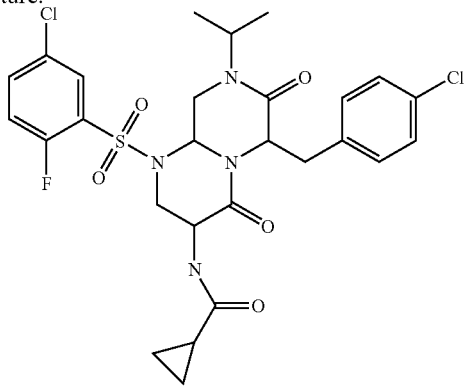

Synthesis takes place in analogy to Example 22 starting from 3-amino-6-(4-chlorobenzyl)-1-(5-chloro-2-fluoroben-zenesulfonyl)-8-isopropylhexahydropyrazino[1,2-a]pyrimi-dine-4,7-dione. The desired product is obtained with MW=610.12 (calculated, monoisotopic); measured value (M+H)$^+$: 611.09

EXAMPLE 79

N-[6-(4-Chlorobenzyl)-1-(5-chloro-2-fluorobenzenesulfonyl)-8-isopropyl-4,7-dioxooctahydropyrazino[1,2-a]pyrimidin-3-yl]cyclobutanecarboxamide Structure:

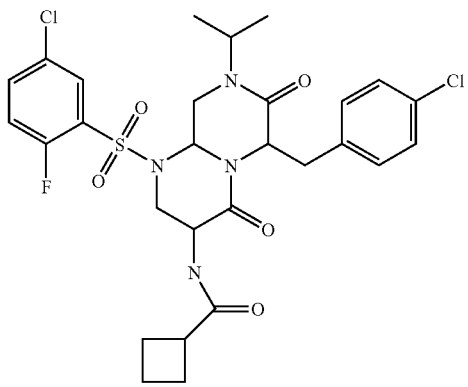

Synthesis takes place in analogy to Example 30 starting from 3-amino-6-(4-chlorobenzyl)-1-(5-chloro-2-fluorobenzenesulfonyl)-8-isopropylhexahydropyrazino[1,2-a]pyrimidine-4,7-dione. The desired product is obtained with MW=624.14 (calculated, monoisotopic); measured value (M+H)$^+$: 625.10

EXAMPLE 80

N-[6-(4-Chlorobenzyl)-1-(5-chloro-2-fluorobenzenesulfonyl)-8-isopropyl-4,7-dioxooctahydropyrazino[1,2-a]pyrimidin-3-yl]cyclopentanecarboxamide Structure:

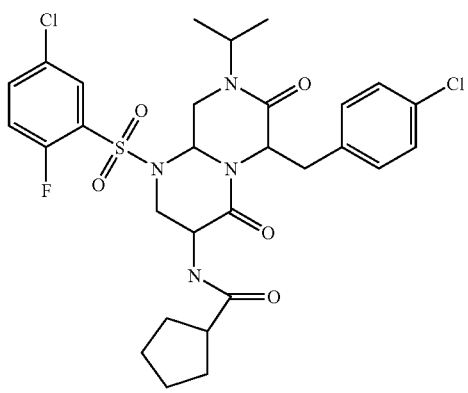

Synthesis takes place in analogy to Example 31 starting from 3-amino-6-(4-chlorobenzyl)-1-(5-chloro-2-fluorobenzenesulfonyl)-8-isopropylhexahydropyrazino[1,2-a]pyrimidine-4,7-dione. The desired product is obtained with MW=638.15 (calculated, monoisotopic); measured value (M+H)$^+$: 639.12

EXAMPLE 81

1-tert-Butyl-3-[6-(4-chlorobenzyl)-1-(5-chloro-2-fluorobenzenesulfonyl)-8-isopropyl-4,7-dioxooctahydropyrazino[1,2-a]pyrimidin-3-yl]urea

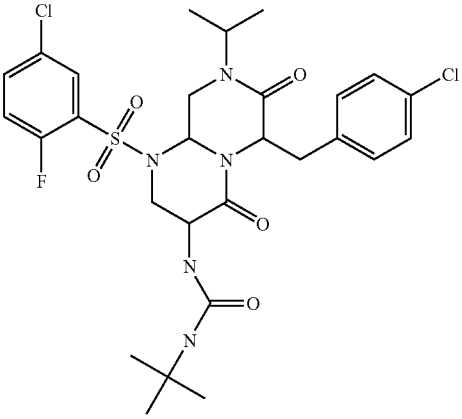

Synthesis takes place in analogy to Example 28 starting from 3-amino-6-(4-chlorobenzyl)-1-(5-chloro-2-fluorobenzenesulfonyl)-8-isopropylhexahydropyrazino[1,2-a]pyrimidine-4,7-dione. The desired product is obtained with MW=641.16 (calculated, monoisotopic); measured value (M+Na)$^+$: 664.12

EXAMPLE 82

6-(4-Chlorobenzyl)-1-(5-chloro-2-fluorobenzenesulfonyl)-3-dimethylamino-8-isopropylhexahydropyrazino[1,2-a]pyrimidine-4,7-dione Structure:

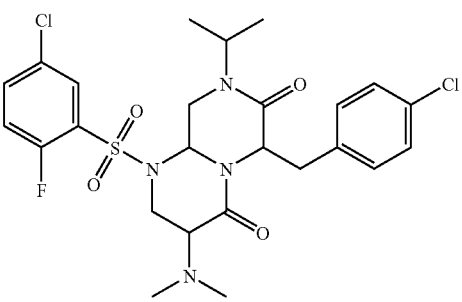

Synthesis takes place in analogy to Example 72 starting from 3-amino-6-(4-chlorobenzyl)-1-(5-chloro-2-fluorobenzenesulfonyl)-8-isopropylhexahydropyrazino[1,2-a]pyrimidine-4,7-dione. The desired product is obtained with MW=570.13 (calculated, monoisotopic); measured value (M+H)$^+$: 571.09.

EXAMPLE 83

3-Azetidin-1-yl-6-(4-chlorobenzyl)-1-(5-chloro-2-fluorobenzenesulfonyl)-8-isopropylhexahydropyrazino[1,2-a]pyrimidine-4,7-dione Structure:

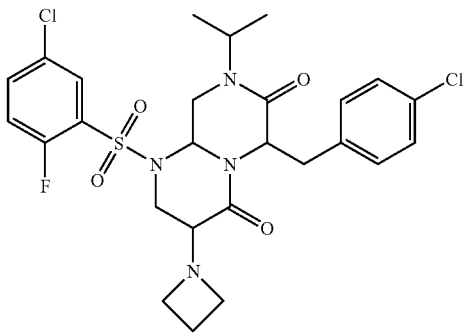

Synthesis takes place in analogy to Example 73 starting from 3-amino-6-(4-chlorobenzyl)-1-(5-chloro-2-fluorobenzenesulfonyl)-8-isopropylhexahydropyrazino[1,2-a]pyrimidine-4,7-dione. The desired product is obtained with MW=582.13 (calculated, monoisotopic); measured value (M+H)$^+$: 583.11.

EXAMPLE 84

6-(4-Chlorobenzyl)-1-(5-chloro-2-fluorobenzenesulfonyl)-8-isopropyl-3-pyrrolidin-1-yl-hexahydropyrazino[1,2-a]pyrimidine-4,7-dione Structure:

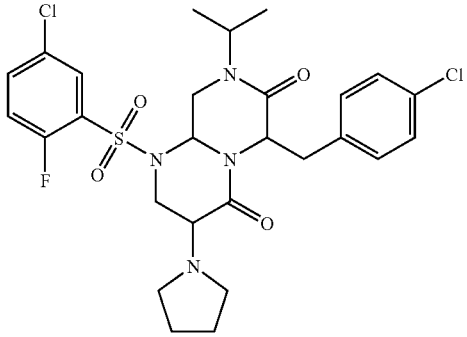

Synthesis takes place in analogy to Example 74 starting from 3-amino-6-(4-chlorobenzyl)-1-(5-chloro-2-fluorobenzenesulfonyl)-8-isopropylhexahydropyrazino[1,2-a]pyrimidine-4,7-dione. The desired product is obtained with MW=596.14 (calculated, monoisotopic); measured value (M+H)$^+$: 597.14.

EXAMPLE 85

6-(4-Chlorobenzyl)-1-(5-chloro-2-fluorobenzenesulfonyl)-8-isopropyl-3-piperidin-1-yl-hexahydropyrazino[1,2-a]pyrimidine-4,7-dione Structure:

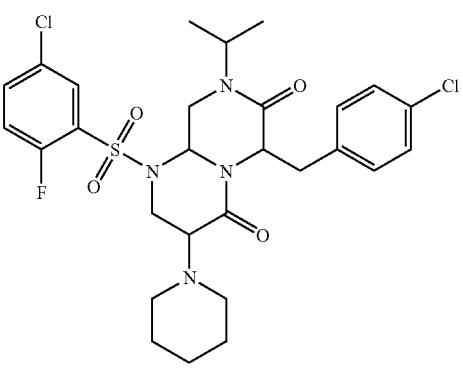

Synthesis takes place in analogy to Example 59 starting from 3-amino-6-(4-chlorobenzyl)-1-(5-chloro-2-fluorobenzenesulfonyl)-8-isopropylhexahydropyrazino[1,2-a]pyrimidine-4,7-dione. The desired product is obtained with MW=610.16 (calculated, monoisotopic); measured value (M+H)$^+$: 611.15

EXAMPLE 86

6-(4-Chlorobenzyl)-1-(5-chloro-2-fluorobenzenesulfonyl)-8-isopropyl-3-morpholin-1-yl-hexahydropyrazino[1,2-a]pyrimidine-4,7-dione Structure:

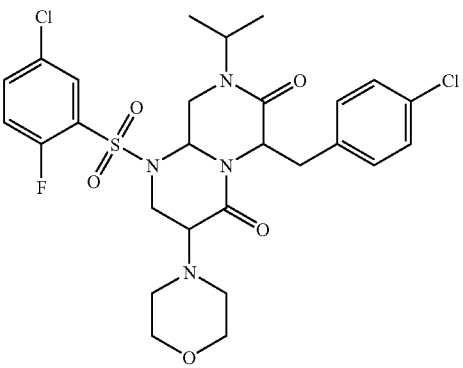

Synthesis takes place in analogy to Example 60 starting from 3-amino-6-(4-chlorobenzyl)-1-(5-chloro-2-fluorobenzenesulfonyl)-8-isopropylhexahydropyrazino[1,2-a]pyrimidine-4,7-dione. The desired product is obtained with MW=612.14 (calculated, monoisotopic); measured value (M+H)$^+$: 613.13.

EXAMPLE 87

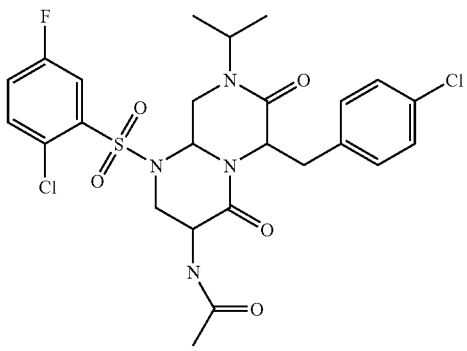

a) 2-Chloro-5-fluorobenzenesulfonyl Chloride 5 g (34.3 mmol) of 2-chloro-5-fluoroaniline were slowly added to a solution of 17 ml of concentrated hydrochloric acid solution and 11 ml of water at 0° C. The reaction mixture was stirred at 0° C. for 1 hour. Addition of 2.49 g (36.1 mmol) of $NaNO_2$ in 6 ml of $H_2O$ was followed by stirring the mixture at 0° C. for 15 minutes and then adding to a solution of 692 mg (5.15 mmol) of sulfur dioxide and copper(II) chloride in 10 ml of acetic acid. The reactants were stirred at 0° C. for 15 minutes and then at room temperature for a further 15 minutes. The reaction mixture was extracted with EtOAc. The organic phase was concentrated, dissolved in EtOAc, washed with 1N $NaHCO_3$ solution, dried over $MgSO_4$ and concentrated. 7.86 g of the desired sulfonyl chloride were obtained as a yellow oil.

b) Benzyl(2-(2-chloro-5-fluorobenzenesulfonylamino)-1-{2-(4-chlorophenyl)-1-[(2,2-diethoxyethyl)isopropylcarbamoyl]ethylcarbamoyl}ethyl)carbamate $Et_3N$ was added to a solution of 800 mg (1.39 mmol) of the amine benzyl(2-amino-1-{2-(4-chlorophenyl)-1-[(2,2-diethoxyethyl)isopropylcarbamoyl]ethylcarbamoyl}ethyl)-carbamate in 4 ml of DCM. The sulfonyl chloride prepared as described above (476 mg, 2.08 mmol) in solution in 3 ml of DCM was then added at room temperature. The reaction mixture was stirred at room temperature for 1 hour and washed with 1N $NaHCO_3$. The organic phase was dried on $MgSO_4$ and concentrated. The residue was chromatographed on 40 g of $SiO_2$ (elution with 30-70% EtOAc in heptane). 860 mg of the desired substance was taken as a white solid.

LC/MS: MG (calculated, monoisotopic)=769.72; measured value $(M^+Na)$=791.

c) Benzyl[6-(4-chlorobenzyl)-1-(2-chloro-5-fluorobenzenesulfonyl)-8-isopropyl-4,7-dioxooctahydropyrazino[1,2-a]pyrimidin-3-yl]carbamate Synthesis takes place in analogy to Example 29f) (Method B) starting from N-{2-(4-chlorophenyl)-1-[(2,2-diethoxyethyl)isopropylcarbamoyl]ethyl}-3-(2-chloro-5-fluorobenzenesulfonylamino)-2-methanesulfonylaminopropionamide. The desired product is obtained when MW=676.13 (calculated, monoisotopic); measured value $(M+H)^+$: 677.16 d) 3-Amino-6-(4-chlorobenzyl)-1-(2-chloro-5-fluorobenzenesulfonyl)-8-isopropylhexahydropyrazino[1,2-a]pyrimidine-4,7-dione Synthesis takes place in analogy to Example 29g) (Method B) starting from benzyl[6-(4-chlorobenzyl)-1-(2-chloro-5-fluorobenzenesulfonyl)-8-isopropyl-4,7-dioxooctahydropyrazino[1,2-a]pyrimidin-3-yl]carbamate. The desired product is obtained with MW=542.1 (calculated, monoisotopic); measured value $(M+H)^+$: 543.10 e) N-[6-(4-Chlorobenzyl)-1-(2-chloro-5-fluorobenzenesulfonyl)-8-isopropyl-4,7-dioxooctahydropyrazino[1,2-a]pyrimidin-3-yl]acetamide Synthesis takes place in analogy to Example 21h) starting from 3-amino-6-(4-chlorobenzyl)-1-(2-chloro-5-fluorobenzenesulfonyl)-8-isopropylhexahydropyrazino[1,2-a]pyrimidine-4,7-dione. The desired product is obtained with MW=584.11 (calculated, monoisotopic); measured value $(M+H)^+$: 585.10

EXAMPLE 88

N-[6-(4-Chlorobenzyl)-1-(2-chloro-5-fluorobenzenesulfonyl)-8-isopropyl-4,7-dioxooctahydropyrazino[1,2-a]pyrimidin-3-yl]cyclopropanecarboxamide Structure:

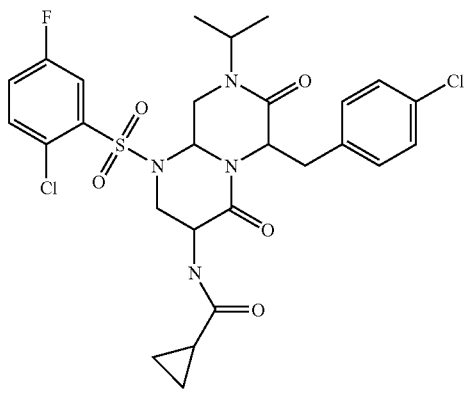

Synthesis takes place in analogy to Example 22 starting from 3-amino-6-(4-chlorobenzyl)-1-(2-chloro-5-fluorobenzenesulfonyl)-8-isopropylhexahydropyrazino[1,2-a]pyrimidine-4,7-dione. The desired product is obtained with MW=610.12 (calculated, monoisotopic); measured value $(M+H)^+$: 611.14

EXAMPLE 89

N-[6-(4-Chlorobenzyl)-1-(2-chloro-5-fluorobenzene-sulfonyl)-8-isopropyl-4,7-dioxooctahydropyrazino[1,2-a]pyrimidin-3-yl]cyclobutanecarboxamide Structure:

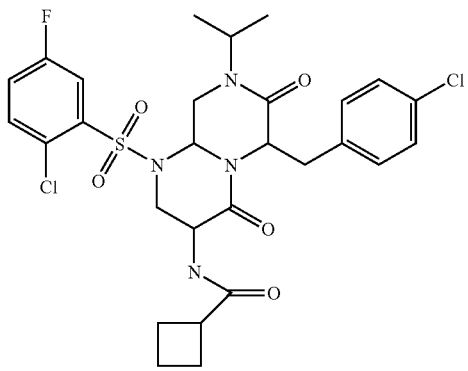

Synthesis takes place in analogy to Example 30 starting from 3-amino-6-(4-chlorobenzyl)-1-(2-chloro-5-fluorobenzenesulfonyl)-8-isopropylhexahydropyrazino[1,2-a]pyrimidine-4,7-dione. The desired product is obtained with MW=624.14 (calculated, monoisotopic); measured value (M+H)$^+$: 625.14

EXAMPLE 90

1-tert-Butyl-3-[6-(4-chlorobenzyl)-1-(2-chloro-5-fluorobenzenesulfonyl)-8-isopropyl-4,7-dioxooctahydropyrazino[1,2-a]pyrimidin-3-yl] urea Structure:

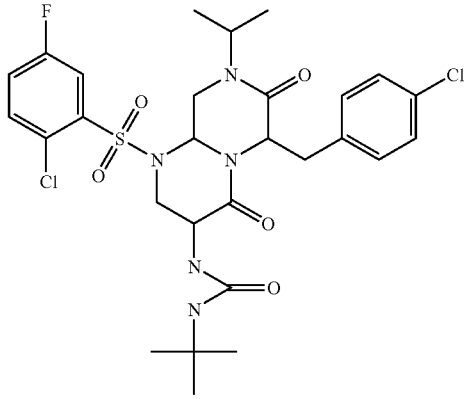

Synthesis takes place in analogy to Example 28 starting from 3-amino-6-(4-chlorobenzyl)-1-(2-chloro-5-fluorobenzenesulfonyl)-8-isopropylhexahydropyrazino[1,2-a]pyrimidine-4,7-dione. The desired product is obtained with MW=641.16 (calculated, monoisotopic); measured value (M+Na)$^+$: 664.15

EXAMPLE 91

N-[6-(4-Chlorobenzyl)-1-(2-chloro-5-fluorobenzene-sulfonyl)-8-isopropyl-4,7-dioxooctahydropyrazino[1,2-a]pyrimidin-3-yl]methanesulfonamide

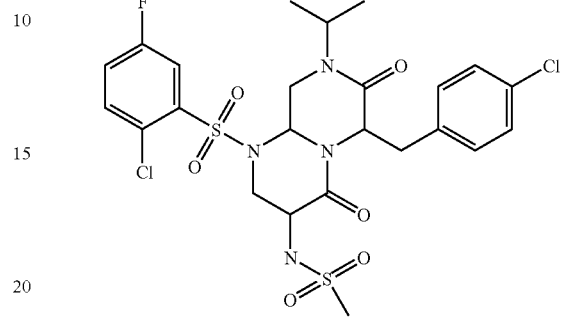

Synthesis takes place in analogy to Example 26 starting from 3-amino-6-(4-chlorobenzyl)-1-(2-chloro-5-fluorobenzenesulfonyl)-8-isopropylhexahydropyrazino[1,2-a]pyrimidine-4,7-dione. The desired product is obtained with MW=620.07 (calculated, monoisotopic); measured value (M+H)$^+$:621.0

EXAMPLE 92

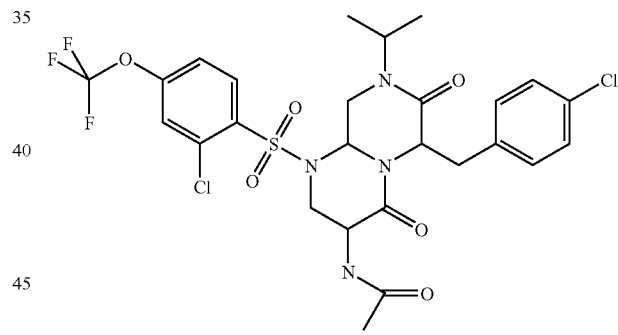

a) 2-Chloro-4-trifluoromethoxybenzenesulfonyl Chloride

2-Chloro-4-trifluoromethoxyaniline was reacted to give the corresponding sulfonyl chloride by the same protocol as in Example 87a).

b) Benzyl[1-{2-(4-chlorophenyl)-1-[(2,2-diethoxy-ethyl)isopropylcarbamoyl]ethylcarbamoyl}-2-(2-chloro-4-trifluoromethoxybenzenesulfonylamino) ethyl]carbamate Synthesis takes place in analogy to Example 87b) starting from 2-chloro-4-trifluoromethoxybenzenesulfonyl chloride. The desired product is obtained with MW=834.21 (calculated, monoisotopic); measured value (M+Na)$^+$: 857.0 c) Benzyl[6-(4-chlorobenzyl)-1-(2-chloro-4-trifluoromethoxybenzenesulfonyl)-8-isopropyl-4,7-dioxooctahydropyrazino [1,2-a]pyrimidin-3-yl]carbamate Synthesis takes place in analogy to Example 29f) (Method B) starting from N-{2-(4-chlorophenyl)-1-[(2,2-diethoxyethyl)isopropylcarbamoyl]ethyl}-3-(2-chloro-4-trifluoromethoxybenzenesulfonylamino)-2-methanesulfonylaminopropionamide. The desired product is obtained with MW=742.12 (calculated, monoisotopic); measured value (M+H)⁺: 743.14 d) 3-Amino-6-(4-chlorobenzyl)-1-(2-chloro-5-trifluoromethoxybenzenesulfonyl)-8-isopropylhexahydropyrazino[1,2-a]pyrimidine-4,7-dione Synthesis takes place in analogy to Example 29g) (Method B) starting from benzyl[6-(4-chlorobenzyl)-1-(2-chloro-4-trifluoromethoxybenzenesulfonyl)-8-isopropyl-4,7-dioxooctahydropyrazino[1,2-a]pyrimidin-3-yl]carbamate. The desired product is obtained with MW=608.09 (calculated, monoisotopic); measured value (M+H)⁺: 609.07 e) N-[6-(4-Chlorobenzyl)-1-(2-chloro-4-trifluoromethoxybenzenesulfonyl)-8-isopropyl-4,7-dioxooctahydropyrazino[1,2-a]pyrimidin-3-yl]acetamide Synthesis takes place in analogy to Example 21h) starting from 3-amino-6-(4-chlorobenzyl)-1-(2-chloro-4-trifluoromethoxybenzenesulfonyl)-8-isopropylhexahydropyrazino[1,2-a]pyrimidine-4,7-dione. The desired product is obtained with MW=650.1 (calculated, monoisotopic); measured value (M+H)⁺: 651.09

EXAMPLE 93

N-[6-(4-Chlorobenzyl)-1-(2-chloro-4-trifluoromethoxybenzenesulfonyl)-8-isopropyl-4,7-dioxooctahydropyrazino[1,2-a]pyrimidin-3-yl]cyclopropanecarboxamide Structure:

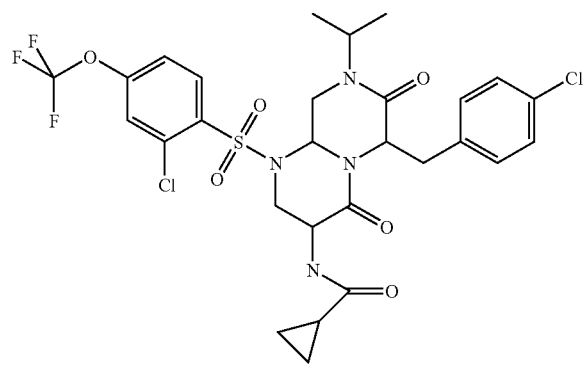

Synthesis takes place in analogy to Example 22 starting from 3-amino-6-(4-chlorobenzyl)-1-(2-chloro-4-trifluoromethoxybenzenesulfonyl)-8-isopropylhexahydropyrazino[1,2-a]pyrimidine-4,7-dione. The desired product is obtained with MW=676.11 (calculated, monoisotopic); measured value (M+H)⁺: 677.13

EXAMPLE 94

N-[6-(4-Chlorobenzyl)-1-(2-chloro-4-trifluoromethoxybenzenesulfonyl)-8-isopropyl-4,7-dioxooctahydropyrazino[1,2-a]pyrimidin-3-yl]cyclobutanecarboxamide Structure:

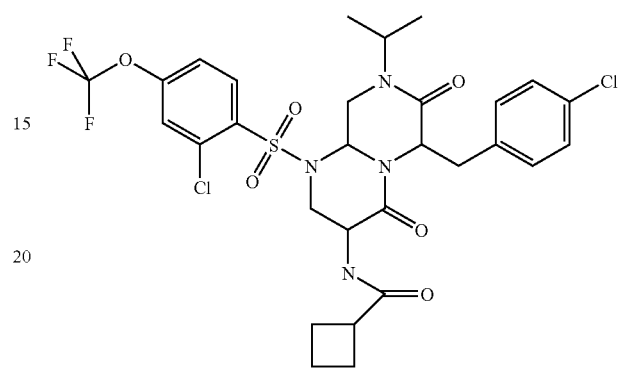

Synthesis takes place in analogy to Example 30 starting from 3-amino-6-(4-chlorobenzyl)-1-(2-chloro-4-trifluoromethoxybenzenesulfonyl)-8-isopropylhexahydropyrazino[1,2-a]pyrimidine-4,7-dione. The desired product is obtained with MW=690.13 (calculated, monoisotopic); measured value (M+H)⁺: 691.13

EXAMPLE 95

1-tert-Butyl-3-[6-(4-chlorobenzyl)-1-(2-chloro-4-trifluoromethoxybenzenesulfonyl)-8-isopropyl-4,7-dioxooctahydropyrazino[1,2-a]pyrimidin-3-yl]urea Structure:

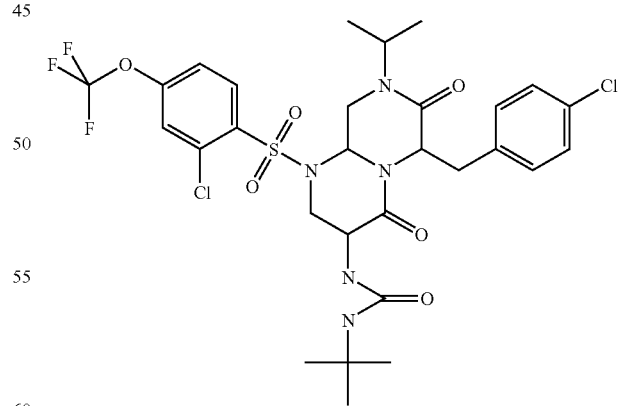

Synthesis takes place in analogy to Example 28 starting from 3-amino-6-(4-chlorobenzyl)-1-(2-chloro-4-trifluoromethoxybenzenesulfonyl)-8-isopropylhexahydropyrazino[1,2-a]pyrimidine-4,7-dione. The desired product is obtained with MW=707.16 (calculated, monoisotopic); measured value (M+Na)⁺: 730.14

EXAMPLE 96

N-[6-(4-Chlorobenzyl)-1-(2-chloro-4-trifluoromethoxybenzenesulfonyl)-8-isopropyl-4,7-dioxooctahydropyrazino[1,2-a]pyrimidin-3-yl]methanesulfonamide Structure:

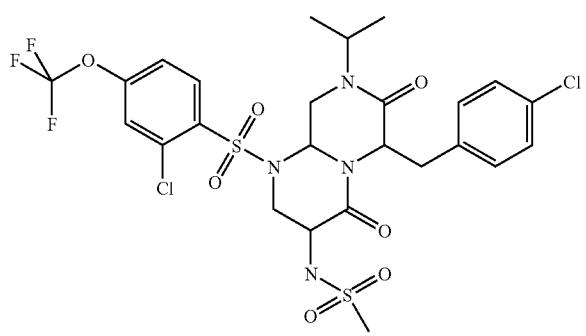

Synthesis takes place in analogy to Example 26 starting from 3-amino-6-(4-chlorobenzyl)-1-(2-chloro-4-trifluoromethoxybenzenesulfonyl)-8-isopropylhexahydropyrazino[1,2-a]pyrimidine-4,7-dione. The desired product is obtained with MW=686.07 (calculated, monoisotopic); measured value (M+H)$^+$: 687.0

EXAMPLE 97

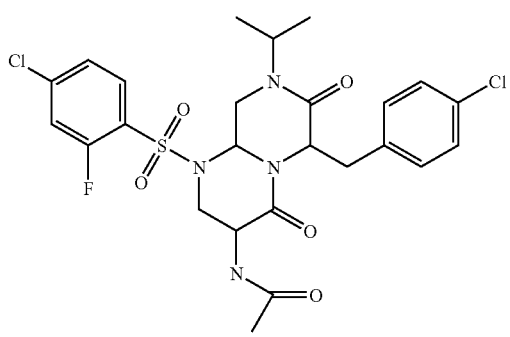

a) Benzyl[1-{2-(4-chlorophenyl)-1-[(2,2-diethoxyethyl)isopropylcarbamoyl]ethylcarbamoyl}-2-(4-chloro-2-fluorobenzenesulfonylamino)ethyl]carbamate Synthesis takes place in analogy to Example 87b) starting from 4-chloro-2-fluorobenzenesulfonyl chloride. The desired product is obtained with MW=768.22 (calculated, monoisotopic); measured value (M+Na)$^+$: 791.0 b) Benzyl[6-(4-chlorobenzyl)-1-(4-chloro-2-fluorobenzenesulfonyl)-8-isopropyl-4,7-dioxooctahydropyrazino[1,2-a]pyrimidin-3-yl]carbamate Synthesis takes place in analogy to Example 29f) (Method B) starting from N-{2-(4-chlorophenyl)-1-[(2,2-diethoxyethyl)isopropylcarbamoyl]ethyl}-3-(4-chloro-2-fluorobenzenesulfonylamino)-2-methanesulfonylaminopropionamide. The desired product is obtained with MW=676.13 (calculated, monoisotopic); measured value (M+H)$^+$: 677.14 c) 3-Amino-6-(4-chlorobenzyl)-1-(4-chloro-2-fluorobenzenesulfonyl)-8-isopropylhexahydropyrazino[1,2-a]pyrimidine-4,7-dione Synthesis takes place in analogy to Example 29g) (Method B) starting from benzyl[6-(4-chlorobenzyl)-1-(4-chloro-2-fluorobenzenesulfonyl)-8-isopropyl-4,7-dioxooctahydropyrazino[1,2-a]pyrimidin-3-yl]carbamate. The desired product is obtained with MW=542.1 (calculated, monoisotopic); measured value (M+H)$^+$: 543.1 d) N-[6-(4-Chlorobenzyl)-1-(4-chloro-2-fluorobenzenesulfonyl)-8-isopropyl-4,7-dioxooctahydropyrazino[1,2-a]pyrimidin-3-yl]acetamide Synthesis takes place in analogy to Example 21h) starting from 3-amino-6-(4-chlorobenzyl)-1-(4-chloro-2-fluorobenzenesulfonyl)-8-isopropylhexahydropyrazino[1,2-a]pyrimidine-4,7-dione. The desired product is obtained with MW=584.11 (calculated, monoisotopic); measured value (M+H)$^+$:585.1

EXAMPLE 98

N-[6-(4-Chlorobenzyl)-1-(4-chloro-2-fluorobenzenesulfonyl)-8-isopropyl-4,7-dioxooctahydropyrazino[1,2-a]pyrimidin-3-yl]cyclopropanecarboxamide Structure:

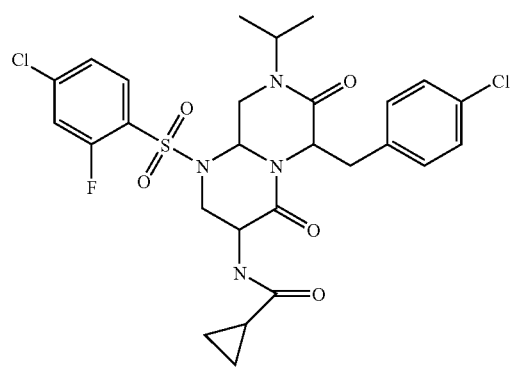

Synthesis takes place in analogy to Example 29e) starting from 3-amino-6-(4-chlorobenzyl)-1-(4-chloro-2-fluorobenzenesulfonyl)-8-isopropylhexahydropyrazino[1,2-a]pyrimidine-4,7-dione. The desired product is obtained with MW=610.12 (calculated, monoisotopic); measured value (M+H)$^+$: 611.14

EXAMPLE 99

N-[6-(4-Chlorobenzyl)-1-(4-chloro-2-fluorobenzene-sulfonyl)-8-isopropyl-4,7-dioxooctahydropyrazino[1,2-a]pyrimidin-3-yl]cyclobutanecarboxamide Structure:

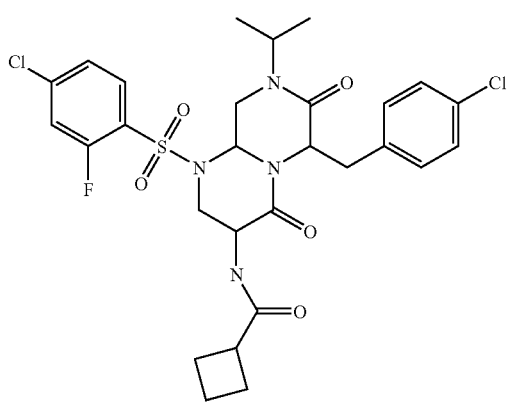

Synthesis takes place in analogy to Example 30 starting from 3-amino-6-(4-chlorobenzyl)-1-(4-chloro-2-fluorobenzenesulfonyl)-8-isopropylhexahydropyrazino[1,2-a]pyrimidine-4,7-dione. The desired product is obtained with MW=624.12 (calculated, monoisotopic); measured value (M+H)$^+$: 625.14

EXAMPLE 100

1-tert-Butyl-3-[6-(4-chlorobenzyl)-1-(4-chloro-2-fluorobenzenesulfonyl)-8-isopropyl-4,7-dioxooctahydropyrazino[1,2-a]pyrimidin-3-yl]urea Structure:

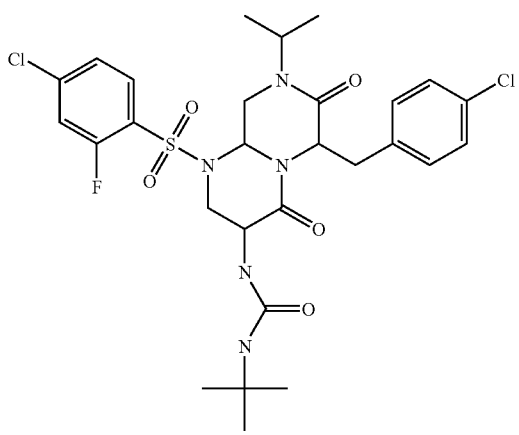

Synthesis takes place in analogy to Example 28 starting from 3-amino-6-(4-chlorobenzyl)-1-(4-chloro-2-fluorobenzenesulfonyl)-8-isopropylhexahydropyrazino[1,2-a]pyrimidine-4,7-dione. The desired product is obtained with MW=641.16 (calculated, monoisotopic); measured value (M+Na)$^+$: 664.14

EXAMPLE 101

N-[6-(4-Chlorobenzyl)-1-(4-chloro-2-fluorobenzene-sulfonyl)-8-isopropyl-4,7-dioxooctahydropyrazino[1,2-a]pyrimidin-3-yl]methanesulfonamide Structure:

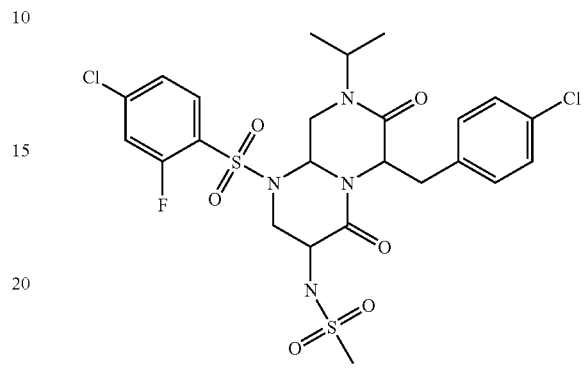

Synthesis takes place in analogy to Example 26 starting from 3-amino-6-(4-chlorobenzyl)-1-(4-chloro-2-fluorobenzenesulfonyl)-8-isopropylhexahydropyrazino[1,2-a]pyrimidine-4,7-dione. The desired product is obtained with MW=620.07 (calculated, monoisotopic); measured value (M+H)$^+$: 621.0

EXAMPLE 102

N-[6-(4-Chlorobenzyl)-1-(2,5-dimethoxybenzene-sulfonyl)-8-isopropyl-4,7-dioxooctahydropyrazino[1,2-a]pyrimidin-3-yl]methanesulfonamide Structure:

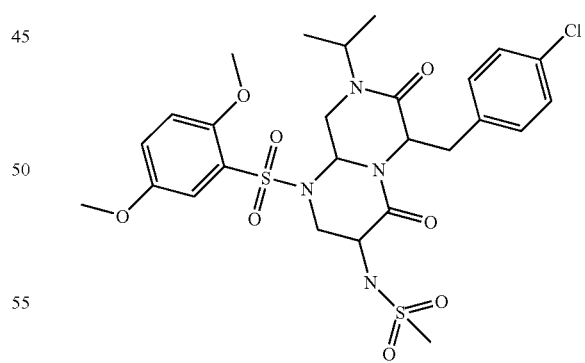

a) 2-Benzyloxycarbonylamino-3-(2,5-dimethoxybenzenesulfonylamino)propionic Acid

Synthesis takes place in analogy to Example 21d) starting from 2,5-dimethoxybenzenesulfonyl chloride. The desired product is obtained with MW=438.46 (calculated, monoisotopic); measured value (M+H)$^+$: 439.1 b) N-{2-(4-Chlorophenyl)-1-[(2,2-diethoxyethyl) isopropylcarbamoyl]ethyl}-3-(2,5-dimethoxybenzenesulfonylamino)-2-methanesulfonylaminopropionamide Synthesis takes place in analogy to Example 21e) starting from 2-benzyloxycarbonylamino-3-(2,5-dimethoxybenzenesulfonylamino)propionic acid. The desired product is obtained with MW=777.34 (calculated, monoisotopic); measured value (M-$C_2H_6O$+H)$^+$: 731.9 c) Benzyl[6-(4-chlorobenzyl)-1-(2,5-dimethoxybenzenesulfonyl)-8-isopropyl-4,7-dioxooctahydropyrazino[1,2-a]pyrimidin-3-yl]carbamate Synthesis takes place in analogy to Example 21f) starting from N-{2-(4-chlorophenyl)-1-[(2,2-diethoxyethyl)isopropylcarbamoyl]ethyl}-3-(2,5-dimethoxybenzenesulfonylamino)-2-methanesulfonylaminopropionamide. The desired product is obtained with MW=684 (calculated, monoisotopic); measured value (M+H)$^+$: 685.38 d) 3-Amino-6-(4-chlorobenzyl)-1-(2,5-dimethoxybenzenesulfonyl)-8-isopropylhexahydropyrazino[1,2-a]pyrimidine-4,7-dione Synthesis takes place in analogy to Example 21g) starting from benzyl[6-(4-chlorobenzyl)-1-(2,5-dimethoxybenzenesulfonyl)-8-isopropyl-4,7-dioxooctahydropyrazino[1,2-a]pyrimidin-3-yl]carbamate. The desired product is obtained with MW=550 (calculated, monoisotopic); measured value (M+H)$^+$: 551.15 e) 3-Amino-6-(4-chlorobenzyl)-1-(2,5-dimethoxybenzenesulfonyl)-8-isopropylhexahydropyrazino[1,2-a]pyrimidine-4,7-dione Synthesis takes place in analogy to Example 26 starting from 3-amino-6-(4-chlorobenzyl)-1-(2,5-dimethoxybenzenesulfonyl)-8-isopropylhexahydropyrazino[1,2-a]pyrimidine-4,7-dione. The desired product is obtained with MW=628.14 (calculated, monoisotopic); measured value (M+H)$^+$: 629.15

EXAMPLE 103

N-[6-(4-Chlorobenzyl)-1-(3-fluorobenzenesulfonyl)-8-isopropyl-4,7-dioxooctahydropyrazino[1,2-a]pyrimidin-3-yl]methanesulfonamide Structure:

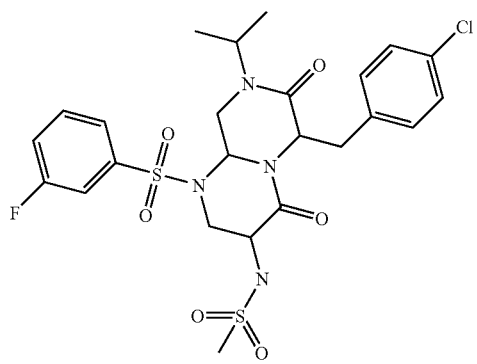

a) 2-Benzyloxycarbonylamino-3-(3-fluorobenzenesulfonylamino)propionic Acid

Synthesis takes place in analogy to Example 21d) starting from 3-fluorobenzenesulfonyl chloride. The desired product is obtained with MW=396.40 (calculated, monoisotopic); measured value (M+H)$^+$: 397.10 b) N-{2-(4-Chlorophenyl)-1-[(2,2-diethoxyethyl) isopropylcarbamoyl]ethyl}-3-(3-fluorobenzenesulfonylamino)-2-methanesulfonylaminopropionamide Synthesis takes place in analogy to Example 21e) starting from 2-benzyloxycarbonylamino-3-(3-fluorobenzenesulfonylamino)propionic acid. The desired product is obtained with MW=735.28 (calculated, monoisotopic); measured value (M-$C_2H_6O$+H)$^+$: 689.8 c) Benzyl[6-(4-chlorobenzyl)-1-(3-fluorobenzenesulfonyl)-8-isopropyl-4,7-dioxooctahydropyrazino[1,2-a]pyrimidin-3-yl]carbamate Synthesis takes place in analogy to Example 21f) starting from N-{2-(4-chlorophenyl)-1-[(2,2-diethoxyethyl)isopropylcarbamoyl]ethyl}-3-(3-fluorobenzenesulfonylamino)-2-methanesulfonylaminopropionamide. The desired product is obtained with MW=642 (calculated, monoisotopic); measured value (M+H)$^+$: 643.31 d) 3-Amino-6-(4-chlorobenzyl)-1-(3-fluorobenzenesulfonyl)-8-isopropylhexahydropyrazino[1,2-a]pyrimidine-4,7-dione Synthesis takes place in analogy to Example 21g) starting from benzyl[6-(4-chlorobenzyl)-1-(3-fluorobenzenesulfonyl)-8-isopropyl-4,7-dioxooctahydropyrazino[1,2-a]pyrimidin-3-yl]carbamate. The desired product is obtained with MW=508 (calculated, monoisotopic); measured value (M+H)$^+$: 509.15 e) 3-Amino-6-(4-chlorobenzyl)-1-(3-fluorobenzenesulfonyl)-8-isopropylhexahydropyrazino[1,2-a]pyrimidine-4,7-dione Synthesis takes place in analogy to Example 26 starting from 3-amino-6-(4-chlorobenzyl)-1-(3-fluorobenzenesulfonyl)-8-isopropylhexahydropyrazino[1,2-a]pyrimidine-4,7-dione. The desired product is obtained with MW=586.11 (calculated, monoisotopic); measured value (M+H)$^+$: 587.41

EXAMPLE 104

N-[1-Benzenesulfonyl-6-(4-chlorobenzyl)-8-isopropyl-4,7-dioxooctahydropyrazino[1,2-a]pyrimidin-3-yl]methanesulfonamide Structure:

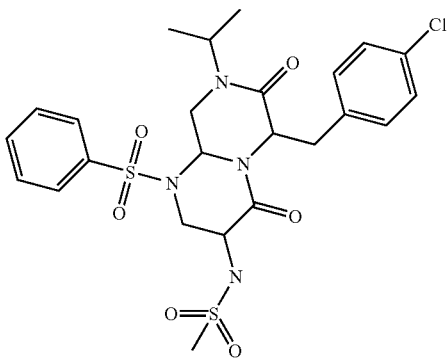

a) 2-Benzyloxycarbonylamino-3-(benzenesulfonylamino)propionic Acid

Synthesis takes place in analogy to Example 21d) starting from benzenesulfonyl chloride. The desired product is obtained with MW=378.41 (calculated, monoisotopic); measured value $(M+H)^+$: 397.10 b) N-{2-(4-Chlorophenyl)-1-[(2,2-diethoxyethyl)isopropylcarbamoyl]ethyl}-3-(benzenesulfonylamino)-2-methanesulfonylaminopropionamide Synthesis takes place in analogy to Example 21e) starting from 2-benzyloxycarbonylamino-3-(benzenesulfonylamino) propionic acid. The desired product is obtained with MW=717.29 (calculated, monoisotopic); measured value $(M-C_2H_6O+H)^+$: 671.7 c) Benzyl[6-(4-chlorobenzyl)-1-(benzenesulfonyl)-8-isopropyl-4,7-dioxooctahydropyrazino[1,2-a]pyrimidin-3-yl]carbamate Synthesis takes place in analogy to Example 21f) starting from N-{2-(4-chlorophenyl)-1-[(2,2-diethoxyethyl)isopropylcarbamoyl]ethyl}-3-(benzenesulfonylamino)-2-methanesulfonylaminopropionamide. The desired product is obtained with MW=642 (calculated, monoisotopic); measured value $(M+H)^+$: 625.33 d) 3-Amino-6-(4-chlorobenzyl)-1-(benzenesulfonyl)-8-isopropylhexahydropyrazino[1,2-a]pyrimidine-4,7-dione Synthesis takes place in analogy to Example 21g) starting from benzyl[6-(4-chlorobenzyl)-1-(benzenesulfonyl)-8-isopropyl-4,7-dioxooctahydropyrazino[1,2-a]pyrimidin-3-yl]carbamate. The desired product is obtained with MW=490 (calculated, monoisotopic); measured value $(M+H)^+$: 491.10 e) 3-Amino-6-(4-chlorobenzyl)-1-(benzenesulfonyl)-8-isopropylhexahydropyrazino[1,2-a]pyrimidine-4,7-dione Synthesis takes place in analogy to Example 26 starting from 3-amino-6-(4-chlorobenzyl)-1-(benzenesulfonyl)-8-isopropylhexahydropyrazino[1,2-a]pyrimidine-4,7-dione. The desired product is obtained with MW=568.12 (calculated, monoisotopic); measured value $(M+H)^+$: 569.13

EXAMPLE 105

N-[6-(4-Chlorobenzyl)-1-(2-fluorobenzenesulfonyl)-8-isopropyl-4,7-dioxooctahydropyrazino[1,2-a]pyrimidin-3-yl]methanesulfonamide Structure:

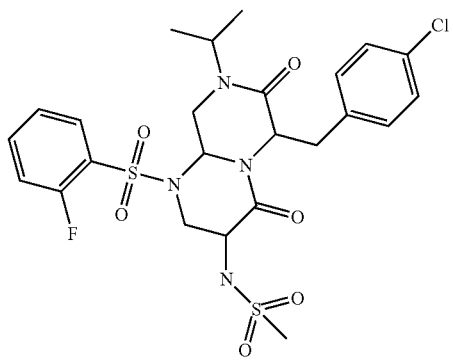

a) 2-Benzyloxycarbonylamino-3-(2-fluorobenzenesulfonylamino)propionic Acid

Synthesis takes place in analogy to Example 21d) starting from 2-fluorobenzenesulfonyl chloride. The desired product is obtained with MW=396.40 (calculated, monoisotopic); measured value $(M+H)^+$: 397.10 b) N-{2-(4-Chlorophenyl)-1-[(2,2-diethoxyethyl)isopropylcarbamoyl]ethyl}-3-(2-fluorobenzenesulfonylamino)-2-methanesulfonylaminopropionamide Synthesis takes place in analogy to Example 21e) starting from 2-benzyloxycarbonylamino-3-(2-fluorobenzenesulfonylamino)propionic acid. The desired product is obtained with MW=735.28 (calculated, monoisotopic); measured value $(M-C_2H_6O+H)^+$: 689.7 c) Benzyl[6-(4-chlorobenzyl)-1-(2-fluorobenzenesulfonyl)-8-isopropyl-4,7-dioxooctahydropyrazino[1,2-a]pyrimidin-3-yl]carbamate Synthesis takes place in analogy to Example 21f) starting from N-{2-(4-chlorophenyl)-1-[(2,2-diethoxyethyl)isopropylcarbamoyl]ethyl}-3-(2-fluorobenzenesulfonylamino)-2-methanesulfonylaminopropionamide. The desired product is obtained with MW=642 (calculated, monoisotopic); measured value $(M+R)^+$: 643.31 d) 3-Amino-6-(4-chlorobenzyl)-1-(2-fluorobenzenesulfonyl)-8-isopropylhexahydropyrazino[1,2-a]pyrimidine-4,7-dione Synthesis takes place in analogy to Example 21g) starting from benzyl[6-(4-chlorobenzyl)-1-(2-fluorobenzenesulfonyl)-8-isopropyl-4,7-dioxooctahydropyrazino[1,2-a]pyrimidin-3-yl]carbamate. The desired product is obtained with MW=508 (calculated, monoisotopic); measured value (M+H)$^+$: 509.15 e) 3-Amino-6-(4-chlorobenzyl)-1-(2-fluorobenzenesulfonyl)-8-isopropylhexahydropyrazino[1,2-a]pyrimidine-4,7-dione Synthesis takes place in analogy to Example 26 starting from 3-amino-6-(4-chlorobenzyl)-1-(2-fluorobenzenesulfonyl)-8-isopropylhexahydropyrazino[1,2-a]pyrimidine-4,7-dione. The desired product is obtained with MW=586.11 (calculated, monoisotopic); measured value (M+H)$^+$: 587.12

EXAMPLE 106

N-[6-(4-Chlorobenzyl)-1-(2,4-difluorobenzenesulfonyl)-8-isopropyl-4,7-dioxooctahydropyrazino[1,2-a]pyrimidin-3-yl]methanesulfonamide Structure:

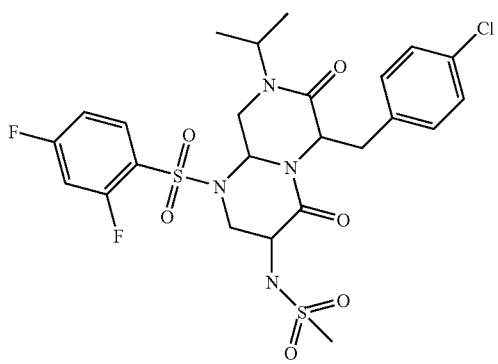

a) 2-Benzyloxycarbonylamino-3-(2,4-difluorobenzenesulfonylamino)propionic Acid

Synthesis takes place in analogy to Example 21d) starting from 2,4-difluorobenzenesulfonyl chloride. The desired product is obtained with MW=414.40 (calculated, monoisotopic); measured value (M+H)$^+$: 415.10 b) N-{2-(4-Chlorophenyl)-1-[(2,2-diethoxyethyl)isopropylcarbamoyl]ethyl}-3-(2,4-difluorobenzenesulfonylamino)-2-methanesulfonylaminopropionamide Synthesis takes place in analogy to Example 21 e) starting from 2-benzyloxycarbonylamino-3-(2,4-difluorobenzenesulfonylamino)propionic acid. The desired product is obtained with MW=753.27 (calculated, monoisotopic); measured value (M-C$_2$H$_6$O+H)$^+$: 707.7 c) Benzyl[6-(4-chlorobenzyl)-1-(2,4-difluorobenzenesulfonyl)-8-isopropyl-4,7-dioxooctahydropyrazino[1,2-a]pyrimidin-3-yl]carbamate Synthesis takes place in analogy to Example 21f) starting from N-{2-(4-chlorophenyl)-1-[(2,2-diethoxyethyl)isopropylcarbamoyl]ethyl}-3-(2,4-difluorobenzenesulfonylamino)-2-methanesulfonylaminopropionamide. The desired product is obtained with MW=660 (calculated, monoisotopic); measured value (M+H)$^+$: 661.32 d) 3-Amino-6-(4-chlorobenzyl)-1-(2,4-difluorobenzenesulfonyl)-8-isopropylhexahydropyrazino[1,2-a]pyrimidine-4,7-dione Synthesis takes place in analogy to Example 21g) starting from benzyl[6-(4-chlorobenzyl)-1-(2,4-difluorobenzenesulfonyl)-8-isopropyl-4,7-dioxooctahydropyrazino[1,2-a]pyrimidin-3-yl]carbamate. The desired product is obtained with MW=526 (calculated, monoisotopic); measured value (M+H)$^+$: 527.10 e) 3-Amino-6-(4-chlorobenzyl)-1-(2,4-difluorobenzenesulfonyl)-8-isopropylhexahydropyrazino[1,2-a]pyrimidine-4,7-dione Synthesis takes place in analogy to Example 26 starting from 3-amino-6-(4-chlorobenzyl)-1-(2,4-difluorobenzenesulfonyl)-8-isopropylhexahydropyrazino[1,2-a]pyrimidine-4,7-dione. The desired product is obtained with MW=604.1 (calculated, monoisotopic); measured value (M+H)$^+$: 605.11

EXAMPLE 107

N-[6-(4-Chlorobenzyl)-1-(3,4-difluorobenzenesulfonyl)-8-isopropyl-4,7-dioxooctahydropyrazino[1,2-a]pyrimidin-3-yl]methanesulfonamide Structure:

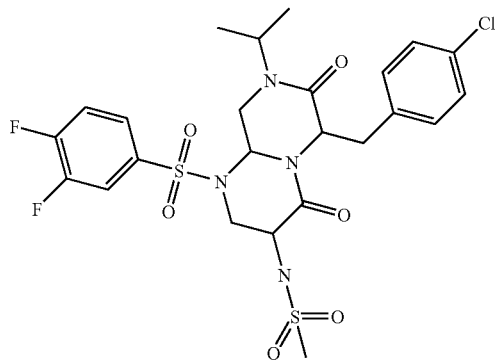

a) 2-Benzyloxycarbonylamino-3-(3,4-difluorobenzenesulfonylamino)propionic Acid

Synthesis takes place in analogy to Example 21d) starting from 3,4-difluorobenzenesulfonyl chloride. The desired product is obtained with MW=414.40 (calculated, monoisotopic); measured value (M+H)$^+$: 415.10 b) N-{2-(4-Chlorophenyl)-1-[(2,2-diethoxyethyl)isopropylcarbamoyl]ethyl}-3-(3,4-difluorobenzenesulfonylamino)-2-methanesulfonylaminopropionamide Synthesis takes place in analogy to Example 21e) starting from 2-benzyloxycarbonylamino-3-(3,4-difluorobenzenesulfonylamino)propionic acid. The desired product is obtained with MW=753.27 (calculated, monoisotopic); measured value (M-C$_2$H$_6$O+H)$^+$: 707.7 c) Benzyl[6-(4-chlorobenzyl)-1-(3,4-difluorobenzenesulfonyl)-8-isopropyl-4,7-dioxooctahydropyrazino[1,2-a]pyrimidin-3-yl]carbamate Synthesis takes place in analogy to Example 21f) starting from N-{2-(4-chlorophenyl)-1-[(2,2-diethoxyethyl)isopropylcarbamoyl]ethyl}-3-(3,4-difluorobenzenesulfonylamino)-2-methanesulfonylaminopropionamide. The desired product is obtained with MW=660 (calculated, monoisotopic); measured value (M+H)$^+$: 661.31 d) 3-Amino-6-(4-chlorobenzyl)-1-(3,4-difluorobenzenesulfonyl)-8-isopropylhexahydropyrazino[1,2-a]pyrimidine-4,7-dione Synthesis takes place in analogy to Example 21g) starting from benzyl[6-(4-chlorobenzyl)-1-(3,4-difluorobenzenesulfonyl)-8-isopropyl-4,7-dioxooctahydropyrazino[1,2-a]pyrimidin-3-yl]carbamate. The desired product is obtained with MW=526 (calculated, monoisotopic); measured value (M+H)$^+$: 527.10 e) 3-Amino-6-(4-chlorobenzyl)-1-(3,4-difluorobenzenesulfonyl)-8-isopropylhexahydropyrazino[1,2-a]pyrimidine-4,7-dione Synthesis takes place in analogy to Example 26 starting from 3-amino-6-(4-chlorobenzyl)-1-(3,4-difluorobenzenesulfonyl)-8-isopropylhexahydropyrazino[1,2-a]pyrimidine-4,7-dione. The desired product is obtained with MW=604.1 (calculated, monoisotopic); measured value (M+H)$^+$: 605.11

EXAMPLE 108

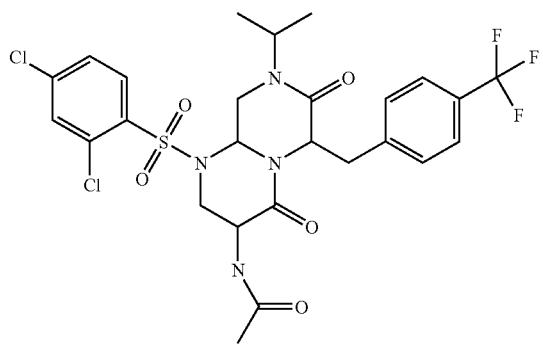

a) 9H-fluoren-9-ylmethyl[1-[(2,2-diethoxyethyl)isopropylcarbamoyl]-2-(4-trifluoromethylphenyl)ethyl]carbamate Synthesis takes place in analogy to Example 29a) (Method B) starting from N-Fmoc-4-CF$_3$-Phe-OH. The desired product is obtained with MW=612.28 (calculated, monoisotopic); measured value (M+Na)$^+$: 635.28 b) 2-Amino-3-(4-trifluoromethylphenyl)-N-(2,2-diethoxyethyl)-N-isopropylpropionamide Synthesis takes place in analogy to Example 29b) (Method B) starting from 9H-fluoren-9-ylmethyl[1-[(2,2-diethoxyethyl)isopropylcarbamoyl]-2-(4-trifluoromethylphenyl)ethyl]-carbamate. The desired product is obtained with MW=390.21 (calculated, monoisotopic); measured value (M+Na)$^+$: 413.22 c) 9H-Fluoren-9-ylmethyl(2-benzyloxycarbonylamino-2-{2-(4-trifluoromethylphenyl)-1-[(2,2-diethoxyethyl)isopropylcarbamoyl]ethylcarbamoyl}ethyl)carbamate Synthesis took place in analogy to Example 29c) (Method B) starting from 2-amino-3-(4-trifluoromethylphenyl)-N-(2,2-diethoxyethyl)-N-isopropylpropionamide. The desired product is obtained with MW=832.37 (calculated, monoisotopic); measured value (M+Na)$^+$: 855.0 d) Benzyl(2-amino-1-{2-(4-trifluoromethylphenyl)-1-[(2,2-diethoxyethyl)isopropylcarbamoyl]ethylcarbamoyl}ethyl)carbamate Synthesis took place in analogy to Example 29d) (Method B) starting from 9H-fluoren-9-ylmethyl(2-benzyloxycarbonylamino-2-{2-(4-trifluoromethylphenyl)-1-[(2,2-diethoxyethyl)isopropylcarbamoyl]ethylcarbamoyl}ethyl)carbamate. The desired product is obtained with MW=610.30 (calculated, monoisotopic); measured value (M+Na)$^+$: 611.33 e) Benzyl[1-{2-(4-trifluoromethylphenyl)-1-[(2,2-diethoxyethyl)isopropylcarbamoyl]-ethylcarbamoyl}-2-(2,4-dichlorobenzenesulfonylamino)ethyl]carbamate Synthesis took place in analogy to Example 29e) (Method B) starting from benzyl (2-amino-1-{2-(4-trifluoromethylphenyl)-1-[(2,2-diethoxyethyl)isopropylcarbamoyl]ethylcarbamoyl}ethyl)carbamate. The desired product is obtained with MW=818.21 (calculated, monoisotopic); measured value (M+Na)$^+$: 841.2 f) Benzyl[6-(4-trifluoromethylbenzyl)-1-(2,4-dichlorobenzenesulfonyl)-8-isopropyl-4,7-dioxooctahydropyrazino[1,2-a]pyrimidin-3-yl]carbamate Synthesis took place in analogy to Example 29f) (Method B) starting from benzyl[1-{2-(4-trifluoromethylphenyl)-1-[(2,2-diethoxyethyl)isopropylcarbamoyl]ethylcarbamoyl}-2-(2,4-dichlorobenzenesulfonylamino)ethyl]carbamate. The desired product is obtained with MW=726.13 (calculated, monoisotopic); measured value (M+H)$^+$: 727.14 g) 3-Amino-6-(4-trifluoromethylbenzyl)-1-(2,4-dichlorobenzenesulfonyl)-8-isopropylhexahydropyrazino[1,2-a]pyrimidine-4,7-dione Synthesis took place in analogy to Example 29g) (Method B) starting from benzyl[6-(4-trifluoromethylbenzyl)-1-(2,4-dichlorobenzenesulfonyl)-8-isopropyl-4,7-dioxooctahydropyrazino[1,2-a]pyrimidin-3-yl]carbamate. The desired product is obtained with MW=592.09 (calculated, monoisotopic); measured value (M+Na)$^+$: 593.09 h) N-[6-(4-Trifluoromethylbenzyl)-1-(2,4-dichlorobenzenesulfonyl)-8-isopropyl-4,7-dioxooctahydropyrazino[1,2-a]pyrimidin-3-yl]acetamide Synthesis takes place in analogy to Example 21h) starting from 3-amino-6-(4-trifluoromethylbenzyl)-1-(2,4-dichlorobenzenesulfonyl)-8-isopropylhexahydropyrazino[1,2-a]pyrimidine-4,7-dione. The desired product is obtained with MW=634.10 (calculated, monoisotopic); measured value (M+H)$^+$: 635.12

EXAMPLE 109

N-[1-(2,4-Dichlorobenzenesulfonyl)-8-isopropyl-4,7-dioxo-6-(4-trifluoromethylbenzyl)-octahydropyrazino[1,2-a]pyrimidin-3-yl]cyclopropanecarboxamide Structure:

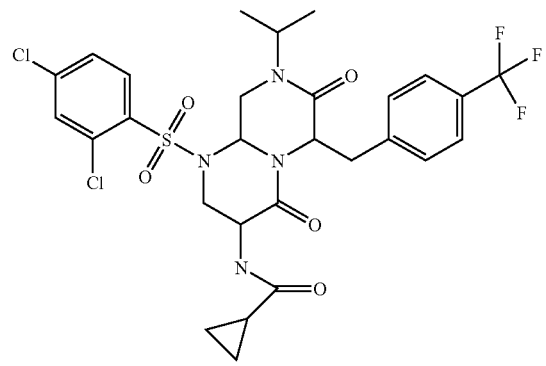

Synthesis takes place in analogy to Example 22 starting from 3-amino-6-(4-trifluoromethylbenzyl)-1-(2,4-dichlorobenzenesulfonyl)-8-isopropylhexahydropyrazino[1,2-a]pyrimidine-4,7-dione. The desired product is obtained with MW=660.12 (calculated, monoisotopic); measured value (M+H)$^+$: 661.13

EXAMPLE 110

N-[1-(2,4-Dichlorobenzenesulfonyl)-8-isopropyl-4,7-dioxo-6-(4-trifluoromethylbenzyl)-octahydropyrazino[1,2-a]pyrimidin-3-yl]cyclobutanecarboxamide Structure:

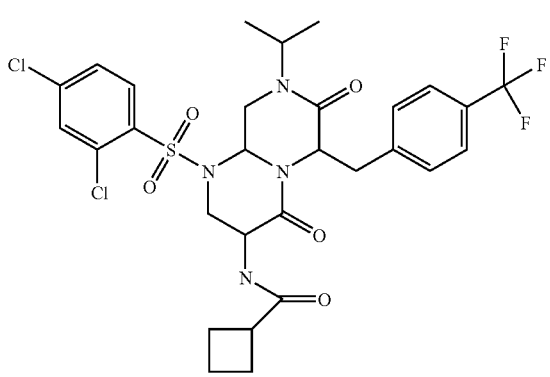

Synthesis takes place in analogy to Example 30 starting from 3-amino-6-(4-trifluoromethylbenzyl)-1-(2,4-dichlorobenzenesulfonyl)-8-isopropylhexahydropyrazino[1,2-a]pyrimidine-4,7-dione. The desired product is obtained with MW=674.13 (calculated, monoisotopic); measured value (M+H)$^+$: 675.15

EXAMPLE 111

N-[1-(2,4-Dichlorobenzenesulfonyl)-8-isopropyl-4,7-dioxo-6-(4-trifluoromethylbenzyl)-octahydropyrazino[1,2-a]pyrimidin-3-yl]cyclopentanecarboxamide Structure:

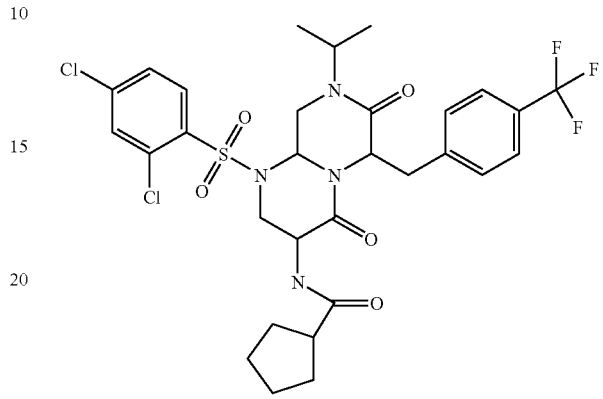

Synthesis takes place in analogy to Example 31 starting from 3-amino-6-(4-trifluoromethylbenzyl)-1-(2,4-dichlorobenzenesulfonyl)-8-isopropylhexahydropyrazino[1,2-a]pyrimidine-4,7-dione. The desired product is obtained with MW=688.15 (calculated, monoisotopic); measured value (M+H)$^+$: 689.16

EXAMPLE 112

N-[1-(2,4-Dichlorobenzenesulfonyl)-8-isopropyl-4,7-dioxo-6-(4-trifluoromethylbenzyl)-octahydropyrazino[1,2-a]pyrimidin-3-yl]pyrrolidine-2-carboxamide Structure:

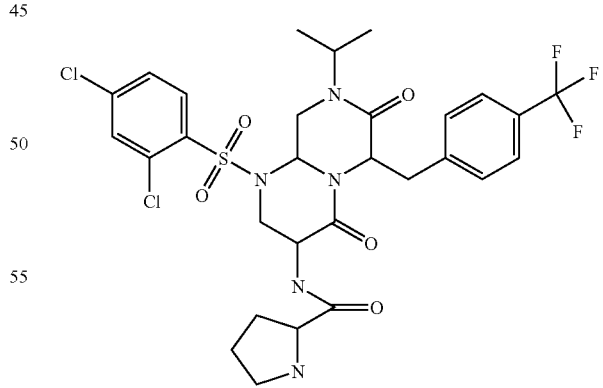

Synthesis takes place in analogy to Example 40 starting from 3-amino-6-(4-trifluoromethylbenzyl)-1-(2,4-dichlorobenzenesulfonyl)-8-isopropylhexahydropyrazino[1,2-a]pyrimidine-4,7-dione. The desired product is obtained with MW=689.15 (calculated, monoisotopic); measured value (M+H)$^+$: 690.10.

EXAMPLE 113

N-[1-(2,4-Dichlorobenzenesulfonyl)-8-isopropyl-4,
7-dioxo-6-(4-trifluoromethylbenzyl)-octahydropy-
razino[1,2-a]pyrimidin-3-yl]4-dimethylaminobenza-
mide Structure:

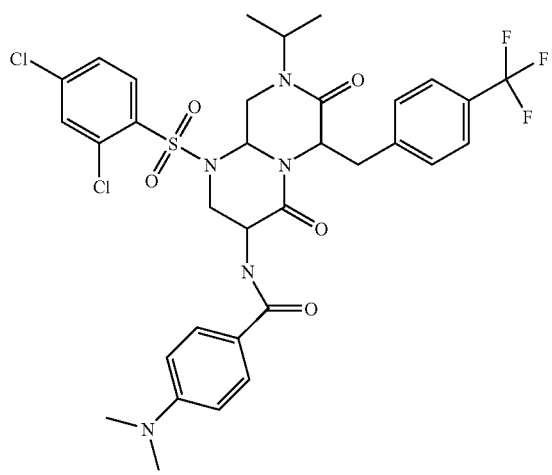

Synthesis takes place in analogy to Example 25 starting from 3-amino-6-(4-trifluoromethylbenzyl)-1-(2,4-dichlorobenzenesulfonyl)-8-isopropylhexahydropyrazino[1,2-a]pyrimidine-4,7-dione. The desired product is obtained with MW=739.16 (calculated, monoisotopic); measured value (M+H)$^+$: 740.15

EXAMPLE 114

1-tert-Butyl-3-[1-(2,4-dichlorobenzenesulfonyl)-8-
isopropyl-4,7-dioxo-6-(4-trifluoromethylbenzyl)-
octahydropyrazino[1,2-a]pyrimidin-3-yl]urea Structure:

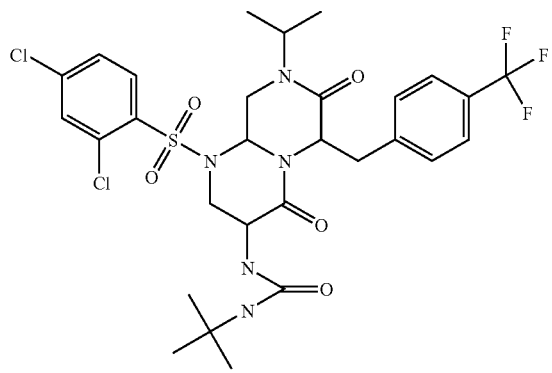

Synthesis takes place in analogy to Example 28 starting from 3-amino-6-(4-trifluoromethylbenzyl)-1-(2,4-dichlorobenzenesulfonyl)-8-isopropylhexahydropyrazino[1,2-a]pyrimidine-4,7-dione. The desired product is obtained with MW=691.16 (calculated, monoisotopic); measured value (M+H)$^+$: 692.18

EXAMPLE 115

N-[1-(2,4-Dichlorobenzenesulfonyl)-8-isopropyl-4,
7-dioxo-6-(4-trifluoromethylbenzyl)-octahydropy-
razino[1,2-a]pyrimidin-3-yl]methane sulfonamide Structure:

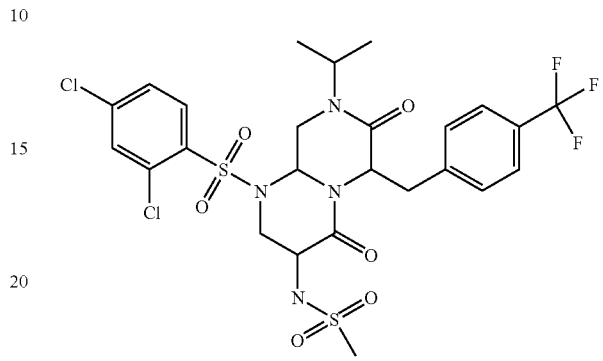

Synthesis takes place in analogy to Example 26 starting from 3-amino-6-(4-trifluoromethylbenzyl)-1-(2,4-dichlorobenzenesulfonyl)-8-isopropylhexahydropyrazino[1,2-a]pyrimidine-4,7-dione. The desired product is obtained with MW=670.07 (calculated, monoisotopic); measured value (M+H)$^+$: 671.08

EXAMPLE 116

N-[1-(2,4-Dichlorobenzenesulfonyl)-8-isopropyl-4,
7-dioxo-6-(4-trifluoromethylbenzyl)-octahydropy-
razino[1,2-a]pyrimidin-3-yl]cyclopropanecarboxam-
ide Structure:

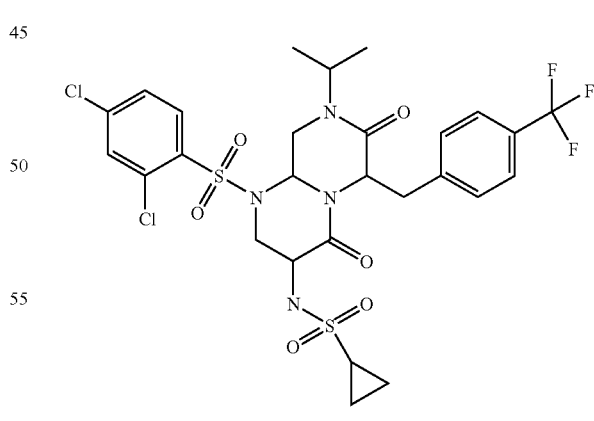

Synthesis takes place in analogy to Example 27 starting from 3-amino-6-(4-trifluoromethylbenzyl)-1-(2,4-dichlorobenzenesulfonyl)-8-isopropylhexahydropyrazino[1,2-a]pyrimidine-4,7-dione. The desired product is obtained with MW=696.09 (calculated, monoisotopic); measured value (M+H)$^+$: 697.0

EXAMPLE 117

1-(2,4-Dichlorobenzenesulfonyl)-3-dimethylamino-8-isopropyl-6-(4-trifluoromethylbenzyl)hexahydropyrazino[1,2-a]pyrimidine-4,7-dione Structure:

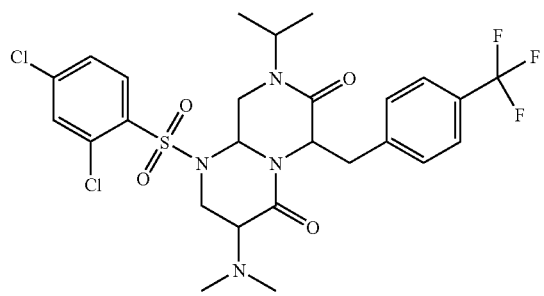

Synthesis takes place in analogy to Example 72 starting from 3-amino-6-(4-trifluoromethylbenzyl)-1-(2,4-dichlorobenzenesulfonyl)-8-isopropylhexahydropyrazino[1,2-a]pyrimidine-4,7-dione. The desired product is obtained with MW=620.12 (calculated, monoisotopic); measured value (M+H)$^+$: 621.09

EXAMPLE 118

3-Azetidin-1-yl-1-(2,4-dichlorobenzenesulfonyl)-8-isopropyl-6-(4-trifluoromethylbenzyl)hexahydropyrazino[1,2-a]pyrimidine-4,7-dione Structure:

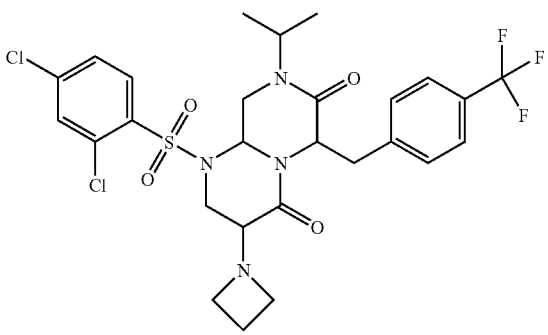

Synthesis takes place in analogy to Example 73 starting from 3-amino-6-(4-trifluoromethylbenzyl)-1-(2,4-dichlorobenzenesulfonyl)-8-isopropylhexahydropyrazino[1,2-a]pyrimidine-4,7-dione. The desired product is obtained with MW=632.12 (calculated, monoisotopic); measured value (M+H)$^+$: 633.0

EXAMPLE 119

1-(2,4-Dichlorobenzenesulfonyl)-8-isopropyl-3-pyrrolidin-1-yl-6-(4-trifluoromethylbenzyl)hexahydropyrazino[1,2-a]pyrimidine-4,7-dione Structure:

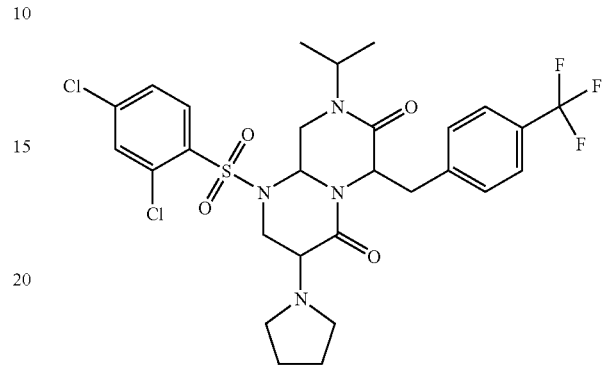

Synthesis takes place in analogy to Example 74 starting from 3-amino-6-(4-trifluoromethylbenzyl)-1-(2,4-dichlorobenzenesulfonyl)-8-isopropylhexahydropyrazino[1,2-a]pyrimidine-4,7-dione. The desired product is obtained with MW=646.14 (calculated, monoisotopic); measured value (M+H)$^+$: 647.14

EXAMPLE 120

1-(2,4-Dichlorobenzenesulfonyl)-8-isopropyl-3-piperidin-1-yl-6-(4-trifluoromethylbenzyl)hexahydropyrazino[1,2-a]pyrimidine-4,7-dione Structure:

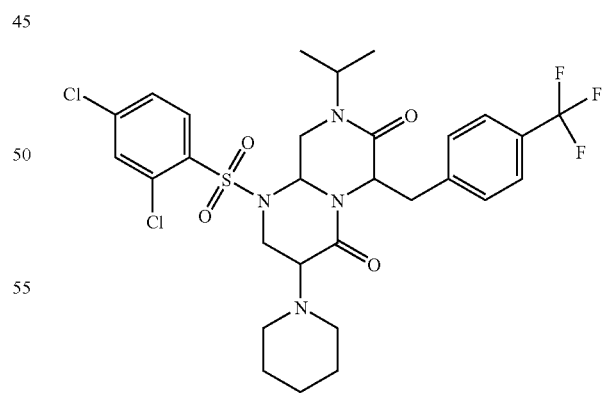

Synthesis takes place in analogy to Example 59 starting from 3-amino-6-(4-trifluoromethylbenzyl)-1-(2,4-dichlorobenzenesulfonyl)-8-isopropylhexahydropyrazino[1,2-a]pyrimidine-4,7-dione. The desired product is obtained with MW=660.16 (calculated, monoisotopic); measured value (M+H)$^+$: 661.13

EXAMPLE 121

1-(2,4-Dichlorobenzenesulfonyl)-8-isopropyl-3-morpholin-4-yl-6-(4-trifluoromethylbenzyl)hexahydropyrazino[1,2-a]pyrimidine-4,7-dione Structure:

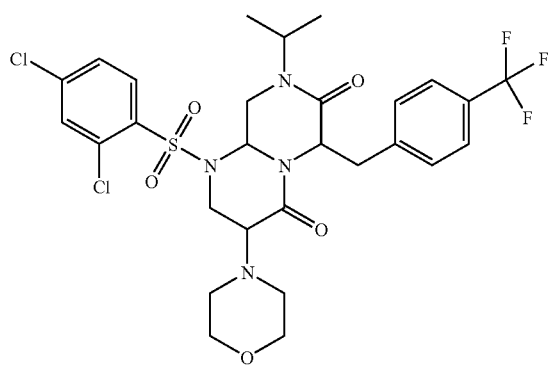

Synthesis takes place in analogy to Example 60 starting from 3-amino-6-(4-trifluoromethylbenzyl)-1-(2,4-dichlorobenzenesulfonyl)-8-isopropylhexahydropyrazino[1,2-a]pyrimidine-4,7-dione. The desired product is obtained with MW=662.13 (calculated, monoisotopic); measured value (M+H)$^+$: 663.07

EXAMPLE 122

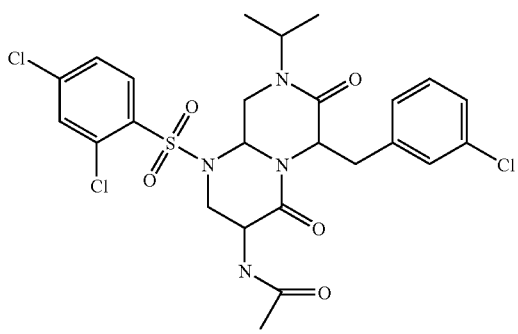

a) 9H-Fluoren-9-ylmethyl[1-[(2,2-diethoxyethyl)isopropylcarbamoyl]-2-(3-chlorophenyl)ethyl]carbamate Synthesis takes place in analogy to Example 29a) (Method B) starting from N-Fmoc-3-Cl-Phe-OH. The desired product is obtained with MW=578.25 (calculated, monoisotopic); measured value (M+H)$^+$: 579.27 b) 2-Amino-3-(3-chlorophenyl)-N-(2,2-diethoxyethyl)-N-isopropylpropionamide

Synthesis takes place in analogy to Example 29b) (Method B) starting from 9H-fluoren-9-ylmethyl[1-[(2,2-diethoxyethyl)isopropylcarbamoyl]-2-(3-chlorophenyl)ethyl]carbamate. The desired product is obtained with MW=356.19 (calculated, monoisotopic); measured value (M+Na)$^+$: 379.18 c) 9H-Fluoren-9-ylmethyl(2-benzyloxycarbonylamino-2-{2-(3-chlorophenyl)-1-[(2,2-diethoxyethyl)isopropylcarbamoyl]ethylcarbamoyl}ethyl)carbamate Synthesis took place in analogy to Example 29c) (Method B) starting from 2-amino-3-(3-chlorophenyl)-N-(2,2-diethoxyethyl)-N-isopropylpropionamide. The desired product is obtained with MW=798.34 (calculated, monoisotopic); measured value (M+H)$^+$: 799.35 d) Benzyl(2-amino-1-{2-(3-chlorophenyl)-1-[(2,2-diethoxyethyl)isopropylcarbamoyl]-ethylcarbamoyl}ethyl)carbamate Synthesis took place in analogy to Example 29d) (Method B) starting from 9H-fluoren-9-ylmethyl(2-benzyloxycarbonylamino-2-{2-(3-chlorophenyl)-1-[(2,2-diethoxyethyl)isopropylcarbamoyl]ethylcarbamoyl}ethyl)carbamate. The desired product is obtained with MW=576.27 (calculated, monoisotopic); measured value (M+H)$^+$: 577.22 e) Benzyl[1-{2-(3-chlorophenyl)-1-[(2,2-diethoxyethyl)isopropylcarbamoyl]ethylcarbamoyl}-2-(2,4-dichlorobenzenesulfonylamino)ethyl]carbamate Synthesis took place in analogy to Example 29e) (Method B) starting from benzyl (2-amino-1-{2-(3-chlorophenyl)-1-[(2,2-diethoxyethyl)isopropylcarbamoyl]ethylcarbamoyl}ethyl)carbamate. The desired product is obtained with MW=784.19 (calculated, monoisotopic); measured value (M+H)$^+$: 785.18 f) Benzyl[6-(3-chlorobenzyl)-1-(2,4-dichlorobenzenesulfonyl)-8-isopropyl-4,7-dioxooctahydropyrazino[1,2-a]pyrimidin-3-yl]carbamate Synthesis took place in analogy to Example 29f) (Method B) starting from benzyl[1-{2-(3-chlorophenyl)-1-[(2,2-diethoxyethyl)isopropylcarbamoyl]ethylcarbamoyl}-2-(2,4-dichlorobenzenesulfonylamino)ethyl]carbamate. The desired product is obtained with MW=692.10 (calculated, monoisotopic); measured value (M+H)$^+$: 693.08 g) 3-Amino-6-(3-chlorobenzyl)-1-(2,4-dichlorobenzenesulfonyl)-8-isopropylhexahydropyrazino[1,2-a]pyrimidine-4,7-dione Synthesis took place in analogy to Example 29g) (Method B) starting from benzyl[6-(3-chlorobenzyl)-1-(2,4-dichlorobenzenesulfonyl)-8-isopropyl-4,7-dioxooctahydropyrazino[1,2-a]pyrimidin-3-yl]carbamate. The desired product is obtained with MW=558.07 (calculated, monoisotopic); measured value (M+H)$^+$: 559.07 h) N-[6-(3-chlorobenzyl)-1-(2,4-dichlorobenzenesulfonyl)-8-isopropyl-4,7-dioxooctahydropyrazino[1,2-a]pyrimidin-3-yl]acetamide Synthesis takes place in analogy to Example 21h) starting from 3-amino-6-(3-chlorobenzyl)-1-(2,4-dichlorobenzenesulfonyl)-8-isopropylhexahydropyrazino[1,2-a]pyrimidine-4,7-dione. The desired product is obtained with MW=600.08 (calculated, monoisotopic); measured value (M+H)$^+$: 601.07

EXAMPLE 123

N-[6-(3-Chlorobenzyl)-1-(2,4-dichlorobenzenesulfo-
nyl)-8-isopropyl-4,7-dioxooctahydropyrazino[1,2-a]
pyrimidin-3-yl]cyclopropanecarboxamide Structure:

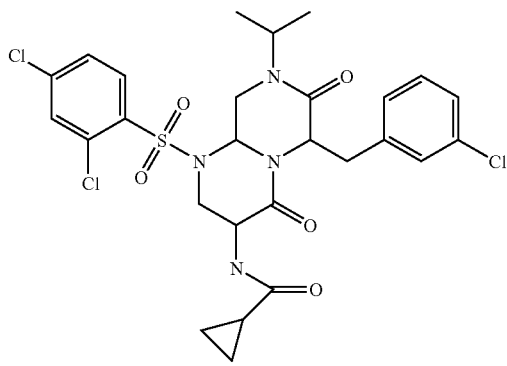

Synthesis takes place in analogy to Example 22 starting from 3-amino-6-(3-chlorobenzyl)-1-(2,4-dichlorobenzenesulfonyl)-8-isopropylhexahydropyrazino[1,2-a]pyrimidine-4,7-dione. The desired product is obtained with MW=626.09 (calculated, monoisotopic); measured value (M+H)$^+$: 627.08

EXAMPLE 124

N-[6-(3-Chlorobenzyl)-1-(2,4-dichlorobenzenesulfo-
nyl)-8-isopropyl-4,7-dioxooctahydropyrazino[1,2-a]
pyrimidin-3-yl]cyclobutanecarboxamide Structure:

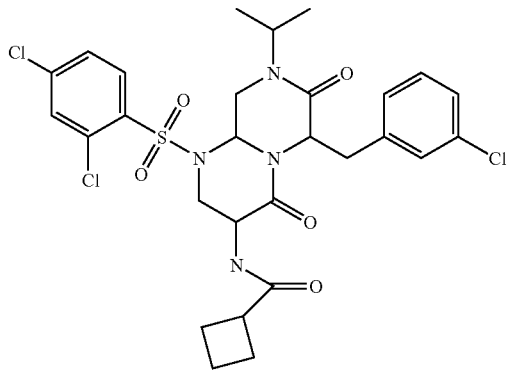

Synthesis takes place in analogy to Example 30 starting from 3-amino-6-(3-chlorobenzyl)-1-(2,4-dichlorobenzenesulfonyl)-8-isopropylhexahydropyrazino[1,2-a]pyrimidine-4,7-dione. The desired product is obtained with MW=640.11 (calculated, monoisotopic); measured value (M+H)$^+$: 641.08

EXAMPLE 125

N-[6-(3-Chlorobenzyl)-1-(2,4-dichlorobenzenesulfo-
nyl)-8-isopropyl-4,7-dioxooctahydropyrazino[1,2-a]
pyrimidin-3-yl]cyclopentanecarboxamide Structure:

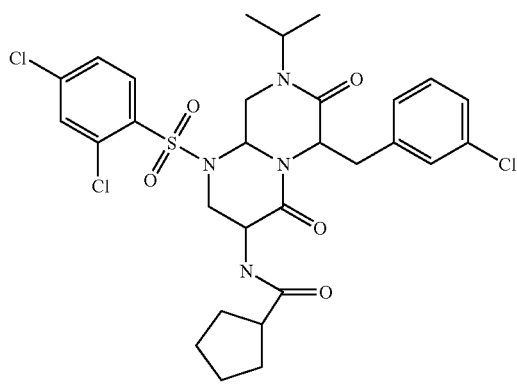

Synthesis takes place in analogy to Example 31 starting from 3-amino-6-(3-chlorobenzyl)-1-(2,4-dichlorobenzenesulfonyl)-8-isopropylhexahydropyrazino[1,2-a]pyrimidine-4,7-dione. The desired product is obtained with MW=654.12 (calculated, monoisotopic); measured value (M+H)$^+$: 655.09

EXAMPLE 126

N-[6-(3-Chlorobenzyl)-1-(2,4-dichlorobenzenesulfo-
nyl)-8-isopropyl-4,7-dioxooctahydropyrazino[1,2-a]
pyrimidin-3-yl]-4-dimethylaminobenzamide Structure:

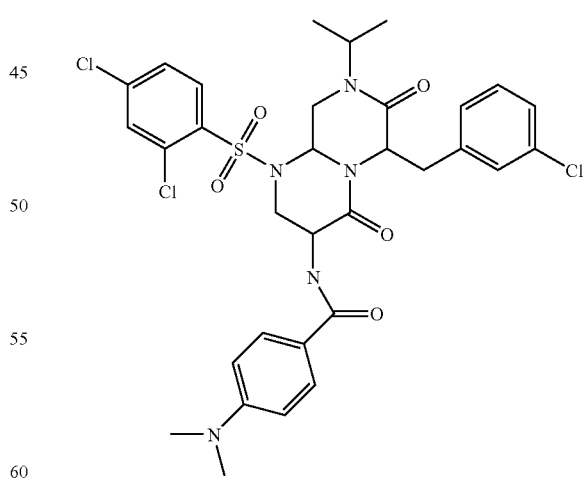

Synthesis takes place in analogy to Example 25 starting from 3-amino-6-(3-chlorobenzyl)-1-(2,4-dichlorobenzenesulfonyl)-8-isopropylhexahydropyrazino[1,2-a]pyrimidine-4,7-dione. The desired product is obtained with MW=705.13 (calculated, monoisotopic); measured value (M+H)$^+$: 706.10

EXAMPLE 127

1-tert-Butyl-3-[6-(3-chlorobenzyl)-1-(2,4-dichlorobenzenesulfonyl)-8-isopropyl-4,7-dioxooctahydropyrazino[1,2-a]pyrimidin-3-yl]urea Structure:

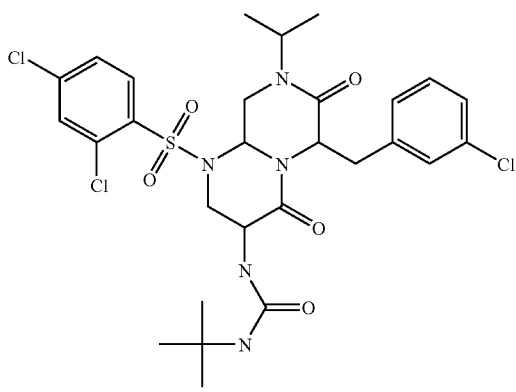

Synthesis takes place in analogy to Example 28 starting from 3-amino-6-(3-chlorobenzyl)-1-(2,4-dichlorobenzenesulfonyl)-8-isopropylhexahydropyrazino[1,2-a]pyrimidine-4,7-dione. The desired product is obtained with MW=657.13 (calculated, monoisotopic); measured value $(M+H)^+$: 658.11

EXAMPLE 128

N-[6-(3-Chlorobenzyl)-1-(2,4-dichlorobenzenesulfonyl)-8-isopropyl-4,7-dioxooctahydropyrazino[1,2-a]pyrimidin-3-yl]methanesulfonamide Structure:

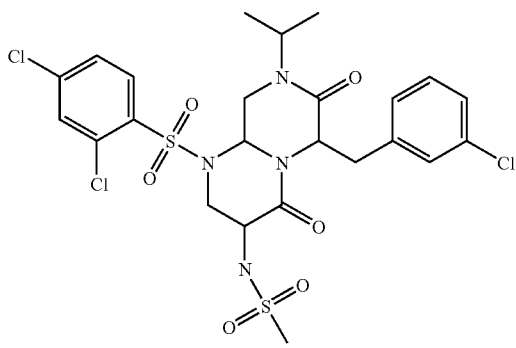

Synthesis takes place in analogy to Example 26 starting from 3-amino-6-(3-chlorobenzyl)-1-(2,4-dichlorobenzenesulfonyl)-8-isopropylhexahydropyrazino[1,2-a]pyrimidine-4,7-dione. The desired product is obtained with MW=636.04 (calculated, monoisotopic); measured value $(M+H)^+$: 637.03

EXAMPLE 129

6-(3-Chlorobenzyl)-1-(2,4-dichlorobenzenesulfonyl)-3-dimethylamino-8-isopropylhexahydropyrazino[1,2-a]pyrimidine-4,7-dione Structure:

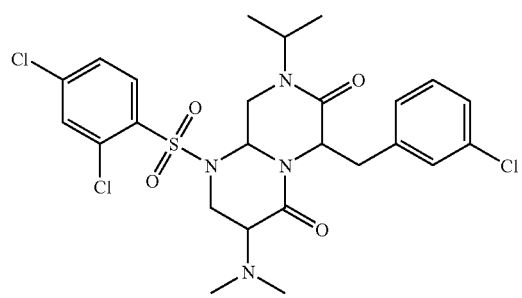

Synthesis takes place in analogy to Example 72 starting from 3-amino-6-(3-chlorobenzyl)-1-(2,4-dichlorobenzenesulfonyl)-8-isopropylhexahydropyrazino[1,2-a]pyrimidine-4,7-dione. The desired product is obtained with MW=586.10 (calculated, monoisotopic); measured value $(M+H)^+$: 587.09

EXAMPLE 130

6-(3-Chlorobenzyl)-1-(2,4-dichlorobenzenesulfonyl)-8-isopropyl-3-pyrrolidin-1-ylhexahydropyrazino[1,2-a]pyrimidine-4,7-dione Structure:

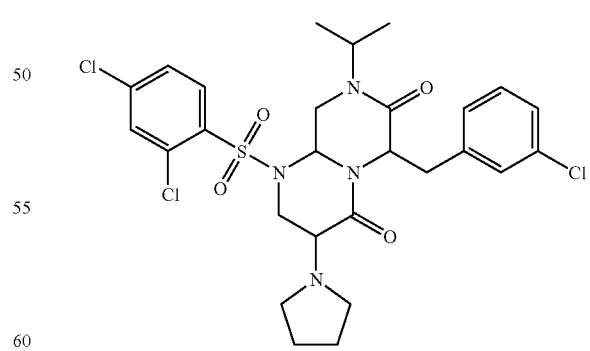

Synthesis takes place in analogy to Example 74 starting from 3-amino-6-(3-chlorobenzyl)-1-(2,4-dichlorobenzenesulfonyl)-8-isopropylhexahydropyrazino[1,2-a]pyrimidine-4,7-dione. The desired product is obtained with MW=612.11 (calculated, monoisotopic); measured value $(M+H)^+$: 613.10

EXAMPLE 131

6-(3-Chlorobenzyl)-1-(2,4-dichlorobenzenesulfo-
nyl)-8-isopropyl-3-piperidin-1-ylhexahydropyrazino
[1,2-a]pyrimidine-4,7-dione Structure:

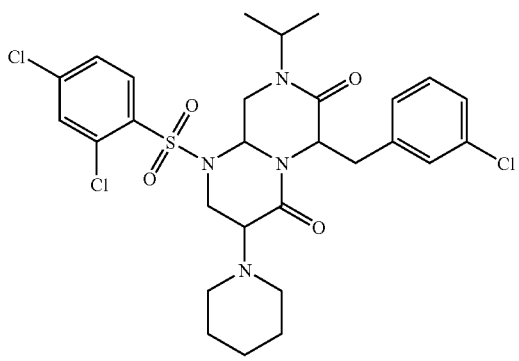

Synthesis takes place in analogy to Example 59 starting from 3-amino-6-(3-chlorobenzyl)-1-(2,4-dichlorobenzene-sulfonyl)-8-isopropylhexahydropyrazino[1,2-a]pyrimidine-4,7-dione. The desired product is obtained with MW=626.13 (calculated, monoisotopic); measured value (M+H)+: 627.13

EXAMPLE 132

6-(3-Chlorobenzyl)-1-(2,4-dichlorobenzenesulfo-
nyl)-8-isopropyl-3-morpholin-4-ylhexahydropy-
razino[1,2-a]pyrimidine-4,7-dione Structure:

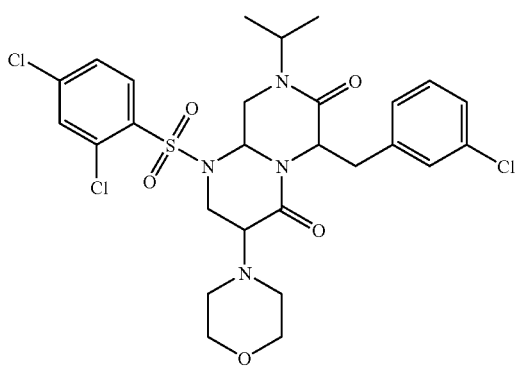

Synthesis takes place in analogy to Example 60 starting from 3-amino-6-(3-chlorobenzyl)-1-(2,4-dichlorobenzene-sulfonyl)-8-isopropylhexahydropyrazino[1,2-a]pyrimidine-4,7-dione. The desired product is obtained with MW=628.11 (calculated, monoisotopic); measured value (M+H)+: 629.09

EXAMPLE 133

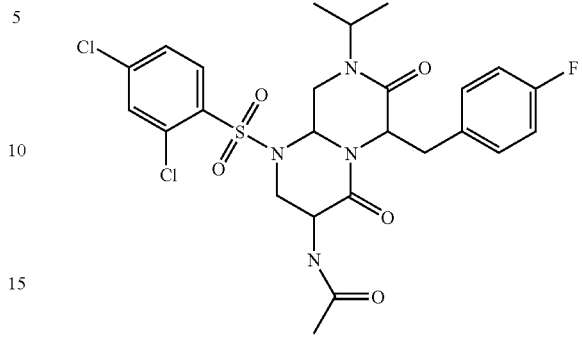

a) 9H-Fluoren-9-ylmethyl[1-[(2,2-diethoxyethyl)
isopropylcarbamoyl]-2-(4-fluorophenyl)ethyl]car-
bamate Synthesis takes place in analogy to Example 29a) (Method B) starting from N-Fmoc-4-FPhe-OH. The desired product is obtained with MW=562.28 (calculated, monoisotopic); measured value (M+H)+: 563.27 b) 2-Amino-3-(4-fluorophenyl)-N-(2,2-diethoxy-
ethyl)-N-isopropylpropionamide

Synthesis takes place in analogy to Example 29b) (Method B) starting from 9H-fluoren-9-ylmethyl[1-[(2,2-diethoxy-ethyl)isopropylcarbamoyl]-2-(4-fluorophenyl)ethyl]car-bamate. The desired product is obtained with MW=340.22 (calculated, monoisotopic); measured value (M+H)+: 341.20 c) 9H-Fluoren-9-ylmethyl(2-benzyloxycarbony-
lamino-2-{2-(4-fluorophenyl)-1-[(2,2-diethoxyethyl)
isopropylcarbamoyl]ethylcarbamoyl}ethyl)carbam-
ate Synthesis took place in analogy to Example 29c) (Method B) starting from 2-amino-3-(4-fluorophenyl)-N-(2,2-di-ethoxyethyl)-N-isopropylpropionamide. The desired product is obtained with MW=782.37 (calculated, monoisotopic); measured value (M+Na)+: 805.37 d) Benzyl(2-amino-1-{2-(4-fluorophenyl)-1-[(2,2-
diethoxyethyl)isopropylcarbamoyl]-
ethylcarbamoyl}ethyl)carbamate Synthesis took place in analogy to Example 29d) (Method B) starting from 9H-fluoren-9-ylmethyl(2-benzyloxycarbo-nylamino-2-{2-(4-fluorophenyl)-1-[(2,2-diethoxyethyl)iso-propylcarbamoyl]ethylcarbamoyl}ethyl)carbamate. The desired product is obtained with MW=560.30 (calculated, monoisotopic); measured value (M+H)+: 561.31 e) Benzyl[1-{2-(4-fluorophenyl)-1-[(2,2-diethoxy-
ethyl)isopropylcarbamoyl]ethylcarbamoyl}-2-(2,4-
dichlorobenzenesulfonylamino)ethyl]carbamate Synthesis took place in analogy to Example 29e) (Method B) starting from benzyl (2-amino-1-{2-(4-fluorophenyl)-1-[(2,2-diethoxyethyl)isopropylcarbamoyl]

ethylcarbamoyl}ethyl)carbamate. The desired product is obtained with MW=768.22 (calculated, monoisotopic); measured value (M+Na)⁺: 791.23 f) Benzyl[6-(4-fluorobenzyl)-1-(2,4-dichlorobenzenesulfonyl)-8-isopropyl-4,7-dioxooctahydropyrazino[1,2-a]pyrimidin-3-yl]carbamate Synthesis took place in analogy to Example 29f) (Method B) starting from benzyl[1-{2-(4-fluorophenyl)-1-[(2,2-diethoxyethyl)isopropylcarbamoyl]ethylcarbamoyl}-2-(2,4-dichlorobenzenesulfonylamino)ethyl]carbamate. The desired product is obtained with MW=676.13 (calculated, monoisotopic); measured value (M+H)⁺: 677.1 g) 3-Amino-6-(4-fluorobenzyl)-1-(2,4-dichlorobenzenesulfonyl)-8-isopropylhexahydropyrazino[1,2-a]pyrimidine-4,7-dione Synthesis took place in analogy to Example 29g) (Method B) starting from benzyl[6-(4-fluorobenzyl)-1-(2,4-dichlorobenzenesulfonyl)-8-isopropyl-4,7-dioxooctahydropyrazino[1,2-a]pyrimidin-3-yl]carbamate. The desired product is obtained with MW=542.1 (calculated, monoisotopic); measured value (M+H)⁺: 543.12 h) N-[6-(4-Fluorobenzyl)-1-(2,4-dichlorobenzenesulfonyl)-8-isopropyl-4,7-dioxooctahydropyrazino[1,2-a]pyrimidin-3-yl]acetamide Synthesis takes place in analogy to Example 21h) starting from 3-amino-6-(4-fluorobenzyl)-1-(2,4-dichlorobenzenesulfonyl)-8-isopropylhexahydropyrazino[1,2-a]pyrimidine-4,7-dione. The desired product is obtained with MW=584.11 (calculated, monoisotopic); measured value (M+H)⁺: 585.08

EXAMPLE 134

N-[1-(2,4-Dichlorobenzenesulfonyl)-6-(4-fluorobenzyl)-8-isopropyl-4,7-dioxooctahydropyrazino[1,2-a]pyrimidin-3-yl]cyclopropanecarboxamide Structure:

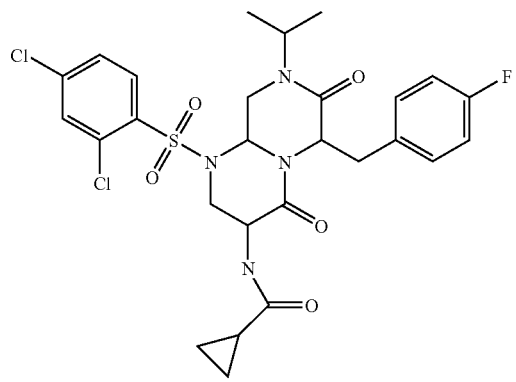

Synthesis takes place in analogy to Example 22 starting from 3-amino-6-(4-fluorobenzyl)-1-(2,4-dichlorobenzenesulfonyl)-8-isopropylhexahydropyrazino[1,2-a]pyrimidine-4,7-dione. The desired product is obtained with MW=610.12 (calculated, monoisotopic); measured value (M+H)⁺: 611.09

EXAMPLE 135

N-[1-(2,4-Dichlorobenzenesulfonyl)-6-(4-fluorobenzyl)-8-isopropyl-4,7-dioxooctahydropyrazino[1,2-a]pyrimidin-3-yl]cyclobutanecarboxamide Structure:

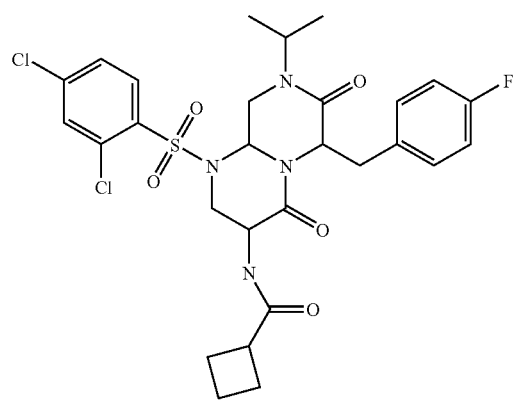

Synthesis takes place in analogy to Example 30 starting from 3-amino-6-(4-fluorobenzyl)-1-(2,4-dichlorobenzenesulfonyl)-8-isopropylhexahydropyrazino[1,2-a]pyrimidine-4,7-dione. The desired product is obtained with MW=624.14 (calculated, monoisotopic); measured value (M+H)⁺: 625.13

EXAMPLE 136

N-[1-(2,4-Dichlorobenzenesulfonyl)-6-(4-fluorobenzyl)-8-isopropyl-4,7-dioxooctahydropyrazino[1,2-a]pyrimidin-3-yl]cyclopentanecarboxamide Structure:

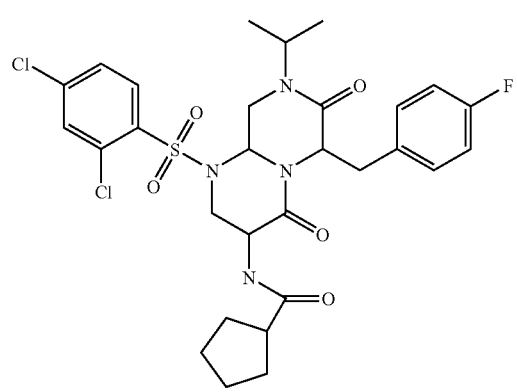

Synthesis takes place in analogy to Example 31 starting from 3-amino-6-(4-fluorobenzyl)-1-(2,4-dichlorobenzenesulfonyl)-8-isopropylhexahydropyrazino[1,2-a]pyrimidine-4,7-dione. The desired product is obtained with MW=638.15 (calculated, monoisotopic); measured value (M+H)⁺: 639.14

EXAMPLE 137

N-[1-(2,4-Dichlorobenzenesulfonyl)-6-(4-fluorobenzyl)-8-isopropyl-4,7-dioxooctahydropyrazino[1,2-a]pyrimidin-3-yl]-4-dimethylaminobenzamide Structure:

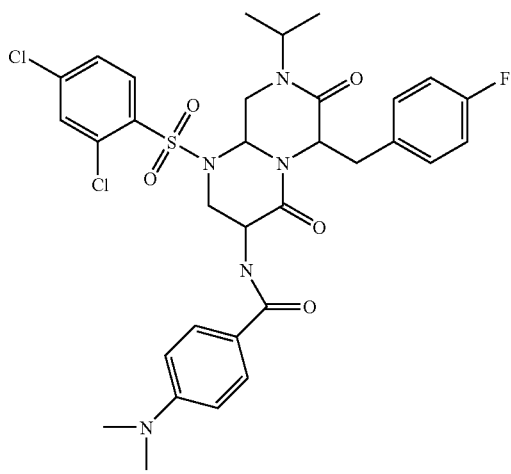

Synthesis takes place in analogy to Example 25 starting from 3-amino-6-(4-fluorobenzyl)-1-(2,4-dichlorobenzenesulfonyl)-8-isopropylhexahydropyrazino[1,2-a]pyrimidine-4,7-dione. The desired product is obtained with MW=689.16 (calculated, monoisotopic); measured value (M+H)$^+$: 690.10

EXAMPLE 138

N-[1-(2,4-Dichlorobenzenesulfonyl)-6-(4-fluorobenzyl)-8-isopropyl-4,7-dioxooctahydropyrazino[1,2-a]pyrimidin-3-yl]methanesulfonamide Structure:

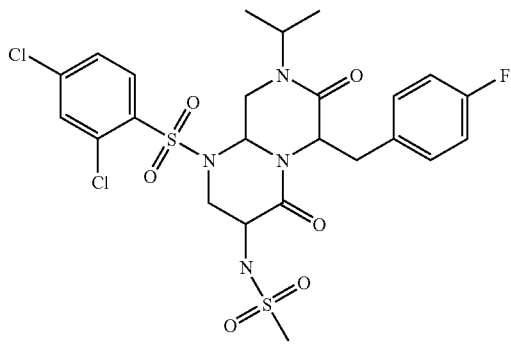

Synthesis takes place in analogy to Example 26 starting from 3-amino-6-(4-fluorobenzyl)-1-(2,4-dichlorobenzenesulfonyl)-8-isopropylhexahydropyrazino[1,2-a]pyrimidine-4,7-dione. The desired product is obtained with MW=620.07 (calculated, monoisotopic); measured value (M+H)$^+$: 621.04

EXAMPLE 139

1-(2,4-Dichlorobenzenesulfonyl)-3-dimethylamino-6-(4-fluorobenzyl)-8-isopropylhexahydropyrazino[1,2-a]pyrimidine-4,7-dione Structure:

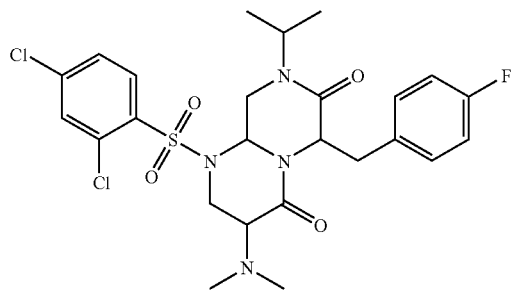

Synthesis takes place in analogy to Example 72 starting from 3-amino-6-(4-fluorobenzyl)-1-(2,4-dichlorobenzenesulfonyl)-8-isopropylhexahydropyrazino[1,2-a]pyrimidine-4,7-dione. The desired product is obtained with MW=570.13 (calculated, monoisotopic); measured value (M+H)$^+$: 571.09

EXAMPLE 140

3-Azetidin-1-yl-1-(2,4-dichlorobenzenesulfonyl)-6-(4-fluorobenzyl)-8-isopropylhexahydropyrazino[1,2-a]pyrimidine-4,7-dione Structure:

Synthesis takes place in analogy to Example 73 starting from 3-amino-6-(4-fluorobenzyl)-1-(2,4-dichlorobenzenesulfonyl)-8-isopropylhexahydropyrazino[1,2-a]pyrimidine-4,7-dione. The desired product is obtained with MW=582.13 (calculated, monoisotopic); measured value (M+H)$^+$: 583.04

EXAMPLE 141

1-(2,4-Dichlorobenzenesulfonyl)-6-(4-fluorobenzyl)-8-isopropyl-3-pyrrolidin-1-ylhexahydropyrazino[1,2-a]pyrimidine-4,7-dione Structure:

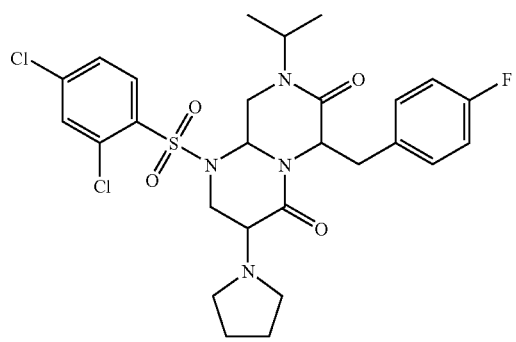

Synthesis takes place in analogy to Example 74 starting from 3-amino-6-(4-fluorobenzyl)-1-(2,4-dichlorobenzenesulfonyl)-8-isopropylhexahydropyrazino[1,2-a]pyrimidine-4,7-dione. The desired product is obtained with MW=596.14 (calculated, monoisotopic); measured value (M+H)$^+$: 597.12

EXAMPLE 142

1-(2,4-Dichlorobenzenesulfonyl)-6-(4-fluorobenzyl)-8-isopropyl-3-piperidin-1-ylhexahydropyrazino[1,2-a]pyrimidine-4,7-dione Structure:

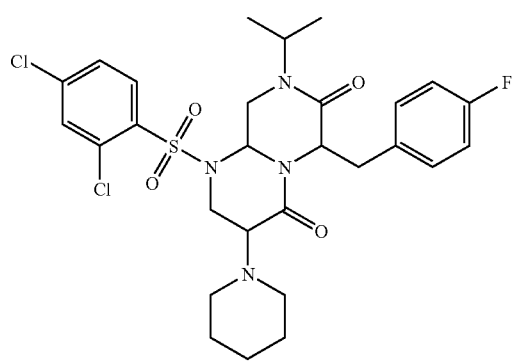

Synthesis takes place in analogy to Example 59 starting from 3-amino-6-(4-fluorobenzyl)-1-(2,4-dichlorobenzenesulfonyl)-8-isopropylhexahydropyrazino[1,2-a]pyrimidine-4,7-dione. The desired product is obtained with MW=610.16 (calculated, monoisotopic); measured value (M+H)$^+$: 611.16

EXAMPLE 143

1-(2,4-Dichlorobenzenesulfonyl)-6-(4-fluorobenzyl)-8-isopropyl-3-morpholin-4-ylhexahydropyrazino[1,2-a]pyrimidine-4,7-dione Structure:

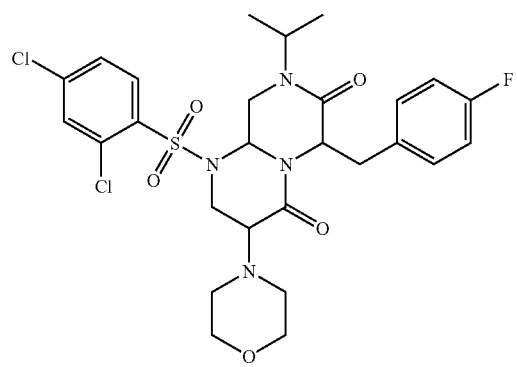

Synthesis takes place in analogy to Example 60 starting from 3-amino-6-(4-fluorobenzyl)-1-(2,4-dichlorobenzenesulfonyl)-8-isopropylhexahydropyrazino[1,2-a]pyrimidine-4,7-dione. The desired product is obtained with MW=612.14 (calculated, monoisotopic); measured value (M+H)$^+$: 613.13

EXAMPLE 144

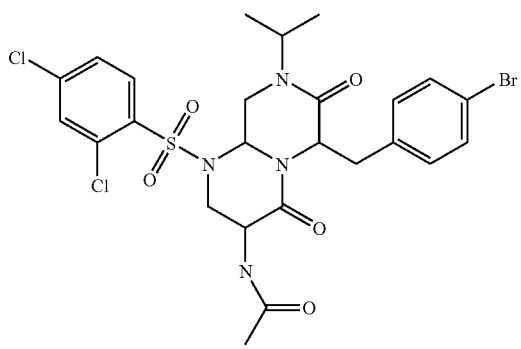

a) 9H-Fluoren-9-ylmethyl[1-[(2,2-diethoxyethyl)isopropylcarbamoyl]-2-(4-bromophenyl)ethyl]carbamate Synthesis takes place in analogy to Example 29a) (Method B) starting from N-Fmoc-4-Br-Phe-OH. The desired product is obtained with MW=622.20 (calculated, monoisotopic); measured value (M+Na)$^+$: 645.30 b) 2-Amino-3-(4-bromophenyl)-N-(2,2-diethoxyethyl)-N-isopropylpropionamide

Synthesis takes place in analogy to Example 29b) (Method B) starting from 9H-fluoren-9-ylmethyl[1-[(2,2-diethoxyethyl)isopropylcarbamoyl]-2-(4-bromophenyl)ethyl]carbamate. The desired product is obtained with MW=400.14 (calculated, monoisotopic); measured value (M+H)$^+$: 401.10 c) 9H-Fluoren-9-ylmethyl(2-benzyloxycarbony-
lamino-2-{2-(4-bromophenyl)-1-[(2,2-diethoxyethyl)
isopropylcarbamoyl]ethylcarbamoyl}ethyl)carbamate Synthesis took place in analogy to Example 29c) (Method B) starting from 2-amino-3-(4-bromophenyl)-N-(2,2-diethoxyethyl)-N-isopropylpropionamide. The desired product is obtained with MW=842.29 (calculated, monoisotopic); measured value (M+Na)+: 865.4 d) Benzyl(2-amino-1-{2-(4-bromophenyl)-1-[(2,2-diethoxyethyl)isopropylcarbamoyl]-
ethylcarbamoyl}ethyl)carbamate Synthesis took place in analogy to Example 29d) (Method B) starting from 9H-fluoren-9-ylmethyl(2-benzyloxycarbonylamino-2-{2-(4-bromophenyl)-1-[(2,2-diethoxyethyl)isopropylcarbamoyl]ethylcarbamoyl}ethyl)carbamate. The desired product is obtained with MW=620.22 (calculated, monoisotopic); measured value (M+H)+: 621.20 e) Benzyl[1-{2-(4-bromophenyl)-1-[(2,2-diethoxyethyl)isopropylcarbamoyl]ethylcarbamoyl}-2-(2,4-dichlorobenzenesulfonylamino)ethyl]carbamate Synthesis took place in analogy to Example 29e) (Method B) starting from benzyl (2-amino-1-{2-(4-bromophenyl)-1-[(2,2-diethoxyethyl)isopropylcarbamoyl]
ethylcarbamoyl}ethyl)carbamate. The desired product is obtained with MW=828.14 (calculated, monoisotopic); measured value (M+H)+: 829.11 f) Benzyl[6-(4-bromobenzyl)-1-(2,4-dichlorobenzenesulfonyl)-8-isopropyl-4,7-dioxooctahydropyrazino
[1,2-a]pyrimidin-3-yl]carbamate Synthesis took place in analogy to Example 29f) (Method B) starting from benzyl[1-{2-(4-bromophenyl)-1-[(2,2-diethoxyethyl)isopropylcarbamoyl]ethylcarbamoyl}-2-(2,4-dichlorobenzenesulfonylamino)ethyl]carbamate. The desired product is obtained with MW=736.05 (calculated, monoisotopic); measured value (M+H)+: 737.1 g) 3-Amino-6-(4-bromobenzyl)-1-(2,4-dichlorobenzenesulfonyl)-8-isopropylhexahydropyrazino[1,2-a]
pyrimidine-4,7-dione Synthesis took place in analogy to Example 29g) (Method B) starting from benzyl[6-(4-bromobenzyl)-1-(2,4-dichlorobenzenesulfonyl)-8-isopropyl-4,7-dioxooctahydropyrazino[1,2-a]pyrimidin-3-yl]carbamate. The desired product is obtained with MW=602.02 (calculated, monoisotopic); measured value (M+H)+: 603.01 h) N-[6-(4-Bromobenzyl)-1-(2,4-dichlorobenzenesulfonyl)-8-isopropyl-4,7-dioxooctahydropyrazino[1,
2-a]pyrimidin-3-yl]acetamide Synthesis takes place in analogy to Example 21h) starting from 3-amino-6-(4-bromobenzyl)-1-(2,4-dichlorobenzenesulfonyl)-8-isopropylhexahydropyrazino[1,2-a]pyrimidine-4,7-dione. The desired product is obtained with MW=644.03 (calculated, monoisotopic); measured value (M+H)+: 645.0

EXAMPLE 145

N-[6-(4-Bromobenzyl)-1-(2,4-dichlorobenzenesulfonyl)-8-isopropyl-4,7-dioxooctahydropyrazino[1,2-a]
pyrimidin-3-yl]cyclopropanecarboxamide Structure:

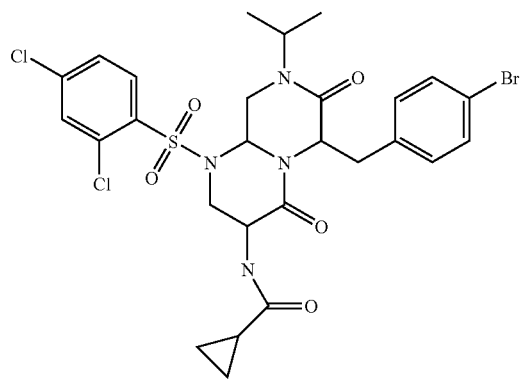

Synthesis takes place in analogy to Example 22 starting from 3-amino-6-(4-bromobenzyl)-1-(2,4-dichlorobenzenesulfonyl)-8-isopropylhexahydropyrazino[1,2-a]pyrimidine-4,7-dione. The desired product is obtained with MW=670.04 (calculated, monoisotopic); measured value (M+H)+: 671.06

EXAMPLE 146

N-[6-(4-Bromobenzyl)-1-(2,4-dichlorobenzenesulfonyl)-8-isopropyl-4,7-dioxooctahydropyrazino[1,2-a]
pyrimidin-3-yl]cyclobutanecarboxamide Structure:

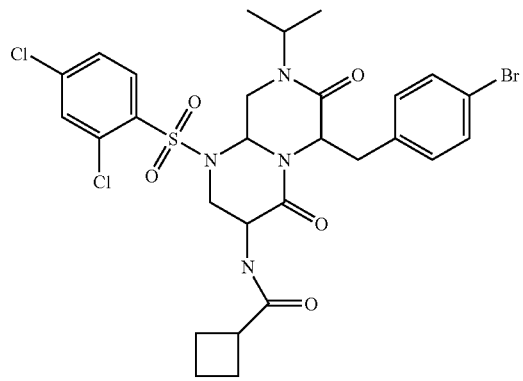

Synthesis takes place in analogy to Example 30 starting from 3-amino-6-(4-bromobenzyl)-1-(2,4-dichlorobenzenesulfonyl)-8-isopropylhexahydropyrazino[1,2-a]pyrimidine-4,7-dione. The desired product is obtained with MW=684.06 (calculated, monoisotopic); measured value (M+H)+: 685.04

EXAMPLE 147

N-[6-(4-Bromobenzyl)-1-(2,4-dichlorobenzenesulfonyl)-8-isopropyl-4,7-dioxooctahydropyrazino[1,2-a]pyrimidin-3-yl]cyclopentanecarboxamide Structure:

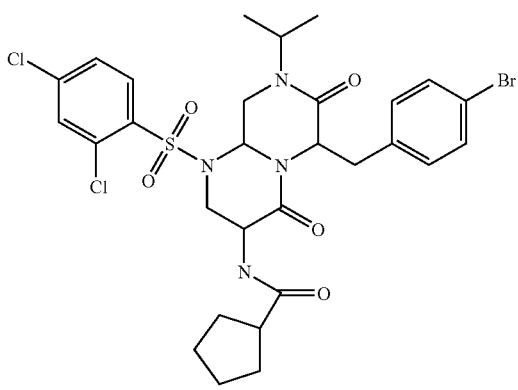

Synthesis takes place in analogy to Example 31 starting from 3-amino-6-(4-bromobenzyl)-1-(2,4-dichlorobenzenesulfonyl)-8-isopropylhexahydropyrazino[1,2-a]pyrimidine-4,7-dione. The desired product is obtained with MW=698.07 (calculated, monoisotopic); measured value (M+H)$^+$: 699.1

EXAMPLE 148

N-[6-(4-Bromobenzyl)-1-(2,4-dichlorobenzenesulfonyl)-8-isopropyl-4,7-dioxooctahydropyrazino[1,2-a]pyrimidin-3-yl]pyrrolidine-2-carboxamide Structure:

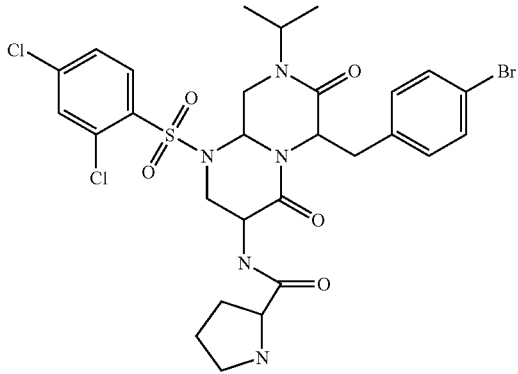

Synthesis takes place in analogy to Example 40 starting from 3-amino-6-(4-bromobenzyl)-1-(2,4-dichlorobenzenesulfonyl)-8-isopropylhexahydropyrazino[1,2-a]pyrimidine-4,7-dione. The desired product is obtained with MW=699.07 (calculated, monoisotopic); measured value (M+H)$^+$: 700.2

EXAMPLE 149

N-[6-(4-Bromobenzyl)-1-(2,4-dichlorobenzenesulfonyl)-8-isopropyl-4,7-dioxooctahydropyrazino[1,2-a]pyrimidin-3-yl]-4-dimethylaminobenzamide Structure:

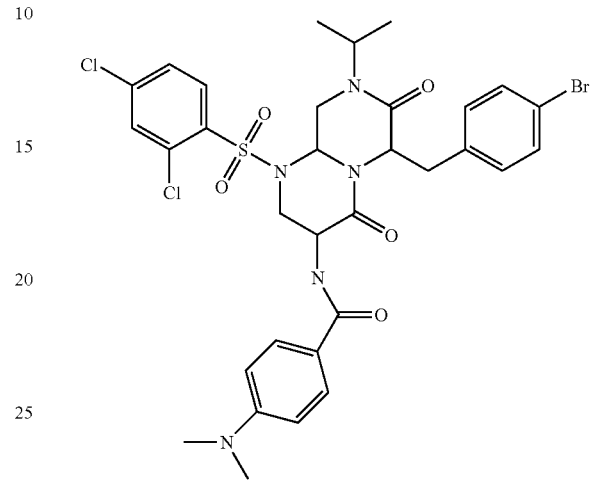

Synthesis takes place in analogy to Example 25 starting from 3-amino-6-(4-bromobenzyl)-1-(2,4-dichlorobenzenesulfonyl)-8-isopropylhexahydropyrazino[1,2-a]pyrimidine-4,7-dione. The desired product is obtained with MW=749.08 (calculated, monoisotopic); measured value (M+H)$^+$: 750.10

EXAMPLE 150

N-[6-(4-Bromobenzyl)-1-(2,4-dichlorobenzenesulfonyl)-8-isopropyl-4,7-dioxooctahydropyrazino[1,2-a]pyrimidin-3-yl]nicotinamide Structure:

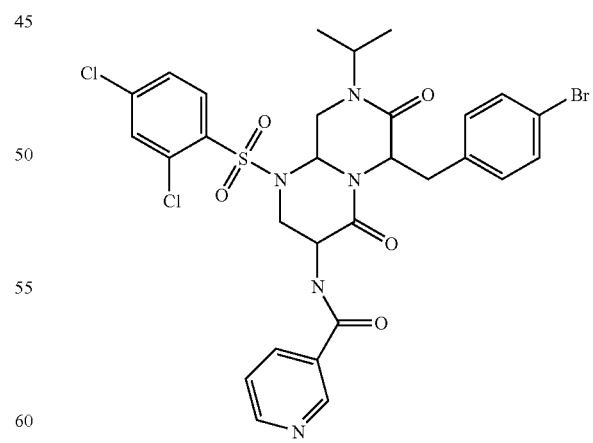

Synthesis takes place in analogy to Example 50 starting from 3-amino-6-(4-bromobenzyl)-1-(2,4-dichlorobenzenesulfonyl)-8-isopropylhexahydropyrazino[1,2-a]pyrimidine-4,7-dione. The desired product is obtained with MW=707.04 (calculated, monoisotopic); measured value (M+H)$^+$: 708.07

EXAMPLE 151

1-[6-(4-Bromobenzyl)-1-(2,4-dichlorobenzenesulfonyl)-8-isopropyl-4,7-dioxooctahydropyrazino[1,2-a]pyrimidin-3-yl]-3-tert-butylurea Structure:

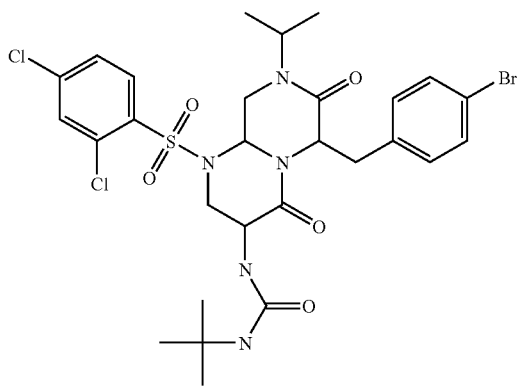

Synthesis takes place in analogy to Example 28 starting from 3-amino-6-(4-bromobenzyl)-1-(2,4-dichlorobenzenesulfonyl)-8-isopropylhexahydropyrazino[1,2-a]pyrimidine-4,7-dione. The desired product is obtained with MW=701.08 (calculated, monoisotopic); measured value (M+H)$^+$: 702.0

EXAMPLE 152

N-[6-(4-Bromobenzyl)-1-(2,4-dichlorobenzenesulfonyl)-8-isopropyl-4,7-dioxooctahydropyrazino[1,2-a]pyrimidin-3-yl]methanesulfonamide Structure:

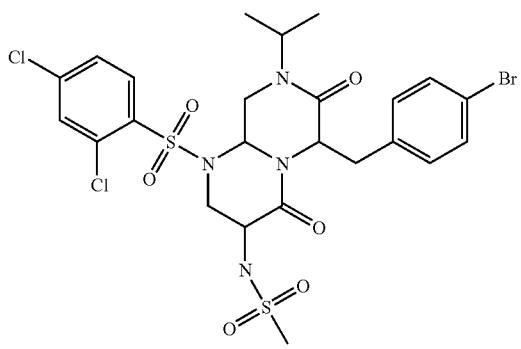

Synthesis takes place in analogy to Example 26 starting from 3-amino-6-(4-bromobenzyl)-1-(2,4-dichlorobenzenesulfonyl)-8-isopropylhexahydropyrazino[1,2-a]pyrimidine-4,7-dione. The desired product is obtained with MW=679.99 (calculated, monoisotopic); measured value (M+H)$^+$: 681.0

EXAMPLE 153

N-[6-(4-Bromobenzyl)-1-(2,4-dichlorobenzenesulfonyl)-8-isopropyl-4,7-dioxooctahydropyrazino[1,2-a]pyrimidin-3-yl]cyclopropanesulfonamide Structure:

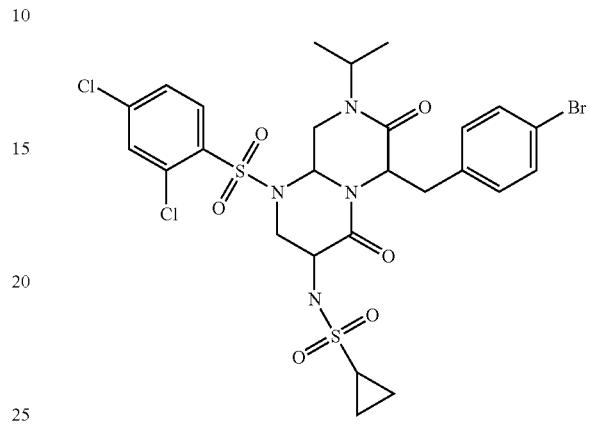

Synthesis takes place in analogy to Example 27 starting from 3-amino-6-(4-bromobenzyl)-1-(2,4-dichlorobenzenesulfonyl)-8-isopropylhexahydropyrazino[1,2-a]pyrimidine-4,7-dione. The desired product is obtained with MW=706.01 (calculated, monoisotopic); measured value (M+H)$^+$: 707.01

EXAMPLE 154

6-(4-Bromobenzyl)-1-(2,4-dichlorobenzenesulfonyl)-8-isopropyl-3-pyrrolidin-1-ylhexahydropyrazino[1,2-a]pyrimidine-4,7-dione Structure:

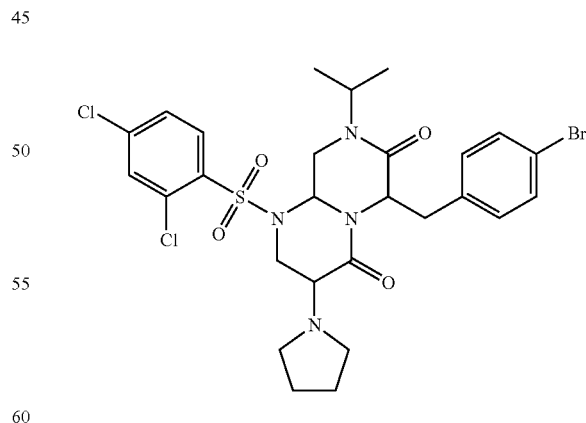

Synthesis takes place in analogy to Example 74 starting from 3-amino-6-(4-bromobenzyl)-1-(2,4-dichlorobenzenesulfonyl)-8-isopropylhexahydropyrazino[1,2-a]pyrimidine4,7-dione. The desired product is obtained with MW=656.06 (calculated, monoisotopic); measured value (M+H)$^+$: 657.06 -

EXAMPLE 155

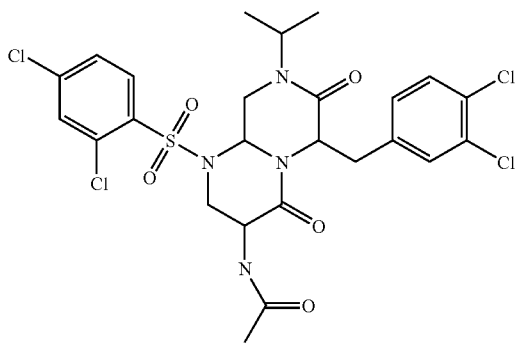

a) 9H-Fluoren-9-ylmethyl[1-[(2,2-diethoxyethyl)isopropylcarbamoyl]-2-(3,4-dichlorophenyl)ethyl]carbamate Synthesis takes place in analogy to Example 29a) (Method B) starting from N-Fmoc-3,4-Cl$_2$-Phe-OH. The desired product is obtained with MW=612.22 (calculated, monoisotopic); measured value (M+Na)$^+$: 635.2 b) 2-Amino-3-(3,4-dichlorophenyl)-N-(2,2-diethoxyethyl)-N-isopropylpropionamide Synthesis takes place in analogy to Example 29b) (Method B) starting from 9H-fluoren-9-ylmethyl[1-[(2,2-diethoxyethyl)isopropylcarbamoyl]-2-(3,4-dichlorophenyl)ethyl]-carbamate. The desired product is obtained with MW=390.34 (calculated, monoisotopic); measured value (M+Na)$^+$: 391.16 c) 9H-Fluoren-9-ylmethyl(2-benzyloxycarbonylamino-2-{2-(3,4-dichlorophenyl)-1-[(2,2-diethoxyethyl)isopropylcarbamoyl]ethylcarbamoyl}ethyl)carbamate Synthesis took place in analogy to Example 29c) (Method B) starting from 2-amino-3-(3,4-dichlorophenyl)-N-(2,2-diethoxyethyl)-N-isopropylpropionamide. The desired product is obtained with MW=832.30 (calculated, monoisotopic); measured value (M+H)$^+$: 833.30 d) Benzyl(2-amino-1-{2-(3,4-dichlorophenyl)-1-[(2,2-diethoxyethyl)isopropylcarbamoyl]-ethylcarbamoyl}ethyl)carbamate Synthesis took place in analogy to Example 29d) (Method B) starting from 9H-fluoren-9-ylmethyl(2-benzyloxycarbonylamino-2-{2-(3,4-dichlorophenyl)-1-[(2,2-diethoxyethyl)isopropylcarbamoyl]ethylcarbamoyl}ethyl)carbamate. The desired product is obtained with MW=610.23 (calculated, monoisotopic); measured value (M+H)$^+$: 611.27 e) Benzyl[1-{2-(3,4-dichlorophenyl)-1-[(2,2-diethoxyethyl)isopropylcarbamoyl]ethylcarbamoyl}-2-(2,4-dichlorobenzenesulfonylamino)ethyl]carbamate Synthesis took place in analogy to Example 29e) (Method B) starting from benzyl(2-amino-1-{2-(3,4-dichlorophenyl)-1-[(2,2-diethoxyethyl)isopropylcarbamoyl]ethylcarbamoyl}ethyl)carbamate. The desired product is obtained with MW=818.15 (calculated, monoisotopic); measured value (M+H)$^+$: 819.20 f) Benzyl[6-(3,4-dichlorobenzyl)-1-(2,4-dichlorobenzenesulfonyl)-8-isopropyl-4,7-dioxooctahydropyrazino[1,2-a]pyrimidin-3-yl]carbamate Synthesis took place in analogy to Example 29f) (Method B) starting from benzyl[1-{2-(3,4-dichlorophenyl)-1-[(2,2-diethoxyethyl)isopropylcarbamoyl]ethylcarbamoyl}-2-(2,4-dichlorobenzenesulfonylamino)ethyl]carbamate. The desired product is obtained with MW=726.06 (calculated, monoisotopic); measured value (M+H)$^+$: 727.1 g) 3-Amino-6-(3,4-dichlorobenzyl)-1-(2,4-dichlorobenzenesulfonyl)-8-isopropylhexahydropyrazino[1,2-a]pyrimidine-4,7-dione Synthesis took place in analogy to Example 29g) (Method B) starting from benzyl[6-(3,4-dichlorobenzyl)-1-(2,4-dichlorobenzenesulfonyl)-8-isopropyl-4,7-dioxooctahydropyrazino[1,2-a]pyrimidin-3-yl]carbamate. The desired product is obtained with MW=592.03 (calculated, monoisotopic); measured value (M+H)$^+$: 593.00 h) N-[6-(3,4-Dichlorobenzyl)-1-(2,4-dichlorobenzenesulfonyl)-8-isopropyl-4,7-dioxooctahydropyrazino[1,2-a]pyrimidin-3-yl]acetamide Synthesis takes place in analogy to Example 21h) starting from 3-amino-6-(3,4-dichlorobenzyl)-1-(2,4-dichlorobenzenesulfonyl)-8-isopropylhexahydropyrazino[1,2-a]pyrimidine-4,7-dione. The desired product is obtained with MW=634.04 (calculated, monoisotopic); measured value (M+H)$^+$: 635.0

EXAMPLE 156

N-[1-(2,4-Dichlorobenzenesulfonyl)-6-(3,4-dichlorobenzyl)-8-isopropyl-4,7-dioxooctahydropyrazino[1,2-a]pyrimidin-3-yl]cyclopropanecarboxamide Structure:

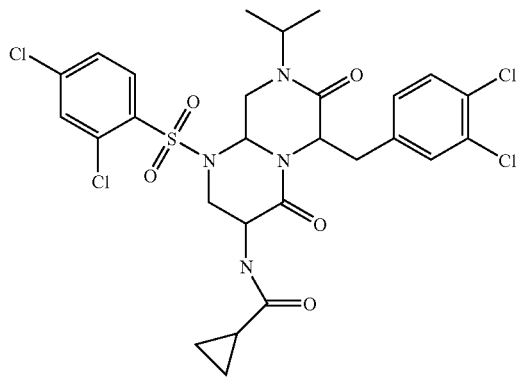

Synthesis takes place in analogy to Example 22 starting from 3-amino-6-(3,4-dichlorobenzyl)-1-(2,4-dichlorobenzenesulfonyl)-8-isopropylhexahydropyrazino[1,2-a]pyrimidine-4,7-dione. The desired product is obtained with MW=660.05 (calculated, monoisotopic); measured value (M+H)$^+$: 661.0

EXAMPLE 157

N-[1-(2,4-Dichlorobenzenesulfonyl)-6-(3,4-dichlorobenzyl)-8-isopropyl-4,7-dioxooctahydropyrazino[1,2-a]pyrimidin-3-yl]cyclobutanecarboxamide Structure:

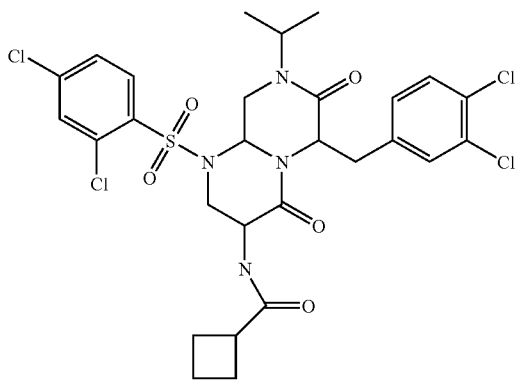

Synthesis takes place in analogy to Example 30 starting from 3-amino-6-(3,4-dichlorobenzyl)-1-(2,4-dichlorobenzenesulfonyl)-8-isopropylhexahydropyrazino[1,2-a]pyrimidine-4,7-dione. The desired product is obtained with MW=674.07 (calculated, monoisotopic); measured value (M+H)$^+$: 675.05

EXAMPLE 158

N-[1-(2,4-Dichlorobenzenesulfonyl)-6-(3,4-dichlorobenzyl)-8-isopropyl-4,7-dioxooctahydropyrazino[1,2-a]pyrimidin-3-yl]cyclopentanecarboxamide Structure:

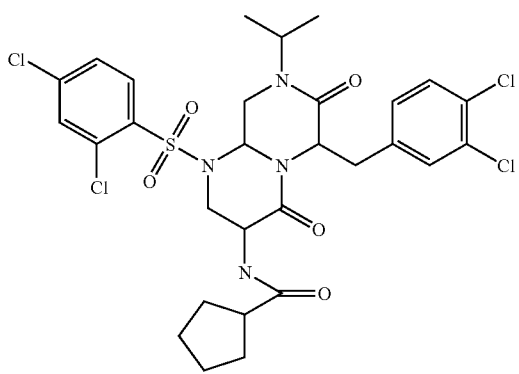

Synthesis takes place in analogy to Example 31 starting from 3-amino-6-(3,4-dichlorobenzyl)-1-(2,4-dichlorobenzenesulfonyl)-8-isopropylhexahydropyrazino[1,2-a]pyrimidine-4,7-dione. The desired product is obtained with MW=688.08 (calculated, monoisotopic); measured value (M+H)$^+$: 689.09

EXAMPLE 159

N-[1-(2,4-Dichlorobenzenesulfonyl)-6-(3,4-dichlorobenzyl)-8-isopropyl-4,7-dioxooctahydropyrazino[1,2-a]pyrimidin-3-yl]-4-dimethylaminobenzamide Structure:

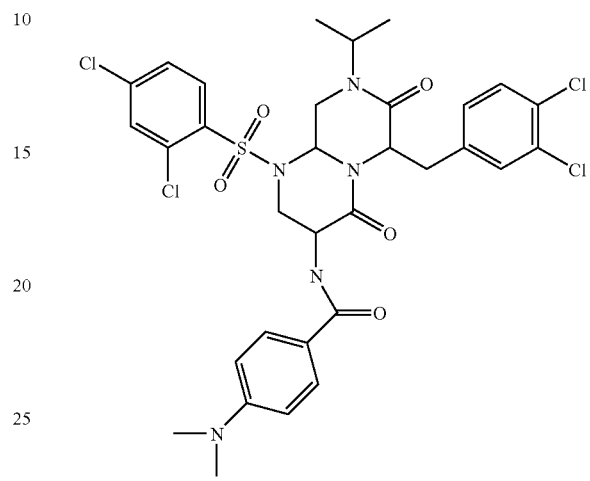

Synthesis takes place in analogy to Example 25 starting from 3-amino-6-(3,4-dichlorobenzyl)-1-(2,4-dichlorobenzenesulfonyl)-8-isopropylhexahydropyrazino[1,2-a]pyrimidine-4,7-dione. The desired product is obtained with MW=739.10 (calculated, monoisotopic); measured value (M+H)$^+$: 740.0

EXAMPLE 160

1-tert-Butyl-3-[1-(2,4-dichlorobenzenesulfonyl)-6-(3,4-dichlorobenzyl)-8-isopropyl-4,7-dioxooctahydropyrazino[1,2-a]pyrimidin-3-yl]urea Structure:

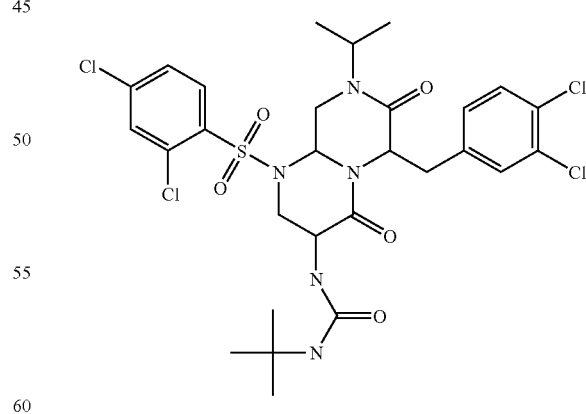

Synthesis takes place in analogy to Example 28 starting from 3-amino-6-(3,4-dichlorobenzyl)-1-(2,4-dichlorobenzenesulfonyl)-8-isopropylhexahydropyrazino[1,2-a]pyrimidine-4,7-dione. The desired product is obtained with MW=691.10 (calculated, monoisotopic); measured value (M+H)$^+$: 692.0

EXAMPLE 161

N-[1-(2,4-Dichlorobenzenesulfonyl)-6-(3,4-dichlorobenzyl)-8-isopropyl-4,7-dioxooctahydropyrazino[1,2-a]pyrimidin-3-yl]methanesulfonamide Structure:

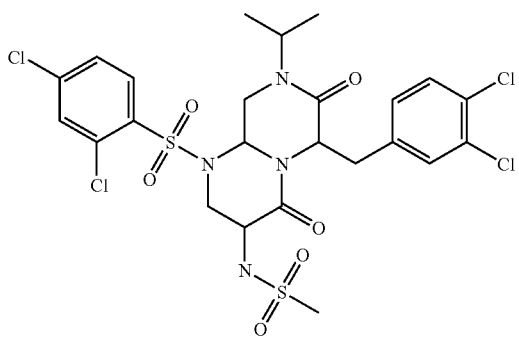

Synthesis takes place in analogy to Example 26 starting from 3-amino-6-(3,4-dichlorobenzyl)-1-(2,4-dichlorobenzenesulfonyl)-8-isopropylhexahydropyrazino[1,2-a]pyrimidine-4,7-dione. The desired product is obtained with MW=670.0 (calculated, monoisotopic); measured value (M+H)$^+$: 670.98

EXAMPLE 162

1-(2,4-Dichlorobenzenesulfonyl)-6-(3,4-dichlorobenzyl)-8-isopropyl-3-pyrrolidin-1-ylhexahydropyrazino[1,2-a]pyrimidine-4,7-dione Structure:

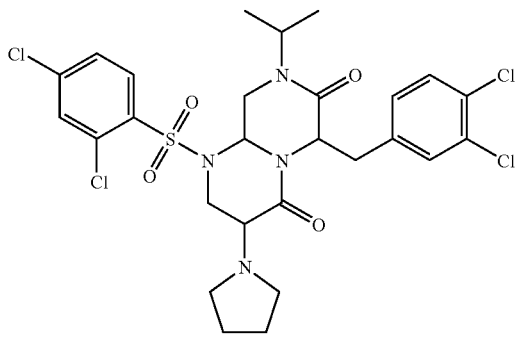

Synthesis takes place in analogy to Example 74 starting from 3-amino-6-(3,4-dichlorobenzyl)-1-(2,4-dichlorobenzenesulfonyl)-8-isopropylhexahydropyrazino[1,2-a]pyrimidine-4,7-dione. The desired product is obtained with MW=646.07 (calculated, monoisotopic); measured value (M+H)$^+$: 647.05

EXAMPLE 163

1-(2,4-Dichlorobenzenesulfonyl)-6-(3,4-dichlorobenzyl)-8-isopropyl-3-morpholin-4-ylhexahydropyrazino[1,2-a]pyrimidine-4,7-dione Structure:

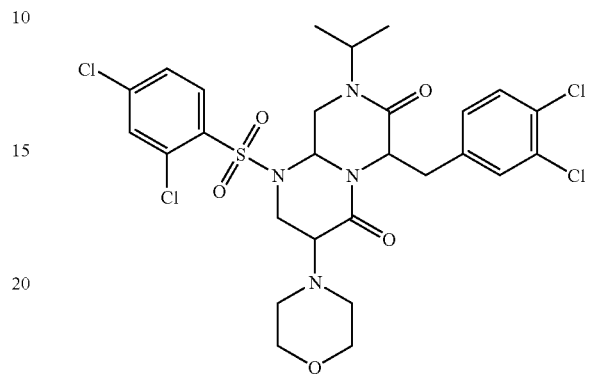

Synthesis takes place in analogy to Example 60 starting from 3-amino-6-(3,4-dichlorobenzyl)-1-(2,4-dichlorobenzenesulfonyl)-8-isopropylhexahydropyrazino[1,2-a]pyrimidine-4,7-dione. The desired product is obtained with MW=662.07 (calculated, monoisotopic); measured value (M+H)$^+$: 663.06

EXAMPLE 164

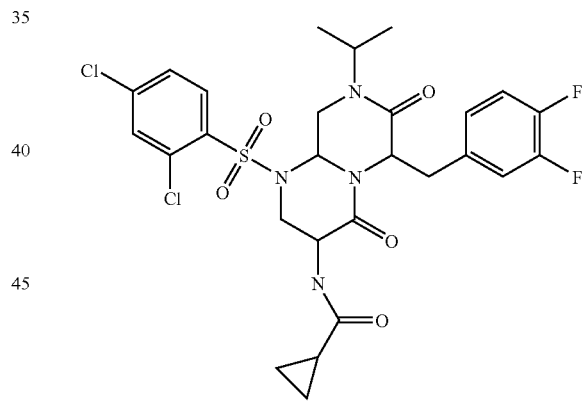

a) 9H-Fluoren-9-ylmethyl[1-[(2,2-diethoxyethyl)isopropylcarbamoyl]-2-(3,4-difluorophenyl)ethyl]carbamate Synthesis takes place in analogy to Example 29a) (Method B) starting from N-Fmoc-3,4-F$_2$-Phe-OH. The desired product is obtained with MW=580.27 (calculated, monoisotopic); measured value (M+Na)$^+$: 603.25 b) 2-Amino-3-(3,4-difluorophenyl)-N-(2,2-diethoxyethyl)-N-isopropylpropionamide

Synthesis takes place in analogy to Example 29b) (Method B) starting from 9H-fluoren-9-ylmethyl[1-[(2,2-diethoxyethyl)isopropylcarbamoyl]-2-(3,4-difluorophenyl)ethyl]-carbamate. The desired product is obtained with MW=358.21 (calculated, monoisotopic); measured value (M+H)$^+$: 359.2 c) 9H-Fluoren-9-ylmethyl(2-benzyloxycarbony-lamino-2-{2-(3,4-difluorophenyl)-1-[(2,2-diethoxy-ethyl)isopropylcarbamoyl]ethylcarbamoyl}ethyl)carbamate Synthesis took place in analogy to Example 29c) (Method B) starting from 2-amino-3-(3,4-difluorophenyl)-N-(2,2-diethoxyethyl)-N-isopropylpropionamide. The desired product is obtained with MW=800.36 (calculated, monoisotopic); measured value (M+H)$^+$: 801.35 d) Benzyl(2-amino-1-{2-(3,4-difluorophenyl)-1-[(2,2-diethoxyethyl)isopropylcarbamoyl]-ethylcarbamoyl}ethyl)carbamate Synthesis took place in analogy to Example 29d) (Method B) starting from 9H-fluoren-9-ylmethyl(2-benzyloxycarbonylamino-2-{2-(3,4-difluorophenyl)-1-[(2,2-diethoxyethyl)isopropylcarbamoyl]ethylcarbamoyl}ethyl)carbamate. The desired product is obtained with MW=578.29 (calculated, monoisotopic); measured value (M+H)$^+$: 579.31 e) Benzyl[1-{2-(3,4-difluorophenyl)-1-[(2,2-diethoxyethyl)isopropylcarbamoyl]ethylcarbamoyl}-2-(2,4-dichlorobenzenesulfonylamino)ethyl]carbamate Synthesis took place in analogy to Example 29e) (Method B) starting from benzyl (2-amino-1-{2-(3,4-difluorophenyl)-1-[(2,2-diethoxyethyl)isopropylcarbamoyl]ethylcarbamoyl}ethyl)carbamate. The desired product is obtained with MW=786.21 (calculated, monoisotopic); measured value (M+Na)$^+$: 809.19 f) Benzyl[6-(3,4-difluorobenzyl)-1-(2,4-dichlorobenzenesulfonyl)-8-isopropyl-4,7-dioxooctahydropyrazino[1,2-a]pyrimidin-3-yl]carbamate Synthesis took place in analogy to Example 29f) (Method B) starting from benzyl[1-{2-(3,4-difluorophenyl)-1-[(2,2-diethoxyethyl)isopropylcarbamoyl]ethylcarbamoyl}-2-(2,4-dichlorobenzenesulfonylamino)ethyl]carbamate. The desired product is obtained with MW=694.12 (calculated, monoisotopic); measured value (M+H)$^+$: 695.10 g) 3-Amino-6-(3,4-difluorobenzyl)-1-(2,4-dichlorobenzenesulfonyl)-8-isopropylhexahydropyrazino[1,2-a]pyrimidine-4,7-dione Synthesis took place in analogy to Example 29g) (Method B) starting from benzyl[6-(3,4-difluorobenzyl)-1-(2,4-dichlorobenzenesulfonyl)-8-isopropyl-4,7-dioxooctahydropyrazino[1,2-a]pyrimidin-3-yl]carbamate. The desired product is obtained with MW=560.09 (calculated, monoisotopic); measured value (M+H)$^+$: 561.13 h) N-[1-(2,4-dichlorobenzenesulfonyl)-6-(3,4-difluorobenzyl)-8-isopropyl-4,7-dioxooctahydropyrazino[1,2-a]pyrimidin-3-yl]cyclopropanecarboxamide Synthesis takes place in analogy to Example 22 starting from 3-amino-6-(3,4-difluorobenzyl)-1-(2,4-dichlorobenzenesulfonyl)-8-isopropylhexahydropyrazino[1,2-a]pyrimidine-4,7-dione. The desired product is obtained with MW=628.11 (calculated, monoisotopic); measured value (M+H)$^+$: 629.18

EXAMPLE 165

N-[1-(2,4-Dichlorobenzenesulfonyl)-6-(3,4-difluorobenzyl)-8-isopropyl-4,7-dioxooctahydropyrazino[1,2-a]pyrimidin-3-yl]cyclobutanecarboxamide Structure:

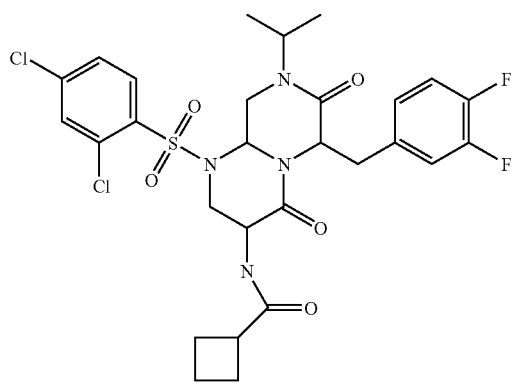

Synthesis takes place in analogy to Example 30 starting from 3-amino-6-(3,4-difluorobenzyl)-1-(2,4-dichlorobenzenesulfonyl)-8-isopropylhexahydropyrazino[1,2-a]pyrimidine-4,7-dione. The desired product is obtained with MW=642.13 (calculated, monoisotopic); measured value (M+H)$^+$: 643.21

EXAMPLE 166

N-[1-(2,4-Dichlorobenzenesulfonyl)-6-(3,4-difluorobenzyl)-8-isopropyl-4,7-dioxooctahydropyrazino[1,2-a]pyrimidin-3-yl]cyclopentanecarboxamide Structure:

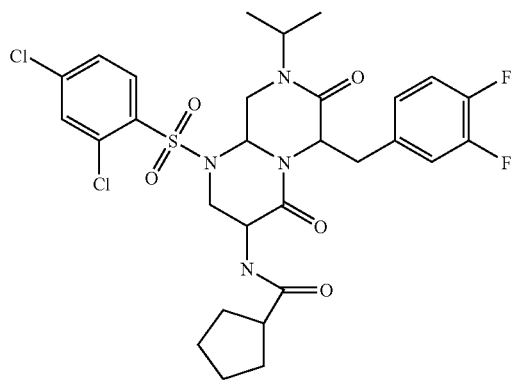

Synthesis takes place in analogy to Example 31 starting from 3-amino-6-(3,4-difluorobenzyl)-1-(2,4-dichlorobenzenesulfonyl)-8-isopropylhexahydropyrazino[1,2-a]pyrimidine-4,7-dione. The desired product is obtained with MW=656.14 (calculated, monoisotopic); measured value (M+H)$^+$: 657.21

EXAMPLE 167

N-[1-(2,4-Dichlorobenzenesulfonyl)-6-(3,4-difluorobenzyl)-8-isopropyl-4,7-dioxooctahydropyrazino[1,2-a]pyrimidin-3-yl]cyclohexanecarboxamide Structure:

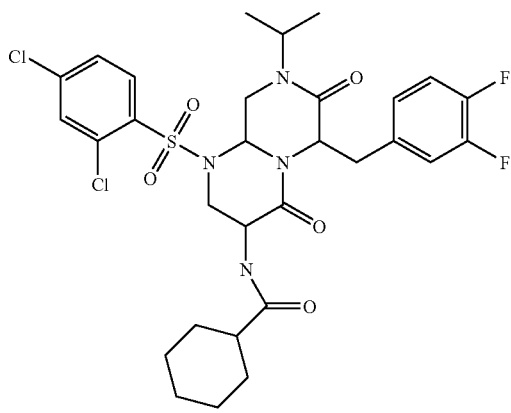

Synthesis takes place in analogy to Example 32 starting from 3-amino-6-(3,4-difluorobenzyl)-1-(2,4-dichlorobenzenesulfonyl)-8-isopropylhexahydropyrazino[1,2-a]pyrimidine-4,7-dione. The desired product is obtained with MW=670.16 (calculated, monoisotopic); measured value (M+H)$^+$: 671.24

EXAMPLE 168

N-[1-(2,4-Dichlorobenzenesulfonyl)-6-(3,4-difluorobenzyl)-8-isopropyl-4,7-dioxooctahydropyrazino[1,2-a]pyrimidin-3-yl]methanesulfonamide Structure:

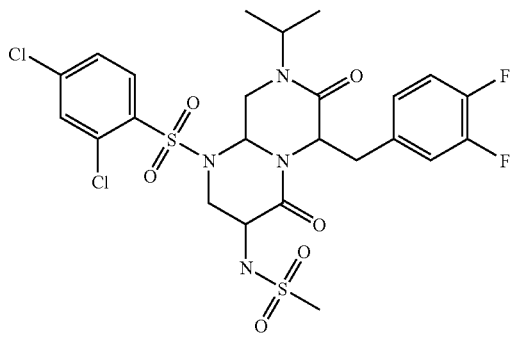

Synthesis takes place in analogy to Example 26 starting from 3-amino-6-(3,4-difluorobenzyl)-1-(2,4-dichlorobenzenesulfonyl)-8-isopropylhexahydropyrazino[1,2-a]pyrimidine-4,7-dione. The desired product is obtained with MW=638.06 (calculated, monoisotopic); measured value (M+H)$^+$: 639.02

EXAMPLE 169

1-(2,4-Dichlorobenzenesulfonyl)-6-(3,4-difluorobenzyl)-3-dimethylamino-8-isopropylhexahydropyrazino[1,2-a]pyrimidine-4,7-dione Structure:

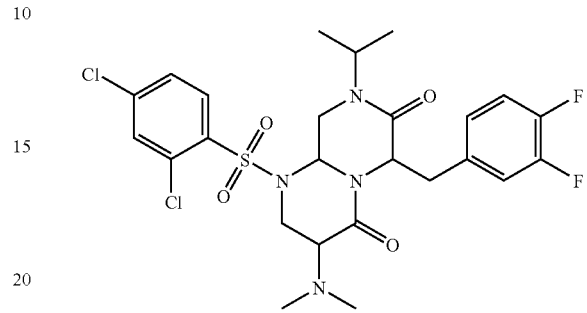

Synthesis takes place in analogy to Example 72 starting from 3-amino-6-(3,4-difluorobenzyl)-1-(2,4-dichlorobenzenesulfonyl)-8-isopropylhexahydropyrazino[1,2-a]pyrimidine-4,7-dione. The desired product is obtained with MW=588.12 (calculated, monoisotopic); measured value (M+H)$^+$: 589.10

EXAMPLE 170

1-(2,4-Dichlorobenzenesulfonyl)-6-(3,4-difluorobenzyl)-8-isopropyl-3-pyrrolidin-1-ylhexahydropyrazino[1,2-a]pyrimidine-4,7-dione Structure:

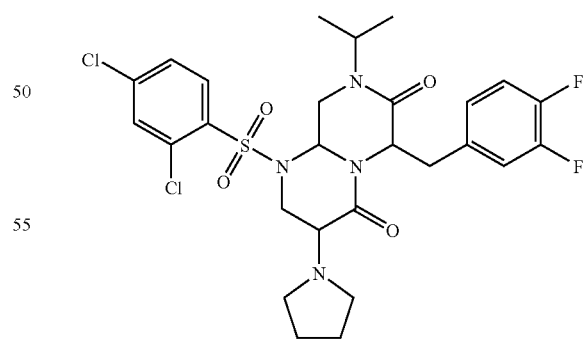

Synthesis takes place in analogy to Example 74 starting from 3-amino-6-(3,4-difluorobenzyl)-1-(2,4-dichlorobenzenesulfonyl)-8-isopropylhexahydropyrazino[1,2-a]pyrimidine-4,7-dione. The desired product is obtained with MW=614.13 (calculated, monoisotopic); measured value (M+H)$^+$: 615.10

EXAMPLE 171

1-(2,4-Dichlorobenzenesulfonyl)-6-(3,4-difluorobenzyl)-8-isopropyl-3-piperidin-1-ylhexahydropyrazino[1,2-a]pyrimidine-4,7-dione Structure:

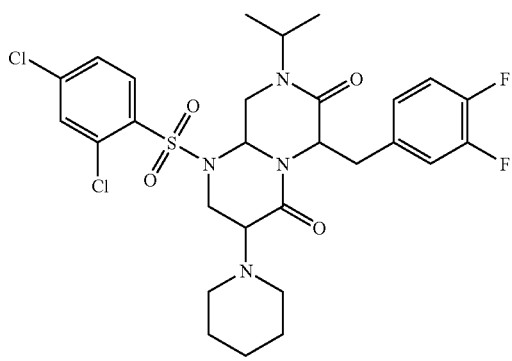

Synthesis takes place in analogy to Example 59 starting from 3-amino-6-(3,4-difluorobenzyl)-1-(2,4-dichlorobenzenesulfonyl)-8-isopropylhexahydropyrazino[1,2-a]pyrimidine-4,7-dione. The desired product is obtained with MW=628.15 (calculated, monoisotopic); measured value (M+H)$^+$: 629.22

EXAMPLE 172

1-(2,4-Dichlorobenzenesulfonyl)-6-(3,4-difluorobenzyl)-8-isopropyl-3-morpholin-4-ylhexahydropyrazino[1,2-a]pyrimidine-4,7-dione Structure:

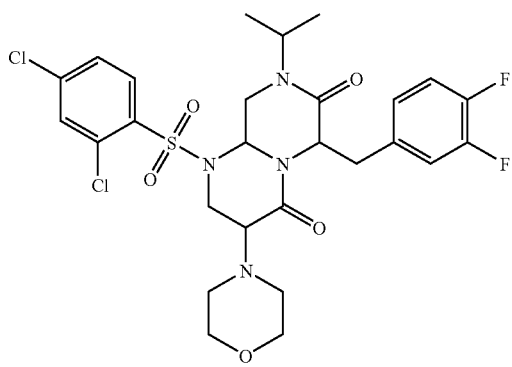

Synthesis takes place in analogy to Example 60 starting from 3-amino-6-(3,4-difluorobenzyl)-1-(2,4-dichlorobenzenesulfonyl)-8-isopropylhexahydropyrazino[1,2-a]pyrimidine-4,7-dione. The desired product is obtained with MW=630.13 (calculated, monoisotopic); measured value (M+H)$^+$: 631.10

EXAMPLE 173

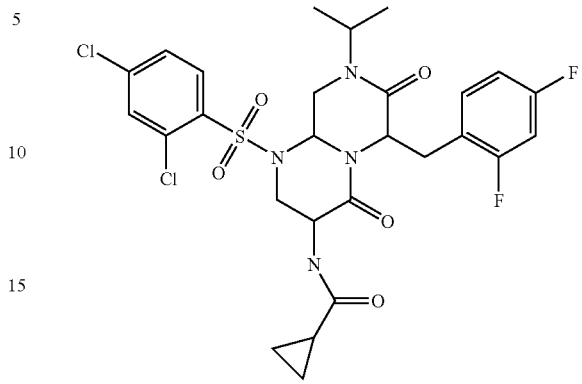

a) 2-Allyloxycarbonylamino-3-(2,4-difluorophenyl) propionic Acid

Synthesis takes place in analogy to Example 21a) starting from 2-amino-3-(2,4-difluorophenyl)propionic acid. The desired product is obtained with MW=285.08 (calculated, monoisotopic); measured value (M+H)$^+$: 286.05 b) Allyl {2-(2,4-difluorophenyl)-1-[(2,2-diethoxyethyl)isopropylcarbamoyl]ethyl}-carbamate Synthesis takes place in analogy to Example 21b) starting from 2-allyloxycarbonylamino-3-(2,4-difluorophenyl)propionic acid. The desired product is obtained with MW=442.23 (calculated, monoisotopic); measured value (M+H)$^+$: 443.2 c) 2-Amino-3-(2,4-difluorophenyl)-N-(2,2-diethoxyethyl)-N-isopropylpropionamide

Synthesis takes place in analogy to Example 21c) starting from allyl {2-(2,4-difluorophenyl)-1-[(2,2-diethoxyethyl)isopropylcarbamoyl]ethyl}carbamate. The desired product is obtained with MW=358.21 (calculated, monoisotopic); measured value (M+H)$^+$: 359.2 d). Benzyl(2-(2,4-dichlorobenzenesulfonylamino)-1-{2-(2,4-difluorophenyl)-1-[(2,2-diethoxyethyl)isopropylcarbamoyl]ethylcarbamoyl}ethyl)carbamate Synthesis takes place in analogy to Example 29b) starting from 2-amino-3-(2,4-difluorophenyl)-N-(2,2-diethoxyethyl)-N-isopropylpropionamide. The desired product is obtained with MW=786.21 (calculated, monoisotopic); measured value (M+H)$^+$: 787.30 e) Benzyl[6-(2,4-difluorobenzyl)-1-(2,4-dichlorobenzenesulfonyl)-8-isopropyl-4,7-dioxooctahydropyrazino[1,2-a]pyrimidin-3-yl]carbamate Synthesis takes place in analogy to Example 21 f) starting from benzyl(2-(2,4-dichlorobenzenesulfonylamino)-1-{2-(2,4-difluorophenyl)-1-[(2,2-diethoxyethyl)isopropylcarbamoyl]ethylcarbamoyl}ethyl)carbamate. The desired product is obtained with MW=694.12 (calculated, monoisotopic); measured value (M+H)$^+$: 695.05 f) 3-Amino-6-(2,4-difluorobenzyl)-1-(2,4-dichlo-robenzenesulfonyl)-8-isopropylhexahydropyrazino[1,2-a]pyrimidine-4,7-dione Synthesis takes place in analogy to Example 21g) starting from benzyl(2-(2,4-dichlorobenzenesulfonylamino)-1-{2-(2,4-difluorophenyl)-1-[(2,2-diethoxyethyl)isopropylcarbamoyl]ethylcarbamoyl}ethyl)carbamate. The desired product is obtained with MW=560.09 (calculated, monoisotopic); measured value (M+H)$^+$: 561.0 g) N-[1-(2,4-Dichlorobenzenesulfonyl)-6-(2,4-difluorobenzyl)-8-isopropyl-4,7-dioxooctahydropyrazino[1,2-a]pyrimidin-3-yl]cyclopropanecarboxamide Synthesis takes place in analogy to Example 29e) (Method A) starting from 3-amino-6-(2,4-difluorobenzyl)-1-(2,4-dichlorobenzenesulfonyl)-8-isopropylhexahydropyrazino[1,2-a]pyrimidine-4,7-dione. The desired product is obtained with MW=628.11 (calculated, monoisotopic); measured value (M+H)$^+$: 629.31

EXAMPLE 174

1-(2,4-Dichlorobenzenesulfonyl)-6-(2,4-difluorobenzyl)-3-dimethylamino-8-isopropylhexahydropyrazino[1,2-a]pyrimidine-4,7-dione Structure:

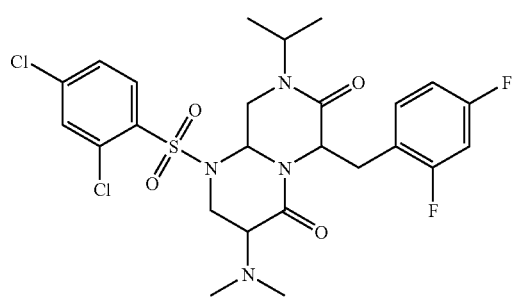

Synthesis takes place in analogy to Example 72 starting from 3-amino-6-(2,4-difluorobenzyl)-1-(2,4-dichlorobenzenesulfonyl)-8-isopropylhexahydropyrazino[1,2-a]pyrimidine-4,7-dione. The desired product is obtained with MW=588.12 (calculated, monoisotopic); measured value (M+H)$^+$: 589.07

EXAMPLE 175

3-Azetidin-1-yl-1-(2,4-dichlorobenzenesulfonyl)-6-(2,4-difluorobenzyl)-8-isopropylhexahydropyrazino[1,2-a]pyrimidine-4,7-dione Structure:

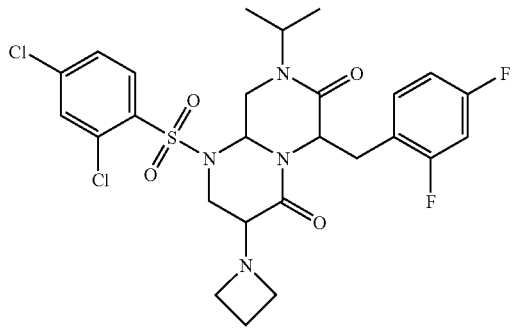

Synthesis takes place in analogy to Example 73 starting from 3-amino-6-(2,4-difluorobenzyl)-1-(2,4-dichlorobenzenesulfonyl)-8-isopropylhexahydropyrazino[1,2-a]pyrimidine-4,7-dione. The desired product is obtained with MW=600.12 (calculated, monoisotopic); measured value (M+H)$^+$: 600.81

EXAMPLE 176

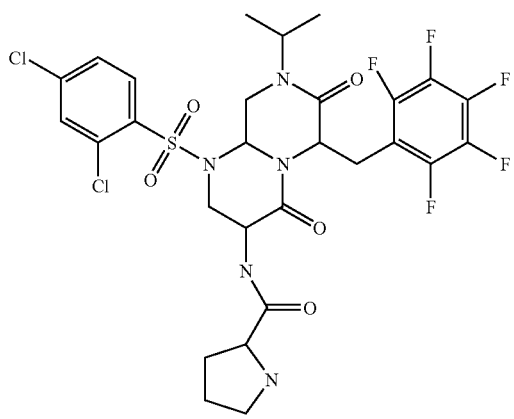

a) 9H-Fluoren-9-ylmethyl[1-[(2,2-diethoxyethyl)isopropylcarbamoyl]-2-pentafluorophenylethyl]carbamate Synthesis takes place in analogy to Example 29a) (Method B) starting from N-Fmoc-2,3,4,5,6-F$_5$-Phe-OH. The desired product is obtained with MW=634.25 (calculated, monoisotopic); measured value (M+Na)$^+$: 657.17 b) 2-Amino-3-pentafluorophenyl-N-(2,2-diethoxyethyl)-N-isopropylpropionamide

Synthesis takes place in analogy to Example 29b) (Method B) starting from 9H-fluoren-9-ylmethyl[1-[(2,2-diethoxyethyl)isopropylcarbamoyl]-2-pentafluorophenylethyl]carbamate. The desired product is obtained with MW=412.18 (calculated, monoisotopic); measured value (M+Na)$^+$: 435.17 c) 9H-Fluoren-9-ylmethyl(2-benzyloxycarbony-
lamino-2-{2-(pentafluorophenyl)-1-[(2,2-diethoxy-
ethyl)isopropylcarbamoyl]ethylcarbamoyl}ethyl)
carbamate Synthesis took place in analogy to Example 29c) (Method B) starting from 2-amino-3-pentafluorophenyl-N-(2,2-diethoxyethyl)-N-isopropylpropionamide. The desired product is obtained with MW=854.33 (calculated, monoisotopic); measured value (M+Na)+: 877.41 d) Benzyl(2-amino-1-{2-pentafluorophenyl-1-[(2,2-
diethoxyethyl)isopropylcarbamoyl]-
ethylcarbamoyl}ethyl)carbamate Synthesis took place in analogy to Example 29d) (Method B) starting from 9H-fluoren-9-ylmethyl(2-benzyloxycarbonylamino-2-{2-pentafluorophenyl-1-[(2,2-diethoxyethyl)isopropylcarbamoyl]ethylcarbamoyl}ethyl)carbamate. The desired product is obtained with MW=632.26 (calculated, monoisotopic); measured value (M+Na)+: 655.24 e) Benzyl[1-{2-pentafluorophenyl-1-[(2,2-diethoxy-
ethyl)isopropylcarbamoyl]ethylcarbamoyl}-2-(2,4-
dichlorobenzenesulfonylamino)ethyl]carbamate Synthesis took place in analogy to Example 29e) (Method B) starting from benzyl (2-amino-1-{2-pentafluorophenyl-1-[(2,2-diethoxyethyl)isopropylcarbamoyl]ethylcarbamoyl}ethyl)carbamate. The desired product is obtained with MW=840.18 (calculated, monoisotopic); measured value (M+Na)+: 863.18.

f) Benzyl[1-(2,4-dichlorobenzenesulfonyl)-8-isopro-
pyl-4,7-dioxo-6-pentafluorophenylmethyloc-
tahydropyrazino[1,2-a]pyrimidin-3-yl]carbamate Synthesis takes place in analogy to Example 29f) starting from benzyl(2-(2,4-dichlorobenzenesulfonylamino)-1-{1-[(2,2-diethoxyethyl)isopropylcarbamoyl]-2-pentafluorophenylethylcarbamoyl}ethyl)carbamate. The desired product is obtained with MW=748.09 (calculated, monoisotopic); measured value (M+H)+: 749.15 g) 3-Amino-1-(2,4-dichlorobenzenesulfonyl)-8-iso-
propyl-6-pentafluorophenylmethyl-
hexahydropyrazino[1,2-a]pyrimidine-4,7-dione Synthesis takes place in analogy to Example 29g) starting from benzyl[1-(2,4-dichlorobenzenesulfonyl)-8-isopropyl-4,7-dioxo-6-pentafluorophenylmethyloctahydropyrazino[1,2-a]pyrimidin-3-yl]carbamate. The desired product is obtained with MW=614.06 (calculated, monoisotopic); measured value (M+1)+: 615.05 h) N-[1-(2,4-Dichlorobenzenesulfonyl)-8-isopropyl-
4,7-dioxo-6-pentafluorophenylmethyloc-
tahydropyrazino[1,2-a]pyrimidin-3-yl]pyrrolidine-2-
carboxamide Synthesis takes place in analogy to Example 40 starting from 3-amino-1-(2,4-dichlorobenzenesulfonyl)-8-isopropyl-6-pentafluorophenylmethylhexahydropyrazino[1,2-a]pyrimidine-4,7-dione. The desired product is obtained with MW=711.11 (calculated, monoisotopic); measured value (M+H)+: 712.06

EXAMPLE 177

1-(2,4-Dichlorobenzenesulfonyl)-3-dimethylamino-
8-isopropyl-6-pentafluorophenylmethyl-
hexahydropyrazino[1,2-a]pyrimidine-4,7-dione Structure:

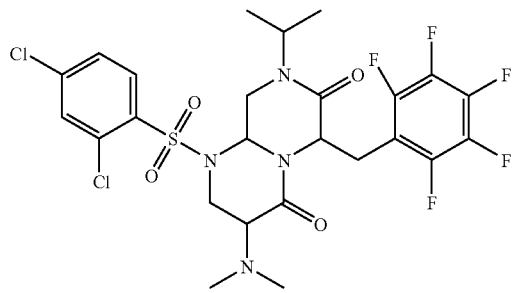

Synthesis takes place in analogy to Example 72 starting from 3-amino-1-(2,4-dichlorobenzenesulfonyl)-8-isopropyl-6-pentafluorophenylmethylhexahydropyrazino[1,2-a]pyrimidine-4,7-dione. The desired product is obtained with MW=620.12 (calculated, monoisotopic); measured value (M+H)+: 621.09

EXAMPLE 178

3-Azetidin-1-yl-1-(2,4-dichlorobenzenesulfonyl)-8-
isopropyl-6-pentafluorophenylmethyl-
hexahydropyrazino[1,2-a]pyrimidine-4,7-dione Structure:

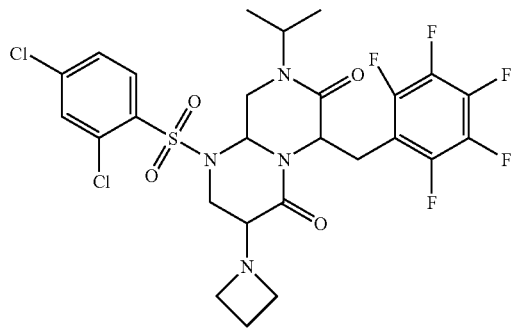

Synthesis takes place in analogy to Example 73 starting from 3-amino-1-(2,4-dichlorobenzenesulfonyl)-8-isopropyl-6-pentafluorophenylmethylhexahydropyrazino[1,2-a]pyrimidine-4,7-dione. The desired product is obtained with MW=654.09 (calculated, monoisotopic); measured value (M+H)+: 655.1

EXAMPLE 179

1-(2,4-Dichlorobenzenesulfonyl)-8-isopropyl-6-pentafluorophenylmethyl-3-pyrrolidin-1-ylhexahydropyrazino[1,2-a]pyrimidine-4,7-dione Structure:

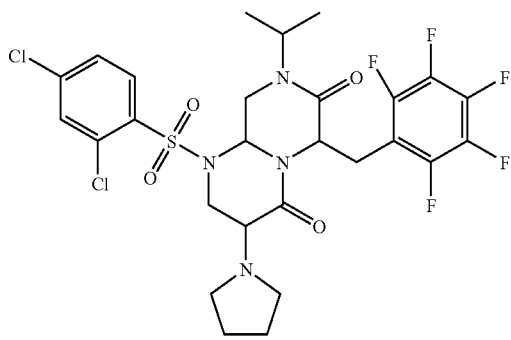

Synthesis takes place in analogy to Example 74 starting from 3-amino-1-(2,4-dichlorobenzenesulfonyl)-8-isopropyl-6-pentafluorophenylmethylhexahydropyrazino[1,2-a]pyrimidine-4,7-dione. The desired product is obtained with MW=668.11 (calculated, monoisotopic); measured value (M+H)$^+$: 669.11

EXAMPLE 180

1-(2,4-Dichlorobenzenesulfonyl)-8-isopropyl-6-pentafluorophenylmethyl-3-piperidin-1-ylhexahydropyrazino[1,2-a]pyrimidine-4,7-dione Structure:

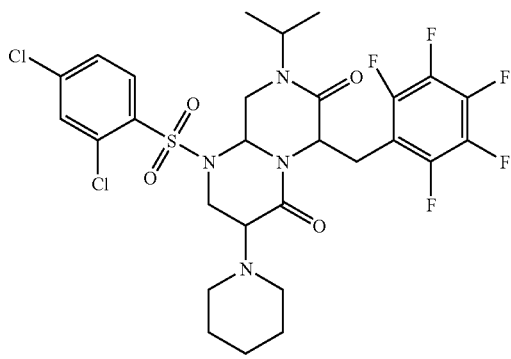

Synthesis takes place in analogy to Example 59 starting from 3-amino-1-(2,4-dichlorobenzenesulfonyl)-8-isopropyl-6-pentafluorophenylmethylhexahydropyrazino[1,2-a]pyrimidine-4,7-dione. The desired product is obtained with MW=682.12 (calculated, monoisotopic); measured value (M+H)$^+$: 683.09

EXAMPLE 181

1-(2,4-Dichlorobenzenesulfonyl)-8-isopropyl-3-morpholin-4-yl-6-pentafluorophenylmethylhexahydropyrazino[1,2-a]pyrimidine-4,7-dione Structure:

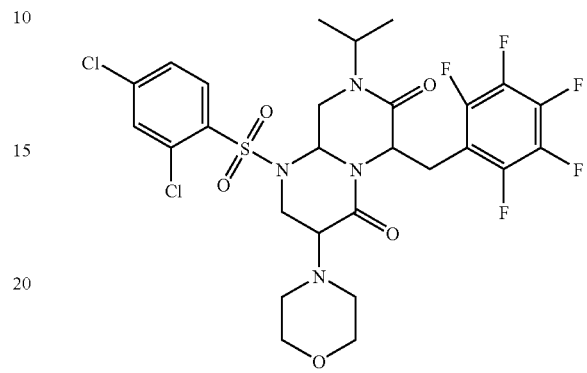

Synthesis takes place in analogy to Example 60 starting from 3-amino-1-(2,4-dichlorobenzenesulfonyl)-8-isopropyl-6-pentafluorophenylmethylhexahydropyrazino[1,2-a]pyrimidine-4,7-dione. The desired product is obtained with MW=684.10 (calculated, monoisotopic); measured value (M+H)$^+$: 685.01

EXAMPLE 182

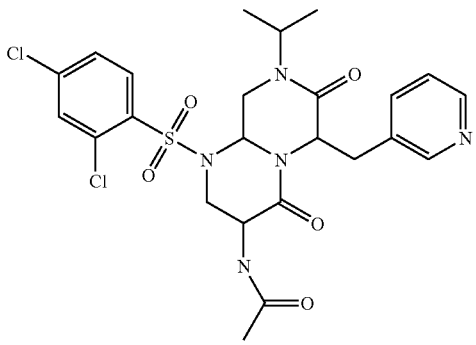

a) 9H-Fluoren-9-ylmethyl{1-[(2,2-diethoxyethyl)isopropylcarbamoyl]-2-pyridin-3-ylethyl} carbamate Synthesis takes place in analogy to Example 29a) (Method B) starting from Fmoc-3-pyridylalanine. The desired product is obtained with MW=545.29 (calculated, monoisotopic); measured value (M+H)$^+$: 546.24 b) 2-Amino-N-(2,2-diethoxyethyl)-N-isopropyl-3-pyridin-3-ylpropionamide

Synthesis takes place in analogy to Example 29b) (Method B) starting from 9H-fluoren-9-ylmethyl{1-[(2,2-diethoxyethyl)isopropylcarbamoyl]-2-pyridin-3-ylethyl}carbamate. The desired product is obtained with MW=323.22 (calculated, monoisotopic); measured value (M+H)$^+$: 324.22 c) Benzyl[1-[(2,2-diethoxyethyl)isopropylcarbamoyl]-2-pyridin-3-ylethylcarbamoyl-2-(9H-fluoren-9-ylmethoxycarbonylamino)ethyl]carbamate Synthesis took place in analogy to Example 29c) (Method B) starting from 2-amino-N-(2,2-diethoxyethyl)-N-isopropyl-3-pyridin-3-ylpropionamide. The desired product is obtained with MW=765.37 (calculated, monoisotopic); measured value (M+H)+: 766.31 d) Benzyl(2-amino-{1-[(2,2-diethoxyethyl)isopropylcarbamoyl]-2-pyridin-3-ylethylcarbamoyl}ethyl) carbamate Synthesis took place in analogy to Example 29d) (Method B) starting from benzyl[1-[(2,2-diethoxyethyl)isopropylcarbamoyl]-2-pyridin-3-ylethylcarbamoyl}-2-(9H-fluoren-9-ylmethoxycarbonylamino)ethyl]carbamate. The desired product is obtained with MW=543.31 (calculated, monoisotopic); measured value (M+H)+: 544.4 e) Benzyl(2-(2,4-dichlorobenzenesulfonylamino)-1-{1-[(2,2-diethoxyethyl)isopropylcarbamoyl]-2-pyridin-3-ylethylcarbamoyl}ethyl)carbamate Synthesis took place in analogy to Example 29e) (Method B) starting from benzyl (2-amino-{1-[(2,2-diethoxyethyl)isopropylcarbamoyl]-2-pyridin-3-ylethylcarbamoyl}ethyl) carbamate. The desired product is obtained with MW=751.22 (calculated, monoisotopic); measured value (M+H)+: 752.19.

f) Benzyl[1-(2,4-dichlorobenzenesulfonyl)-8-isopropyl-4,7-dioxo-6-pyridin-3-ylmethyloctahydropyrazino[1,2-a]pyrimidin-3-yl]carbamate Synthesis takes place in analogy to Example 29f) starting from benzyl(2-(2,4-dichlorobenzenesulfonylamino)-1-{1-[(2,2-diethoxyethyl)isopropylcarbamoyl]-2-pyridin-3-ylethylcarbamoyl}ethyl)carbamate. The desired product is obtained with MW=659.14 (calculated, monoisotopic); measured value (M+H)+: 660.10 g) 3-Amino-1-(2,4-dichlorobenzenesulfonyl)-8-isopropyl-6-pyridin-3-ylmethylhexahydropyrazino[1,2-a]pyrimidine-4,7-dione Synthesis takes place in analogy to Example 29g) starting from benzyl[1-(2,4-dichlorobenzenesulfonyl)-8-isopropyl-4,7-dioxo-6-pyridin-3-ylmethyloctahydropyrazino[1,2-a]pyrimidin-3-yl]carbamate. The desired product is obtained with MW=525.10 (calculated, monoisotopic); measured value (M+H)+: 526.1 h) N-[1-(2,4-Dichlorobenzenesulfonyl)-8-isopropyl-4,7-dioxo-6-pyridin-3-ylmethyloctahydropyrazino[1,2-a]pyrimidin-3-yl]acetamide Synthesis takes place in analogy to Example 21h) starting from 3-amino-1-(2,4-dichlorobenzenesulfonyl)-8-isopropyl-6-pyridin-3-ylmethylhexahydropyrazino[1,2-a]pyrimidine-4,7-dione. The desired product is obtained with MW=567.11 (calculated, monoisotopic); measured value (M+H)+: 568.11

EXAMPLE 183

N-[1-(2,4-Dichlorobenzenesulfonyl)-8-isopropyl-4,7-dioxo-6-pyridin-3-ylmethyloctahydropyrazino[1,2-a]pyrimidin-3-yl]cyclopropanecarboxamide Structure:

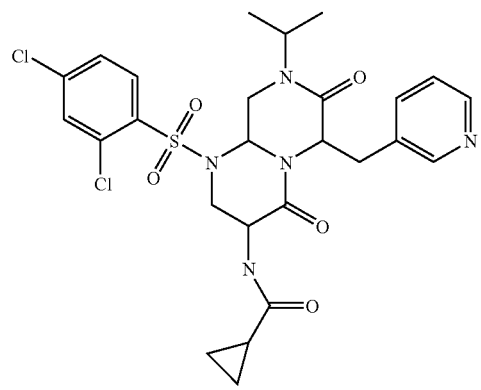

Synthesis takes place in analogy to Example 22 starting from 3-amino-1-(2,4-dichlorobenzenesulfonyl)-8-isopropyl-6-pyridin-3-ylmethylhexahydropyrazino[1,2-a]pyrimidine-4,7-dione. The desired product is obtained with MW=593.13 (calculated, monoisotopic); measured value (M+H)+: 594.13

EXAMPLE 184

N-[1-(2,4-Dichlorobenzenesulfonyl)-8-isopropyl-4,7-dioxo-6-pyridin-3-ylmethyloctahydropyrazino[1,2-a]pyrimidin-3-yl]cyclobutanecarboxamide Structure:

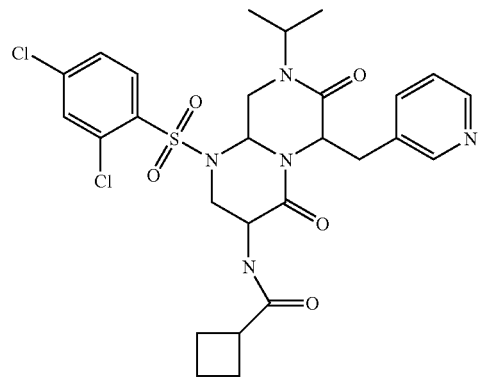

Synthesis takes place in analogy to Example 30 starting from 3-amino-1-(2,4-dichlorobenzenesulfonyl)-8-isopropyl-6-pyridin-3-ylmethylhexahydropyrazino[1,2-a]pyrimidine-4,7-dione. The desired product is obtained with MW=607.14 (calculated, monoisotopic); measured value (M+H)+: 608.15

EXAMPLE 185

N-[1-(2,4-Dichlorobenzenesulfonyl)-8-isopropyl-4,7-dioxo-6-pyridin-3-ylmethyloctahydropyrazino[1,2-a]pyrimidin-3-yl]cyclopentanecarboxamide Structure:

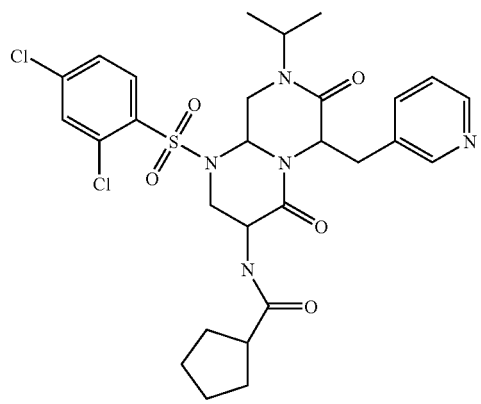

Synthesis takes place in analogy to Example 31 starting from 3-amino-1-(2,4-dichlorobenzenesulfonyl)-8-isopropyl-6-pyridin-3-ylmethylhexahydropyrazino[1,2-a]pyrimidine-4,7-dione. The desired product is obtained with MW=621.16 (calculated, monoisotopic); measured value (M+H)$^+$: 622.17

EXAMPLE 186

N-[1-(2,4-Dichlorobenzenesulfonyl)-8-isopropyl-4,7-dioxo-6-pyridin-3-ylmethyloctahydropyrazino[1,2-a]pyrimidin-3-yl]pyrrolidine-2-carboxamide Structure:

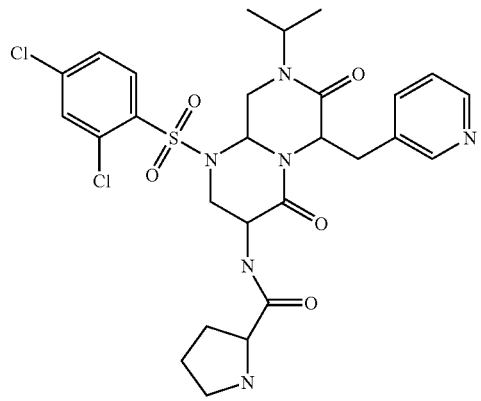

Synthesis takes place in analogy to Example 40 starting from 3-amino-1-(2,4-dichlorobenzenesulfonyl)-8-isopropyl-6-pyridin-3-ylmethylhexahydropyrazino[1,2-a]pyrimidine-4,7-dione. The desired product is obtained with MW=622.15 (calculated, monoisotopic); measured value (M+H)$^+$: 623.14

EXAMPLE 187

N-[1-(2,4-Dichlorobenzenesulfonyl)-8-isopropyl-4,7-dioxo-6-pyridin-3-ylmethyloctahydropyrazino[1,2-a]pyrimidin-3-yl]-4-dimethylaminobenzamide Structure:

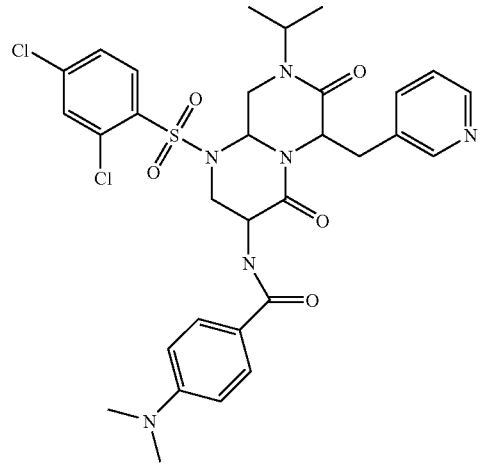

Synthesis takes place in analogy to Example 25 starting from 3-amino-1-(2,4-dichlorobenzenesulfonyl)-8-isopropyl-6-pyridin-3-ylmethylhexahydropyrazino[1,2-a]pyrimidine-4,7-dione. The desired product is obtained with MW=672.17 (calculated, monoisotopic); measured value (M+H)$^+$: 673.18

EXAMPLE 188

N-[1-(2,4-Dichlorobenzenesulfonyl)-8-isopropyl-4,7-dioxo-6-pyridin-3-ylmethyloctahydropyrazino[1,2-a]pyrimidin-3-yl]nicotinamide Structure:

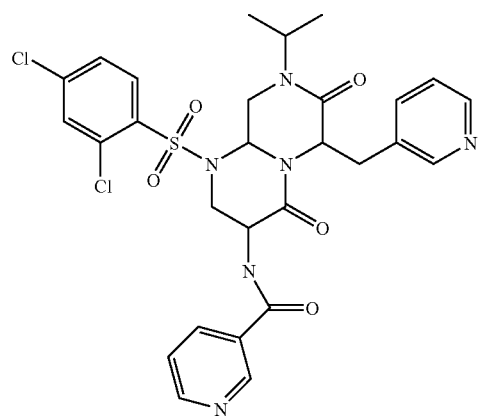

Synthesis takes place in analogy to Example 50 starting from 3-amino-1-(2,4-dichlorobenzenesulfonyl)-8-isopropyl-6-pyridin-3-ylmethylhexahydropyrazino[1,2-a]pyrimidine-4,7-dione. The desired product is obtained with MW=630.12 (calculated, monoisotopic); measured value (M+H)$^+$: 631.16

EXAMPLE 189

1-tert-Butyl-3-[1-(2,4-dichlorobenzenesulfonyl)-8-isopropyl-4,7-dioxo-6-pyridin-3-ylmethyloctahydropyrazino[1,2-a]pyrimidin-3-yl]urea Structure:

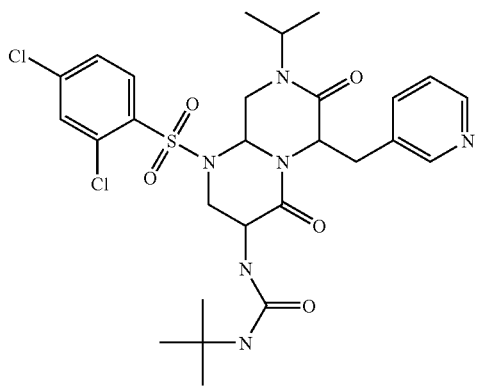

Synthesis takes place in analogy to Example 28 starting from 3-amino-1-(2,4-dichlorobenzenesulfonyl)-8-isopropyl-6-pyridin-3-ylmethylhexahydropyrazino[1,2-a]pyrimidine-4,7-dione. The desired product is obtained with MW=624.17 (calculated, monoisotopic); measured value (M+H)$^+$: 625.1

EXAMPLE 190

N-[1-(2,4-Dichlorobenzenesulfonyl)-8-isopropyl-4,7-dioxo-6-pyridin-3-ylmethyloctahydropyrazino[1,2-a]pyrimidin-3-yl]methanesulfonamide Structure:

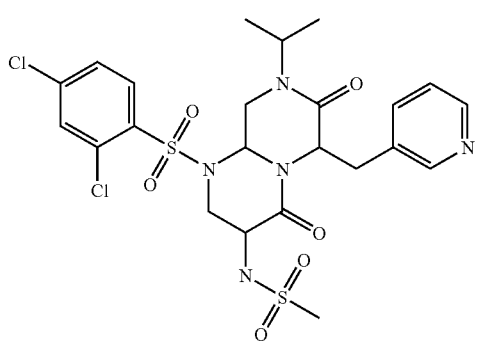

Synthesis takes place in analogy to Example 26 starting from 3-amino-1-(2,4-dichlorobenzenesulfonyl)-8-isopropyl-6-pyridin-3-ylmethylhexahydropyrazino[1,2-a]pyrimidine-4,7-dione. The desired product is obtained with MW=603.08 (calculated, monoisotopic); measured value (M+H)$^+$: 604.06

EXAMPLE 191

N-[1-(2,4-Dichlorobenzenesulfonyl)-8-isopropyl-4,7-dioxo-6-pyridin-3-ylmethyloctahydropyrazino[1,2-a]pyrimidin-3-yl]cyclopropanesulfonamide Structure:

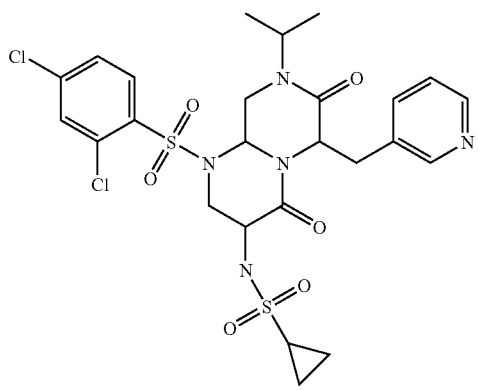

Synthesis takes place in analogy to Example 27 starting from 3-amino-1-(2,4-dichlorobenzenesulfonyl)-8-isopropyl-6-pyridin-3-ylmethylhexahydropyrazino[1,2-a]pyrimidine-4,7-dione. The desired product is obtained with MW=629.09 (calculated, monoisotopic); measured value (M+H)$^+$: 630.09

EXAMPLE 192

1-(2,4-Dichlorobenzenesulfonyl)-3-dimethylamino-8-isopropyl-6-pyridin-3-ylmethylhexahydropyrazino[1,2-a]pyrimidine-4,7-dione Structure:

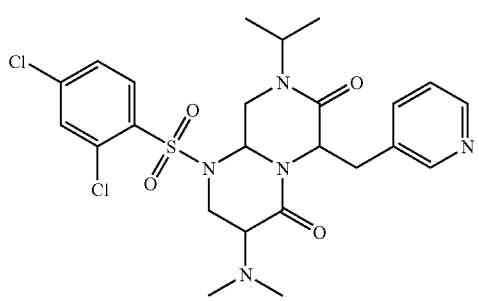

Synthesis takes place in analogy to Example 72 starting from 3-amino-1-(2,4-dichlorobenzenesulfonyl)-8-isopropyl-6-pyridin-3-ylmethylhexahydropyrazino[1,2-a]pyrimidine-4,7-dione. The desired product is obtained with MW=553.13 (calculated, monoisotopic); measured value (M+H)$^+$: 554.08

EXAMPLE 193

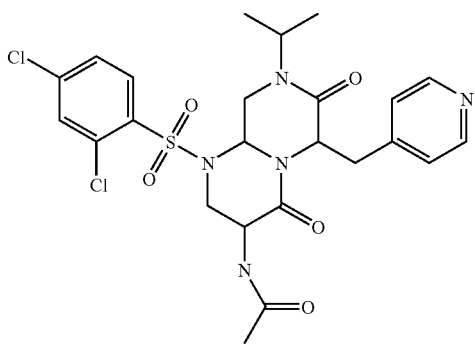

a) 9H-Fluoren-9-ylmethyl{1-[(2,2-diethoxyethyl)isopropylcarbamoyl]-2-pyridin-4-ylethyl}carbamate Synthesis takes place in analogy to Example 29a) (Method B) starting from Fmoc-4-pyridylalanine. The desired product is obtained with MW=545.29 (calculated, monoisotopic); measured value (M+H)$^+$: 546.26 b) 2-Amino-N-(2,2-diethoxyethyl)-N-isopropyl-3-pyridin-4-ylpropionamide

Synthesis takes place in analogy to Example 29b) (Method B) starting from 9H-fluoren-9-ylmethyl{1-[(2,2-diethoxyethyl)isopropylcarbamoyl]-2-pyridin-4-ylethyl}carbamate. The desired product is obtained with MW=323.22 (calculated, monoisotopic); measured value (M+H)$^+$: 324.22 c) Benzyl[1-[(2,2-diethoxyethyl)isopropylcarbamoyl]-2-pyridin-4-ylethylcarbamoyl}-2-(9H-fluoren-9-ylmethoxycarbonylamino)ethyl]carbamate Synthesis took place in analogy to Example 29c) (Method B) starting from 2-amino-N-(2,2-diethoxyethyl)-N-isopropyl-3-pyridin-4-ylpropionamide. The desired product is obtained with MW=809.36 (calculated, monoisotopic); measured value (M+Na)$^+$: 832.3 d) Benzyl(2-amino-{1-[(2,2-diethoxyethyl)isopropylcarbamoyl]-2-pyridin-4-ylethylcarbamoyl}ethyl)carbamate Synthesis took place in analogy to Example 29d) (Method B) starting from benzyl[1-[(2,2-diethoxyethyl)isopropylcarbamoyl]-2-pyridin-4-ylethylcarbamoyl}-2-(9H-fluoren-9-ylmethoxycarbonylamino)ethyl]carbamate. The desired product is obtained with MW=543.31 (calculated, monoisotopic); measured value (M+H)$^+$: 544.4 e) Benzyl(2-(2,4-dichlorobenzenesulfonylamino)-1-{1-[(2,2-diethoxyethyl)isopropylcarbamoyl]-2-pyridin-4-ylethylcarbamoyl}ethyl)carbamate Synthesis took place in analogy to Example 29e) (Method B) starting from benzyl (2-amino-{1-[(2,2-diethoxyethyl)isopropylcarbamoyl]-2-pyridin-4-ylethylcarbamoyl}ethyl)carbamate. The desired product is obtained with MW=751.22 (calculated, monoisotopic); measured value (M+H)$^+$: 752.19.

f) Benzyl[1-(2,4-dichlorobenzenesulfonyl)-8-isopropyl-4,7-dioxo-6-pyridin-4-ylmethyloctahydropyrazino[1,2-a]pyrimidin-3-yl]carbamate Synthesis takes place in analogy to Example 29f) (Method B) starting from benzyl(2-(2,4-dichloro-benzenesulfonylamino)-1-{1-[(2,2-diethoxyethyl)isopropylcarbamoyl]-2-pyridin-4-ylethylcarbamoyl}ethyl)carbamate. The desired product is obtained with MW=659.14 (calculated, monoisotopic); measured value (M+H)$^+$: 660.17 g) 3-Amino-1-(2,4-dichlorobenzenesulfonyl)-8-isopropyl-6-pyridin-4-ylmethylhexahydropyrazino[1,2-a]pyrimidine-4,7-dione Synthesis takes place in analogy to Example 29g) (Method B) starting from benzyl[1-(2,4-dichlorobenzenesulfonyl)-8-isopropyl-4,7-dioxo-6-pyridin-4-ylmethyloctahydropyrazino[1,2-a]pyrimidin-3-yl]carbamate. The desired product is obtained with MW=525.10 (calculated, monoisotopic); measured value (M+H)$^+$: 526.10 h) N-[1-(2,4-Dichlorobenzenesulfonyl)-8-isopropyl-4,7-dioxo-6-pyridin-4-ylmethyloctahydropyrazino[1,2-a]pyrimidin-3-yl]acetamide Synthesis takes place in analogy to Example 21h) starting from 3-amino-1-(2,4-dichlorobenzenesulfonyl)-8-isopropyl-6-pyridin-4-ylmethylhexahydropyrazino[1,2-a]pyrimidine-4,7-dione. The desired product is obtained with MW=567.11 (calculated, monoisotopic); measured value (M+H)$^+$: 568.13

EXAMPLE 194

N-[1-(2,4-Dichlorobenzenesulfonyl)-8-isopropyl-4,7-dioxo-6-pyridin-4-ylmethyloctahydropyrazino[1,2-a]pyrimidin-3-yl]cyclopropanecarboxamide Structure:

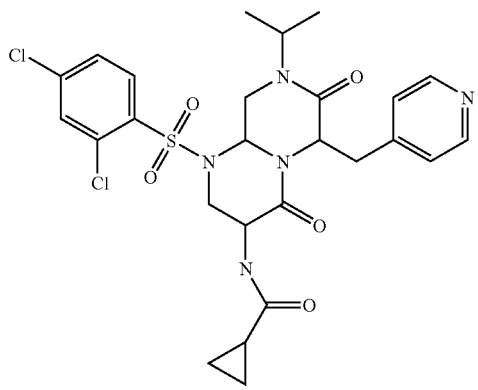

Synthesis takes place in analogy to Example 22 starting from 3-amino-1-(2,4-dichlorobenzenesulfonyl)-8-isopropyl-6-pyridin-4-ylmethylhexahydropyrazino[1,2-a]pyrimidine-4,7-dione. The desired product is obtained with MW=593.13 (calculated, monoisotopic); measured value (M+H)$^+$: 594.13

EXAMPLE 195

N-[1-(2,4-Dichlorobenzenesulfonyl)-8-isopropyl-4,7-dioxo-6-pyridin-4-ylmethyloctahydropyrazino[1,2-a]pyrimidin-3-yl]cyclopentanecarboxamide Structure:

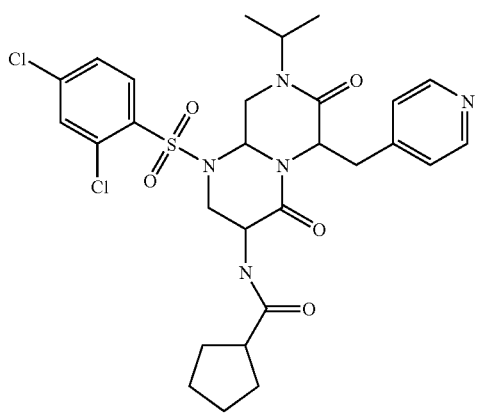

Synthesis takes place in analogy to Example 31 starting from 3-amino-1-(2,4-dichlorobenzenesulfonyl)-8-isopropyl-6-pyridin-4-ylmethylhexahydropyrazino[1,2-a]pyrimidine-4,7-dione. The desired product is obtained with MW=621.16 (calculated, monoisotopic); measured value (M+H)$^+$: 622.17

EXAMPLE 196

N-[1-(2,4-Dichlorobenzenesulfonyl)-8-isopropyl-4,7-dioxo-6-pyridin-4-ylmethyloctahydropyrazino[1,2-a]pyrimidin-3-yl]4-dimethylaminobenzamide Structure:

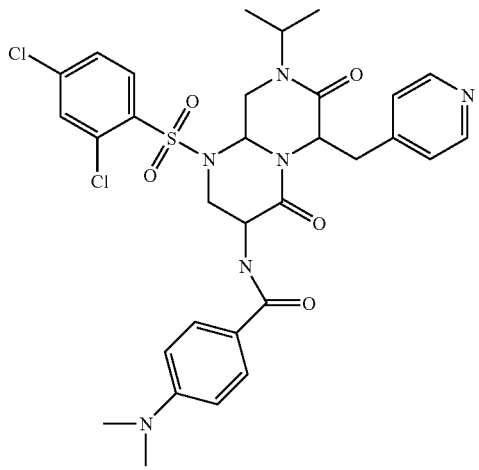

Synthesis takes place in analogy to Example 25 starting from 3-amino-1-(2,4-dichlorobenzenesulfonyl)-8-isopropyl-6-pyridin-4-ylmethylhexahydropyrazino[1,2-a]pyrimidine-4,7-dione. The desired product is obtained with MW=672.17 (calculated, monoisotopic); measured value (M+H)$^+$: 673.2

EXAMPLE 197

1-tert-Butyl-3-[1-(2,4-dichlorobenzenesulfonyl)-8-isopropyl-4,7-dioxo-6-pyridin-4-ylmethyloctahydropyrazino[1,2-a]pyrimidin-3-yl]urea Structure:

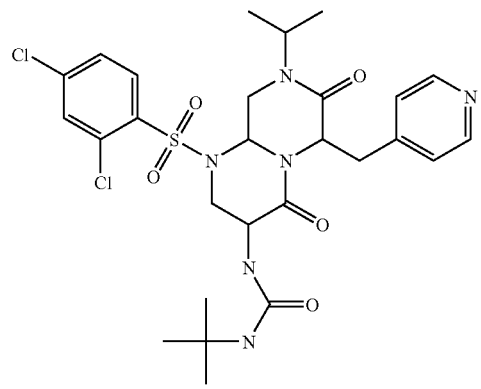

Synthesis takes place in analogy to Example 28 starting from 3-amino-1-(2,4-dichlorobenzenesulfonyl)-8-isopropyl-6-pyridin-4-ylmethylhexahydropyrazino[1,2-a]pyrimidine-4,7-dione. The desired product is obtained with MW=624.17 (calculated, monoisotopic); measured value (M+H)$^+$: 625.2

EXAMPLE 198

N-[1-(2,4-Dichlorobenzenesulfonyl)-8-isopropyl-4,7-dioxo-6-pyridin-4-ylmethyloctahydropyrazino[1,2-a]pyrimidin-3-yl]methanesulfonamide Structure:

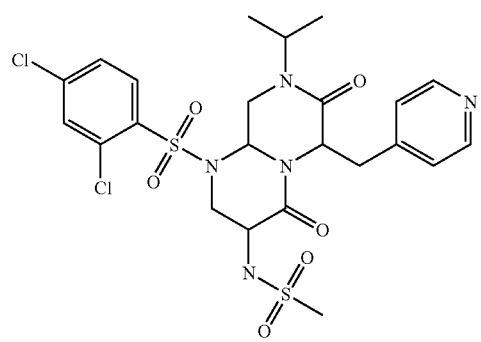

Synthesis takes place in analogy to Example 26 starting from 3-amino-1-(2,4-dichlorobenzenesulfonyl)-8-isopropyl-6-pyridin-4-ylmethylhexahydropyrazino[1,2-a]pyrimidine-4,7-dione. The desired product is obtained with MW=603.08 (calculated, monoisotopic); measured value (M+H)$^+$: 604.08

EXAMPLE 199

N-[1-(2,4-Dichlorobenzenesulfonyl)-8-isopropyl-4,7-dioxo-6-pyridin-4-ylmethyloctahydropyrazino[1,2-a]pyrimidin-3-yl]cyclopropanesulfonamide Structure:

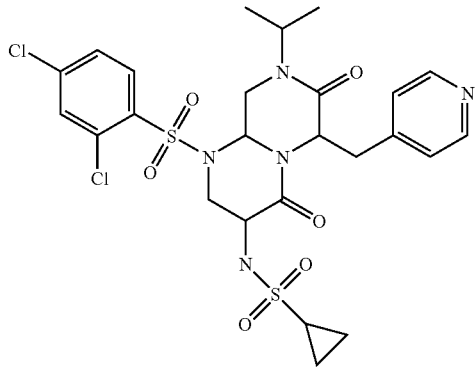

Synthesis takes place in analogy to Example 27 starting from 3-amino-1-(2,4-dichlorobenzenesulfonyl)-8-isopropyl-6-pyridin-4-ylmethylhexahydropyrazino[1,2-a]pyrimidine-4,7-dione. The desired product is obtained with MW=629.09 (calculated, monoisotopic); measured value (M+H)$^+$: 630.06

EXAMPLE 200

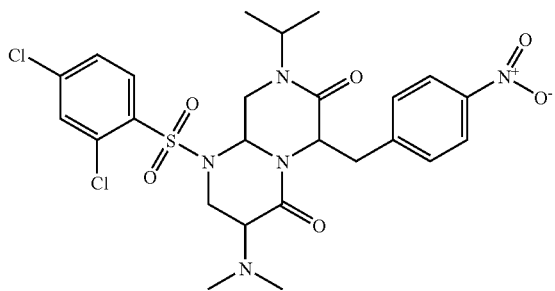

a) 9H-Fluoren-9-ylmethyl[1-[(2,2-diethoxyethyl)isopropylcarbamoyl]-2-(4-nitrophenyl)ethyl]carbamate Synthesis takes place in analogy to Example 29a) (Method B) starting from N-Fmoc-4-nitro-Phe-OH. The desired product is obtained with MW=589.28 (calculated, monoisotopic); measured value (M+H)$^+$: 590.3 b) 2-Amino-N-(2,2-diethoxyethyl)-N-isopropyl-3-(4-nitrophenyl)propionamide

Synthesis takes place in analogy to Example 29b) (Method B) starting from 9H-fluoren-9-ylmethyl[1-[(2,2-diethoxyethyl)isopropylcarbamoyl]-2-(4-nitrophenyl)ethyl]carbamate.

c) Benzyl[1-[1-[(2,2-diethoxyethyl)isopropylcarbamoyl]-2-(4-nitrophenyl)ethylcarbamoyl]-2-(9H-fluoren-9-ylmethoxycarbonylamino)ethyl]carbamate Synthesis took place in analogy to Example 29c) (Method B) starting from 2-amino-N-(2,2-diethoxyethyl)-N-isopropyl-3-(4-nitrophenyl)propionamide. The desired product is obtained with MW=765.37 (calculated, monoisotopic); measured value (M+H)$^+$: 766.31 d) Benzyl{2-amino-1-[1-[(2,2-diethoxyethyl)isopropylcarbamoyl]-2-(4-nitrophenyl)ethylcarbamoyl]ethyl)carbamate Synthesis took place in analogy to Example 29d) (Method B) starting from benzyl 1-[(2,2-diethoxyethyl)isopropylcarbamoyl]-2-pyridin-4-ylethylcarbamoyl}-2-(9H-fluoren-9-ylmethoxycarbonylamino)ethyl]carbamate. The desired product is obtained with MW=587.68 (calculated, monoisotopic); measured value (M-OEt): 542 e) Benzyl{2-(2,4-dichlorobenzenesulfonylamino)-1-[1-[(2,2-diethoxyethyl)isopropylcarbamoyl]-2-(4-nitrophenyl)ethylcarbamoyl]ethyl}carbamate Synthesis took place in analogy to Example 29e) (Method B) starting from benzyl {2-amino-1-[1-[(2,2-diethoxyethyl)isopropylcarbamoyl]-2-(4-nitrophenyl)ethylcarbamoyl]ethyl}carbamate. The desired product is obtained with MW=795.21 (calculated, monoisotopic); measured value (M+Na)$^+$: 818.21 f) Benzyl[1-(2,4-dichlorobenzenesulfonyl)-8-isopropyl-6-(4-nitrobenzyl)-4,7-dioxooctahydropyrazino[1,2-a]pyrimidin-3-yl]carbamate Synthesis takes place in analogy to Example 29f) (Method B) starting from benzyl {2-(2,4-dichlorobenzenesulfonylamino)-1-[1-[(2,2-diethoxyethyl)isopropylcarbamoyl]-2-(4-nitrophenyl)ethylcarbamoyl]ethyl}carbamate. The desired product is obtained with MW=703.13 (calculated, monoisotopic); measured value (M+H)$^+$: 704.1 g) 3-Amino-1-(2,4-dichlorobenzenesulfonyl)-8-isopropyl-6-(4-nitrobenzyl)hexahydropyrazino[1,2-a]pyrimidine-4,7-dione Synthesis takes place in analogy to Example 29g) (Method B) starting from benzyl[1-(2,4-dichlorobenzenesulfonyl)-8-isopropyl-6-(4-nitrobenzyl)-4,7-dioxooctahydropyrazino[1,2-a]pyrimidin-3-yl]carbamate. The desired product is obtained with MW=525.10 (calculated, monoisotopic); measured value (M+H)$^+$: 526.10 h) 1-(2,4-Dichlorobenzenesulfonyl)-3-dimethylamino-8-isopropyl-6-(4-nitrobenzyl)hexahydropyrazino[1,2-a]pyrimidine-4,7-dione 0.15 ml of acetic acid and then 0.15 ml of formaldehyde (37% in H$_2$O) and 1 ml of sodium cyanoborohydride (1M in THF) were added to a solution of 100 mg (0.17 mmol) of 3-amino-1-(2,4-dichlorobenzenesulfonyl)-8-isopropyl-6-(4-nitrobenzyl)hexahydropyrazino[1,2-a]pyrimidine-4,7-dione in 5 ml of methanol. The mixture was stirred at room temperature for 1 hour, concentrated in vacuo, diluted with ethyl acetate and washed with water and brine. It was then dried (MgSO$_4$) and concentrated in vacuo. The residue was chromatographed on 12 g of SiO$_2$ (elution with ethyl acetate/methanol, gradient 0-5% methanol). 25 mg of the dimethylamine were obtained. The amine was treated with 1 ml of 1M HCl in ether. The mixture was concentrated in vacuo. 35 mg of dimethylamine HCl salt were obtained as a white solid. LC/MS MW=597.12 (calculated, monoisotopic) measured value (M$^+$H)=598.12

EXAMPLE 201

N-[6-(4-Aminobenzyl)-1-(2,4-dichlorobenzenesulfonyl)-8-isopropyl-4,7-dioxooctahydropyrazino[1,2-a]pyrimidin-3-yl]cyclopentanecarboxamide

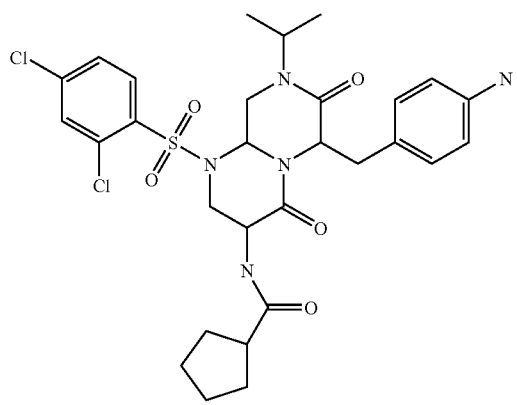

3-Amino-1-(2,4-dichlorobenzenesulfonyl)-8-isopropyl-6-(4-nitrobenzyl)hexahydropyrazino[1,2-a]pyrimidine-4,7-dione was reacted in analogy to Example 31 to give the cyclopentane carboxamide. The latter was reacted further in the following way: 71 mg (0.3 mmol) of tin(II) chloride were added to a solution of 50 mg (0.07 mmol) of N-[1-(2,4-dichlorobenzenesulfonyl)-8-isopropyl-6-(4-nitrobenzyl)-4,7-dioxooctahydropyrazino[1,2-a]pyrimidin-3-yl]cyclopentanecarboxamide (Example 200) in 3 ml of ethanol. The mixture was heated at 100° C. in a microwave oven for 5 minutes and concentrated in vacuo. The residue was diluted with ethyl acetate, filtered through kieselguhr and concentrated in vacuo. It was then chromatographed on 4 g of SiO$_2$ (elution with ethyl acetate/heptane, gradient 0-100% ethyl acetate). 25 mg of the desired aniline were obtained as an oil. LC/MS MW (calculated, monoisotopic)=635.17 and measured value (M$^+$H)=636.14.

EXAMPLE 202

6-(4-Aminobenzyl)-1-(2,4-dichlorobenzenesulfonyl)-3-dimethylamino-8-isopropylhexahydropyrazino[1,2-a]pyrimidine-4,7-dione

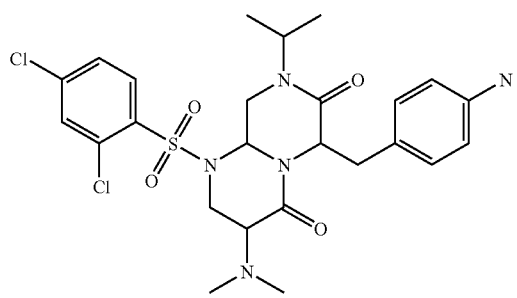

Example 202 was reduced in analogy to Example 201 starting from compound 1-(2,4-dichlorobenzenesulfonyl)-3-dimethylamino-8-isopropyl-6-(4-nitrobenzyl)hexahydropyrazino[1,2-a]pyrimidine-4,7-dione. The desired product is obtained with MW=567.15 (calculated, monoisotopic); measured value (M+H)$^+$: 568.1

EXAMPLE 203

6-(4-Aminobenzyl)-1-(2,4-dichlorobenzenesulfonyl)-8-isopropyl-3-piperidin-1-ylhexahydropyrazino[1,2-a]pyrimidine-4,7-dione

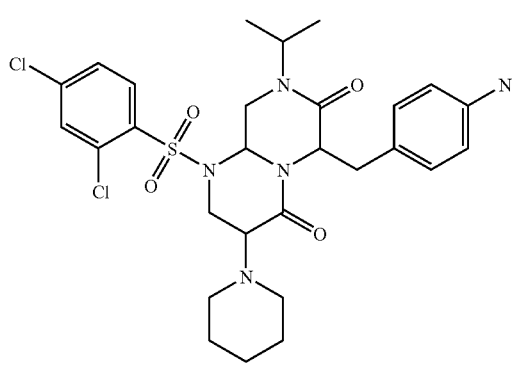

Synthesis takes place in analogy to Example 59 starting from 3-amino-1-(2,4-dichlorobenzenesulfonyl)-8-isopropyl-6-(4-nitrobenzyl)hexahydropyrazino[1,2-a]pyrimidine-4,7-dione to give the corresponding piperidine derivative. Subsequent reduction of the nitro group took place as described in Example 201. The desired product is obtained with MW=607.18 (calculated, monoisotopic); measured value (M+H)$^+$: 608.2

EXAMPLE 204

4-Chloro-N-{4-[3-(cyclopentanecarbonylamino)-1-(2,4-dichlorobenzenesulfonyl)-8-isopropyl-4,7-dioxooctahydropyrazino[1,2-a]pyrimidin-6-ylmethyl]phenyl} benzamide

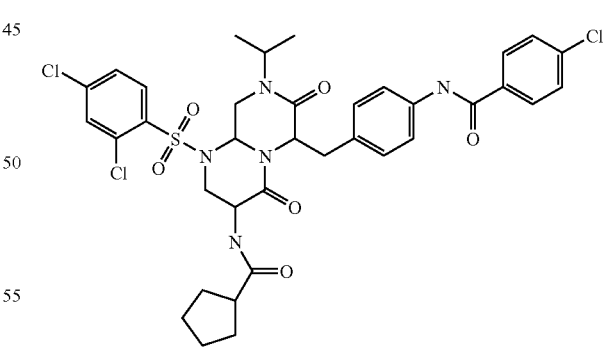

5 mg (0.04 mmol) of diisopropylethylamine and then 7 mg (0.04 mmol) of 4-chlorobenzoyl chloride were added to a solution of 25 mg (0.03 mmol) of benzyl[6-(4-aminobenzyl)-1-(2,4-dichlorobenzenesulfonyl)-8-isopropyl-4,7-dioxooctahydropyrazino[1,2-a]pyrimidin-3-yl]carbamate in 1 ml of dichloromethane. The mixture was stirred at room temperature overnight, diluted with dichloromethane and washed with brine. The organic phase was isolated, dried (MgSO$_4$) and concentrated in vacuo. The residue was chromatographed on 8 g of SiO$_2$ (elution with ethyl acetate/heptane, gradient 0-100% ethyl acetate). 28.5 mg of amide were obtained as oil. This compound was used directly in the next step.

28 mg (0.14 mmol) of TMSI were added to a solution of 28.5 mg (0.03 mmol) of the abovementioned Cbz-carbamate in 2 ml of acetonitrile at 0° C. The mixture was left to stand at room temperature overnight, concentrated in vacuo, diluted with methanol and filtered through an SCX (5 g) cartridge (elution with 5 ml of methanol and then with 15 ml of 7N ammonia in methanol). 18 mg of the desired amine were obtained as a brown oil. This compound was used without further purification in the next step.

3 mg (0.02 mmol) of DIEA and then 2.7 mg (0.02 mmol) of cyclopentanecarbonyl chloride were added to a solution of 18 mg (0.02 mmol) of the deblocked compound in 1 ml of DCM. The mixture was stirred at room temperature overnight and concentrated in vacuo. The residue was dissolved in 2 ml of ethyl acetate, washed with water, dried (MgSO$_4$) and concentrated in vacuo. It was then chromatographed on 4 g of SiO$_2$ (elution with ethyl acetate/heptane, gradient 0-100% ethyl acetate). 11 mg of the desired amide were obtained as an oil. LC/MS MW=773.16 (calculated, monoisotopic); measured value (M$^+$H)=774.12

EXAMPLE 205

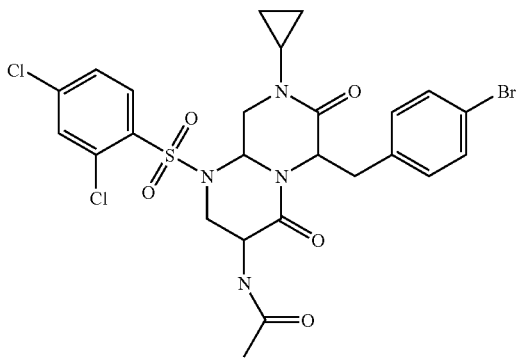

a) Cyclopropyl(2,2-diethoxyethyl)amine

A solution of 2.36 g (12 mmol) of 2-bromoacetaldehyde diethyl acetal and 4.94 g (86.6 mmol) of cyclopropylamine was heated in a closed vessel at 120° C. for 2 h. The reaction mixture was cooled to room temperature and diluted with 75 ml of ether and washed with 5% aq NaOH, followed by water and saturated sodium chloride solution. The organic phase was dried (MgSO$_4$) and concentrated in vacuo. The residue was distilled in vacuo (130° C.-140° C.). 2.01 g of the desired compound were obtained. LC/MS M+H=173 b) 9H-Fluoren-9-ylmethyl[1-[cyclopropyl(2,2-diethoxyethyl)carbamoyl]-2-(4-bromophenyl)ethyl]carbamate Synthesis takes place in analogy to Example 29a) (Method B) starting from N-Fmoc-4-Br-Phe-OH and cyclopropyl(2,2-diethoxyethyl)amine. The desired product is obtained with MW=629.19 (calculated, monoisotopic); measured value (M+Na)$^+$: 643.16 c) 2-Amino-3-(4-bromophenyl)-N-cyclopropyl-N-(2,2-diethoxyethyl)propionamide

Synthesis takes place in analogy to Example 29b) (Method B) starting from 9H-fluoren-9-ylmethyl[1-[cyclopropyl(2,2-diethoxyethyl)carbamoyl]-2-(4-bromophenyl)ethyl]-carbamate. The desired product is obtained with MW=398.12 (calculated, monoisotopic); measured value (M+H)$^+$: 399.11 d) Benzyl[1-{2-(4-bromophenyl)-1-[cyclopropyl(2,2-diethoxyethyl)carbamoyl]ethylcarbamoyl}-2-(9H-fluoren-9-ylmethoxycarbonylamino)ethyl]carbamate Synthesis took place in analogy to Example 29c) (Method B) starting from 2-amino-3-(4-bromophenyl)-N-cyclopropyl-N-(2,2-diethoxyethyl)propionamide. The desired product is obtained with MW=840.27 (calculated, monoisotopic); measured value (M+Na)$^+$: 863.23 e) Benzyl(2-amino-1-{2-(4-bromophenyl)-1-[cyclopropyl(2,2-diethoxyethyl)carbamoyl]-ethylcarbamoyl}ethyl)carbamate Synthesis took place in analogy to Example 29d) (Method B) starting from benzyl[1-{2-(4-bromophenyl)-1-[cyclopropyl(2,2-diethoxyethyl)carbamoyl]ethylcarbamoyl}-2-(9H-fluoren-9-ylmethoxycarbonylamino)ethyl]carbamate. The desired product is obtained with MW=618.21 (calculated, monoisotopic); measured value (M+H)$^+$: 619.2 f) Benzyl[1-{2-(4-bromophenyl)-1-[cyclopropyl(2,2-diethoxyethyl)carbamoyl]ethylcarbamoyl}-2-(2,4-dichlorobenzenesulfonylamino)ethyl]carbamate Synthesis took place in analogy to Example 29e) (Method B) starting from benzyl (2-amino-1-{2-(4-bromophenyl)-1-[cyclopropyl(2,2-diethoxyethyl)carbamoyl]ethylcarbamoyl}ethyl)carbamate. The desired product is obtained with MW=826.12 (calculated, monoisotopic); measured value (M+Na)$^+$: 849.14.

g) Benzyl[6-(4-bromobenzyl)-8-cyclopropyl-1-(2,4-dichlorobenzenesulfonyl)-4,7-dioxooctahydropyrazino[1,2-a]pyrimidin-3-yl]carbamate Synthesis took place in analogy to Example 29f) (Method B) starting from benzyl[1-{2-(4-bromophenyl)-1-[cyclopropyl(2,2-diethoxyethyl)carbamoyl]ethylcarbamoyl}-2-(2,4-dichlorobenzenesulfonylamino)ethyl]carbamate. The desired product is obtained with MW=734.04 (calculated, monoisotopic); measured value (M+H)$^+$: 735.02 h) 3-Amino-6-(4-bromobenzyl)-8-cyclopropyl-1-(2,4-dichlorobenzenesulfonyl)hexahydropyrazino[1,2-a]pyrimidine-4,7-dione Synthesis took place in analogy to Example 29g) (Method B) starting from benzyl[6-(4-bromobenzyl)-8-cyclopropyl-1-(2,4-dichlorobenzenesulfonyl)-4,7-dioxooctahydropyrazino[1,2-a]pyrimidin-3-yl]carbamate. The desired product is obtained with MW=600.0 (calculated, monoisotopic); measured value (M+H)$^+$: 600.99 i) N-[6-(4-Bromobenzyl)-8-cyclopropyl-1-(2,4-dichlorobenzenesulfonyl)-4,7-dioxooctahydropyrazino[1,2-a]pyrimidin-3-yl]acetamide Synthesis takes place in analogy to Example 21h) starting from 3-amino-6-(4-bromobenzyl)-8-cyclopropyl-1-(2,4-dichlorobenzenesulfonyl)hexahydropyrazino[1,2-a]pyrimidine-4,7-dione. The desired product is obtained with MW=642.01 (calculated, monoisotopic); measured value (M+H)$^+$: 643.02

EXAMPLE 206

N-[6-(4-Bromobenzyl)-8-cyclopropyl-1-(2,4-dichlorobenzenesulfonyl)-4,7-dioxooctahydropyrazino[1,2-a]pyrimidin-3-yl]cyclopropanecarboxamide Structure:

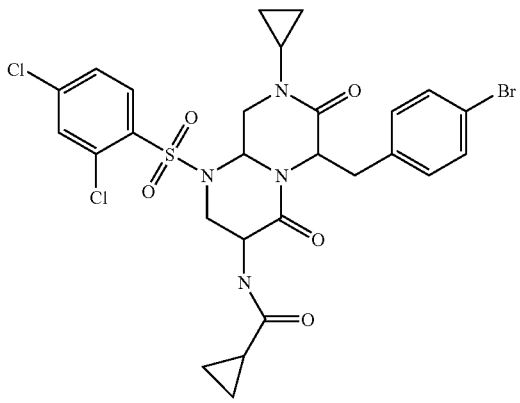

Synthesis takes place in analogy to Example 22 starting from 3-amino-6-(4-bromobenzyl)-8-cyclopropyl-1-(2,4-dichlorobenzenesulfonyl)hexahydropyrazino[1,2-a]pyrimidine-4,7-dione. The desired product is obtained with MW=668.03 (calculated, monoisotopic); measured value (M+H)$^+$: 669.04

EXAMPLE 207

N-[6-(4-Bromobenzyl)-8-cyclopropyl-1-(2,4-dichlorobenzenesulfonyl)-4,7-dioxooctahydropyrazino[1,2-a]pyrimidin-3-yl]cyclobutanecarboxamide Structure:

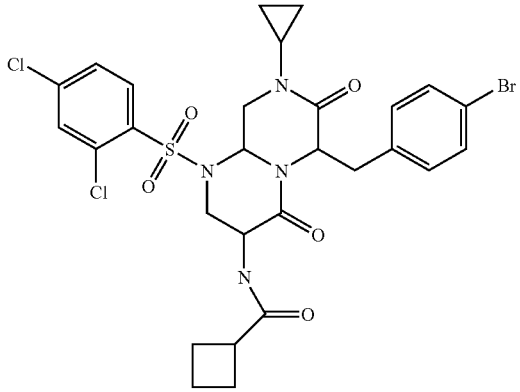

Synthesis takes place in analogy to Example 30 starting from 3-amino-6-(4-bromobenzyl)-8-cyclopropyl-1-(2,4-dichlorobenzenesulfonyl)hexahydropyrazino[1,2-a]pyrimidine-4,7-dione. The desired product is obtained with MW=682.04 (calculated, monoisotopic); measured value (M+H)$^+$: 683.06

EXAMPLE 208

N-[6-(4-Bromobenzyl)-8-cyclopropyl-1-(2,4-dichlorobenzenesulfonyl)-4,7-dioxooctahydropyrazino[1,2-a]pyrimidin-3-yl]cyclopentanecarboxamide Structure:

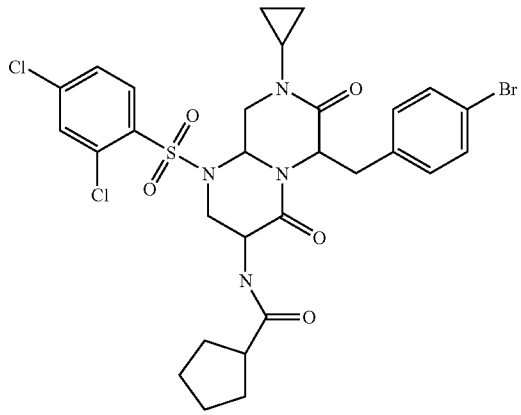

Synthesis takes place in analogy to Example 31 starting from 3-amino-6-(4-bromobenzyl)-8-cyclopropyl-1-(2,4-dichlorobenzenesulfonyl)hexahydropyrazino[1,2-a]pyrimidine-4,7-dione. The desired product is obtained with MW=696.06 (calculated, monoisotopic); measured value (M+H)$^+$: 697.08

EXAMPLE 209

N-[6-(4-Bromobenzyl)-8-cyclopropyl-1-(2,4-dichlorobenzenesulfonyl)-4,7-dioxooctahydropyrazino[1,2-a]pyrimidin-3-yl]pyrrolidine-2-carboxamide Structure:

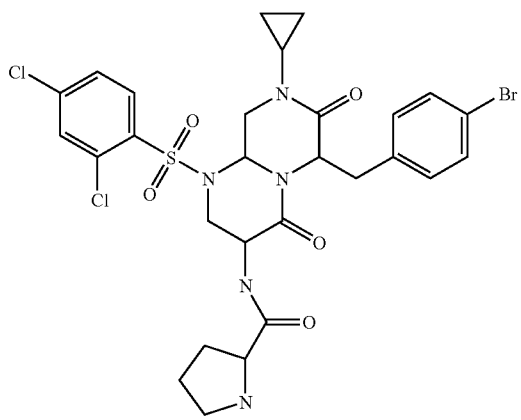

Synthesis takes place in analogy to Example 40 starting from 3-amino-6-(4-bromobenzyl)-8-cyclopropyl-1-(2,4-dichlorobenzenesulfonyl)hexahydropyrazino[1,2-a]pyrimidine-4,7-dione. The desired product is obtained with MW=697.05 (calculated, monoisotopic); measured value (M+H)$^+$: 698.02

EXAMPLE 210

N-[6-(4-Bromobenzyl)-8-cyclopropyl-1-(2,4-dichlorobenzenesulfonyl)-4,7-dioxooctahydropyrazino[1,2-a]pyrimidin-3-yl]-4-dimethylaminobenzamide Structure:

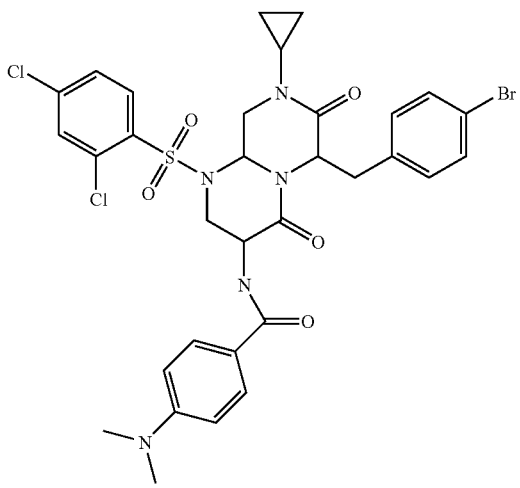

Synthesis takes place in analogy to Example 47 starting from 3-amino-6-(4-bromobenzyl)-8-cyclopropyl-1-(2,4-dichlorobenzenesulfonyl)hexahydropyrazino[1,2-a]pyrimidine-4,7-dione. The desired product is obtained with MW=747.07 (calculated, monoisotopic); measured value (M+H)$^+$: 748.08

EXAMPLE 211

N-[6-(4-Bromobenzyl)-8-cyclopropyl-1-(2,4-dichlorobenzenesulfonyl)-4,7-dioxooctahydropyrazino[1,2-a]pyrimidin-3-yl]nicotinamide Structure:

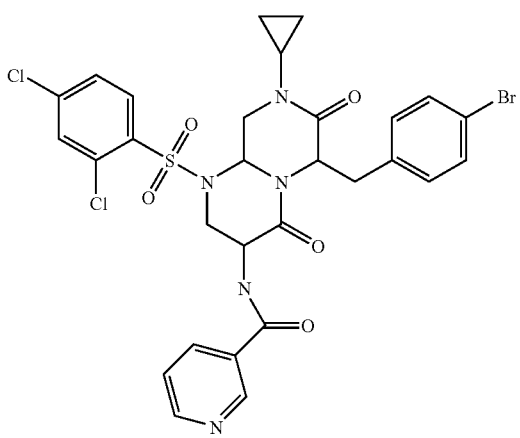

Synthesis takes place in analogy to Example 50 starting from 3-amino-6-(4-bromobenzyl)-8-cyclopropyl-1-(2,4-dichlorobenzenesulfonyl)hexahydropyrazino[1,2-a]pyrimidine-4,7-dione. The desired product is obtained with MW=705.02 (calculated, monoisotopic); measured value (M+H)$^+$: 706.06

EXAMPLE 212

1-[6-(4-Bromobenzyl)-8-cyclopropyl-1-(2,4-dichlorobenzenesulfonyl)-4,7-dioxooctahydropyrazino[1,2-a]pyrimidin-3-yl]-3-tert-butylurea Structure:

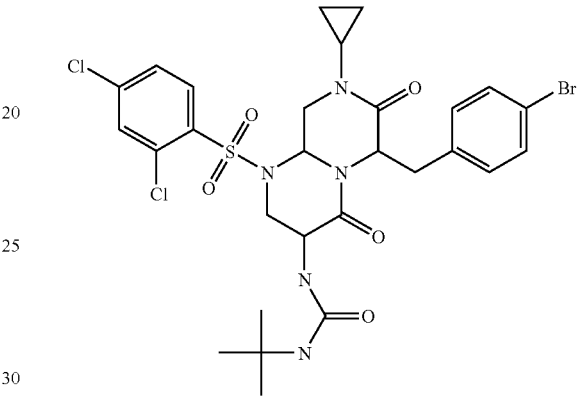

Synthesis takes place in analogy to Example 28 starting from 3-amino-6-(4-bromobenzyl)-8-cyclopropyl-1-(2,4-dichlorobenzenesulfonyl)hexahydropyrazino[1,2-a]pyrimidine-4,7-dione. The desired product is obtained with MW=699.07 (calculated, monoisotopic); measured value (M+H)$^+$: 700.09

EXAMPLE 213

N-[6-(4-Bromobenzyl)-8-cyclopropyl-1-(2,4-dichlorobenzenesulfonyl)-4,7-dioxooctahydropyrazino[1,2-a]pyrimidin-3-yl]methanesulfonamide Structure:

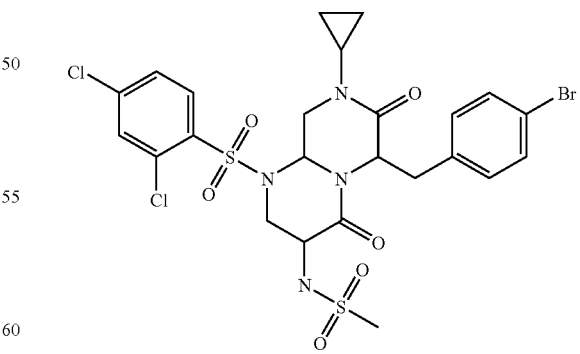

Synthesis takes place in analogy to Example 26 starting from 3-amino-6-(4-bromobenzyl)-8-cyclopropyl-1-(2,4-dichlorobenzenesulfonyl)hexahydropyrazino[1,2-a]pyrimidine-4,7-dione. The desired product is obtained with MW=677.98 (calculated, monoisotopic); measured value (M+H)$^+$: 679.0

EXAMPLE 214

N-[6-(4-Bromobenzyl)-8-cyclopropyl-1-(2,4-dichlorobenzenesulfonyl)-4,7-dioxooctahydropyrazino[1,2-a]pyrimidin-3-yl]cyclopropanesulfonamide Structure:

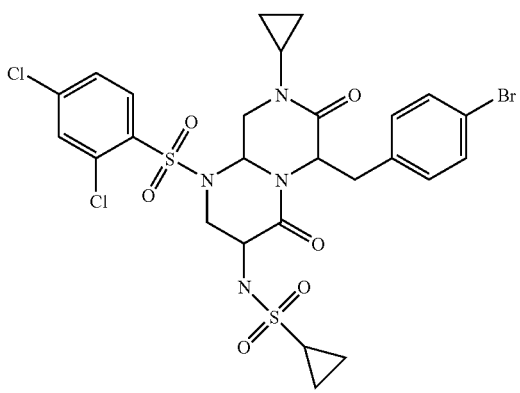

Synthesis takes place in analogy to Example 27 starting from 3-amino-6-(4-bromobenzyl)-8-cyclopropyl-1-(2,4-dichlorobenzenesulfonyl)hexahydropyrazino[1,2-a]pyrimidine-4,7-dione. The desired product is obtained with MW=703.99 (calculated, monoisotopic); measured value (M+H)$^+$: 705.01

EXAMPLE 215

6-(4-Bromobenzyl)-8-cyclopropyl-1-(2,4-dichlorobenzenesulfonyl)-3-dimethylaminohexahydropyrazino[1,2-a]pyrimidine-4,7-dione Structure:

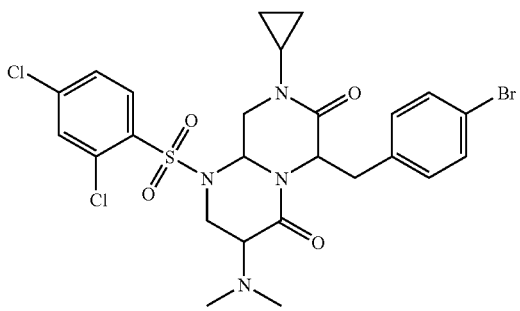

Synthesis takes place in analogy to Example 72 starting from 3-amino-6-(4-bromobenzyl)-8-cyclopropyl-1-(2,4-dichlorobenzenesulfonyl)hexahydropyrazino[1,2-a]pyrimidine-4,7-dione. The desired product is obtained with MW=628.03 (calculated, monoisotopic); measured value (M+H)$^+$: 629.04

EXAMPLE 216

3-Azetidin-1-yl-6-(4-bromobenzyl)-8-cyclopropyl-1-(2,4-dichlorobenzenesulfonyl)hexahydropyrazino[1,2-a]pyrimidine-4,7-dione Structure:

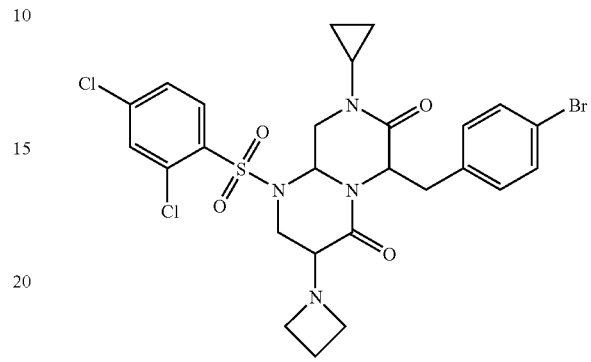

Synthesis takes place in analogy to Example 73 starting from 3-amino-6-(4-bromobenzyl)-8-cyclopropyl-1-(2,4-dichlorobenzenesulfonyl)hexahydropyrazino[1,2-a]pyrimidine-4,7-dione. The desired product is obtained with MW=636.08 (calculated, monoisotopic); measured value (M+H)$^+$: 637.1

EXAMPLE 217

6-(4-Bromobenzyl)-8-cyclopropyl-1-(2,4-dichlorobenzenesulfonyl)-3-pyrrolidin-1-ylhexahydropyrazino[1,2-a]pyrimidine-4,7-dione Structure:

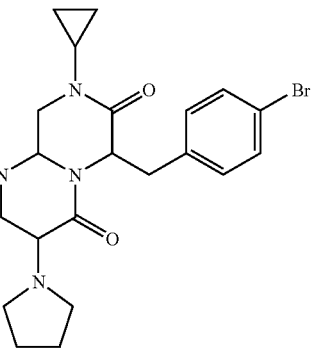

Synthesis takes place in analogy to Example 74 starting from 3-amino-6-(4-bromobenzyl)-8-cyclopropyl-1-(2,4-dichlorobenzenesulfonyl)hexahydropyrazino[1,2-a]pyrimidine-4,7-dione. The desired product is obtained with MW=654.05 (calculated, monoisotopic); measured value (M+H)$^+$: 655.04

EXAMPLE 218

6-(4-Bromobenzyl)-8-cyclopropyl-1-(2,4-dichlorobenzenesulfonyl)-3-piperidin-1-ylhexahydropyrazino[1,2-a]pyrimidine-4,7-dione Structure:

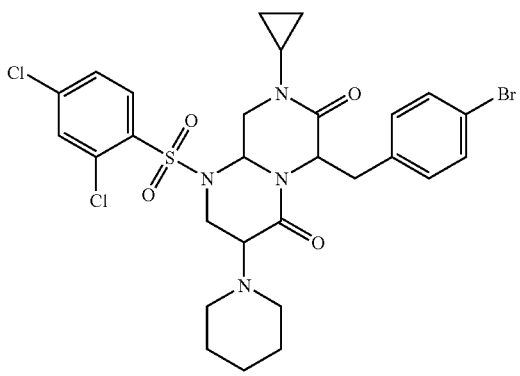

Synthesis takes place in analogy to Example 59 starting from 3-amino-6-(4-bromobenzyl)-8-cyclopropyl-1-(2,4-dichlorobenzenesulfonyl)hexahydropyrazino[1,2-a]pyrimidine-4,7-dione. The desired product is obtained with MW=668.06 (calculated, monoisotopic); measured value (M+H)$^+$: 669.08

EXAMPLE 219

6-(4-Bromobenzyl)-8-cyclopropyl-1-(2,4-dichlorobenzenesulfonyl)-3-morpholin-4-ylhexahydropyrazino[1,2-a]pyrimidine-4,7-dione Structure:

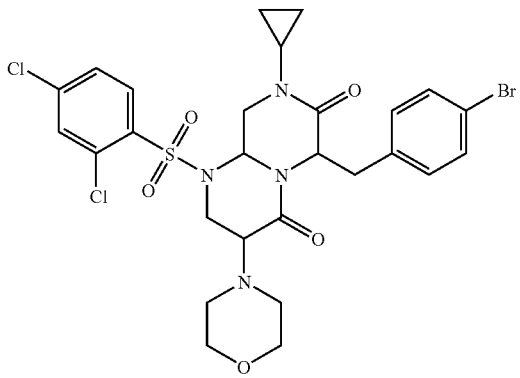

Synthesis takes place in analogy to Example 60 starting from 3-amino-6-(4-bromobenzyl)-8-cyclopropyl-1-(2,4-dichlorobenzenesulfonyl)hexahydropyrazino[1,2-a]pyrimidine-4,7-dione. The desired product is obtained with MW=670.04 (calculated, monoisotopic); measured value (M+H)$^+$: 670.97

EXAMPLE 220

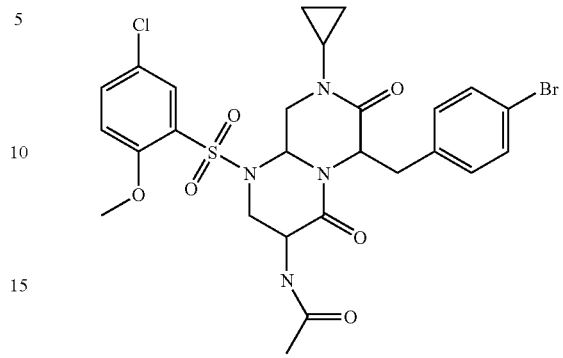

a) Benzyl[1-{2-(4-bromophenyl)-1-[cyclopropyl(2,2-diethoxyethyl)carbamoyl]ethylcarbamoyl}-2-(5-chloro-2-methoxybenzenesulfonylamino)ethyl]carbamate Synthesis takes place in analogy to Example 29e) (Method B) starting from benzyl (2-amino-1-{2-(4-bromophenyl)-1-[cyclopropyl(2,2-diethoxyethyl)carbamoyl]ethylcarbamoyl}ethyl)carbamate. The desired product is obtained with MW=822.17 (calculated, monoisotopic); measured value (M+Na)$^+$: 845.19 b) Benzyl[6-(4-bromobenzyl)-1-(5-chloro-2-methoxybenzenesulfonyl)-8-cyclopropyl-4,7-dioxooctahydropyrazino[1,2-a]pyrimidin-3-yl]carbamate Synthesis takes place in analogy to Example 29f) (Method B) starting from benzyl[1-{2-(4-bromophenyl)-1-[cyclopropyl(2,2-diethoxyethyl)carbamoyl]ethylcarbamoyl}-2-(5-chloro-2-methoxybenzenesulfonylamino)ethyl]carbamate. The desired product is obtained with MW=730.09 (calculated, monoisotopic); measured value (M+H)$^+$: 731.09 c) 3-Amino-6-(4-bromobenzyl)-1-(5-chloro-2-methoxybenzenesulfonyl)-8-cyclopropylhexahydropyrazino[1,2-a]pyrimidine-4,7-dione Synthesis takes place in analogy to Example 29g) (Method B) starting from benzyl[6-(4-bromobenzyl)-1-(5-chloro-2-methoxybenzenesulfonyl)-8-cyclopropyl-4,7-dioxooctahydropyrazino[1,2-a]pyrimidin-3-yl]carbamate. The desired product is obtained with MW=596.05 (calculated, monoisotopic); measured value (M+H)$^+$: 597.04 d) N-[6-(4-Bromobenzyl)-1-(5-chloro-2-methoxybenzenesulfonyl)-8-cyclopropyl-4,7-dioxooctahydropyrazino[1,2-a]pyrimidin-3-yl]acetamide Synthesis takes place in analogy in Example 21h) starting from 3-amino-6-(4-bromobenzyl)-1-(5-chloro-2-methoxybenzenesulfonyl)-8-cyclopropylhexahydropyrazino[1,2-a]pyrimidine-4,7-dione. The desired product is obtained with MW=638.06 (calculated, monoisotopic); measured value (M+H)$^+$: 639.11

EXAMPLE 221

N-[6-(4-Bromobenzyl)-1-(5-chloro-2-methoxybenzenesulfonyl)-8-cyclopropyl-4,7-dioxooctahydropyrazino[1,2-a]pyrimidin-3-yl]cyclopropanecarboxamide Structure:

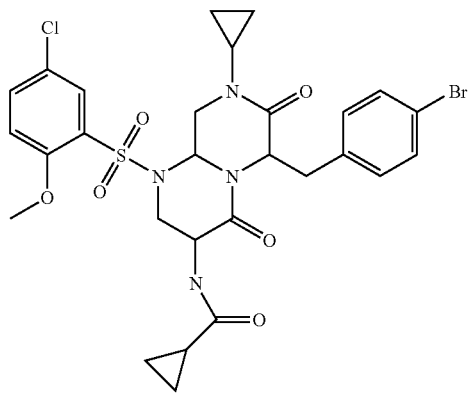

Synthesis takes place in analogy to Example 22 starting from 3-amino-6-(4-bromobenzyl)-1-(5-chloro-2-methoxybenzenesulfonyl)-8-cyclopropylhexahydropyrazino[1,2-a]pyrimidine-4,7-dione. The desired product is obtained with MW=664.08 (calculated, monoisotopic); measured value (M+H)$^+$: 665.13

EXAMPLE 222

N-[6-(4-Bromobenzyl)-1-(5-chloro-2-methoxybenzenesulfonyl)-8-cyclopropyl-4,7-dioxooctahydropyrazino[1,2-a]pyrimidin-3-yl]cyclobutanecarboxamide Structure:

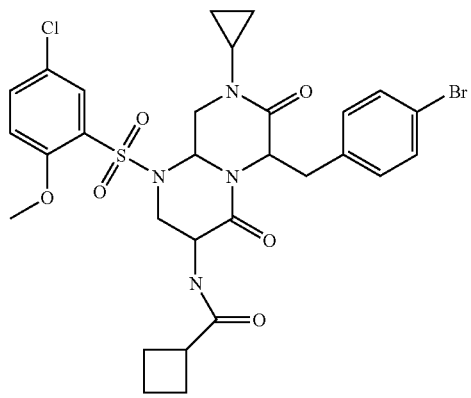

Synthesis takes place in analogy to Example 30 starting from 3-amino-6-(4-bromobenzyl)-1-(5-chloro-2-methoxybenzenesulfonyl)-8-cyclopropylhexahydropyrazino[1,2-a]pyrimidine-4,7-dione. The desired product is obtained with MW=678.09 (calculated, monoisotopic); measured value (M+H)$^+$: 679.15

EXAMPLE 223

N-[6-(4-Bromobenzyl)-1-(5-chloro-2-methoxybenzenesulfonyl)-8-cyclopropyl-4,7-dioxooctahydropyrazino[1,2-a]pyrimidin-3-yl]cyclopentanecarboxamide Structure:

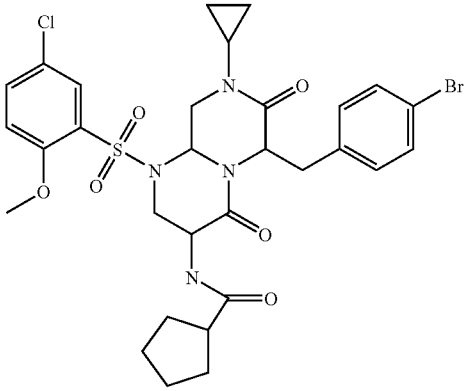

Synthesis takes place in analogy to Example 31 starting from 3-amino-6-(4-bromobenzyl)-1-(5-chloro-2-methoxybenzenesulfonyl)-8-cyclopropylhexahydropyrazino[1,2-a]pyrimidine-4,7-dione. The desired product is obtained with MW=692.11 (calculated, monoisotopic); measured value (M+H)$^+$: 693.16

EXAMPLE 224

N-[6-(4-Bromobenzyl)-1-(5-chloro-2-methoxybenzenesulfonyl)-8-cyclopropyl-4,7-dioxooctahydropyrazino[1,2-a]pyrimidin-3-yl]pyrrolidine-2-carboxamide Structure:

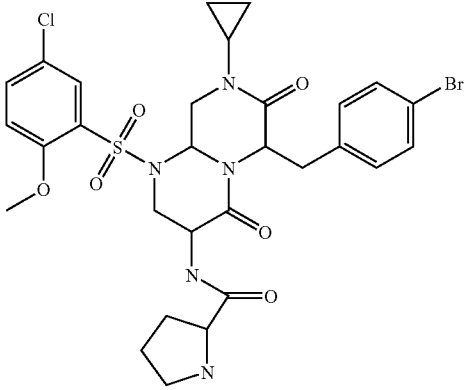

Synthesis takes place in analogy to Example 40 starting from 3-amino-6-(4-bromobenzyl)-1-(5-chloro-2-methoxybenzenesulfonyl)-8-cyclopropylhexahydropyrazino[1,2-a]pyrimidine-4,7-dione. The desired product is obtained with MW=693.10 (calculated, monoisotopic); measured value (M+H)$^+$: 694.06

EXAMPLE 225

N-[6-(4-Bromobenzyl)-1-(5-chloro-2-methoxybenzenesulfonyl)-8-cyclopropyl-4,7-dioxooctahydropyrazino[1,2-a]pyrimidin-3-yl]-4-dimethylaminobenzamide Structure:

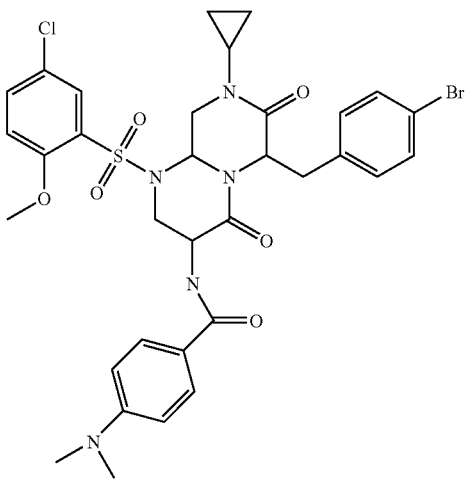

Synthesis takes place in analogy to Example 25 starting from 3-amino-6-(4-bromobenzyl)-1-(5-chloro-2-methoxybenzenesulfonyl)-8-cyclopropylhexahydropyrazino[1,2-a]pyrimidine-4,7-dione. The desired product is obtained with MW=743.12 (calculated, monoisotopic); measured value (M+H)$^+$: 744.17

EXAMPLE 226

N-[6-(4-Bromobenzyl)-1-(5-chloro-2-methoxybenzenesulfonyl)-8-cyclopropyl-4,7-dioxooctahydropyrazino[1,2-a]pyrimidin-3-yl]nicotinamide Structure:

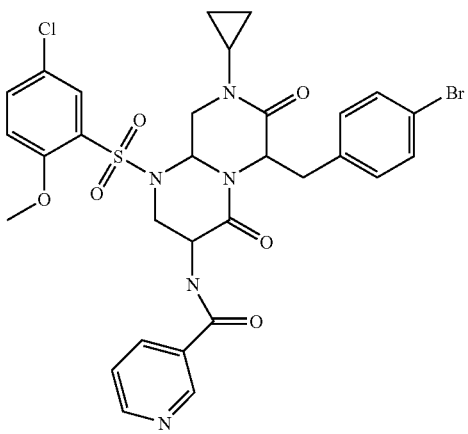

Synthesis takes place in analogy to Example 50 starting from 3-amino-6-(4-bromobenzyl)-1-(5-chloro-2-methoxybenzenesulfonyl)-8-cyclopropylhexahydropyrazino[1,2-a]pyrimidine-4,7-dione. The desired product is obtained with MW=701.07 (calculated, monoisotopic); measured value (M+H)$^+$: 702.08

EXAMPLE 227

1-[6-(4-Bromobenzyl)-1-(5-chloro-2-methoxybenzenesulfonyl)-8-cyclopropyl-4,7-dioxooctahydropyrazino[1,2-a]pyrimidin-3-yl]-3-tert-butylurea Structure:

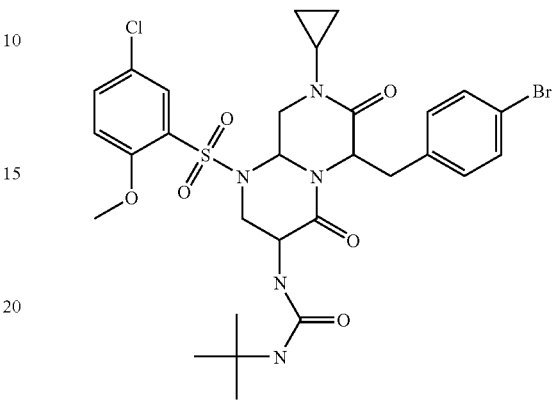

Synthesis takes place in analogy to Example 28 starting from 3-amino-6-(4-bromobenzyl)-1-(5-chloro-2-methoxybenzenesulfonyl)-8-cyclopropylhexahydropyrazino[1,2-a]pyrimidine-4,7-dione. The desired product is obtained with MW=695.12 (calculated, monoisotopic); measured value (M+H)$^+$: 696.17

EXAMPLE 228

N-[6-(4-Bromobenzyl)-1-(5-chloro-2-methoxybenzenesulfonyl)-8-cyclopropyl-4,7-dioxooctahydropyrazino[1,2-a]pyrimidin-3-yl]methanesulfonamide Structure:

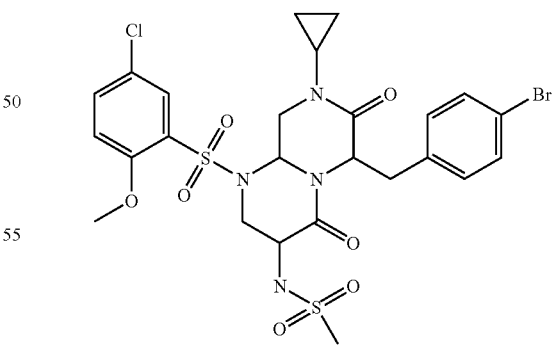

Synthesis takes place in analogy to Example 26 starting from 3-amino-6-(4-bromobenzyl)-1-(5-chloro-2-methoxybenzenesulfonyl)-8-cyclopropylhexahydropyrazino[1,2-a]pyrimidine-4,7-dione. The desired product is obtained with MW=674.03 (calculated, monoisotopic); measured value (M+H)$^+$: 675.08

EXAMPLE 229

N-[6-(4-Bromobenzyl)-1-(5-chloro-2-methoxybenzenesulfonyl)-8-cyclopropyl-4,7-dioxooctahydropyrazino[1,2-a]pyrimidin-3-yl]cyclopropanesulfonamide Structure:

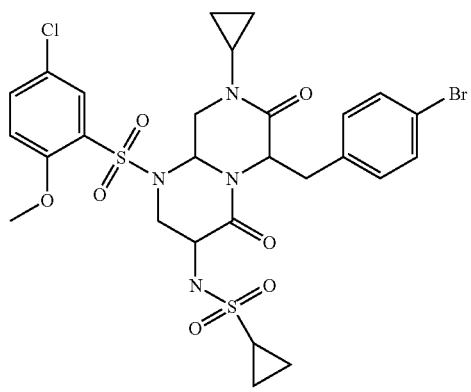

Synthesis takes place in analogy to Example 27 starting from 3-amino-6-(4-bromobenzyl)-1-(5-chloro-2-methoxybenzenesulfonyl)-8-cyclopropylhexahydropyrazino[1,2-a]pyrimidine-4,7-dione. The desired product is obtained with MW=700.04 (calculated, monoisotopic); measured value (M+H)$^+$: 701.1

EXAMPLE 230

6-(4-Bromobenzyl)-1-(5-chloro-2-methoxybenzenesulfonyl)-8-cyclopropyl-3-dimethylaminohexahydropyrazino[1,2-a]pyrimidine-4,7-dione Structure:

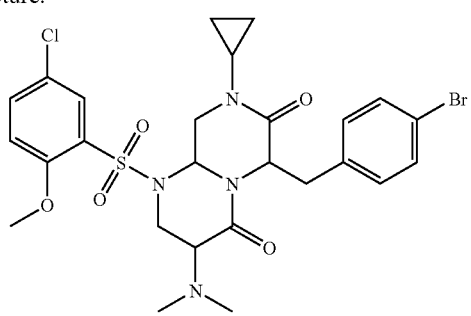

Synthesis takes place in analogy to Example 72 starting from 3-amino-6-(4-bromobenzyl)-1-(5-chloro-2-methoxybenzenesulfonyl)-8-cyclopropylhexahydropyrazino[1,2-a]pyrimidine-4,7-dione. The desired product is obtained with MW=743.12 (calculated, monoisotopic); measured value (M+H)$^+$: 744.17

EXAMPLE 231

3-Azetidin-1-yl-6-(4-bromobenzyl)-1-(5-chloro-2-methoxybenzenesulfonyl)-8-cyclopropylhexahydropyrazino[1,2-a]pyrimidine-4,7-dione Structure:

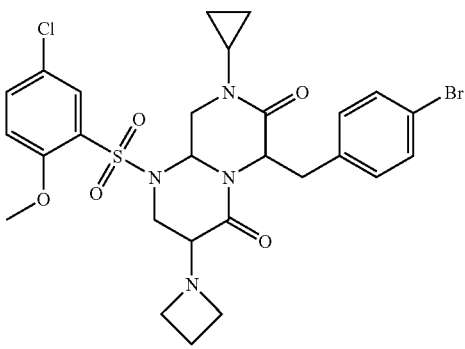

Synthesis takes place in analogy to Example 73 starting from 3-amino-6-(4-bromobenzyl)-1-(5-chloro-2-methoxybenzenesulfonyl)-8-cyclopropylhexahydropyrazino[1,2-a]pyrimidine-4,7-dione. The desired product is obtained with MW=640.03 (calculated, monoisotopic); measured value (M+H)$^+$: 641.0

EXAMPLE 232

6-(4-Bromobenzyl)-1-(5-chloro-2-methoxybenzenesulfonyl)-8-cyclopropyl-3-pyrrolidin-1-ylhexahydropyrazino[1,2-a]pyrimidine-4,7-dione Structure:

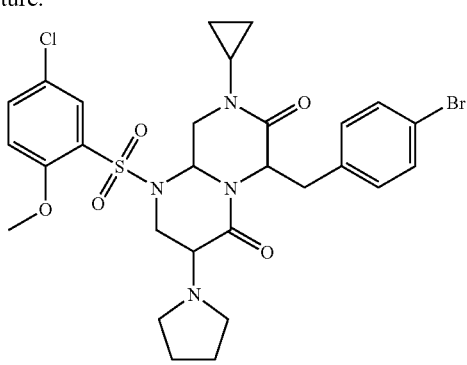

Synthesis takes place in analogy to Example 74 starting from 3-amino-6-(4-bromobenzyl)-1-(5-chloro-2-methoxybenzenesulfonyl)-8-cyclopropylhexahydropyrazino[1,2-a]pyrimidine-4,7-dione. The desired product is obtained with MW=650.10 (calculated, monoisotopic); measured value (M+H)$^+$: 651.07

EXAMPLE 233

6-(4-Bromobenzyl)-1-(5-chloro-2-methoxybenzene-
sulfonyl)-8-cyclopropyl-3-piperidin-1-ylhexahydro-
pyrazino[1,2-a]pyrimidine-4,7-dione Structure:

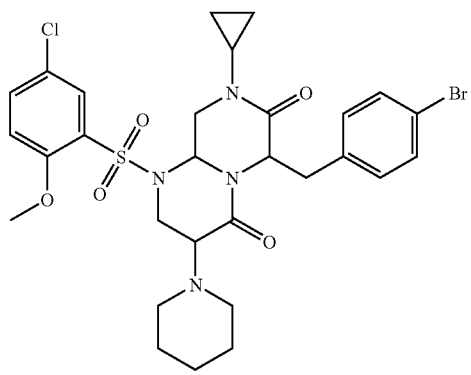

Synthesis takes place in analogy to Example 59 starting from 3-amino-6-(4-bromobenzyl)-1-(5-chloro-2-methoxy-benzenesulfonyl)-8-cyclopropylhexahydropyrazino[1,2-a]pyrimidine-4,7-dione. The desired product is obtained with MW=664.11 (calculated, monoisotopic); measured value (M+H)$^+$: 665.12

EXAMPLE 234

6-(4-Bromobenzyl)-1-(5-chloro-2-methoxybenzene-
sulfonyl)-8-cyclopropyl-3-morpholin-4-ylhexahydro-
pyrazino[1,2-a]pyrimidine-4,7-dione Structure:

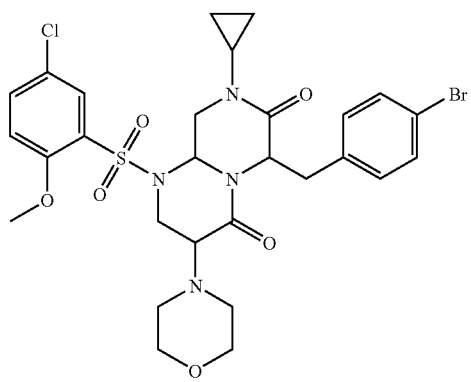

Synthesis takes place in analogy to Example 60 starting from 3-amino-6-(4-bromobenzyl)-1-(5-chloro-2-methoxy-benzenesulfonyl)-8-cyclopropylhexahydropyrazino[1,2-a]pyrimidine-4,7-dione. The desired product is obtained with MW=666.09 (calculated, monoisotopic); measured value (M+H)$^+$: 667.02

EXAMPLE 235

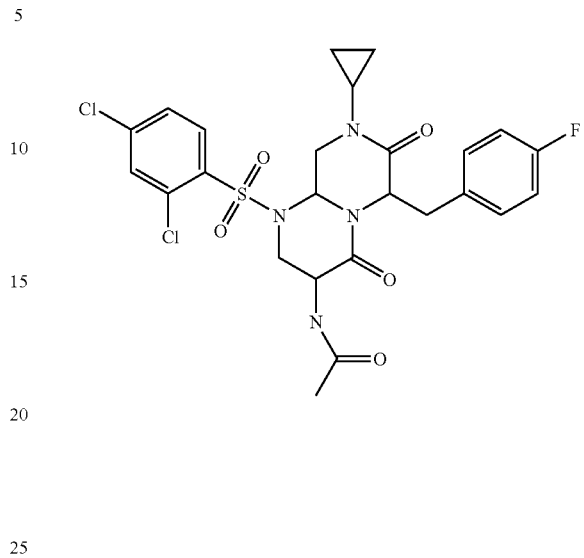

a) Benzyl[6-(4-fluorobenzyl)-8-cyclopropyl-1-(2,4-
dichlorobenzenesulfonyl)-4,7-dioxooctahydropy-
razino[1,2-a]pyrimidin-3-yl]carbamate Synthesis takes place in analogy to Example 66a. The desired product is obtained with MW=689.16 (calculated, monoisotopic); measured value (M+H)$^+$: 690.10 b) 3-Amino-6-(4-fluorobenzyl)-8-cyclopropyl-1-(2,
4-dichlorobenzenesulfonyl)hexahydropyrazino[1,2-
a]pyrimidine-4,7-dione Synthesis takes place in analogy to Example 66b) starting from benzyl[6-(4-fluorobenzyl)-8-cyclopropyl-1-(2,4-dichlorobenzenesulfonyl)-4,7-dioxooctahydropyrazino[1,2-a]pyrimidin-3-yl]carbamate. The desired product is obtained with MW=540.08 (calculated, monoisotopic); measured value (M+H)$^+$: 541.06 c) N-[6-(4-Fluorobenzyl)-8-cyclopropyl-1-(2,4-
dichlorobenzenesulfonyl)-4,7-dioxooctahydropy-
razino[1,2-a]pyrimidin-3-yl]acetamide Synthesis takes place in analogy to Example 21h) starting from 3-amino-6-(4-fluorobenzyl)-8-cyclopropyl-1-(2,4-dichlorobenzenesulfonyl)hexahydropyrazino[1,2-a]pyrimi-dine-4,7-dione. The desired product is obtained with MW=582.09 (calculated, monoisotopic); measured value (M+H)$^+$: 583.10

EXAMPLE 236

N-[8-Cyclopropyl-1-(2,4-dichlorobenzenesulfonyl)-6-(4-fluorobenzyl)-4,7-dioxooctahydropyrazino[1,2-a]pyrimidin-3-yl]cyclopropanecarboxamide Structure:

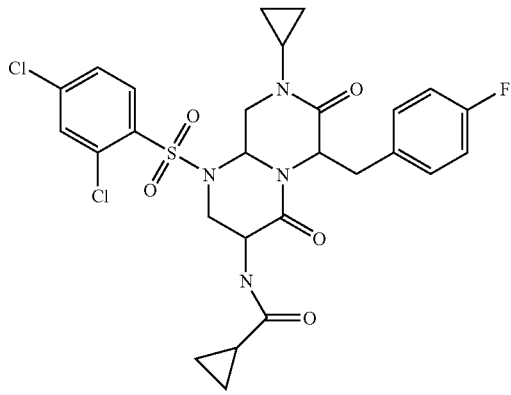

Synthesis takes place in analogy to Example 22 starting from 3-amino-6-(4-fluorobenzyl)-8-cyclopropyl-1-(2,4-dichlorobenzenesulfonyl)hexahydropyrazino[1,2-a]pyrimidine-4,7-dione. The desired product is obtained with MW=608.11 (calculated, monoisotopic); measured value (M+H)$^+$: 609.11

EXAMPLE 237

N-[8-Cyclopropyl-1-(2,4-dichlorobenzenesulfonyl)-6-(4-fluorobenzyl)-4,7-dioxooctahydropyrazino[1,2-a]pyrimidin-3-yl]cyclobutanecarboxamide Structure:

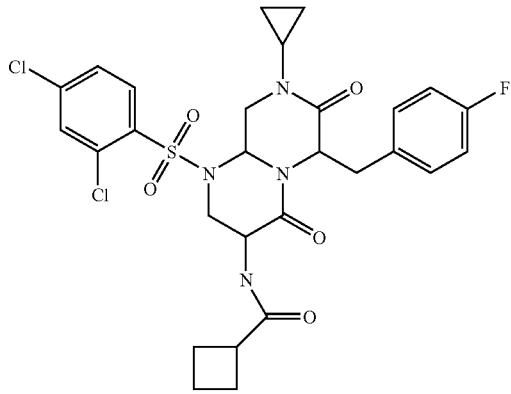

Synthesis takes place in analogy to Example 30 starting from 3-amino-6-(4-fluorobenzyl)-8-cyclopropyl-1-(2,4-dichlorobenzenesulfonyl)hexahydropyrazino[1,2-a]pyrimidine-4,7-dione. The desired product is obtained with MW=622.12 (calculated, monoisotopic); measured value (M+H)$^+$: 623.13

EXAMPLE 238

N-[8-Cyclopropyl-1-(2,4-dichlorobenzenesulfonyl)-6-(4-fluorobenzyl)-4,7-dioxooctahydropyrazino[1,2-a]pyrimidin-3-yl]cyclopentanecarboxamide Structure:

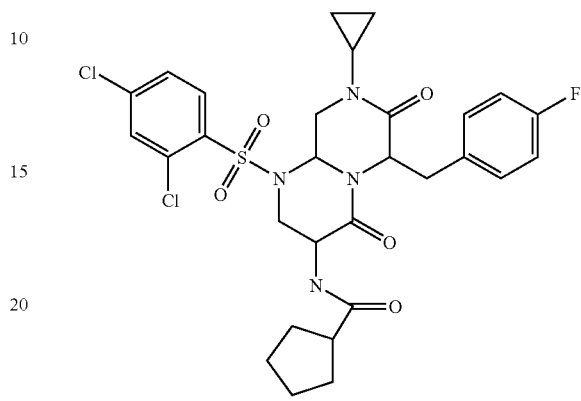

Synthesis takes place in analogy to Example 31 starting from 3-amino-6-(4-fluorobenzyl)-8-cyclopropyl-1-(2,4-dichlorobenzenesulfonyl)hexahydropyrazino[1,2-a]pyrimidine-4,7-dione. The desired product is obtained with MW=636.14 (calculated, monoisotopic); measured value (M+H)$^+$: 637.14

EXAMPLE 239

N-[8-Cyclopropyl-1-(2,4-dichlorobenzenesulfonyl)-6-(4-fluorobenzyl)-4,7-dioxooctahydropyrazino[1,2-a]pyrimidin-3-yl]-4-dimethylaminobenzamide Structure:

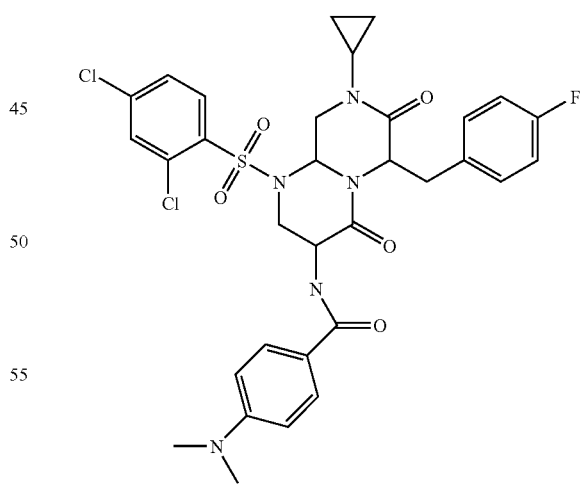

Synthesis takes place in analogy to Example 25 starting from 3-amino-6-(4-fluorobenzyl)-8-cyclopropyl-1-(2,4-dichlorobenzenesulfonyl)hexahydropyrazino[1,2-a]pyrimidine-4,7-dione. The desired product is obtained with MW=687.15 (calculated, monoisotopic); measured value (M+H)$^+$: 688.15

EXAMPLE 240

1-tert-Butyl-3-[8-cyclopropyl-1-(2,4-dichlorobenzenesulfonyl)-6-(4-fluorobenzyl)-4,7-dioxooctahydropyrazino[1,2-a]pyrimidin-3-yl]urea Structure:

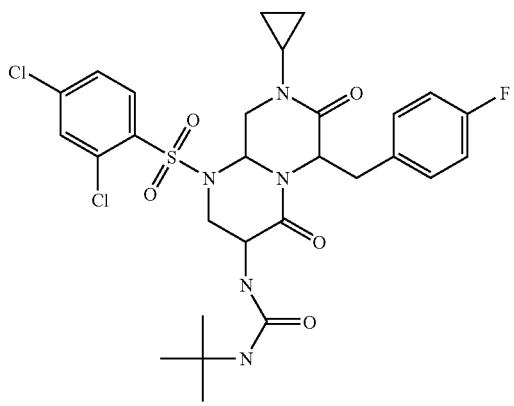

Synthesis takes place in analogy to Example 28 starting from 3-amino-6-(4-fluorobenzyl)-8-cyclopropyl-1-(2,4-dichlorobenzenesulfonyl)hexahydropyrazino[1,2-a]pyrimidine-4,7-dione. The desired product is obtained with MW=639.15 (calculated, monoisotopic); measured value (M+H)$^+$: 640.18

EXAMPLE 241

N-[8-Cyclopropyl-1-(2,4-dichlorobenzenesulfonyl)-6-(4-fluorobenzyl)-4,7-dioxooctahydropyrazino[1,2-a]pyrimidin-3-yl]methanesulfonamide Structure:

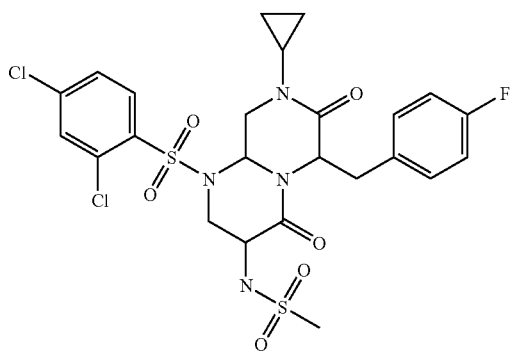

Synthesis takes place in analogy to Example 26 starting from 3-amino-6-(4-fluorobenzyl)-8-cyclopropyl-1-(2,4-dichlorobenzenesulfonyl)hexahydropyrazino[1,2-a]pyrimidine-4,7-dione. The desired product is obtained with MW=618.06 (calculated, monoisotopic); measured value (M+H)$^+$: 619.08

EXAMPLE 242

8-Cyclopropyl-1-(2,4-dichlorobenzenesulfonyl)-3-dimethylamino-6-(4-fluorobenzyl)hexahydropyrazino[1,2-a]pyrimidine-4,7-dione Structure:

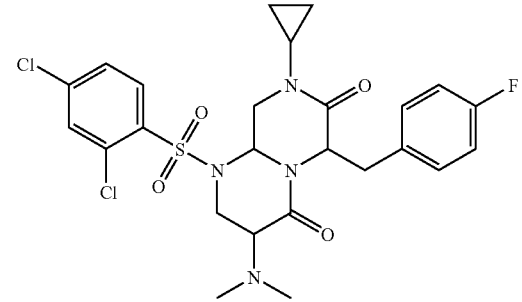

Synthesis takes place in analogy to Example 72 starting from 3-amino-6-(4-fluorobenzyl)-8-cyclopropyl-1-(2,4-dichlorobenzenesulfonyl)hexahydropyrazino[1,2-a]pyrimidine-4,7-dione. The desired product is obtained with MW=568.11 (calculated, monoisotopic); measured value (M+H)$^+$: 569.12

EXAMPLE 243

8-Cyclopropyl-1-(2,4-dichlorobenzenesulfonyl)-6-(4-fluorobenzyl)-3-piperidin-1-ylhexahydropyrazino[1,2-a]pyrimidine-4,7-dione Structure:

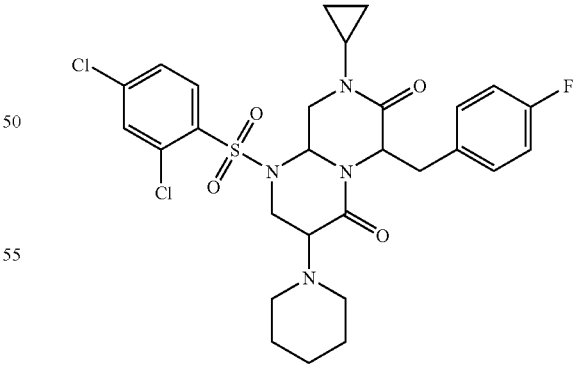

Synthesis takes place in analogy to Example 59 starting from 3-amino-6-(4-fluorobenzyl)-8-cyclopropyl-1-(2,4-dichlorobenzenesulfonyl)hexahydropyrazino[1,2-a]pyrimidine-4,7-dione. The desired product is obtained with MW=608.14 (calculated, monoisotopic); measured value (M+H)$^+$: 609.14

EXAMPLE 244

8-Cyclopropyl-1-(2,4-dichlorobenzenesulfonyl)-6-(4-fluorobenzyl)-3-morpholin-4-ylhexahydropyrazino[1,2-a]pyrimidine-4,7-dione Structure:

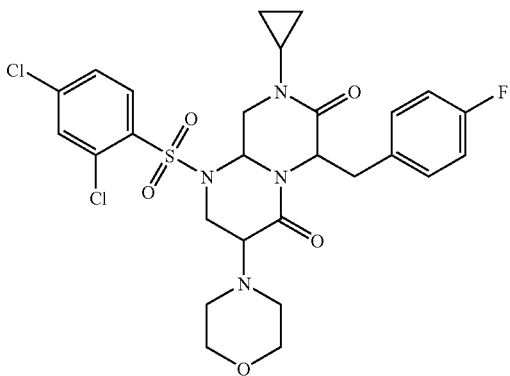

Synthesis takes place in analogy to Example 60 starting from 3-amino-6-(4-fluorobenzyl)-8-cyclopropyl-1-(2,4-dichlorobenzenesulfonyl)hexahydropyrazino[1,2-a]pyrimidine-4,7-dione. The desired product is obtained with MW=610.12 (calculated, monoisotopic); measured value (M+H)$^+$: 611.1

EXAMPLE 245

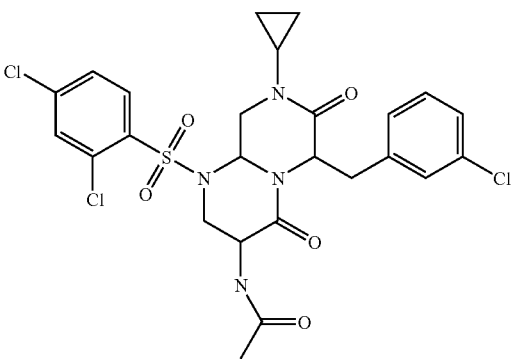

a) Benzyl[6-(3-chlorobenzyl)-8-cyclopropyl-1-(2,4-dichlorobenzenesulfonyl)-4,7-dioxooctahydropyrazino[1,2-a]pyrimidin-3-yl]carbamate Synthesis takes place in analogy to Example 66a). The desired product is obtained with MW=690.09 (calculated, monoisotopic); measured value (M+H)$^+$: 691.0 b) 3-Amino-6-(3-chlorobenzyl)-8-cyclopropyl-1-(2,4-dichlorobenzenesulfonyl)hexahydropyrazino[1,2-a]pyrimidine-4,7-dione Synthesis takes place in analogy to Example 66b) starting from benzyl[6-(3-chlorobenzyl)-8-cyclopropyl-1-(2,4-dichlorobenzenesulfonyl)-4,7-dioxooctahydropyrazino[1,2-a]pyrimidin-3-yl]carbamate. The desired product is obtained with MW=556.05 (calculated, monoisotopic); measured value (M+H)$^+$: 557.04 c) N-[6-(3-Chlorobenzyl)-8-cyclopropyl-1-(2,4-dichlorobenzenesulfonyl)-4,7-dioxooctahydropyrazino[1,2-a]pyrimidin-3-yl]acetamide Synthesis takes place in analogy to Example 21h) starting from 3-amino-6-(3-chlorobenzyl)-8-cyclopropyl-1-(2,4-dichlorobenzenesulfonyl)hexahydropyrazino[1,2-a]pyrimidine-4,7-dione. The desired product is obtained with MW=598.06 (calculated, monoisotopic); measured value (M+H)$^+$: 599.0

EXAMPLE 246

N-[6-(3-Chlorobenzyl)-8-cyclopropyl-1-(2,4-dichlorobenzenesulfonyl)-4,7-dioxooctahydropyrazino[1,2-a]pyrimidin-3-yl]cyclopropanecarboxamide Structure:

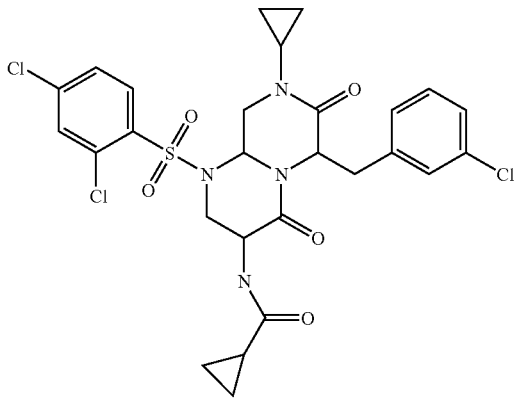

Synthesis takes place in analogy to Example 22 starting from 3-amino-6-(3-chlorobenzyl)-8-cyclopropyl-1-(2,4-dichlorobenzenesulfonyl)hexahydropyrazino[1,2-a]pyrimidine-4,7-dione. The desired product is obtained with MW=624.08 (calculated, monoisotopic); measured value (M+H)$^+$: 625.0

EXAMPLE 247

N-[6-(3-Chlorobenzyl)-8-cyclopropyl-1-(2,4-dichlorobenzenesulfonyl)-4,7-dioxooctahydropyrazino[1,2-a]pyrimidin-3-yl]cyclobutanecarboxamide Structure:

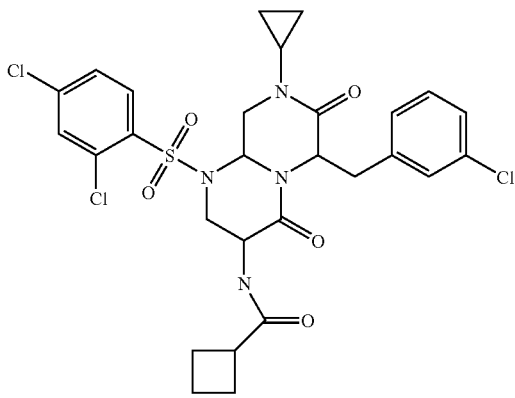

Synthesis takes place in analogy to Example 30 starting from 3-amino-6-(3-chlorobenzyl)-8-cyclopropyl-1-(2,4- dichlorobenzenesulfonyl)hexahydropyrazino[1,2-a]pyrimidine-4,7-dione. The desired product is obtained with MW=638.09 (calculated, monoisotopic); measured value (M+H)+: 639.08

EXAMPLE 248

N-[6-(3-Chlorobenzyl)-8-cyclopropyl-1-(2,4-dichlorobenzenesulfonyl)-4,7-dioxooctahydropyrazino[1,2-a]pyrimidin-3-yl]cyclopentanecarboxamide Structure:

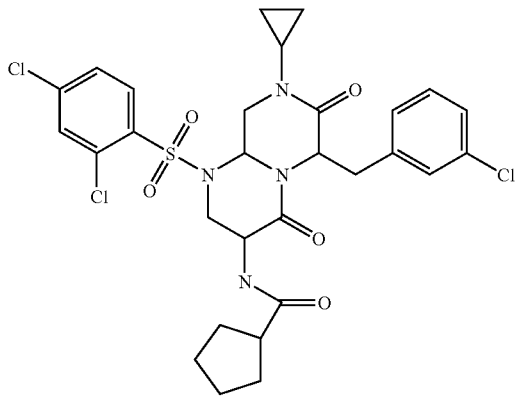

Synthesis takes place in analogy to Example 31 starting from 3-amino-6-(3-chlorobenzyl)-8-cyclopropyl-1-(2,4-dichlorobenzenesulfonyl)hexahydropyrazino[1,2-a]pyrimidine-4,7-dione. The desired product is obtained with MW=652.11 (calculated, monoisotopic); measured value (M+H)+: 653.0

EXAMPLE 249

N-[6-(3-Chlorobenzyl)-8-cyclopropyl-1-(2,4-dichlorobenzenesulfonyl)-4,7-dioxooctahydropyrazino[1,2-a]pyrimidin-3-yl]-4-dimethylaminobenzamide Structure:

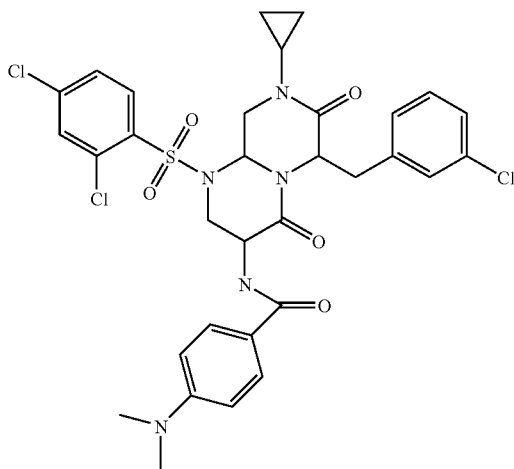

Synthesis takes place in analogy to Example 25 starting from 3-amino-6-(3-chlorobenzyl)-8-cyclopropyl-1-(2,4-dichlorobenzenesulfonyl)hexahydropyrazino[1,2-a]pyrimidine-4,7-dione. The desired product is obtained with MW=703.12 (calculated, monoisotopic); measured value (M+H)+: 704.0

EXAMPLE 250

1-tert-Butyl-3-[6-(3-chlorobenzyl)-8-cyclopropyl-1-(2,4-dichlorobenzenesulfonyl)-4,7-dioxooctahydropyrazino[1,2-a]pyrimidin-3-yl]urea Structure:

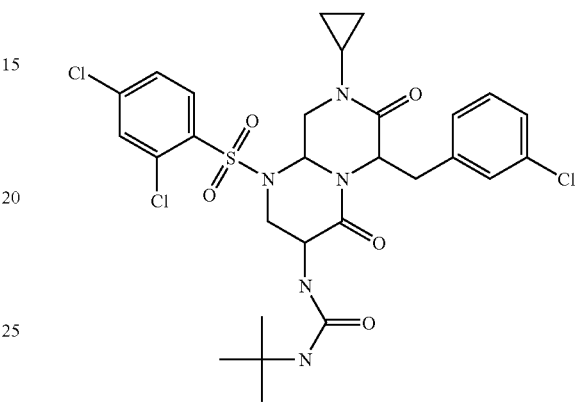

Synthesis takes place in analogy to Example 28 starting from 3-amino-6-(3-chlorobenzyl)-8-cyclopropyl-1-(2,4-dichlorobenzenesulfonyl)hexahydropyrazino[1,2-a]pyrimidine-4,7-dione. The desired product is obtained with MW=655.12 (calculated, monoisotopic); measured value (M+H)+: 656.11

EXAMPLE 251

N-[6-(3-Chlorobenzyl)-8-cyclopropyl-1-(2,4-dichlorobenzenesulfonyl)-4,7-dioxooctahydropyrazino[1,2-a]pyrimidin-3-yl]methanesulfonamide Structure:

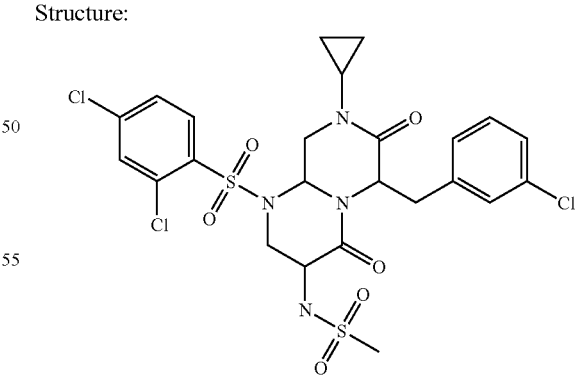

Synthesis takes place in analogy to Example 26 starting from 3-amino-6-(3-chlorobenzyl)-8-cyclopropyl-1-(2,4-dichlorobenzenesulfonyl)hexahydropyrazino[1,2-a]pyrimidine-4,7-dione. The desired product is obtained with MW=634.03 (calculated, monoisotopic); measured value (M+H)+: 635.0

EXAMPLE 252

6-(3-Chlorobenzyl)-8-cyclopropyl-1-(2,4-dichlorobenzenesulfonyl)-3-dimethylaminohexahydropyrazino[1,2-a]pyrimidine-4,7-dione Structure:

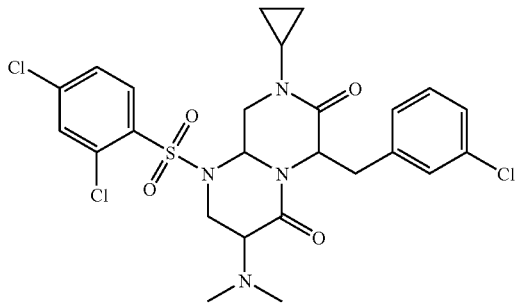

Synthesis takes place in analogy to Example 72 starting from 3-amino-6-(3-chlorobenzyl)-8-cyclopropyl-1-(2,4-dichlorobenzenesulfonyl)hexahydropyrazino[1,2-a]pyrimidine-4,7-dione. The desired product is obtained with MW=584.08 (calculated, monoisotopic); measured value (M+H)$^+$: 585.1

EXAMPLE 253

3-Azetidin-1-yl-6-(3-chlorobenzyl)-8-cyclopropyl-1-(2,4-dichlorobenzenesulfonyl)hexahydropyrazino[1,2-a]pyrimidine-4,7-dione Structure:

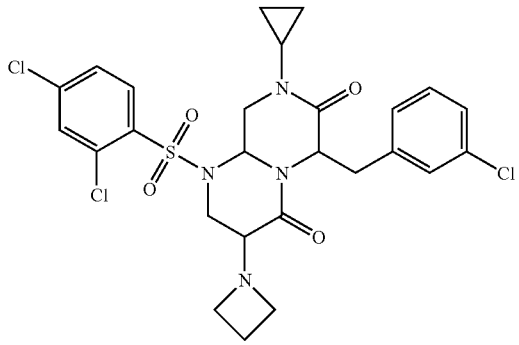

Synthesis takes place in analogy to Example 73 starting from 3-amino-6-(3-chlorobenzyl)-8-cyclopropyl-1-(2,4-dichlorobenzenesulfonyl)hexahydropyrazino[1,2-a]pyrimidine-4,7-dione. The desired product is obtained with MW=596.08 (calculated, monoisotopic); measured value (M+H)$^+$: 597.07

EXAMPLE 254

6-(3-Chlorobenzyl)-8-cyclopropyl-1-(2,4-dichlorobenzenesulfonyl)-3-pyrrolidin-1-ylhexahydropyrazino[1,2-a]pyrimidine-4,7-dione Structure:

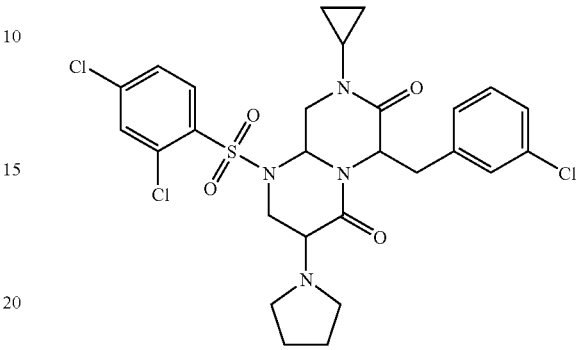

Synthesis takes place in analogy to Example 74 starting from 3-amino-6-(3-chlorobenzyl)-8-cyclopropyl-1-(2,4-dichlorobenzenesulfonyl)hexahydropyrazino[1,2-a]pyrimidine-4,7-dione. The desired product is obtained with MW=610.10 (calculated, monoisotopic); measured value (M+H)$^+$: 611.09

EXAMPLE 255

6-(3-Chlorobenzyl)-8-cyclopropyl-1-(2,4-dichlorobenzenesulfonyl)-3-piperidin-1-ylhexahydropyrazino[1,2-a]pyrimidine-4,7-dione Structure:

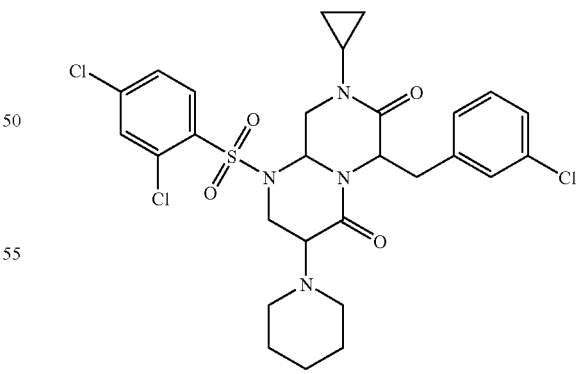

Synthesis takes place in analogy to Example 59 starting from 3-amino-6-(3-chlorobenzyl)-8-cyclopropyl-1-(2,4-dichlorobenzenesulfonyl)hexahydropyrazino[1,2-a]pyrimidine-4,7-dione. The desired product is obtained with MW=624.11 (calculated, monoisotopic); measured value (M+H)$^+$: 625.11

EXAMPLE 256

6-(3-Chlorobenzyl)-8-cyclopropyl-1-(2,4-dichlorobenzenesulfonyl)-3-morpholin-4-ylhexahydropyrazino[1,2-a]pyrimidine-4,7-dione Structure:

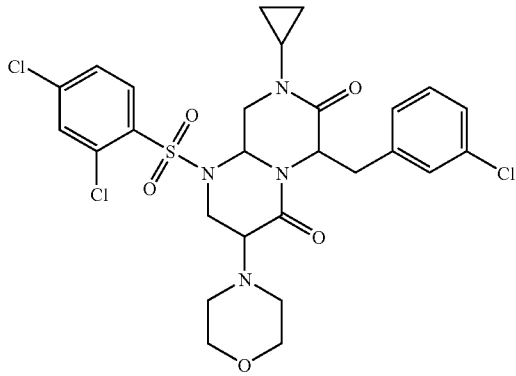

Synthesis takes place in analogy to Example 60 starting from 3-amino-6-(3-chlorobenzyl)-8-cyclopropyl-1-(2,4-dichlorobenzenesulfonyl)hexahydropyrazino[1,2-a]pyrimidine-4,7-dione. The desired product is obtained with MW=626.09 (calculated, monoisotopic); measured value $(M+H)^+$: 627.09

EXAMPLE 257

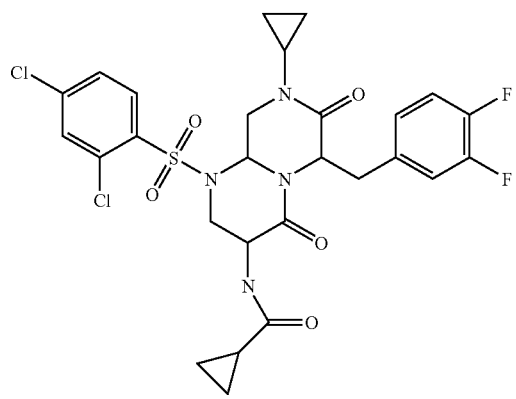

a) 9H-Fluoren-9-ylmethyl[1-[cyclopropyl(2,2-diethoxyethyl)carbamoyl]-2-(3,4-difluorophenyl)ethyl]carbamate Synthesis takes place in analogy to Example 29a) (Method B) starting from N-Fmoc-3,4-$F_2$-Phe-OH and cyclopropyl(2,2-diethoxyethyl)amine. The desired product is obtained with MW=578.26 (calculated, monoisotopic); measured value $(M+H)^+$: 579.3 b) 2-Amino-3-(3,4-difluorophenyl)-N-cyclopropyl-N-(2,2-diethoxyethyl)propionamide Synthesis takes place in analogy to Example 29b) (Method B) starting from 9H-fluoren-9-ylmethyl[1-[cyclopropyl(2,2-diethoxyethyl)carbamoyl]-2-(3,4-difluorophenyl)ethyl]-carbamate. The desired product is obtained with MW=356.19 (calculated, monoisotopic); measured value $(M+H)^+$: 357.23 c) Benzyl[1-{2-(3,4-difluorophenyl)-1-[cyclopropyl(2,2-diethoxyethyl)carbamoyl]ethylcarbamoyl}-2-(9H-fluoren-9-ylmethoxycarbonylamino)ethyl]carbamate Synthesis took place in analogy to Example 29c) (Method B) starting from 2-amino-3-(3,4-difluorophenyl)-N-cyclopropyl-N-(2,2-diethoxyethyl)propionamide. The desired product is obtained with MW=798.34 (calculated, monoisotopic); measured value $(M+Na)^+$: 821.35 d) Benzyl(2-amino-1-{2-(3,4-difluorophenyl)-1-[cyclopropyl(2,2-diethoxyethyl)carbamoyl]ethylcarbamoyl}ethyl)carbamate Synthesis took place in analogy to Example 29d) (Method B) starting from benzyl[1-{2-(3,4-difluorophenyl)-1-[cyclopropyl(2,2-diethoxyethyl)carbamoyl]ethylcarbamoyl}-2-(9H-fluoren-9-ylmethoxycarbonylamino)ethyl]carbamate. The desired product is obtained with MW=576.28 (calculated, monoisotopic); measured value $(M+Na)^+$: 599.27 f) Benzyl[1-{2-(3,4-difluorophenyl)-1-[cyclopropyl(2,2-diethoxyethyl)carbamoyl]ethylcarbamoyl}-2-(2,4-dichlorobenzenesulfonylamino)ethyl]carbamate Synthesis took place in analogy to Example 29e) (Method B) starting from benzyl (2-amino-1-{2-(3,4-difluorophenyl)-1-[cyclopropyl(2,2-diethoxyethyl)carbamoyl]ethylcarbamoyl}ethyl)carbamate. The desired product is obtained with MW=784.19 (calculated, monoisotopic); measured value $(M+Na)^+$: 807.18.

e) Benzyl[6-(3,4-difluorobenzyl)-8-cyclopropyl-1-(2,4-dichlorobenzenesulfonyl)-4,7-dioxooctahydropyrazino[1,2-a]pyrimidin-3-yl]carbamate Synthesis takes place in analogy to Example 29f) (Method B) starting from benzyl[1-{2-(3,4-difluorophenyl)-1-[cyclopropyl(2,2-diethoxyethyl)carbamoyl]ethylcarbamoyl}-2-(2,4-dichlorobenzenesulfonylamino)ethyl]carbamate. The desired product is obtained with MW=692.11 (calculated, monoisotopic); measured value $(M+H)^+$: 693.0 f) 3-Amino-6-(3,4-difluorobenzyl)-8-cyclopropyl-1-(2,4-dichlorobenzenesulfonyl)hexahydropyrazino[1,2-a]pyrimidine-4,7-dione Synthesis takes place in analogy to Example 29g) (Method B) starting from benzyl[6-(3,4-difluorobenzyl)-8-cyclopropyl-1-(2,4-dichlorobenzenesulfonyl)-4,7-dioxooctahydropyrazino[1,2-a]pyrimidin-3-yl]carbamate. The desired product is obtained with MW=558.07 (calculated, monoisotopic); measured value $(M+H)^+$: 559.05 g) N-[8-Cyclopropyl-1-(2,4-dichlorobenzenesulfonyl)-6-(3,4-difluorobenzyl)-4,7-dioxooctahydropyrazino[1,2-a]pyrimidin-3-yl]cyclopropanecarboxamide Synthesis takes place in analogy to Example 22 starting from 3-amino-6-(3,4-difluorobenzyl)-8-cyclopropyl-1-(2,4-dichlorobenzenesulfonyl)hexahydropyrazino[1,2-a]pyrimidine-4,7-dione. The desired product is obtained with MW=626.10 (calculated, monoisotopic); measured value $(M+H)^+$: 627.18

EXAMPLE 258

N-[8-Cyclopropyl-1-(2,4-dichlorobenzenesulfonyl)-6-(3,4-difluorobenzyl)-4,7-dioxooctahydropyrazino[1,2-a]pyrimidin-3-yl]cyclobutanecarboxamide Structure:

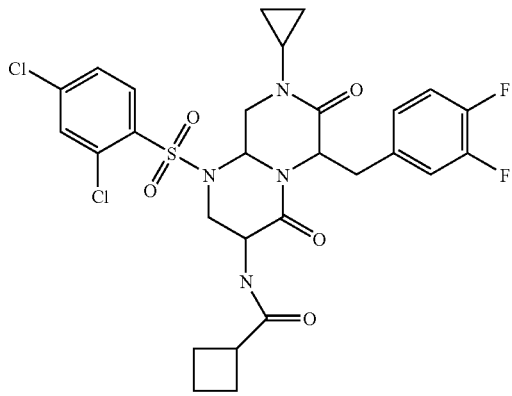

Synthesis takes place in analogy to Example 30 starting from 3-amino-6-(3,4-difluorobenzyl)-8-cyclopropyl-1-(2,4-dichlorobenzenesulfonyl)hexahydropyrazino[1,2-a]pyrimidine-4,7-dione. The desired product is obtained with MW=640.11 (calculated, monoisotopic); measured value $(M+H)^+$: 641.1

EXAMPLE 259

N-[8-Cyclopropyl-1-(2,4-dichlorobenzenesulfonyl)-6-(3,4-difluorobenzyl)-4,7-dioxooctahydropyrazino[1,2-a]pyrimidin-3-yl]cyclopentanecarboxamide Structure:

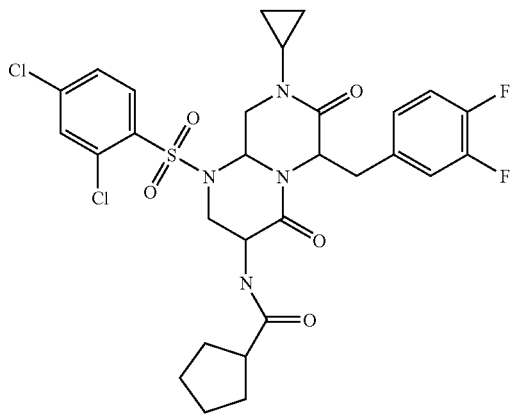

Synthesis takes place in analogy to Example 31 starting from 3-amino-6-(3,4-difluorobenzyl)-8-cyclopropyl-1-(2,4-dichlorobenzenesulfonyl)hexahydropyrazino[1,2-a]pyrimidine-4,7-dione. The desired product is obtained with MW=654.13 (calculated, monoisotopic); measured value $(M+H)^+$: 655.21

EXAMPLE 260

N-[8-Cyclopropyl-1-(2,4-dichlorobenzenesulfonyl)-6-(3,4-difluorobenzyl)-4,7-dioxooctahydropyrazino[1,2-a]pyrimidin-3-yl]cyclohexanecarboxamide Structure:

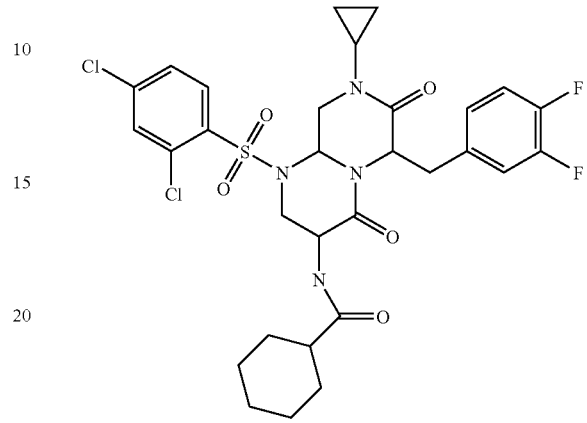

Synthesis takes place in analogy to Example 32 starting from 3-amino-6-(3,4-difluorobenzyl)-8-cyclopropyl-1-(2,4-dichlorobenzenesulfonyl)hexahydropyrazino[1,2-a]pyrimidine-4,7-dione. The desired product is obtained with MW=668.14 (calculated, monoisotopic); measured value $(M+H)^+$: 669.22

EXAMPLE 261

N-[8-Cyclopropyl-1-(2,4-dichlorobenzenesulfonyl)-6-(3,4-difluorobenzyl)-4,7-dioxooctahydropyrazino[1,2-a]pyrimidin-3-yl]methanesulfonamide Structure:

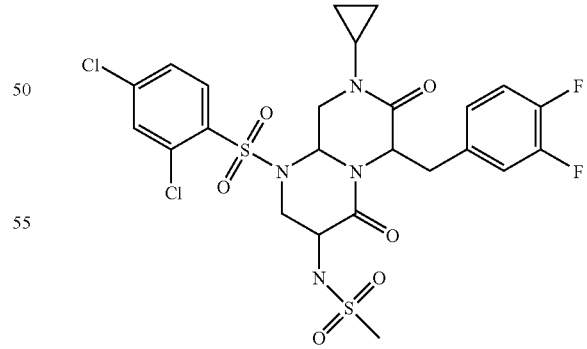

Synthesis takes place in analogy to Example 26 starting from 3-amino-6-(3,4-difluorobenzyl)-8-cyclopropyl-1-(2,4-dichlorobenzenesulfonyl)hexahydropyrazino[1,2-a]pyrimidine-4,7-dione. The desired product is obtained with MW=636.05 (calculated, monoisotopic); measured value $(M+H)^+$: 637.07

EXAMPLE 262

8-Cyclopropyl-1-(2,4-dichlorobenzenesulfonyl)-6-(3,4-difluorobenzyl)-3-dimethylaminohexahydropyrazino[1,2-a]pyrimidine-4,7-dione Structure:

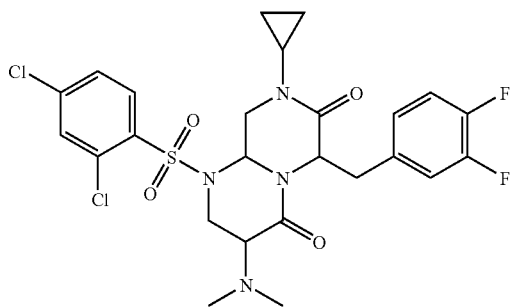

Synthesis takes place in analogy to Example 72 starting from 3-amino-6-(3,4-difluorobenzyl)-8-cyclopropyl-1-(2,4-dichlorobenzenesulfonyl)hexahydropyrazino[1,2-a]pyrimidine-4,7-dione. The desired product is obtained with MW=586.10 (calculated, monoisotopic); measured value (M+H)$^+$: 587.10

EXAMPLE 263

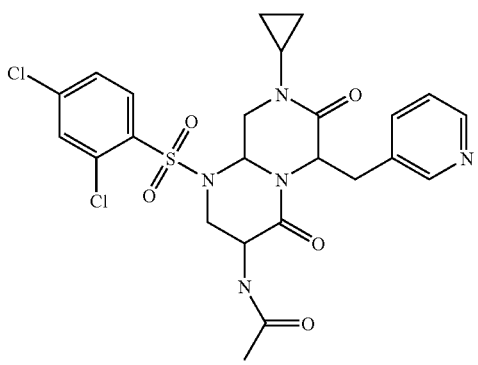

a) 9H-Fluoren-9-ylmethyl{1-[cyclopropyl(2,2-diethoxyethyl)carbamoyl]-2-pyridin-3-ylethyl}carbamate Synthesis takes place in analogy to Example 29a) (Method B) starting from Fmoc-PAL-OH and cyclopropyl(2,2-diethoxyethyl)amine. The desired product is obtained with MW=543.27 (calculated, monoisotopic), measured value (M+H)$^+$: 544.21 b) 2-Amino-N-cyclopropyl-N-(2,2-diethoxyethyl)-3-pyridin-3-ylpropionamide

Synthesis takes place in analogy to Example 29b) (Method B) starting from 9H-fluoren-9-ylmethyl{1-[cyclopropyl(2,2-diethoxyethyl)carbamoyl]-2-pyridin-3-yl-ethyl}carbamate. The desired product is obtained with MW=321.21 (calculated, monoisotopic); measured value (M+H)$^+$: 322.20 c) Benzyl[1-{1-[cyclopropyl(2,2-diethoxyethyl)carbamoyl]-2-pyridin-3-ylethylcarbamoyl}-2-(9H-fluoren-9-ylmethoxycarbonylamino)ethyl]carbamate Synthesis took place in analogy to Example 29c) (Method B) starting from 2-amino-N-cyclopropyl-N-(2,2-diethoxyethyl)-3-pyridin-3-ylpropionamide. The desired product is obtained with MW=798.34 (calculated, monoisotopic); measured value (M+Na)$^+$: 821.35 d) Benzyl(2-amino-1-{1-[cyclopropyl(2,2-diethoxyethyl)carbamoyl]-2-pyridin-3-ylethylcarbamoyl}ethyl)carbamate Synthesis took place in analogy to Example 29d) (Method B) starting from benzyl[1-{1-[cyclopropyl(2,2-diethoxyethyl)carbamoyl]-2-pyridin-3-ylethylcarbamoyl}-2-(9H-fluoren-9-ylmethoxycarbonylamino)ethyl]carbamate. The desired product is obtained with MW=541.29 (calculated, monoisotopic); measured value (M+H)$^+$: 542.30 e) Benzyl[1-{1-[cyclopropyl(2,2-diethoxyethyl)carbamoyl]-2-pyridin-3-ylethylcarbamoyl}-2-(2,4-dichlorobenzenesulfonylamino)ethyl]carbamate Synthesis took place in analogy to Example 29e) (Method B) starting from benzyl (2-amino-1-{-[cyclopropyl(2,2-diethoxyethyl)carbamoyl]-2-pyridin-3-ylethylcarbamoyl}-ethyl)carbamate. The desired product is obtained with MW=826.12 (calculated, monoisotopic); measured value (M+Na)$^+$: 849.14.

f) Benzyl[8-cyclopropyl-1-(2,4-dichlorobenzenesulfonyl)-4,7-dioxo-6-pyridin-3-ylmethyloctahydropyrazino[1,2-a]pyrimidin-3-yl]carbamate Synthesis takes place in analogy to Example 29f) (Method B) starting from benzyl[1-{1-[cyclopropyl(2,2-diethoxyethyl)carbamoyl]-2-pyridin-3-ylethylcarbamoyl}-2-(2,4-dichlorobenzenesulfonylamino)ethyl]carbamate. The desired product is obtained with MW=657.12 (calculated, monoisotopic); measured value (M+H)$^+$: 658.11 g) 3-Amino-8-cyclopropyl-1-(2,4-dichlorobenzenesulfonyl)-6-pyridin-3-ylmethylhexahydropyrazino[1,2-a]pyrimidine-4,7-dione Synthesis takes place in analogy to Example 29g) (Method B) starting from benzyl [8-cyclopropyl-1-(2,4-dichlorobenzenesulfonyl)-4,7-dioxo-6-pyridin-3-ylmethyloctahydropyrazino[1,2-a]pyrimidin-3-yl]carbamate. The desired product is obtained with MW=523.08 (calculated, monoisotopic); measured value (M+H)$^+$: 524.09 h) N-[8-Cyclopropyl-1-(2,4-dichlorobenzenesulfonyl)-4,7-dioxo-6-pyridin-3-ylmethyloctahydropyrazino[1,2-a]pyrimidin-3-yl]acetamide Synthesis takes place in analogy to Example 21h) starting from 3-amino-8-cyclopropyl-1-(2,4-dichlorobenzenesulfonyl)-6-pyridin-3-ylmethylhexahydropyrazino[1,2-a]pyrimidine-4,7-dione. The desired product is obtained with MW=565.10 (calculated, monoisotopic); measured value (M+H)$^+$: 566.10

EXAMPLE 264

N-[8-Cyclopropyl-1-(2,4-dichlorobenzenesulfonyl)-4,7-dioxo-6-pyridin-3-ylmethyloctahydropyrazino[1,2-a]pyrimidin-3-yl]cyclopropanecarboxamide Structure:

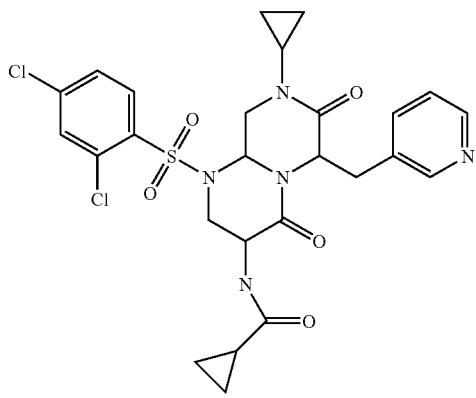

Synthesis takes place in analogy to Example 22 starting from 3-amino-8-cyclopropyl-1-(2,4-dichlorobenzenesulfonyl)-6-pyridin-3-ylmethylhexahydropyrazino[1,2-a]pyrimidine-4,7-dione. The desired product is obtained with MW=591.11 (calculated, monoisotopic); measured value (M+H)$^+$: 592.09

EXAMPLE 265

N-[8-Cyclopropyl-1-(2,4-dichlorobenzenesulfonyl)-4,7-dioxo-6-pyridin-3-ylmethyloctahydropyrazino[1,2-a]pyrimidin-3-yl]cyclobutanecarboxamide Structure:

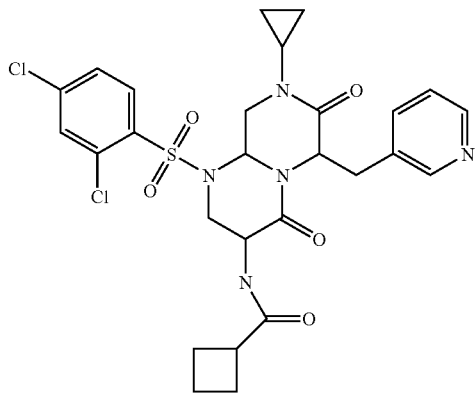

Synthesis takes place in analogy to Example 30 starting from 3-amino-8-cyclopropyl-1-(2,4-dichlorobenzenesulfonyl)-6-pyridin-3-ylmethylhexahydropyrazino[1,2-a]pyrimidine-4,7-dione. The desired product is obtained with MW=605.13 (calculated, monoisotopic); measured value (M+H)$^+$: 606.12

EXAMPLE 266

N-[8-Cyclopropyl-1-(2,4-dichlorobenzenesulfonyl)-4,7-dioxo-6-pyridin-3-ylmethyloctahydropyrazino[1,2-a]pyrimidin-3-yl]cyclopentanecarboxamide Structure:

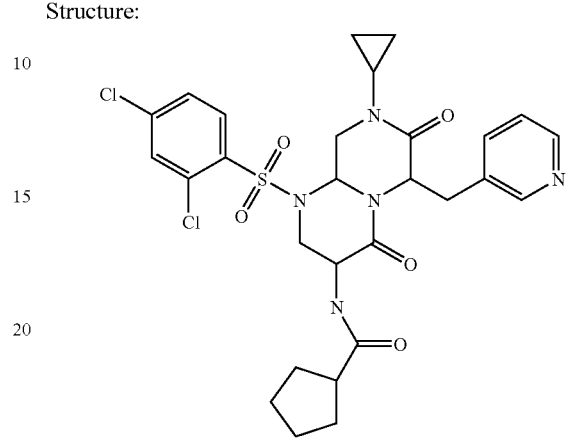

Synthesis takes place in analogy to Example 31 starting from 3-amino-8-cyclopropyl-1-(2,4-dichlorobenzenesulfonyl)-6-pyridin-3-ylmethylhexahydropyrazino[1,2-a]pyrimidine-4,7-dione. The desired product is obtained with MW=619.14 (calculated, monoisotopic); measured value (M+H)$^+$: 620.14

EXAMPLE 267

N-[8-Cyclopropyl-1-(2,4-dichlorobenzenesulfonyl)-4,7-dioxo-6-pyridin-3-ylmethyloctahydropyrazino[1,2-a]pyrimidin-3-yl]pyrrolidine-2-carboxamide Structure:

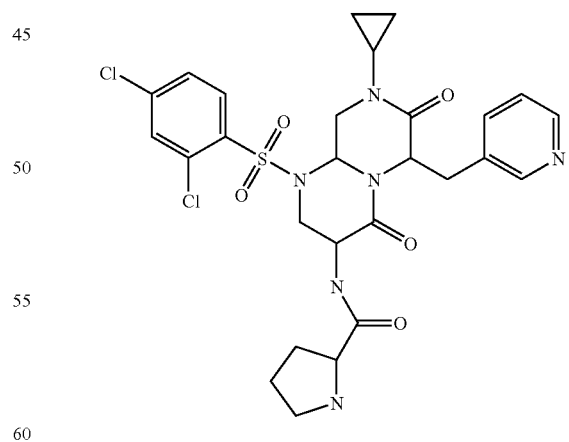

Synthesis takes place in analogy to Example 40 starting from 3-amino-8-cyclopropyl-1-(2,4-dichlorobenzenesulfonyl)-6-pyridin-3-ylmethylhexahydropyrazino[1,2-a]pyrimidine-4,7-dione. The desired product is obtained with MW=620.14 (calculated, monoisotopic); measured value (M+H)$^+$: 621.12

EXAMPLE 268

N-[8-Cyclopropyl-1-(2,4-dichlorobenzenesulfonyl)-4,7-dioxo-6-pyridin-3-ylmethyloctahydropyrazino[1,2-a]pyrimidin-3-yl]-4-dimethylaminobenzamide Structure:

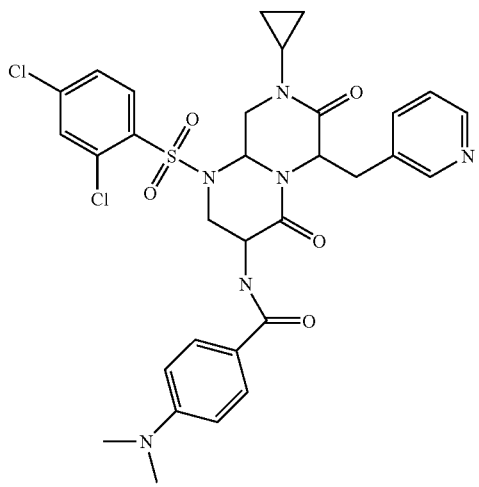

Synthesis takes place in analogy to Example 25 starting from 3-amino-8-cyclopropyl-1-(2,4-dichlorobenzenesulfonyl)-6-pyridin-3-ylmethylhexahydropyrazino[1,2-a]pyrimidine-4,7-dione. The desired product is obtained with MW=670.15 (calculated, monoisotopic); measured value (M+H)$^+$: 671.16

EXAMPLE 269

N-[8-Cyclopropyl-1-(2,4-dichlorobenzenesulfonyl)-4,7-dioxo-6-pyridin-3-ylmethyloctahydropyrazino[1,2-a]pyrimidin-3-yl]pyridine-2-carboxamide Structure:

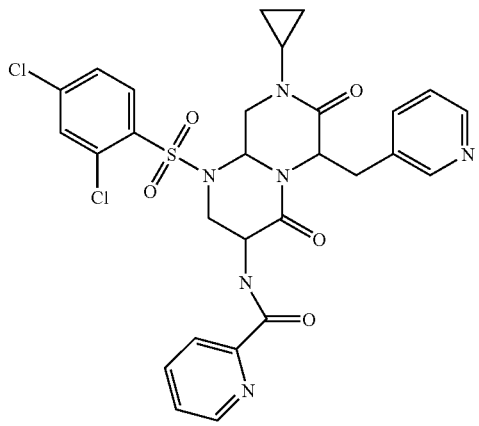

Synthesis takes place in analogy to Example 49 starting from 3-amino-8-cyclopropyl-1-(2,4-dichlorobenzenesulfonyl)-6-pyridin-3-ylmethylhexahydropyrazino[1,2-a]pyrimidine-4,7-dione. The desired product is obtained with MW=628.11 (calculated, monoisotopic); measured value (M+H)$^+$: 629.14

EXAMPLE 270

1-tert-Butyl-3-[8-cyclopropyl-1-(2,4-dichlorobenzenesulfonyl)-4,7-dioxo-6-pyridin-3-ylmethyloctahydropyrazino[1,2-a]pyrimidin-3-yl]urea Structure:

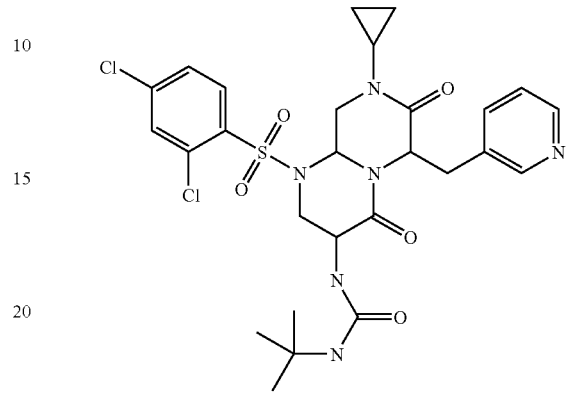

Synthesis takes place in analogy to Example 28 starting from 3-amino-8-cyclopropyl-1-(2,4-dichlorobenzenesulfonyl)-6-pyridin-3-ylmethylhexahydropyrazino[1,2-a]pyrimidine-4,7-dione. The desired product is obtained with MW=622.15 (calculated, monoisotopic); measured value (M+H)$^+$: 623.16

EXAMPLE 271

N-[8-Cyclopropyl-1-(2,4-dichlorobenzenesulfonyl)-4,7-dioxo-6-pyridin-3-ylmethyloctahydropyrazino[1,2-a]pyrimidin-3-yl]methanesulfonamide Structure:

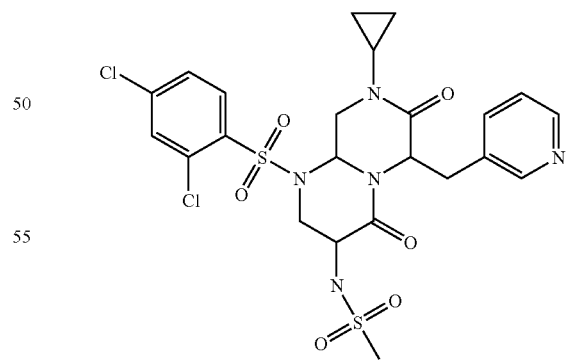

Synthesis takes place in analogy to Example 26 starting from 3-amino-8-cyclopropyl-1-(2,4-dichlorobenzenesulfonyl)-6-pyridin-3-ylmethylhexahydropyrazino[1,2-a]pyrimidine-4,7-dione. The desired product is obtained with MW=601.06 (calculated, monoisotopic); measured value (M+H)$^+$: 602.06

EXAMPLE 272

N-[8-Cyclopropyl-1-(2,4-dichlorobenzenesulfonyl)-4,7-dioxo-6-pyridin-3-ylmethyloctahydropyrazino[1,2-a]pyrimidin-3-yl]cyclopropanesulfonamide Structure:

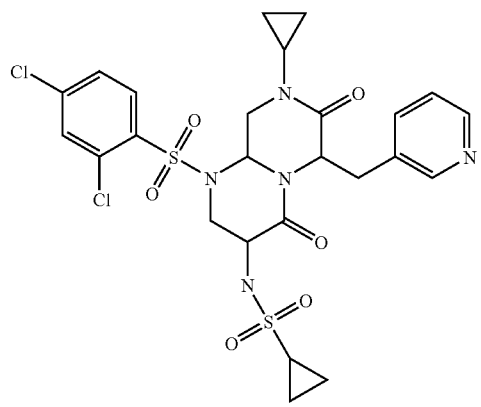

Synthesis takes place in analogy to Example 27 starting from 3-amino-8-cyclopropyl-1-(2,4-dichlorobenzenesulfonyl)-6-pyridin-3-ylmethylhexahydropyrazino[1,2-a]pyrimidine-4,7-dione. The desired product is obtained with MW=627.08 (calculated, monoisotopic); measured value (M+H)$^+$: 628.09

EXAMPLE 273

8-Cyclopropyl-1-(2,4-dichlorobenzenesulfonyl)-3-dimethylamino-6-pyridin-3-ylmethylhexahydropyrazino[1,2-a]pyrimidine-4,7-dione Structure:

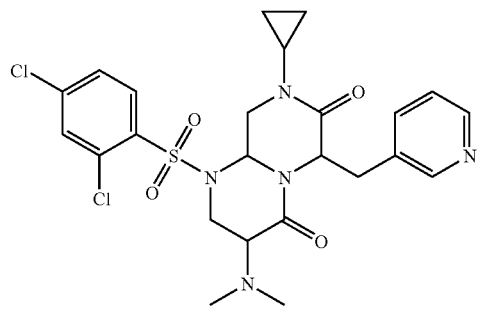

Synthesis takes place in analogy to Example 72 starting from 3-amino-8-cyclopropyl-1-(2,4-dichlorobenzenesulfonyl)-6-pyridin-3-ylmethylhexahydropyrazino[1,2-a]pyrimidine-4,7-dione. The desired product is obtained with MW=551.12 (calculated, monoisotopic); measured value (M+H)$^+$: 552.14

EXAMPLE 274

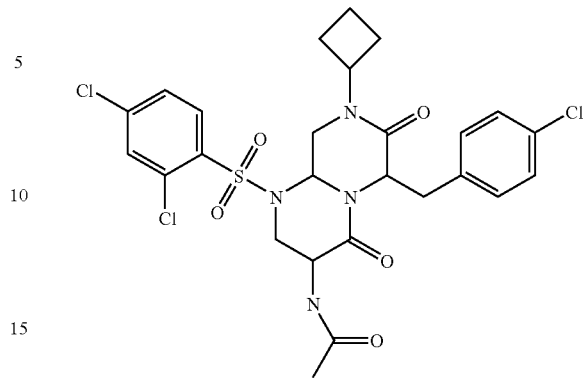

a) Cyclobutyl(2,2-diethoxyethyl)amine

A solution of 1.75 ml (11.65 mmol) of 1-bromo-2,2-diethoxyethane and 2 ml (23.3 mmol) of cyclobutylamine was heated at 80° C. in a closed vessel overnight. The reaction mixture was mixed with 40% NaOH (in $H_2O$) and extracted, with ether. The organic phase was isolated, dried (MgSO$_4$) and concentrated in vacuo. 2.39 g of substance were obtained as an orange liquid.

b) 2-Amino-3-(4-chlorophenyl)-N-cyclobutyl-N-(2,2-diethoxyethyl)propionamide A solution of 1.0 g (2.37 mmol) of Fmoc-Phe(4-Cl)—OH and 489 mg (2.61 mmol) of the amine cyclobutyl(2,2-diethoxyethyl)amine was dissolved in 9.5 ml of dimethylformamide. 722 mg (2.61 mmol) of DMTMM were added to this solution. The mixture was stirred at room temperature overnight, diluted with ethyl acetate and washed with water and brine. The organic phase was isolated, dried (MgSO$_4$) and concentrated in vacuo. The residue was chromatographed on 40 g of SiO$_2$ (elution with EtOAc/heptane, gradient 10-70%). 890 mg of the substance were obtained as a white foam. LC/MS M$^+$=591, measured value (M$^+$Na)=613 and M-OEt=545 agreed with the desired substance. A solution of 890 mg (1.5 mmol) of said substance was dissolved in 7.5 ml of dimethylformamide, and 0.8 ml of diethylamine was added. The reaction mixture was stirred at room temperature for 10 minutes and concentrated in vacuo. The residue was subjected to a flash chromatography on 12 g of SiO$_2$ (elution with MeOH in DCM, gradient 1-10%). 470 mg of the desired amine 2-amino-3-(4-chlorophenyl)-N-cyclobutyl-N-(2,2-diethoxyethyl)propionamide were obtained as a colorless oil. LC/MS M$^+$=368, measured value (M$^+$Na)=391 and M-OEt=323 agree with the structure.

c) Benzyl[1-{2-(4-chlorophenyl)-1-[cyclobutyl(2,2-diethoxyethyl)carbamoyl]ethylcarbamoyl}-2-(2,4-dichlorobenzenesulfonylamino)ethyl]carbamate A solution of 2.5 g (10.5 mmol) of Z-Dap-OH in 21 ml of 1N NaOH was stirred until homogeneous. A solution of 2.83 g (11.5 mmol) of 2,4-dichlorophenylsulfonyl chloride in 29 ml of dioxane was slowly added to the Z-Dap-OH solution. The mixture was then stirred for 2 hours. The reaction mixture was acidified with citric acid and extracted with DCM. The organic phase was dried (MgSO$_4$) and concentrated in vacuo. 4.08 g of the desired sulfonamide were obtained and were employed without further purification in the process described below. 755 mg (2.73 mmol) of DMTMM were added to a solution of 840 mg (2.28 mmol) of 2-amino-3-(4-chlorophenyl)-N-cyclobutyl-N-(2,2-diethoxyethyl)propionamide and 1.22 g (2.73 mmol) of said sulfonamide in 9 ml of DMF. The mixture was stirred at room temperature for 2 days, diluted with ethyl acetate and washed with water and brine. The organic phase was isolated, dried (MgSO$_4$) and concentrated in vacuo. 1.9 g of crude substance were obtained as a white foam. The residue was subjected to a flash chromatography on 40 g of SiO$_2$ (elution with EtOAc/heptane, gradient 10-80%). 1.09 g of the desired substance benzyl[1-{2-(4-chlorophenyl)-1-[cyclobutyl-(2,2-diethoxyethyl)carbamoyl]ethylcarbamoyl}-2-(2,4-dichlorobenzenesulfonylamino)ethyl]-carbamate were obtained as a white solid. LC/MS M$^+$=798, measured value (M$^+$Na)=819 and M-OEt=753 agree with the structure.

d) Benzyl[6-(4-chlorobenzyl)-8-cyclobutyl-1-(2,4-dichlorobenzenesulfonyl)-4,7-dioxooctahydropyrazino[1,2-a]pyrimidin-3-yl]carbamate Synthesis takes place in analogy to Example 29f) (Method B) starting from benzyl[1-{2-(4-chlorophenyl)-1-[cyclobutyl(2,2-diethoxyethyl)carbamoyl]ethylcarbamoyl}-2-(2,4-dichlorobenzenesulfonylamino)ethyl]carbamate. The desired product is obtained with MW=704.10 (calculated, monoisotopic); measured value (M+H)$^+$: 705.1 e) 3-Amino-6-(4-chlorobenzyl)-8-cyclobutyl-1-(2,4-dichlorobenzenesulfonyl)hexahydropyrazino[1,2-a]pyrimidine-4,7-dione Synthesis takes place in analogy to Example 29g) (Method B) starting from benzyl[6-(4-chlorobenzyl)-8-cyclobutyl-1-(2,4-dichlorobenzenesulfonyl)-4,7-dioxooctahydropyrazino[1,2-a]pyrimidin-3-yl]carbamate. The desired product is obtained with MW=570.07 (calculated, monoisotopic); measured value (M+H)$^+$: 570.99 f) N-[6-(4-Chlorobenzyl)-8-cyclobutyl-1-(2,4-dichlorobenzenesulfonyl)-4,7-dioxooctahydropyrazino[1,2-a]pyrimidin-3-yl]acetamide Synthesis takes place in analogy to Example 21h) starting from 3-amino-6-(4-chlorobenzyl)-8-cyclobutyl-1-(2,4-dichlorobenzenesulfonyl)hexahydropyrazino[1,2-a]pyrimidine-4,7-dione. The desired product is obtained with MW=612.08 (calculated, monoisotopic); measured value (M+H)$^+$: 613.07

EXAMPLE 275

N-[6-(4-Chlorobenzyl)-8-cyclobutyl-1-(2,4-dichlorobenzenesulfonyl)-4,7-dioxooctahydropyrazino[1,2-a]pyrimidin-3-yl]cyclopropanecarboxamide Structure:

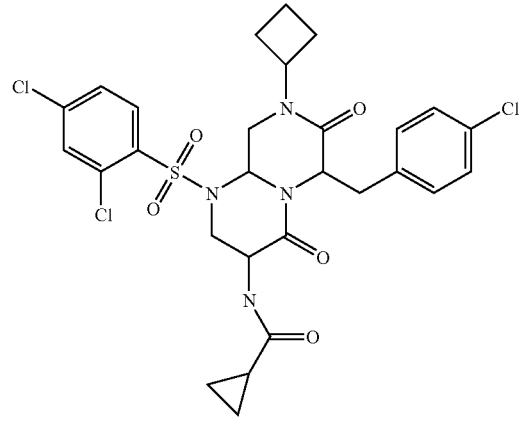

Synthesis takes place in analogy to Example 22 starting from 3-amino-6-(4-chlorobenzyl)-8-cyclobutyl-1-(2,4-dichlorobenzenesulfonyl)hexahydropyrazino[1,2-a]pyrimidine-4,7-dione. The desired product is obtained with MW=638.09 (calculated, monoisotopic); measured value (M+H)$^+$: 639.09

EXAMPLE 276

1-[6-(4-Chlorobenzyl)-8-cyclobutyl-1-(2,4-dichlorobenzenesulfonyl)-4,7-dioxooctahydropyrazino[1,2-a]pyrimidin-3-yl]-3-ethylurea Structure:

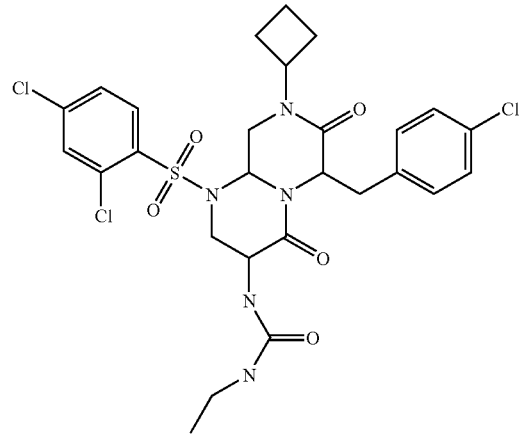

Synthesis takes place in analogy to Example 57 starting from 3-amino-6-(4-chlorobenzyl)-8-cyclobutyl-1-(2,4-dichlorobenzenesulfonyl)hexahydropyrazino[1,2-a]pyrimidine-4,7-dione. The desired product is obtained with MW=641.10 (calculated, monoisotopic); measured value (M+H)$^+$: 642.09

EXAMPLE 277

N-[6-(4-Chlorobenzyl)-8-cyclobutyl-1-(2,4-dichlorobenzenesulfonyl)-4,7-dioxooctahydropyrazino[1,2-a]pyrimidin-3-yl]methanesulfonamide Structure:

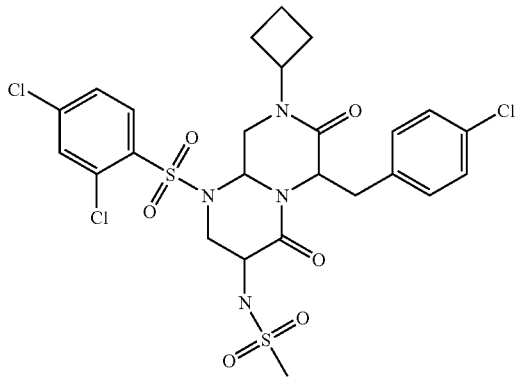

Synthesis takes place in analogy to Example 26 starting from 3-amino-6-(4-chlorobenzyl)-8-cyclobutyl-1-(2,4-dichlorobenzenesulfonyl)hexahydropyrazino[1,2-a]pyrimidine-4,7-dione. The desired product is obtained with MW=648.04 (calculated, monoisotopic); measured value (M+H)$^+$: 649.15

EXAMPLE 278

6-(4-Chlorobenzyl)-8-cyclobutyl-1-(2,4-dichlorobenzenesulfonyl)-3-dimethylaminohexahydropyrazino[1,2-a]pyrimidine-4,7-dione Structure:

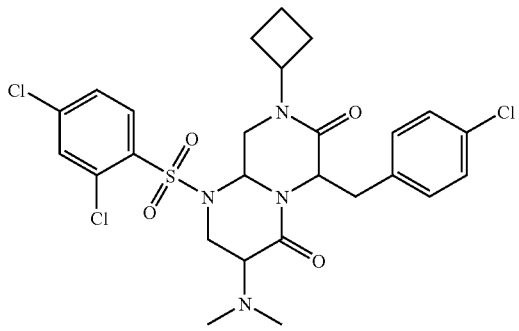

Synthesis takes place in analogy to Example 72 starting from 3-amino-6-(4-chlorobenzyl)-8-cyclobutyl-1-(2,4-dichlorobenzenesulfonyl)hexahydropyrazino[1,2-a]pyrimidine-4,7-dione. The desired product is obtained with MW=598.10 (calculated, monoisotopic); measured value (M+H)$^+$: 599.07

EXAMPLE 279

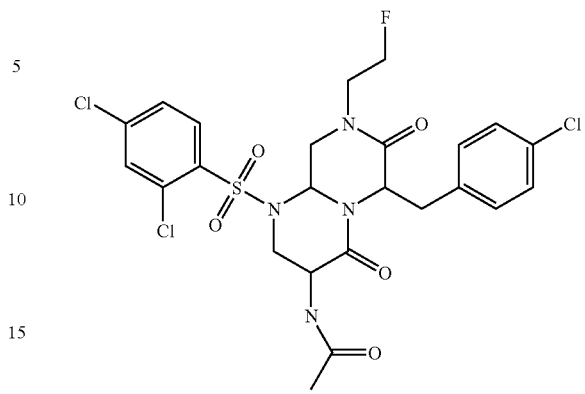

a) (2,2-Diethoxyethyl)-(2-fluoroethyl)amine

A solution of 3.1 ml (21.5 mmol) of 1-amino-2,2-diethoxyethane, 3.0 g (23.6 mmol) of 1-bromo-2-fluoroethane and 5.56 g (43 mmol) of diisopropylethylamine was heated at 100° C. in a closed vessel for 6 hours. The reaction mixture was diluted with ether and washed with 1N NaOH and water. The organic phase was dried (MgSO$_4$) and concentrated in vacuo. The residue was distilled in vacuo. 1.3 g of substance were obtained as a clear liquid.

b) 2-Amino-3-(4-chlorophenyl)-N-(2,2-diethoxyethyl)-N-(2-fluoroethyl)propionamide Synthesis takes place in analogy to Example 274b). The desired product is obtained with MW=360.16 (calculated, monoisotopic); measured value (M+H)$^+$: 361.2 c) Benzyl[1-{2-(4-chlorophenyl)-1-[(2,2-diethoxyethyl)-(2-fluoroethyl)carbamoyl]ethylcarbamoyl}-2-(2,4-dichlorobenzenesulfonylamino)ethyl]carbamate Synthesis takes place in analogy to Example 274c). The desired product is obtained with MW=788.16 (calculated, monoisotopic); measured value (M+Na)$^+$: 811.19 d) Benzyl[6-(4-chlorobenzyl)-1-(2,4-dichlorobenzenesulfonyl)-8-(2-fluoroethyl)-4,7-dioxooctahydropyrazino[1,2-a]pyrimidin-3-yl]carbamate Synthesis takes place in analogy to Example 29f) (Method B) starting from benzyl[1-{2-(4-chlorophenyl)-1-[(2,2-diethoxyethyl)-(2-fluoroethyl)carbamoyl]ethylcarbamoyl}-2-(2,4-dichlorobenzenesulfonylamino)ethyl]carbamate. The desired product is obtained with MW=696.08 (calculated, monoisotopic); measured value (M+H)$^+$: 697.04 e) 3-Amino-6-(4-chlorobenzyl)-1-(2,4-dichlorobenzenesulfonyl)-8-(2-fluoroethyl)hexahydropyrazino[1,2-a]pyrimidine-4,7-dione Synthesis takes place in analogy to Example 29e) (Method B) starting from benzyl[6-(4-chlorobenzyl)-1-(2,4-dichlorobenzenesulfonyl)-8-(2-fluoroethyl)-4,7-dioxooctahydropyrazino[1,2-a]pyrimidin-3-yl]carbamate. The desired product is obtained with MW=562.04 (calculated, monoisotopic); measured value (M+H)$^+$: 563.03 f) N-[6-(4-Chlorobenzyl)-1-(2,4-dichlorobenzenesulfonyl)-8-(2-fluoroethyl)-4,7-dioxooctahydropyrazino[1,2-a]pyrimidin-3-yl]acetamide Synthesis takes place in analogy to Example 21h) starting from 3-amino-6-(4-chlorobenzyl)-1-(2,4-dichlorobenzenesulfonyl)-8-(2-fluoroethyl)hexahydropyrazino[1,2-a]pyrimidine-4,7-dione. The desired product is obtained with MW=604.05 (calculated, monoisotopic); measured value (M+H)⁺: 605.07

EXAMPLE 280

N-[6-(4-Chlorobenzyl)-1-(2,4-dichlorobenzenesulfonyl)-8-(2-fluoroethyl)-4,7-dioxooctahydropyrazino[1,2-a]pyrimidin-3-yl]cyclopropanecarboxamide Structure:

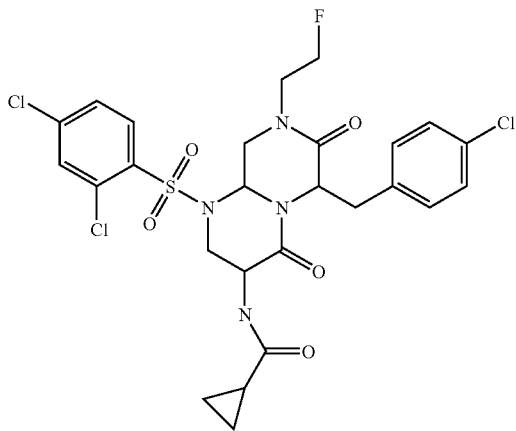

Synthesis takes place in analogy to Example 22 starting from 3-amino-6-(4-chlorobenzyl)-1-(2,4-dichlorobenzenesulfonyl)-8-(2-fluoroethyl)hexahydropyrazino[1,2-a]pyrimidine-4,7-dione. The desired product is obtained with MW=630.07 (calculated, monoisotopic); measured value (M+H)⁺: 631.06

EXAMPLE 281

N-[6-(4-Chlorobenzyl)-1-(2,4-dichlorobenzenesulfonyl)-8-(2-fluoroethyl)-4,7-dioxooctahydropyrazino[1,2-a]pyrimidin-3-yl]cyclobutanecarboxamide Structure:

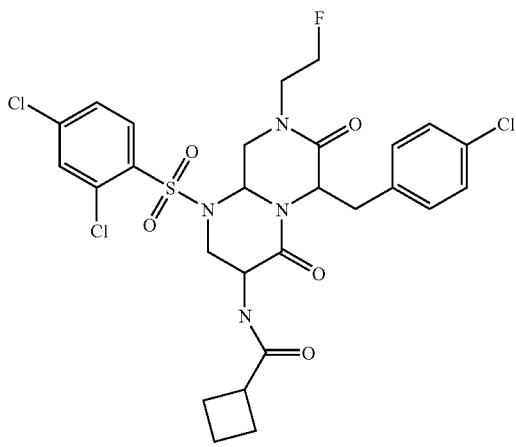

Synthesis takes place in analogy to Example 30 starting from 3-amino-6-(4-chlorobenzyl)-1-(2,4-dichlorobenzenesulfonyl)-8-(2-fluoroethyl)hexahydropyrazino[1,2-a]pyrimidine-4,7-dione. The desired product is obtained with MW=644.08 (calculated, monoisotopic); measured value (M+H)⁺: 645.11

EXAMPLE 282

1-tert-Butyl-3-[6-(4-chlorobenzyl)-1-(2,4-dichlorobenzenesulfonyl)-8-(2-fluoroethyl)-4,7-dioxooctahydropyrazino[1,2-a]pyrimidin-3-yl]urea Structure:

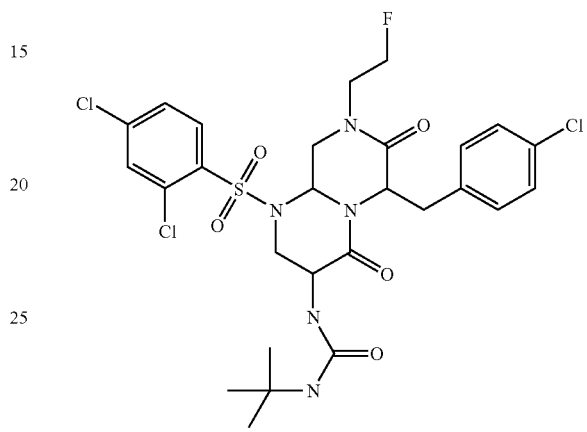

Synthesis takes place in analogy to Example 28 starting from 3-amino-6-(4-chlorobenzyl)-1-(2,4-dichlorobenzenesulfonyl)-8-(2-fluoroethyl)hexahydropyrazino[1,2-a]pyrimidine-4,7-dione. The desired product is obtained with MW=661.11 (calculated, monoisotopic); measured value (M+H)⁺: 662.1

EXAMPLE 283

N-[6-(4-Chlorobenzyl)-1-(2,4-dichlorobenzenesulfonyl)-8-(2-fluoroethyl)-4,7-dioxooctahydropyrazino[1,2-a]pyrimidin-3-yl]methanesulfonamide Structure:

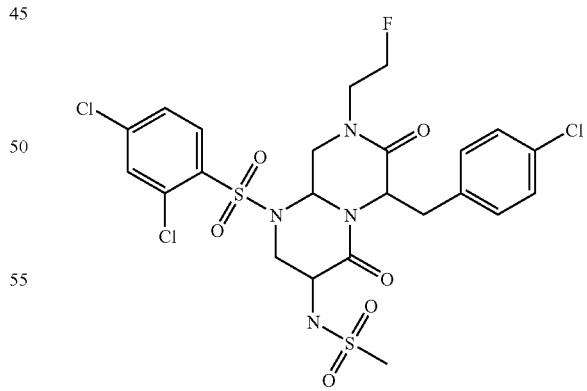

Synthesis takes place in analogy to Example 26 starting from 3-amino-6-(4-chlorobenzyl)-1-(2,4-dichlorobenzenesulfonyl)-8-(2-fluoroethyl)hexahydropyrazino[1,2-a]pyrimidine-4,7-dione. The desired product is obtained with MW=640.02 (calculated, monoisotopic); measured value (M+H)⁺: 641.03

EXAMPLE 284

6-(4-Chlorobenzyl)-1-(2,4-dichlorobenzenesulfo-
nyl)-3-dimethylamino-8-(2-fluoroethyl)hexahydro-
pyrazino[1,2-a]pyrimidine-4,7-dione Structure:

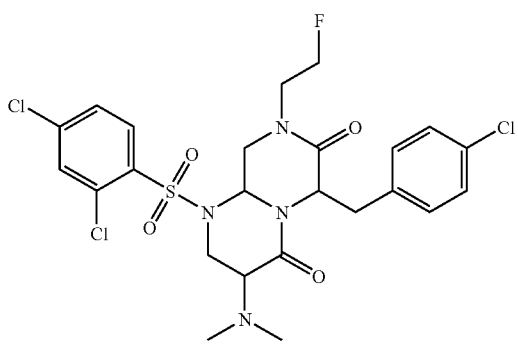

Synthesis takes place in analogy to Example 72 starting from 3-amino-6-(4-chlorobenzyl)-1-(2,4-dichlorobenzenesulfonyl)-8-(2-fluoroethyl)hexahydropyrazino[1,2-a]pyrimidine-4,7-dione. The desired product is obtained with MW=590.07 (calculated, monoisotopic); measured value (M+H)$^+$: 591.04

EXAMPLE 285

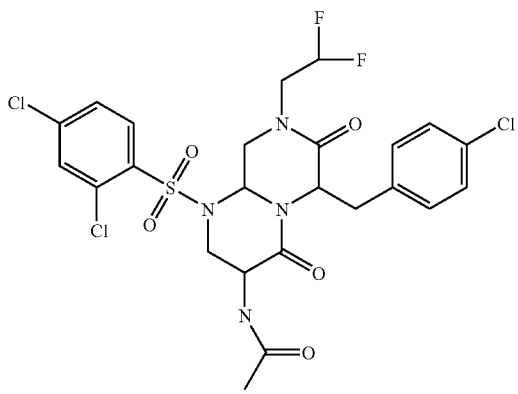

a) (2,2-Diethoxyethyl)-(2,2-difluoroethyl)amine

A solution of 3 g (22.5 mmol) of 1-amino-2,2-diethoxyethane, 3.1 g (24.8 mmol) of difluoroacetaldehyde ethyl hemiacetal and 1 pellet of solid NaOH in 44 ml of toluene was heated at 120° C. with a Dean-Stark trap for 1.5 hours. The mixture was left to stand until it had cooled to room temperature and was concentrated in vacuo. The residue was diluted with 80 ml of methanol, and 3.4 g (90 mmol) of sodium borohydride were added in small quantities. The reaction mixture was then stirred overnight, concentrated in vacuo and partitioned between ethyl acetate and water. The organic phase was isolated, dried (MgSO$_4$) and concentrated in vacuo. 3.7 g of crude substance were obtained as a colorless oil. The residue was subjected to a flash chromatography on 40 g of SiO$_2$ (elution with DCM/MeOH, gradient 1-8%). 3.1 g of the desired amine were obtained as a colorless oil.

b) 2-Amino-3-(4-chlorophenyl)-N-(2,2-diethoxy-ethyl)-N-(2,2-difluoroethyl)propionamide Synthesis takes place in analogy to Example 274b). The desired product is obtained with MW=378.15 (calculated, monoisotopic); measured value (M+H)$^+$: 379.18 c) Benzyl[1-{2-(4-chlorophenyl)-1-[(2,2-diethoxy-ethyl)-(2,2-difluoroethyl)carbamoyl]-ethylcarbamoyl}-2-(2,4-dichlorobenzenesulfonylamino)ethyl]carbamate Synthesis takes place in analogy to Example 274c). The desired product is obtained with MW=806.15 (calculated, monoisotopic); measured value (M+Na)$^+$: 829.11 d) Benzyl[6-(4-chlorobenzyl)-1-(2,4-dichlorobenzenesulfonyl)-8-(2,2-difluoroethyl)-4,7-dioxooctahydropyrazino[1,2-a]pyrimidin-3-yl]carbamate Synthesis takes place in analogy to Example 29f) (Method B) starting from benzyl[1-{2-(4-chlorophenyl)-1-[(2,2-diethoxyethyl)-(2,2-difluoroethyl)carbamoyl]ethylcarbamoyl}-2-(2,4-dichlorobenzenesulfonylamino)ethyl]carbamate. The desired product is obtained with MW=714.07 (calculated, monoisotopic); measured value (M+H)$^+$: 715.02 e) 3-Amino-6-(4-chlorobenzyl)-1-(2,4-dichlorobenzenesulfonyl)-8-(2,2-difluoroethyl)hexahydropyrazino[1,2-a]pyrimidine-4,7-dione Synthesis takes place in analogy to Example 29e) (Method B) starting from benzyl[6-(4-chlorobenzyl)-1-(2,4-dichlorobenzenesulfonyl)-8-(2,2-difluoroethyl)-4,7-dioxooctahydropyrazino[1,2-a]pyrimidin-3-yl]carbamate. The desired product is obtained with MW=580.03 (calculated, monoisotopic); measured value (M+H)$^+$: 580.99 f) N-[6-(4-Chlorobenzyl)-1-(2,4-dichlorobenzenesulfonyl)-8-(2,2-difluoroethyl)-4,7-dioxooctahydropyrazino[1,2-a]pyrimidin-3-yl]acetamide Synthesis takes place in analogy to Example 21h) starting from 3-amino-6-(4-chlorobenzyl)-1-(2,4-dichlorobenzenesulfonyl)-8-(2,2-difluoroethyl)hexahydropyrazino[1,2-a]pyrimidine-4,7-dione. The desired product is obtained with MW=622.04 (calculated, monoisotopic); measured value (M+H)$^+$: 623.03

EXAMPLE 286

N-[6-(4-Chlorobenzyl)-1-(2,4-dichlorobenzenesulfonyl)-8-(2,2-difluoroethyl)-4,7-dioxooctahydropyrazino[1,2-a]pyrimidin-3-yl]cyclopropanecarboxamide Structure:

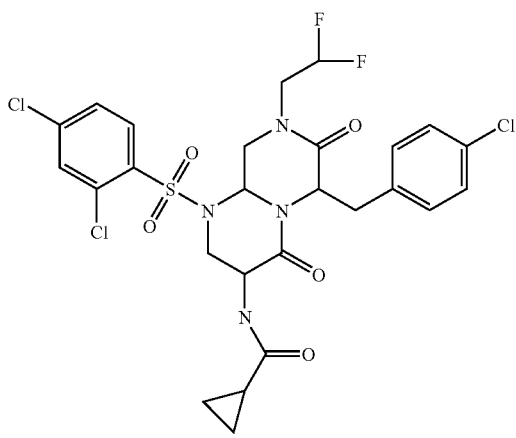

Synthesis takes place in analogy to Example 22 starting from 3-amino-6-(4-chlorobenzyl)-1-(2,4-dichlorobenzenesulfonyl)-8-(2,2-difluoroethyl)hexahydropyrazino[1,2-a]pyrimidine-4,7-dione. The desired product is obtained with MW=648.06 (calculated, monoisotopic); measured value (M+H)$^+$: 649.04

EXAMPLE 287

N-[6-(4-Chlorobenzyl)-1-(2,4-dichlorobenzenesulfonyl)-8-(2,2-difluoroethyl)-4,7-dioxooctahydropyrazino[1,2-a]pyrimidin-3-yl]cyclobutanecarboxamide

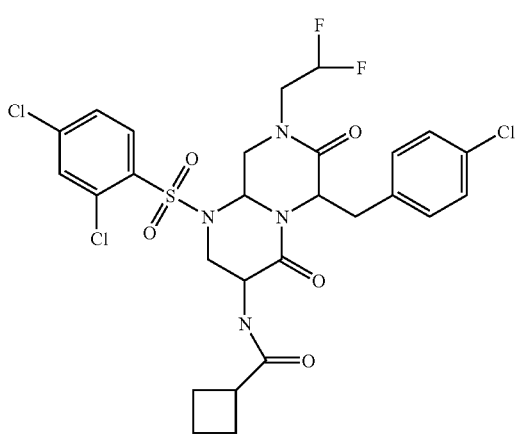

Synthesis takes place in analogy to Example 30 starting from 3-amino-6-(4-chlorobenzyl)-1-(2,4-dichlorobenzenesulfonyl)-8-(2,2-difluoroethyl)hexahydropyrazino[1,2-a]pyrimidine-4,7-dione. The desired product is obtained with MW=662.07 (calculated, monoisotopic); measured value (M+H)$^+$: 663.06

EXAMPLE 288

N-[6-(4-Chlorobenzyl)-1-(2,4-dichlorobenzenesulfonyl)-8-(2,2-difluoroethyl)-4,7-dioxooctahydropyrazino[1,2-a]pyrimidin-3-yl]cyclopentanecarboxamide

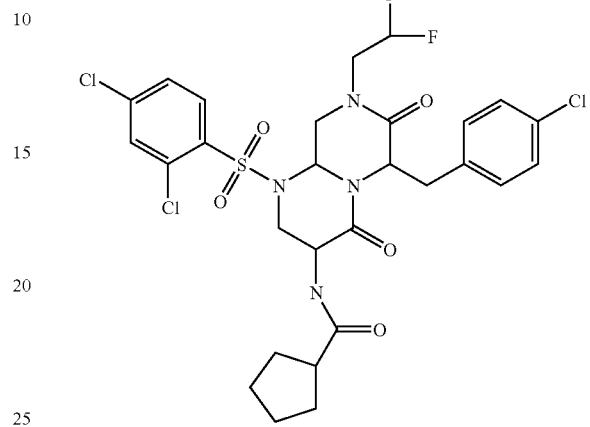

Synthesis takes place in analogy to Example 31 starting from 3-amino-6-(4-chlorobenzyl)-1-(2,4-dichlorobenzenesulfonyl)-8-(2,2-difluoroethyl)hexahydropyrazino[1,2-a]pyrimidine-4,7-dione. The desired product is obtained with MW=676.09 (calculated, monoisotopic); measured value (M+H)$^+$: 677.07

EXAMPLE 289

N-[6-(4-Chlorobenzyl)-1-(2,4-dichlorobenzenesulfonyl)-8-(2,2-difluoroethyl)4,7-dioxooctahydropyrazino[1,2-a]pyrimidin-3-yl]pyrrolidine-2-carboxamide

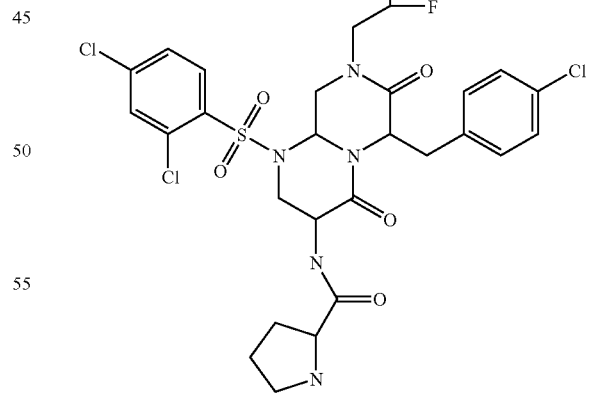

Synthesis takes place in analogy to Example 40 starting from 3-amino-6-(4-chlorobenzyl)-1-(2,4-dichlorobenzenesulfonyl)-8-(2,2-difluoroethyl)hexahydropyrazino[1,2-a]pyrimidine-4,7-dione. The desired product is obtained with MW=677.08 (calculated, monoisotopic); measured value (M+H)$^+$: 678.08

EXAMPLE 290

6-(4-Chlorobenzyl)-1-(2,4-dichlorobenzenesulfonyl)-8-(2,2-difluoroethyl)-3-dimethylaminohexahydropyrazino[1,2-a]pyrimidine-4,7-dione

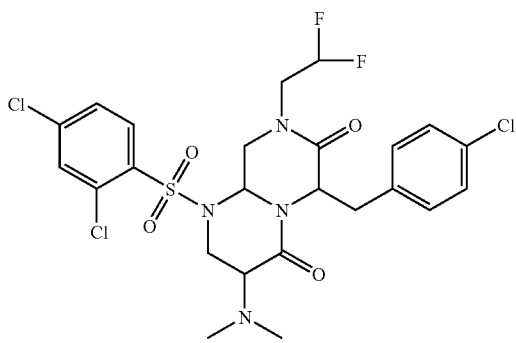

Synthesis takes place in analogy to Example 72 starting from 3-amino-6-(4-chlorobenzyl)-1-(2,4-dichlorobenzenesulfonyl)-8-(2,2-difluoroethyl)hexahydropyrazino[1,2-a]pyrimidine-4,7-dione. The desired product is obtained with MW=608.06 (calculated, monoisotopic); measured value (M+H)$^+$: 609.05

EXAMPLE 291

6-(4-Chlorobenzyl)-1-(2,4-dichlorobenzenesulfonyl)-8-(2,2-difluoroethyl)-3-morpholin-4-ylhexahydropyrazino[1,2-a]pyrimidine-4,7-dione

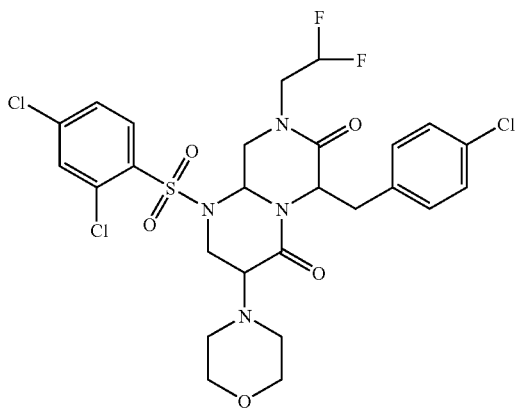

Synthesis takes place in analogy to Example 60 starting from 3-amino-6-(4-chlorobenzyl)-1-(2,4-dichlorobenzenesulfonyl)-8-(2,2-difluoroethyl)hexahydropyrazino[1,2-a]pyrimidine-4,7-dione. The desired product is obtained with MW=650.07 (calculated, monoisotopic); measured value (M+H)$^+$: 651.07

EXAMPLE 292

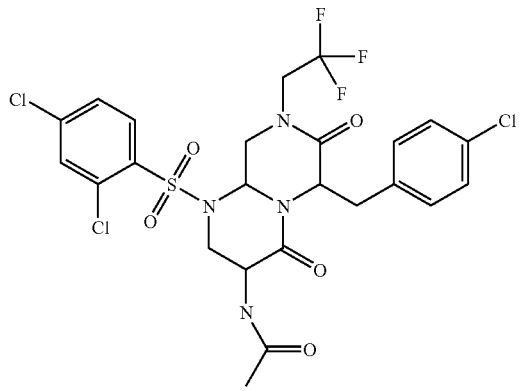

a) (2,2-Diethoxyethyl)-(2,2,2-trifluoroethyl)amine

A solution of 1 g (7.5 mmol) of 1-amino-2,2-diethoxyethane, 1.26 g (7.9 mmol) of trifluoroacetaldehyde ethyl hemiacetal and 1 pellet of NaOH in 15 ml of toluene was heated at 110° C. with a Dean-Stark trap for 3 hours. The mixture was heated at 125° C. for a further 3 hours. The reaction mixture was left to stand until it had cooled to room temperature and was concentrated in vacuo. The residue was diluted with 25 ml of methanol, and 1.13 g (30 mmol) of sodium borohydride were added. The reaction mixture was then heated to 70° C. and stirred overnight, concentrated in vacuo and partitioned between water and ethyl acetate. The organic phase was isolated, dried (MgSO$_4$) and concentrated in vacuo. 740 mg of the desired amine were obtained as a clear oil.

b) 2-Amino-3-(4-chlorophenyl)-N-(2,2-diethoxyethyl)-N-(2,2,2-trifluoroethyl)propionamide Synthesis takes place in analogy to Example 274b). The desired product is obtained with MW=378.15 (calculated, monoisotopic); measured value (M+H)$^+$: 379.18 c) Benzyl[1-{2-(4-chlorophenyl)-1-[(2,2-diethoxyethyl)-(2,2,2-trifluoroethyl)carbamoyl]-ethylcarbamoyl}-2-(2,4-dichlorobenzenesulfonylamino)ethyl]carbamate Synthesis takes place in analogy to Example 274c). The desired product is obtained with MW=806.15 (calculated, monoisotopic); measured value (M+Na)$^+$: 829.11 d) Benzyl[6-(4-chlorobenzyl)-1-(2,4-dichlorobenzenesulfonyl)-8-(2,2,2-trifluoroethyl)-4,7-dioxooctahydropyrazino[1,2-a]pyrimidin-3-yl]carbamate Synthesis takes place in analogy to Example 29f) (Method B) starting from benzyl[1-{2-(4-chlorophenyl)-1-[(2,2-diethoxyethyl)-(2,2,2-trifluoroethyl)carbamoyl]ethylcarbamoyl}-2-(2,4-dichlorobenzenesulfonylamino)ethyl]carbamate. The desired product is obtained with MW=732.06 (calculated, monoisotopic); measured value (M+H)$^+$: 732.12 e) 3-Amino-6-(4-chlorobenzyl)-1-(2,4-dichlorobenzenesulfonyl)-8-(2,2,2-trifluoroethyl)hexahydro pyrazino[1,2-a]pyrimidine-4,7-dione Synthesis takes place in analogy to Example 29e) (Method B) starting from benzyl[6-(4-chlorobenzyl)-1-(2,4-dichlorobenzenesulfonyl)-8-(2,2,2-trifluoroethyl)-4,7-dioxooctahydropyrazino[1,2-a]pyrimidin-3-yl]carbamate. The desired product is obtained with MW=598.02 (calculated, monoisotopic); measured value (M+H)+: 599.06 f) N-[6-(4-Chlorobenzyl)-1-(2,4-dichlorobenzenesulfonyl)-8-(2,2,2-trifluoroethyl)-4,7-dioxooctahydropyrazino[1,2-a]pyrimidin-3-yl]acetamide Synthesis takes place in analogy to Example 21b) starting from 3-amino-6-(4-chlorobenzyl)-1-(2,4-dichlorobenzenesulfonyl)-8-(2,2,2-trifluoroethyl)hexahydropyrazino[1,2-a]pyrimidine-4,7-dione. The desired product is obtained with MW=640.03 (calculated, monoisotopic); measured value (M+H)+: 641.06

EXAMPLE 293

N-[6-(4-Chlorobenzyl)-1-(2,4-dichlorobenzenesulfonyl)-4,7-dioxo-8-(2,2,2-trifluoroethyl)-octahydropyrazino[1,2-a]pyrimidin-3-yl]cyclopropanecarboxamide

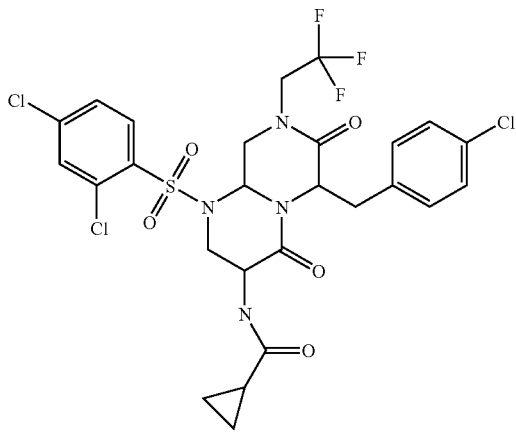

Synthesis takes place in analogy to Example 22 starting from 3-amino-6-(4-chlorobenzyl)-1-(2,4-dichlorobenzenesulfonyl)-8-(2,2,2-trifluoroethyl)hexahydropyrazino[1,2-a]pyrimidine-4,7-dione. The desired product is obtained with MW=666.05 (calculated, monoisotopic); measured value (M+H)+: 667.07

EXAMPLE 294

N-[6-(4-Chlorobenzyl)-1-(2,4-dichlorobenzenesulfonyl)-4,7-dioxo-8-(2,2,2-trifluoroethyl)-octahydropyrazino[1,2-a]pyrimidin-3-yl]cyclobutanecarboxamide

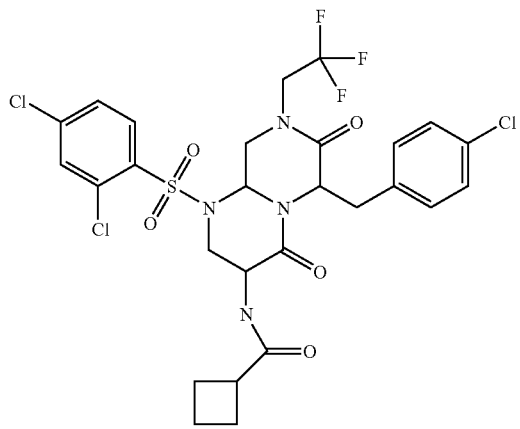

Synthesis takes place in analogy to Example 30 starting from 3-amino-6-(4-chlorobenzyl)-1-(2,4-dichlorobenzenesulfonyl)-8-(2,2,2-trifluoroethyl)hexahydropyrazino[1,2-a]pyrimidine-4,7-dione. The desired product is obtained with MW=680.06 (calculated, monoisotopic); measured value (M+H)+: 681.02

EXAMPLE 295

N-[6-(4-Chlorobenzyl)-1-(2,4-dichlorobenzenesulfonyl)-4,7-dioxo-8-(2,2,2-trifluoroethyl)-octahydropyrazino[1,2-a]pyrimidin-3-yl]cyclopentanecarboxamide

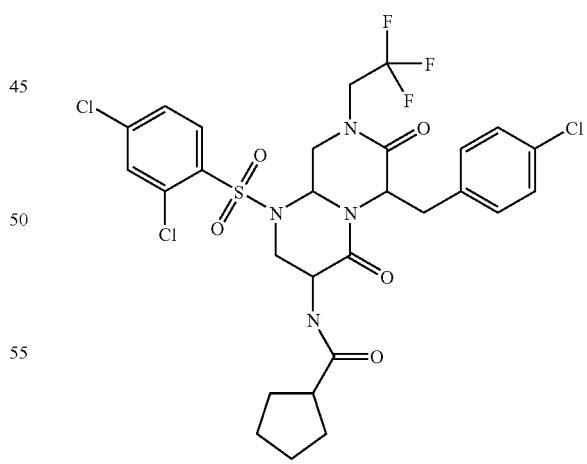

Synthesis takes place in analogy to Example 31 starting from 3-amino-6-(4-chlorobenzyl)-1-(2,4-dichlorobenzenesulfonyl)-8-(2,2,2-trifluoroethyl)hexahydropyrazino[1,2-a]pyrimidine-4,7-dione. The desired product is obtained with MW=694.08 (calculated, monoisotopic); measured value (M+H)+: 695.10

EXAMPLE 296

N-[6-(4-Chlorobenzyl)-1-(2,4-dichlorobenzenesulfonyl)-4,7-dioxo-8-(2,2,2-trifluoroethyl)octahydropyrazino[1,2-a]pyrimidin-3-yl]piperidine-4-carboxamide

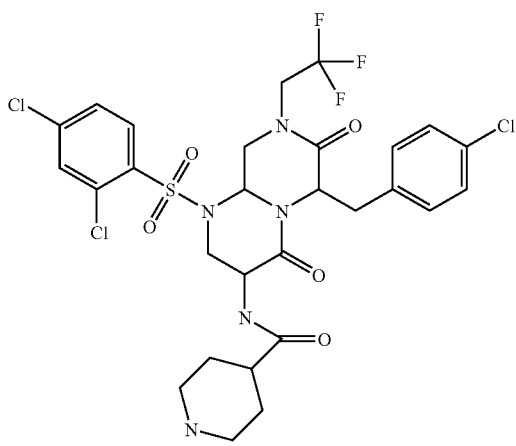

Synthesis takes place in analogy to Example 37 starting from 3-amino-6-(4-chlorobenzyl)-1-(2,4-dichlorobenzenesulfonyl)-8-(2,2,2-trifluoroethyl)hexahydropyrazino[1,2-a]pyrimidine-4,7-dione. The desired product is obtained with MW=709.09 (calculated, monoisotopic); measured value (M+H)$^+$: 710.09

EXAMPLE 297

6-(4-Chlorobenzyl)-1-(2,4-dichlorobenzenesulfonyl)-3-dimethylamino-8-(2,2,2-trifluoroethyl)hexahydropyrazino[1,2-a]pyrimidine-4,7-dione

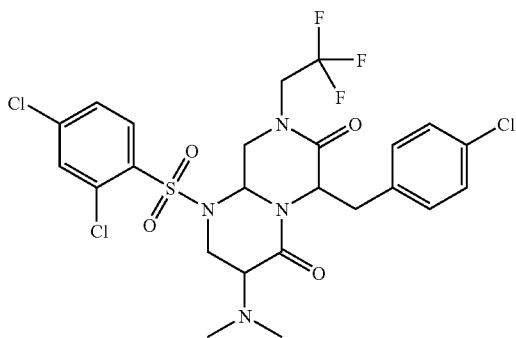

Synthesis takes place in analogy to Example 72 starting from 3-amino-6-(4-chlorobenzyl)-1-(2,4-dichlorobenzenesulfonyl)-8-(2,2,2-trifluoroethyl)hexahydropyrazino[1,2-a]pyrimidine-4,7-dione. The desired product is obtained with MW=626.05 (calculated, monoisotopic); measured value (M+H)$^+$: 627.05

EXAMPLE 298

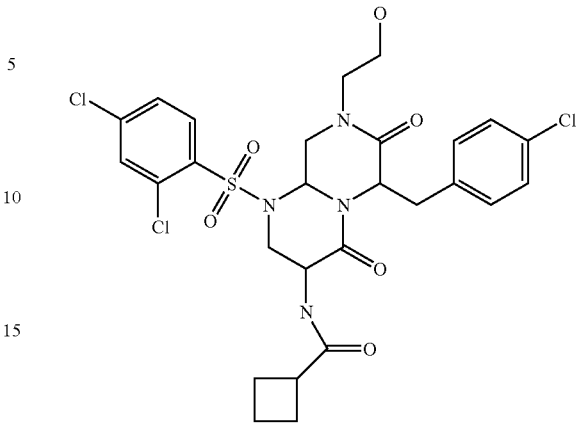

a) Benzyl[6-(4-chlorobenzyl)-1-(2,4-dichlorobenzenesulfonyl)-8-(2-hydroxyethyl)-4,7-dioxooctahydropyrazino[1,2-a]pyrimidin-3-yl]carbamate A solution of 3.13 g (3.96 mmol) of benzyl[1-{2-(4-chlorophenyl)-1-[(2,2-diethoxyethyl)(2-fluoroethyl)carbamoyl]ethylcarbamoyl}-2-(2,4-dichlorobenzenesulfonylamino)ethyl]carbamate in 20 ml of formic acid was heated to 60° C. and stirred for 6 hours. The reaction mixture was concentrated in vacuo, diluted with EtOAc and washed with 1N NaHCO$_3$ solution and brine. The organic phase was isolated, dried (MgSO$_4$) and concentrated in vacuo. This crude substance was subjected to a flash chromatography on 120 g of SiO$_2$ (elution with EtOAc/heptane, gradient 50-100%). 350 mg of the substance benzyl[6-(4-chlorobenzyl)-1-(2,4-dichlorobenzenesulfonyl)-8-(2-fluoroethyl)-4,7-dioxooctahydropyrazino[1,2-a]pyrimidin-3-yl]carbamate were obtained. Further elution of the column provided 980 mg of the compound corresponding to the benzyl[6-(4-chlorobenzyl)-1-(2,4-dichlorobenzenesulfonyl)-8-(2-hydroxyethyl)-4,7-dioxooctahydropyrazino[1,2-a]pyrimidin-3-yl]carbamate byproduct. The monoisotopic MW expected in the LC/MS=694 and the measured value of (M$^+$H)=695 agree with the structure.

b) 3-Amino-6-(4-chlorobenzyl)-1-(2,4-dichlorobenzenesulfonyl)-8-(2-hydroxyethyl)hexahydropyrazino[1,2-a]pyrimidine-4,7-dione Synthesis takes place in analogy to Example 29g) (Method B) starting from benzyl[6-(4-chlorobenzyl)-1-(2,4-dichlorobenzenesulfonyl)-8-(2-hydroxyethyl)-4,7-dioxooctahydropyrazino[1,2-a]pyrimidin-3-yl]carbamate. The desired product is obtained with MW=560.04 (calculated, monoisotopic); measured value (M+H)$^+$: 561.03 c) N-[6-(4-Chlorobenzyl)-1-(2,4-dichlorobenzenesulfonyl)-8-(2-hydroxyethyl)-4,7-dioxooctahydropyrazino[1,2-a]pyrimidin-3-yl]cyclobutanecarboxamide Synthesis takes place in analogy to Example 30 starting from 3-amino-6-(4-chlorobenzyl)-1-(2,4-dichlorobenzenesulfonyl)-8-(2-hydroxyethyl)hexahydropyrazino[1,2-a]pyrimidine-4,7-dione. The desired product is obtained with MW=642.09 (calculated, monoisotopic); measured value (M+H)$^+$: 643.11

EXAMPLE 299

N-[6-(4-Chlorobenzyl)-1-(2,4-dichlorobenzenesulfonyl)-8-(2-hydroxyethyl)-4,7-dioxooctahydropyrazino[1,2-a]pyrimidin-3-yl]cyclopentanecarboxamide

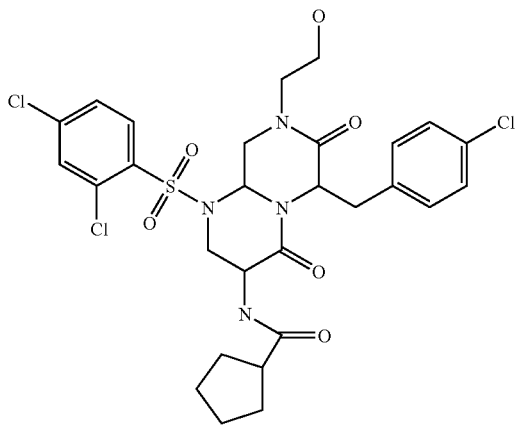

Synthesis takes place in analogy to Example 31 starting from 3-amino-6-(4-chlorobenzyl)-1-(2,4-dichlorobenzenesulfonyl)-8-(2-hydroxyethyl)hexahydropyrazino[1,2-a]pyrimidine-4,7-dione. The desired product is obtained with MW=656.10 (calculated, monoisotopic); measured value $(M+H)^+$: 657.12

EXAMPLE 300

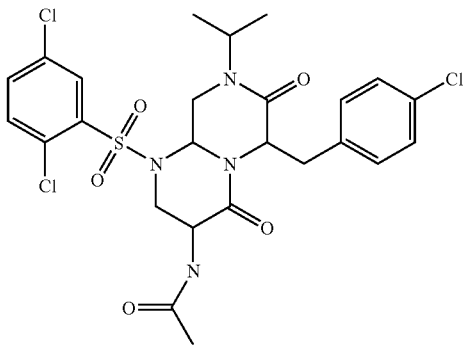

a) 2-Benzyloxycarbonylamino-3-(2,5-dichlorobenzenesulfonylamino)propionic Acid

Synthesis takes place in analogy to Example 21d) starting from 2,5-dichlorobenzenesulfonyl chloride. The desired product is obtained with MW=446.01 (calculated, monoisotopic); measured value $(M+H-CO_2)^+$: 403.00.

a) N-{2-(4-Chlorophenyl)-1-[(2,2-diethoxyethyl)isopropylcarbamoyl]ethyl}-3-(2,5-dichlorobenzenesulfonylamino)-2-methanesulfonylaminopropionamide Synthesis takes place in analogy to Example 21e) starting from 2-benzyloxycarbonylamino-3-(2,6-dichlorobenzenesulfonylamino)propionic acid. The desired product is obtained with MW=784.186 (calculated, monoisotopic); measured value $(M-CO_2+H)^+$: 741.10 b) Benzyl[6-(4-chlorobenzyl)-1-(2,5-dichlorobenzenesulfonyl)-8-isopropyl-4,7-dioxooctahydropyrazino[1,2-a]pyrimidin-3-yl]carbamate Synthesis takes place in analogy to Example 21f) starting from N-{2-(4-chlorophenyl)-1-[(2,2-diethoxyethyl)isopropylcarbamoyl]ethyl}-3-(2,5-dichlorobenzenesulfonylamino)-2-methanesulfonylaminopropionamide. The desired product is obtained with MW=692.10 (calculated, monoisotopic); measured value $(M+H)^+$: 693.05 d) 3-Amino-6-(4-chlorobenzyl)-1-(2,5-dichlorobenzenesulfonyl)-8-isopropylhexahydropyrazino[1,2-a]pyrimidine-4,7-dione Synthesis takes place in analogy to Example 21g) starting from benzyl[6-(4-chlorobenzyl)-1-(2,5-dichlorobenzenesulfonyl)-8-isopropyl-4,7-dioxooctahydropyrazino[1,2-a]pyrimidin-3-yl]carbamate. The desired product is obtained with MW=558.07 (calculated, monoisotopic); measured value $(M+H)^+$: 559.10 e) N-[6-(4-Chlorobenzyl)-1-(2,5-dichlorobenzenesulfonyl)-8-isopropyl-4,7-dioxooctahydropyrazino[1,2-a]pyrimidin-3-yl]acetamide Synthesis takes place in analogy to Example 21h) starting from 3-amino-6-(4-chlorobenzyl)-1-(2,5-dichlorobenzenesulfonyl)-8-isopropylhexahydropyrazino[1,2-a]pyrimidine-4,7-dione. The desired product is obtained with MW=600.08 (calculated, monoisotopic); measured value $(M+H)^+$: 601.13.

EXAMPLE 301

N-[6-(4-Chlorobenzyl)-1-(2,5-dichlorobenzenesulfonyl)-8-isopropyl-4,7-dioxooctahydropyrazino[1,2-a]pyrimidin-3-yl]methanesulfonamide

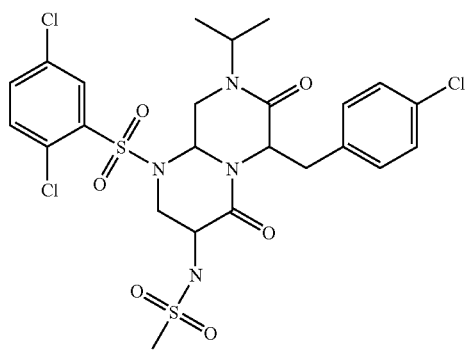

Synthesis takes place in analogy to Example 26 starting from 3-amino-6-(4-chlorobenzyl)-1-(2,5-dichlorobenzenesulfonyl)-8-isopropylhexahydropyrazino[1,2-a]pyrimidine- 4,7-dione. The desired product is obtained with MW=636.04 (calculated, monoisotopic); measured value (M+H)⁺: 637.02.

EXAMPLE 302

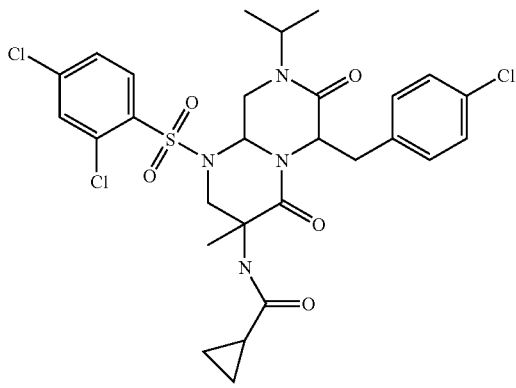

a) Methyl 2-benzyloxycarbonylamino-3-hydroxy-2-methylpropionate 250 mg (2.1 mmol) of 2-amino-3-methylhydroxypropanoic acid are dissolved in 9 ml of anhydrous MeOH. The reaction solution is cooled in an ice bath, and 0.153 ml (2.1 mmol) of SOCl₂ is slowly added dropwise. The solution is allowed to reach room temperature slowly overnight. The reaction solution is concentrated in vacuo and then mixed with 1 ml of EtOAc and 5 ml of saturated NaHCO₃ (aqueous), followed by 0.285 ml (1.995 mmol) of benzyl chloroformate. The solution is stirred at room temperature overnight. Then 5 ml of EtOAc are added, and the organic phase is separated off and washed twice with 1 ml of 1N HCl (aq) each time and twice with 2 ml of a saturated NaHCO₃ (aq) each time, dried over MgSO₄ and concentrated in vacuo. Purification took place by chromatography (40 g of SiO₂, eluent MeOH/DCM (gradient 0-10%). The desired product is obtained as colorless oil (0.130 g) with MW=267 (calculated, monoisotopic), measured value: (M+Na)⁺ 290.

b) Methyl 2-benzyloxycarbonylamino-2-methyl-3-oxopropionate

A solution of 97.7 mg (0.23 mmol) of Dess Martin periodinane reagent (Aldrich) in 1 ml of DCM is slowly added dropwise to a solution of 56 mg (0.21 mmol) of methyl 2-benzyloxycarbonylamino-3-hydroxy-2-methylpropionate in 1 ml of DCM, and the mixture is left to stir at room temperature for 30 min. 5 ml of diethyl ether and a mixture of 4 ml of saturated NaHCO₃ and 0.36 g of Na₂S₂O₃.5H₂O are then added to the solution. It is stirred for 15 min until the solid has dissolved, and then the ether phase is washed with saturated NaHCO₃ and water, dried over MgSO₄ and concentrated in vacuo. The crude product is purified by chromatography on 4 g of SiO₂ with EtOAc/heptane (gradient 0-50%). 40 mg of the desired aldehyde are obtained.

c) Methyl 3-allylamino-2-benzyloxycarbonylamino-2-methylpropionate 1.237 ml (16.5 mmol) of allylamine and 0.9 g (7.48 mmol) of MgSO₄ are added to a solution of 0.874 g (3.3 mmol) of methyl 2-benzyloxycarbonylamino-2-methyl-3-oxopropionate in 15 ml of DCM. The mixture is stirred at room temperature overnight. The reaction mixture was then filtered and concentrated in vacuo. 50 ml of anhydrous MeOH, 6 ml of NaCNBH₃ (1.0M in THF) and 1.8 ml of acetic acid are added to the crude product. This mixture is stirred at RT for 2 h. The reaction solution is concentrated in vacuo, and then EtOAc and water are added. The organic phase is separated off and dried over MgSO₄, and the solvent is removed in vacuo. Purification takes place by chromatography (25 g of SiO₂, eluent MeOH/DCM (gradient 0-10%). 1.035 g of the desired product are obtained as an oil. MW=306 (calculated, monoisotopic), measured value: (M+H)⁺307.

d) Methyl 3-amino-2-benzyloxycarbonylamino-2-methylpropionate

A solution of 0.22 g (1.42 mmol) of N,N-dimethylbarbituric acid, 0.02 g (0.017 mmol) of Pd(PPh₃)₄, 1.5 ml of DCM and 0.145 g (0.47 mmol) of methyl 3-allylamino-2-benzyloxycarbonylamino-2-methylpropionate is heated at 35° C. for 2 h. The reaction solution is subsequently concentrated in vacuo, and then 20 ml of diethyl ether are added, and the solution is washed 3 times with 20 ml of saturated Na₂CO₃ each time. A pH of 2 is adjusted by dropwise addition of 4N HCl. The aqueous phase is separated off and extracted with 2 ml of EtOAc, and the solvent is removed in vacuo. 0.105 g of the desired product are obtained. MW (calculated, monoisotopic)=266, measured value: (M+H)⁺ 267.

e) Methyl 2-benzyloxycarbonylamino-3-(2,4-dichlorobenzenesulfonylamino)-2-methylpropionate 0.103 g (0.341 mmol) of methyl 3-amino-2-benzyloxycarbonylamino-2-methylpropionate, 0.109 g (0.443 mmol) of 2,4 dichlorobenzenesulfonyl chloride and 0.237 ml (1.36 mmol) of DIEA are dissolved in 2 ml of DCM. The mixture is stirred at room temperature overnight. 2 ml are added to the reaction solution, and then the organic phase is separated off and dried over MgSO₄, and the solvent is removed in vacuo. The crude product is purified by chromatography on 4 g of SiO₂, EtOAc/DCM as eluent (gradient of 0-40%). 0.081 g of the desired product is obtained as an oil. MW=474 (calculated, monoisotopic), measured value: (M+H)⁺ 475.

f) 2-Benzyloxycarbonylamino-3-(2,4-dichlorobenzenesulfonylamino)-2-methylpropionic Acid 0.08 g (0.168 mmol) of methyl 2-benzyloxycarbonylamino-3-(2,4-dichlorobenzenesulfonylamino)-2-methylpropionate and 0.093 g (0.674 mmol) of potassium carbonate are stirred in a mixture of 4.5 ml of MeOH and 0.5 ml of water for 90 min. Then 3 ml of saturated NaHCO₃ solution are added, and the mixture is stirred at 60° C. for 2 h. 0.5 ml of water is added, followed by 4N HCl (aq) until a pH of 2 is reached. The solution is extracted 3 times with 10 ml of EtOAc each time, the combined organic phases are dried over MgSO₄, and the solvent is removed in vacuo. 68 mg of the desired product are obtained. MW=460 (calculated, monoisotopic), measured value: (M+H)⁺461.

g) Benzyl[1-{2-(4-chlorophenyl)-1-[(2,2-diethoxyethyl)isopropylcarbamoyl]-ethylcarbamoyl-2-(2,4-dichlorobenzenesulfonylamino)-1-methylethyl]carbamate 52.6 mg (0.15 mmol) of 2-amino-3-(4-chlorophenyl)-N-(2,2-diethoxyethyl)-N-isopropylpropionamide and 41 mg of 4-(4-6-dimethoxy[1,3,5]triazine-2-yl)4-methylmorpholinium chloride xH₂O (DMTMM) are added to a solution of 68 mg (0.15 mmol) of 2-benzyloxycarbonylamino-3-(2,4-dichlorobenzenesulfonylamino)-2-methylpropionic acid in 3 ml of DMF. This reaction solution is stirred at room temperature overnight and, after addition of 10 ml of diethyl ether, the organic phase is separated off and dried over MgSO$_4$. The solvent is removed in vacuo, and the crude product is purified by chromatography on 4 g of SiO$_2$ (eluent MeOH/DCM, gradient 0-1%). 83 mg of the desired product are obtained. MW=798 (calculated, monoisotopic), measured value: (M+H)$^+$799.

h) Benzyl[6-(4-chlorobenzyl)-1-(2,4-dichlorobenzenesulfonyl)-8-isopropyl-3-methyl-4,7-dioxooctahydropyrazino[1,2-a]pyrimidin-3-yl]carbamate A solution of 80 mg (0.1 mmol) of benzyl[1-{2-(4-chlorophenyl)-1-[(2,2-diethoxyethyl)isopropylcarbamoyl]ethylcarbamoyl}-2-(2,4-dichlorobenzenesulfonylamino)-1-methylethyl]carbamate in 1.5 ml of HCOOH (99%) is stirred at 60° C. for 24 h. The reaction solution is concentrated in vacuo, and the crude product is purified by chromatography (4 g of SiO$_2$, eluent EtOAc/heptane (gradient 0-50%)). 30 mg of the desired product are obtained as a white solid. MW (calculated, monoisotopic)=706, measured value: (M+H)$^+$=707 i) 3-Amino-6-(4-chlorobenzyl)-1-(2,4-dichlorobenzenesulfonyl)-8-isopropyl-3-methylhexahydropyrazino[1,2-a]pyrimidine-4,7-dione A solution of benzyl[6-(4-chlorobenzyl)-1-(2,4-dichlorobenzenesulfonyl)-8-isopropyl-3-methyl-4,7-dioxooctahydropyrazino[1,2-a]pyrimidin-3-yl]carbamate in 2 ml of acetonitrile is cooled to 0° C. in an ice bath, and 0.05 ml (0.35 mmol) of TMSI is added.

The solution is stirred at room temperature overnight and then concentrated in vacuo, dissolved in 1 ml of MeOH and put on a 1 g SCX column, and impurities are washed out with 5 ml of MeOH, followed by 5 ml of 2N NH$_3$ in MeOH to elute the product. Concentration in vacuo results in 15 mg of the desired product. MW (calculated, monoisotopic)=572, measured value: (M+H)$^+$ 573.

N-[1-Benzenesulfonyl-6-(4-chlorobenzyl)-8-isopropyl-3-methyl-4,7-dioxooctahydropyrazino[1,2-a]pyrimidin-3-yl]cyclopropanecarboxamide Synthesis takes place in analogy to Example 22 starting from 3-amino-6-(4-chlorobenzyl)-1-(2,4-dichlorobenzenesulfonyl)-8-isopropyl-3-methylhexahydropyrazino[1,2-a]pyrimidine-4,7-dione. The desired product is obtained with MW=640 (calculated, monoisotopic); measured value (M+H)$^+$: 641

We claim:
1. A compound of the formula I:

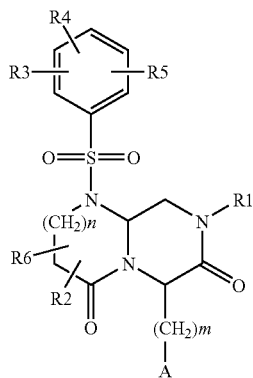

I wherein
A is a 3-, 4-, 5-, 6-, 7-, 8-, 9-, 10-, 11-, and 12-membered mono-, bi- or spirobicyclic ring containing one or more heteroatoms selected from the group of N, O and S, and is optionally substituted with F, Cl, Br, NO$_2$, CF$_3$, OCF$_3$, CN, (C$_1$-C$_6$)-alkyl, aryl, CON(R11)(R12), N(R13)(R14), OH, O—(C$_1$-C$_6$)-alkyl, S—(C$_1$-C$_6$)-alkyl, N(R15)CO(C$_1$-C$_6$)-alkyl or COO—(C$_1$-C$_6$)-alkyl;
R11, R12, R13, R14, R15 are each independently H, (C$_1$-C$_6$)-alkyl or a heterocycle;
n is 1;
m is 0, 1, 2, 3, 4, 5 or 6;
R1 is R8, (C$_1$-C$_6$)-alkylene-R8, (C$_2$-C$_6$)-alkenylene-R9, (SO$_2$)—R8, (SO$_2$)—(C$_1$-C$_6$)-alkylene-R8, (SO$_2$)—(C$_2$-C$_6$)-alkenylene-R9, (C═O)—R8, (C═O)—(C$_1$-C$_6$)-alkylene-R8, (C═O)NH—R8, (C═O)—(C$_2$-C$_6$)-alkenylene-R9, (C═O)—NH—(C$_1$-C$_6$)-alkylene-R8, (C═O)—NH—(C$_2$-C$_6$)-alkenylene-R9, COO—R8, COO—(C$_1$-C$_6$)-alkylene-R8, COO—(C$_2$-C$_6$)-alkenylene-R9, alkynylene-R9 or (C$_1$-C$_4$-alkyl)-heterocycle, wherein the alkylene component of said (C$_1$-C$_6$)-alkylene-R8, (C$_2$-C$_6$)-alkenylene-R9, (SO$_2$)—(C$_1$-C$_6$)-alkylene-R8, (SO$_2$)—(C$_2$-C$_6$)-alkenylene-R9, (C═O)—(C$_1$-C$_6$)-alkylene-R8, (C═O)—(C$_2$-C$_6$)-alkenylene-R9, (C═O)—NH—(C$_1$-C$_6$)-alkylene-R8, (C═O)—NH—(C$_2$-C$_6$)-alkenylene-R9, COO—(C$_1$-C$_6$)-alkylene-R8, COO—(C$_2$-C$_6$)-alkenylene-R9 and alkynylene-R9 groups is optionally substituted by F;
R8, R9 are each independently H, F, Cl, Br, I, OH, CF$_3$ aryl, heterocycle or (C$_3$-C$_8$)-cycloalkyl, wherein said aryl, heterocycle and (C$_3$-C$_8$)-cycloalkyl groups are optionally mono-, di- or tri-substituted by F, Cl, Br, I, OH, CF$_3$, NO$_2$, CN, OCF$_3$, O—(C$_1$-C$_6$)-alkyl, (C$_1$-C$_6$)-alkyl, NH$_2$, CON(R11)(R12), N(R13)(R14), SO$_2$—CH$_3$, COOH, COO—(C$_1$-C$_6$)-alkyl or CONH$_2$;
R2 is NH$_2$, NO$_2$, N(R13)(R14), NH—SO$_2$—CH$_3$, NH—SO$_2$—R$_{12}$, NR11-SO$_2$—R12, N(CO)R11, NHCONR11, N(C$_1$-C$_6$-alkyl)N$^+$(C$_1$-C$_4$-alkyl)$_3$ or a nitrogen-containing heterocycle, wherein said heterocycle is bonded via a nitrogen atom;
R3, R4, R5 are each independently H, F, Cl, Br, I, OH, CF$_3$, NO$_2$, CN, OCF$_3$, O—(C$_1$-C$_6$)-alkyl, O—(C$_1$-C$_4$)-alkoxy-(C$_1$-C$_4$)-alkyl, S—(C$_1$-C$_6$)-alkyl, (C$_1$-C$_6$)-alkyl, (C$_2$-C$_6$)-alkenyl, (C$_3$-C$_8$)-cycloalkyl, O—(C$_3$-C$_8$)-cycloalkyl, (C$_3$-C$_8$)-cycloalkenyl, O—(C$_3$-C$_8$)-cycloalkenyl, (C$_2$-C$_6$)-alkynyl, aryl, O-aryl (C$_1$-C$_8$)-alkylene-aryl, O—(C$_1$-C$_8$)-alkylene-aryl, S-aryl, N((C$_1$-C$_6$)-alkyl)$_2$, SO$_2$—CH$_3$, COOH, COO—(C$_1$-C$_6$)-alkyl or CO—N((C$_1$-C$_6$)-alkyl)$_2$;
R6 is H, F, Cl, Br, I, OH, CF$_3$, NO$_2$, CN, OCF$_3$, O—(C$_1$-C$_6$)-alkyl, O—(C$_1$-C$_4$)-alkoxy-(C$_1$-C$_4$)-alkyl, S—(C$_1$-C$_6$)-alkyl, (C$_1$-C$_6$)-alkyl, (C$_2$-C$_6$)-alkenyl, (C$_3$-C$_8$)-cycloalkyl, O—(C$_3$-C$_8$)-cycloalkyl, (C$_3$-C$_8$)-cycloalkenyl, O—(C$_3$-C$_8$)-cycloalkenyl, (C$_2$-C$_6$)-alkynyl, (C$_0$-C$_8$)-alkylene-aryl, O—(C$_0$-C$_8$)-alkylene-aryl, S-aryl, N((C$_1$-C$_6$)-alkyl)$_2$, SO$_2$—CH$_3$, COOH, COO—(C$_1$-C$_6$)-alkyl or CO—N((C$_1$-C$_6$)-alkyl)$_2$;
Aryl is phenyl or naphthyl;
Heterocycle is acridinyl, azocinyl, benzimidazolyl, benzofuryl, benzothienyl, benzothiophenyl, benzoxazolyl, benzthiazolyl, benztriazolyl, benztetrazolyl, benzisoxazolyl, benzisothiazolyl, benzimidazalinyl, carbazolyl, 4aH-carbazolyl, carbolinyl, quinazolinyl, quinolinyl, 4H-quinolizinyl, quinoxalinyl, quinuclidinyl, chromanyl, chromenyl, cinnolinyl, decahydroquinolinyl, 2H,6H-1,5,2-dithiazinyl, dihydrofuro[2,3-b]-tetrahydrofuran, furyl, furazanyl, imidazolidinyl, imidazolinyl, imidazolyl, 1H-indazolyl, indolinyl, indolizinyl, indolyl, 3H-indolyl, isobenzofuranyl, isochromanyl, isoindazolyl, isoindolinyl, isoindolyl, isoquinolinyl, benzimidazolyl, isothiazolyl, isoxazolyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxazolidinyl, pyrimidinyl, phenanthridinyl, phenanthrolinyl, phenazinyl, phenothiazinyl, phenoxathiinyl, phenoxazinyl, phthalazinyl, piperazinyl, piperidinyl, pteridinyl, purinyl, pyranyl, pyrazinyl, pyrazolidinyl, pyrazolinyl, pyrazolyl, pyridazinyl, pyridooxazoles, pyridoimidazoles, pyridothiazoles, pyridinyl, pyridyl, pyrimidinyl, pyrrolidinyl, pyrrolinyl, 2H-pyrrolyl, pyrrolyl, tetrahydrofuranyl, tetrahydroisoquinolinyl, tetrahydroquinolinyl, 6H-1,2,5-thiadazinyl, thiazolyl, 1,2,3-thiadiazolyl, 1,2,4-thiadiazolyl, 1,2,5-thiadiazolyl, 1,3,4-thiadiazolyl, thienyl, triazolyl, tetrazolyl and xanthenyl and corresponding N-oxides;

wherein said heterocycle is optionally substituted one or more times, each substituent independently chosen from F, Cl, Br, I, $CF_3$, $NO_2$, $N_3$, CN, COOH, COO($C_1$-$C_6$)alkyl, $CONH_2$, $CONH(C_1$-$C_6)$alkyl, CON[($C_1$-$C_6$)alkyl]$_2$, ($C_1$-$C_6$)-alkyl, ($C_2$-$C_6$)-alkenyl, ($C_2$-$C_6$)-alkynyl, O—($C_1$-$C_6$)-alkyl, wherein one or more than one, or all hydrogen(s) in the alkyl radicals may be replaced by fluorine;

$PO_3H_2$, $SO_3H$, $SO_2$—$NH_2$, $SO_2NH(C_1$-$C_6)$-alkyl, $SO_2N[(C_1$-$C_6)$-alkyl]$_2$, S—($C_1$-$C_6$)-alkyl, S—($CH_2$)$_n$-phenyl, SO—($C_1$-$C_6$)-alkyl, SO—($CH_2$)$_n$-phenyl, $SO_2$—($C_1$-$C_6$)-alkyl, $SO_2$—($CH_2$)$_n$-phenyl, wherein n can be 0-6, and the phenyl radical may be substituted up to two times by F, Cl, Br, OH, $CF_3$, $NO_2$, CN, $OCF_3$, O—($C_1$-$C_6$)-alkyl, ($C_1$-$C_6$)-alkyl or $NH_2$; C(NH)($NH_2$), $NH_2$, NH—($C_1$-$C_6$)-alkyl, N(($C_1$-$C_6$)-alkyl)$_2$, NH($C_1$-$C_7$)-acyl, phenyl and O—($CH_2$)$_n$-phenyl, wherein n may be 0-6, and wherein the phenyl ring may be substituted one to 3 times by F, Cl, Br, I, OH, $CF_3$, $NO_2$, CN, $OCF_3$, O—($C_1$-$C_6$)-alkyl, ($C_1$-$C_6$)alkyl, $NH_2$, NH($C_1$-$C_6$)-alkyl, N(($C_1$-$C_6$)-alkyl)$_2$-$SO_2$—$CH_3$, COOH, COO—($C_1$-$C_6$)-alkyl or $CONH_2$;

or a pharmaceutically acceptable salt thereof.

2. The compound of claim 1 having the following structure Ia

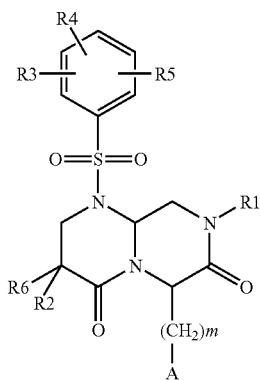

Ia wherein

A is a 3-, 4-, 5-, 6-, 7-, 8-, 9-, 10-, 11-, and 12-membered mono-, bi- or spirobicyclic ring containing one or more heteroatoms selected from the group of N, O and S, and is optionally substituted with F, Cl, Br, $NO_2$, $CF_3$, $OCF_3$, CN, ($C_1$-$C_6$)-alkyl, aryl, CON(R11)(R12), N(R13)(R14), OH, O—($C_1$-$C_6$)-alkyl, S—($C_1$-$C_6$)-alkyl, N(R15)CO($C_1$-$C_6$)-alkyl or COO—($C_1$-$C_6$)-alkyl;

R11, R12, R13, R14, R15 are each independently H, ($C_1$-$C_6$)-alkyl or a heterocycle;

m is 0, 1, 2, 3, 4, 5 or 6;

R1 is R8, ($C_1$-$C_6$)-alkylene-R8, ($C_2$-$C_6$)-alkenylene-R9, ($SO_2$)—R8, ($SO_2$)—($C_1$-$C_6$)-alkylene-R8, ($SO_2$)—($C_2$-$C_6$)-alkenylene-R9, (C=O)—R8, (C=)—($C_1$-$C_6$)-alkylene-R8, (C=O)NH—R8, (C=O)—($C_2$-$C_6$)-alkenylene-R9, (C=O)—NH—($C_1$-$C_6$)-alkylene-R8, (C=O)—NH—($C_2$-$C_6$)-alkenylene-R9, COO—R8, COO—($C_1$-$C_6$)-alkylene-R8, COO—($C_2$-$C_6$)-alkenylene-R9, alkynylene-R9 or ($C_1$-$C_4$-alkyl)-heterocycle;

R8, R9 are each independently H, F, Cl, Br, I, OH, $CF_3$ aryl, heterocycle or ($C_3$-$C_8$)-cycloalkyl, wherein said aryl, heterocycle and ($C_3$-$C_8$)-cycloalkyl groups are optionally mono-, di- or tri-substituted by F, Cl, Br, I, OH, $CF_3$, $NO_2$, CN, $OCF_3$, O—($C_1$-$C_6$)-alkyl, ($C_1$-$C_6$)-alkyl, $NH_2$, CON(R11)(R12), N(R13)(R14), $SO_2$—$CH_3$, COOH, COO—($C_1$-$C_6$)-alkyl or $CONH_2$;

R2 is $NH_2$, $NO_2$, N(R13)(R14), NH—$SO_2$—$CH_3$, NH—$SO_2$—R12, NR11—$SO_2$—R12, N(CO)R11, NHCONR11, N(($C_1$-$C_6$alkyl)N$^+$($C_1$-$C_4$-alkyl)$_3$ or a nitrogen-containing heterocycle, wherein said heterocycle is bonded via a nitrogen atom;

R3, R4, R5 are each independently H, F, Cl, Br, I, OH, $CF_3$, $NO_2$, CN, $OCF_3$, O—($C_1$-$C_6$)-alkyl, O—($C_1$-$C_4$)-alkoxy-($C_1$-$C_4$)-alkyl, S—($C_1$-$C_6$)-alkyl, ($C_1$-$C_6$)-alkyl, ($C_2$-$C_6$)-alkenyl, ($C_3$-$C_8$)-cycloalkyl, O—($C_3$-$C_8$)-cycloalkyl, ($C_3$-$C_8$)-cycloalkenyl, O—($C_3$-$C_8$)-cycloalkenyl, ($C_2$-$C_6$)-alkynyl, aryl, O-aryl, ($C_1$-$C_8$)-alkylene-aryl, O—($C_1$-$C_8$)-alkylene-aryl, S-aryl, N(($C_1$-$C_6$)-alkyl)$_2$, $SO_2$—$CH_3$, COOH, COO—($C_1$-$C_6$)-alkyl or CO—N(($C_1$-$C_6$)-alkyl)$_2$;

R6 is H, F, Cl, Br, I, OH, $CF_3$, $NO_2$, CN, $OCF_3$, O—($C_1$-$C_6$)-alkyl, O—($C_1$-$C_4$)-alkoxy-($C_1$-$C_4$)-alkyl, S—($C_1$-$C_6$)-alkyl, ($C_1$-$C_6$)-alkyl, ($C_2$-$C_6$)-alkenyl, ($C_3$-$C_8$)-cycloalkyl, O—($C_3$-$C_8$)-cycloalkyl, ($C_3$-$C_8$)-cycloalkenyl, O—($C_3$-$C_8$)-cycloalkenyl, ($C_2$-$C_6$)-alkynyl, aryl, O-aryl, ($C_1$-$C_8$)-alkylene-aryl, O—($C_1$-$C_8$)-alkylene-aryl, S-aryl, N(($C_1$-$C_6$)-alkyl)$_2$, $SO_2$—$CH_3$, COOH, COO—($C_1$-$C_6$)-alkyl or CO—N(($C_1$-$C_6$)-alkyl)$_2$;

or a pharmaceutically acceptable salt thereof.

3. The compound of claim 2 wherein

A is aryl wherein said aryl is optionally substituted by F, Cl, Br, $NO_2$, $CF_3$, $OCF_3$, CN, ($C_1$-$C_6$)-alkyl, aryl, CON(R11)(R12), N(R13)(R14), OH, O—($C_1$-$C_6$)-alkyl, S—($C_1$-$C_6$)-alkyl, N(R15)CO($C_1$-$C_6$)-alkyl or COO—($C_1$-$C_6$)-alkyl;

R11, R12, R13, R14, R15 are each independently H, ($C_1$-$C_6$)-alkyl or heterocycle;

m is 1;

R1 is R8, ($C_1$-$C_6$)-alkylene-R8, ($C_2$-$C_6$)-alkenylene-R9, ($SO_2$)—R8, ($SO_2$)—($C_1$-$C_6$)-alkylene-R8, ($SO_2$)—($C_2$-$C_6$)-alkenylene-R9, (C=O)—R8, (C=O)—($C_1$-$C_6$)-alkylene-R8, (C=O)NH—R8, (C=O)—($C_2$-$C_6$)-alkenylene-R9, (C=O)—NH—($C_1$-$C_6$)-alkylene-R8, (C=O)—NH—($C_2$-$C_6$)-alkenylene-R9, COO—R8, COO—($C_1$-$C_6$)-alkylene-R8, COO—($C_2$-$C_6$)-alkenylene-R9, alkynylene-R9 or ($C_1$-$C_4$-alkyl)-heterocycle;

R8, R9 are each independently H, F, Cl, Br, I, OH, $CF_3$ aryl, heterocycle or ($C_3$-$C_8$)-cycloalkyl, wherein said aryl, heterocycle and ($C_3$-$C_8$)-cycloalkyl groups are optionally mono-, di-, or tri-substituted by F, Cl, Br, I, OH, $CF_3$, $NO_2$, CN, $OCF_3$, O—$(C_1-C_6)$-alkyl, $(C_1C_6)$-alkyl, $NH_2$, CON(R11)(R12), N(R13)(R14), $SO_2$—$CH_3$, COOH, COO—$(C_1C_6)$-alkyl or $CONH_2$;

R2 is $NH_2$, $NO_2$, N(R13)(R14), NH—$SO_2$—$CH_3$, NH—$SO_2$—R12, NR11-$SO_2$—R12, N(CO)R11, NHCONR11, $N(C_1-C_6$-alkyl$)N^+(C_1-C_4$-alkyl$)_3$ or a nitrogen-containing heterocycle, wherein said heterocycle is bonded via a nitrogen atom, R3 is H R4, R5 are each independently H, F, Cl, Br, OH, $CF_3$, $OCF_3$, O—$(C_1-C_6)$-alkyl or $(C_1-C_6)$—alkyl;

R6 is H;

or a pharmaceutically acceptable salt thereof.

4. The compound of claim 3 wherein

A is aryl, wherein said aryl group is optionally substituted by F, Cl, Br, $NO_2$, $CF_3$, $OCF_3$, CN, $(C_1-C_6)$-alkyl, aryl, CON(R11)(R12), N(R13)(R14), OH, O—$(C_1-C_6)$-alkyl, S—$(C_1-C_6)$-alkyl, N(R15)CO$(C_1-C_6)$-alkyl or COO—$(C_1-C_6)$-alkyl;

R11, R12, R13, R14, R15 are each independently H, $(C_1-C_6)$-alkyl or heterocycle;

m is 1;

R1 is $(C_1-C_6)$-alkyl or $(C_1-C_6)$-alkylene-R8;

R8, R9 are each independently F, Cl, Br, I, OH or $CF_3$;

R2 is $NH_2$, $NO_2$, CN, N(R13)(R14), NH—$SO_2$—$CH_3$, NH—$SO_2$—R12, NR11—$SO_2$—R12, N(CO)R11, NHCONR11, $N(C_1-C_6$-alkyl$)N^+(C_1-C_4$-alkyl$)_3$ or a nitrogen-containing heterocycle, wherein said heterocycle is bonded via a nitrogen atom, R3 is H;

R4 is F, Cl, Br, OH, $CF_3$, $OCF_3$, O—$(C_1-C_6)$-alkyl or $(C_1-C_6)$-alkyl;

R5 is H, F, Cl, Br, OH, $CF_3$, $OCF_3$, O—$(C_1-C_6)$-alkyl or $(C_1-C6)$-alkyl;

R6 is H;

or a pharmaceutically acceptable salt thereof.

5. A pharmaceutical composition comprising a compound of claim 1 or a pharmaceutically acceptable salt thereof.

* * * * *

UNITED STATES PATENT AND TRADEMARK OFFICE
CERTIFICATE OF CORRECTION

PATENT NO.       : 7,652,007 B2         Page 1 of 1
APPLICATION NO.  : 10/779439
DATED            : January 26, 2010
INVENTOR(S)      : Flohr et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 670 days.

Signed and Sealed this

Twenty-third Day of November, 2010

David J. Kappos
*Director of the United States Patent and Trademark Office*

UNITED STATES PATENT AND TRADEMARK OFFICE
CERTIFICATE OF CORRECTION

| | | |
|---|---|---|
| PATENT NO. | : 7,652,007 B2 | Page 1 of 1 |
| APPLICATION NO. | : 10/779439 | |
| DATED | : January 26, 2010 | |
| INVENTOR(S) | : Stefanie Flohr et al. | |

It is certified that error appears in the above-identified patent and that said Letters Patent is hereby corrected as shown below:

In column 4, line 16, delete "N+" and insert -- $N^+$ --, therefor.

In column 11, line 4-5, delete "The Peptides," and insert -- the peptides, --, therefor.

In column 12, line 9, delete "sofware)" and insert -- software) --, therefor.

In column 59, line 59, delete "DEA" and insert -- DIEA --, therefor.

In column 179, line 56, delete "monoisotopic)," and insert -- monoisotopic); --, therefor.

In column 180, line 28, delete "1-{-[cyclopropyl" and insert -- 1-{1-[cyclopropyl --, therefor.

In column 196, line 39, delete ")4,7" and insert -- )-4,7 --, therefor.

In column 199, line 19, delete "21b)" and insert -- 21h) --, therefor.

In column 203, line 53, delete "2 Id)" and insert -- 21d) --, therefor.

In column 208, line 29, in claim 1, delete "CF$_3$" and insert -- CF$_3$, --, therefor.

In column 210, line 9, in claim 2, delete "(C=)" and insert -- (C=O) --, therefor.

In column 210, line 16, in claim 2, delete "CF$_3$" and insert -- CF$_3$, --, therefor.

In column 210, line 25, in claim 2, delete "C$_6$alkyl)" and insert -- C$_6$-alkyl) --, therefor.

In column 210, line 65, in claim 3, delete "CF$_3$" and insert -- CF$_3$, --, therefor.

In column 211, line 2, in claim 3, delete "(C$_1$C$_6$)" and insert -- (C$_1$-C$_6$) --, therefor.

In column 211, line 4, in claim 3, delete "(C$_1$C$_6$)" and insert -- (C$_1$-C$_6$) --, therefor.

In column 212, line 5, in claim 4, delete "(C$_1$-C6)" and insert -- (C$_1$-C$_6$) --, therefor.

Signed and Sealed this
Thirty-first Day of May, 2011

David J. Kappos
*Director of the United States Patent and Trademark Office*